US012690981B2

(12) United States Patent
Donner et al.

(10) Patent No.: US 12,690,981 B2
(45) Date of Patent: Jul. 28, 2026

(54) MINIMALLY INVASIVE SYSTEMS FOR AND METHODS OF PREPARING AND FUSING A SACROILIAC JOINT DURING INTERVENTIONAL PROCEDURES

(71) Applicant: JCBD, LLC, Fort Collins, CO (US)

(72) Inventors: Edward Jeffrey Donner, Fort Collins, CO (US); Christopher Thomas Donner, Fort Collins, CO (US); Bradley Austin Donner, Fort Collins, CO (US)

(73) Assignee: JCBD, LLC

( * ) Notice: Subject to any disclaimer, the term of this patent is extended or adjusted under 35 U.S.C. 154(b) by 0 days.

(21) Appl. No.: 18/659,806

(22) Filed: May 9, 2024

(65) Prior Publication Data

US 2024/0366240 A1     Nov. 7, 2024

Related U.S. Application Data

(63) Continuation of application No. 17/149,821, filed on Jan. 15, 2021, now Pat. No. 11,998,222, which is a continuation-in-part of application No. 16/822,997, filed on Mar. 18, 2020, now Pat. No. 11,376,026, which is a continuation of application No.

(Continued)

(51) Int. Cl.

| | |
|---|---|
| *A61F 2/44* | (2006.01) |
| *A61B 17/16* | (2006.01) |
| *A61B 17/17* | (2006.01) |
| *A61B 17/70* | (2006.01) |
| *A61B 17/86* | (2006.01) |
| *A61F 2/30* | (2006.01) |
| *A61F 2/46* | (2006.01) |

(Continued)

(52) U.S. Cl.
CPC ............ *A61F 2/44* (2013.01); *A61B 17/1659* (2013.01); *A61B 17/1662* (2013.01); *A61B 17/1671* (2013.01); *A61B 17/1739* (2013.01); *A61B 17/1757* (2013.01); *A61B 17/7055* (2013.01); *A61B 17/7076* (2013.01); *A61B 17/8625* (2013.01); *A61F 2/30* (2013.01); *A61F 2/30749* (2013.01); *A61F 2/30988* (2013.01); *A61F 2/4603* (2013.01); *A61B 2017/0256* (2013.01); *A61B 2017/0275* (2013.01); *A61B 2090/062* (2016.02); *A61F 2002/30179* (2013.01); *A61F 2002/30261* (2013.01); *A61F 2002/30593* (2013.01); *A61F 2002/30622* (2013.01); *A61F 2002/30769* (2013.01); *A61F 2002/30858* (2013.01); *A61F 2002/30995* (2013.01)

(58) Field of Classification Search
CPC ....... A61B 17/1757; A61F 2002/30995; A61F 2/30; A61F 2/44
See application file for complete search history.

(56) References Cited

U.S. PATENT DOCUMENTS

| | | | | | |
|---|---|---|---|---|---|
| 6,053,916 | A | * | 4/2000 | Moore | ................ A61F 2/30988 606/86 R |
| 11,998,222 | B2 | * | 6/2024 | Donner | .............. A61B 17/8625 |

(Continued)

*Primary Examiner* — Christian A Sevilla
(74) *Attorney, Agent, or Firm* — Polsinelli PC

(57) ABSTRACT

A system for performing a minimally invasive interventional fusion procedure on a sacroiliac joint of a patient. The system may include a disposable sterile packed implant and kit including access, bone cutting, accessory and extraction instruments.

32 Claims, 119 Drawing Sheets

Related U.S. Application Data

16/133,605, filed on Sep. 17, 2018, now Pat. No. 10,603,055.

(60) Provisional application No. 63/134,971, filed on Jan. 8, 2021, provisional application No. 62/938,344, filed on Nov. 21, 2019, provisional application No. 62/640,026, filed on Mar. 8, 2018, provisional application No. 62/632,635, filed on Feb. 20, 2018, provisional application No. 62/609,095, filed on Dec. 21, 2017, provisional application No. 62/608,476, filed on Dec. 20, 2017, provisional application No. 62/559,386, filed on Sep. 15, 2017.

(51) Int. Cl.
  *A61B 17/02*     (2006.01)
  *A61B 90/00*     (2016.01)

(56)          References Cited

U.S. PATENT DOCUMENTS

| | | | |
|---|---|---|---|
| 2006/0079908 A1* | 4/2006 | Lieberman | A61B 17/1757 606/99 |
| 2009/0216238 A1* | 8/2009 | Stark | A61F 2/4657 606/329 |
| 2009/0259261 A1* | 10/2009 | Reiley | A61B 17/7055 606/329 |
| 2011/0184518 A1* | 7/2011 | Trieu | A61B 17/562 623/17.11 |

* cited by examiner

800

804

802

803

800

800

800

802

802

305

300

311

301

302

B

307

306

DETAIL A
SCALE 8 : 1

302

300

303

300

305

302

304

302   A

301

300

DETAIL B
SCALE 8 : 1

302

302

302

C

D

305

300

DETAIL C
SCALE 6 : 1

302

300

300

303

303

305

300

301

301

DETAIL D
SCALE 6 : 1

300

305

300

99

DETAIL A
SCALE 2 : 1

A

C
900
100
90
80
70
60
50
40
30
20
10
900
SECTION C-C
C
FIG. 17

900

101

150

102

105

160

107

104

103

400

400

400
400
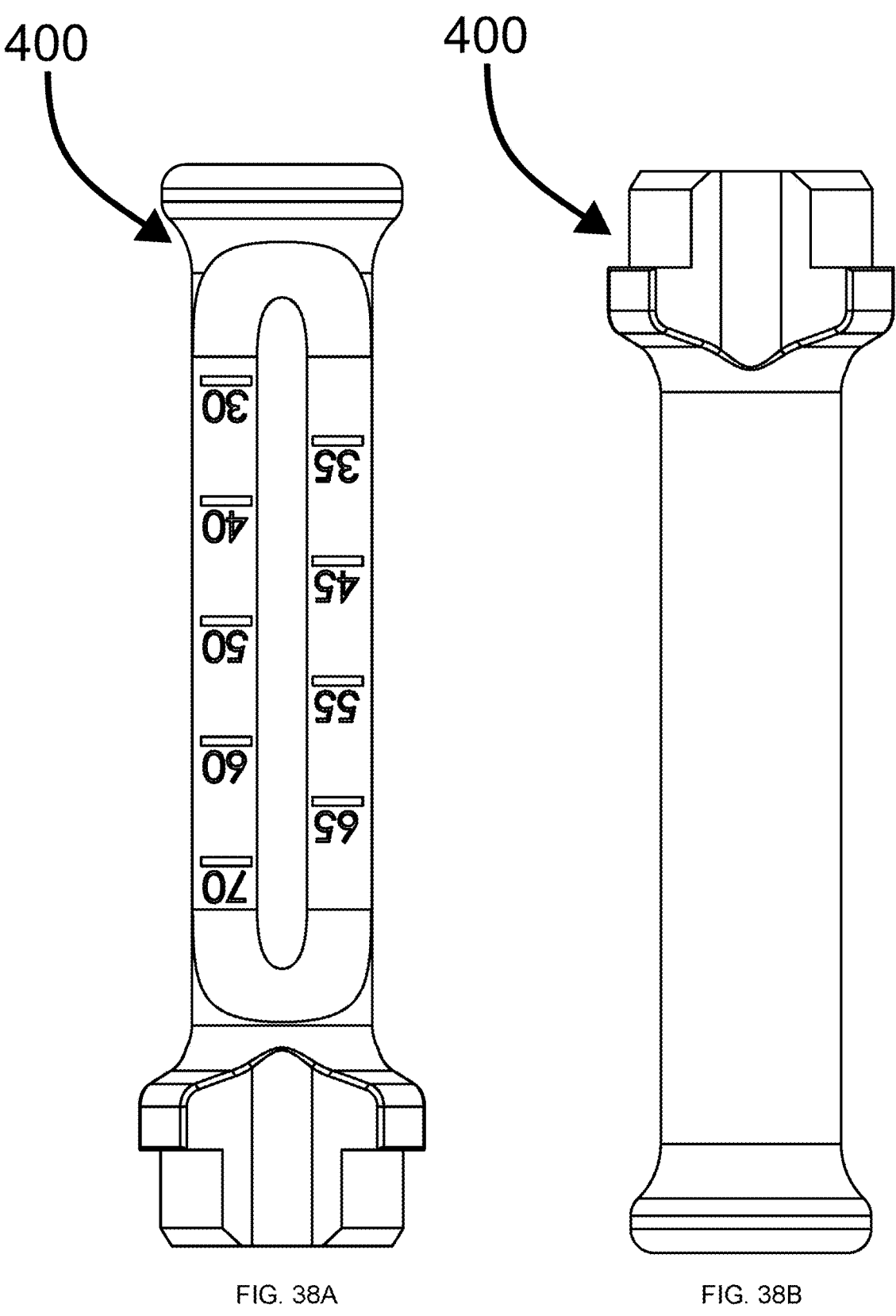
FIG. 38A                    FIG. 38B 400
400
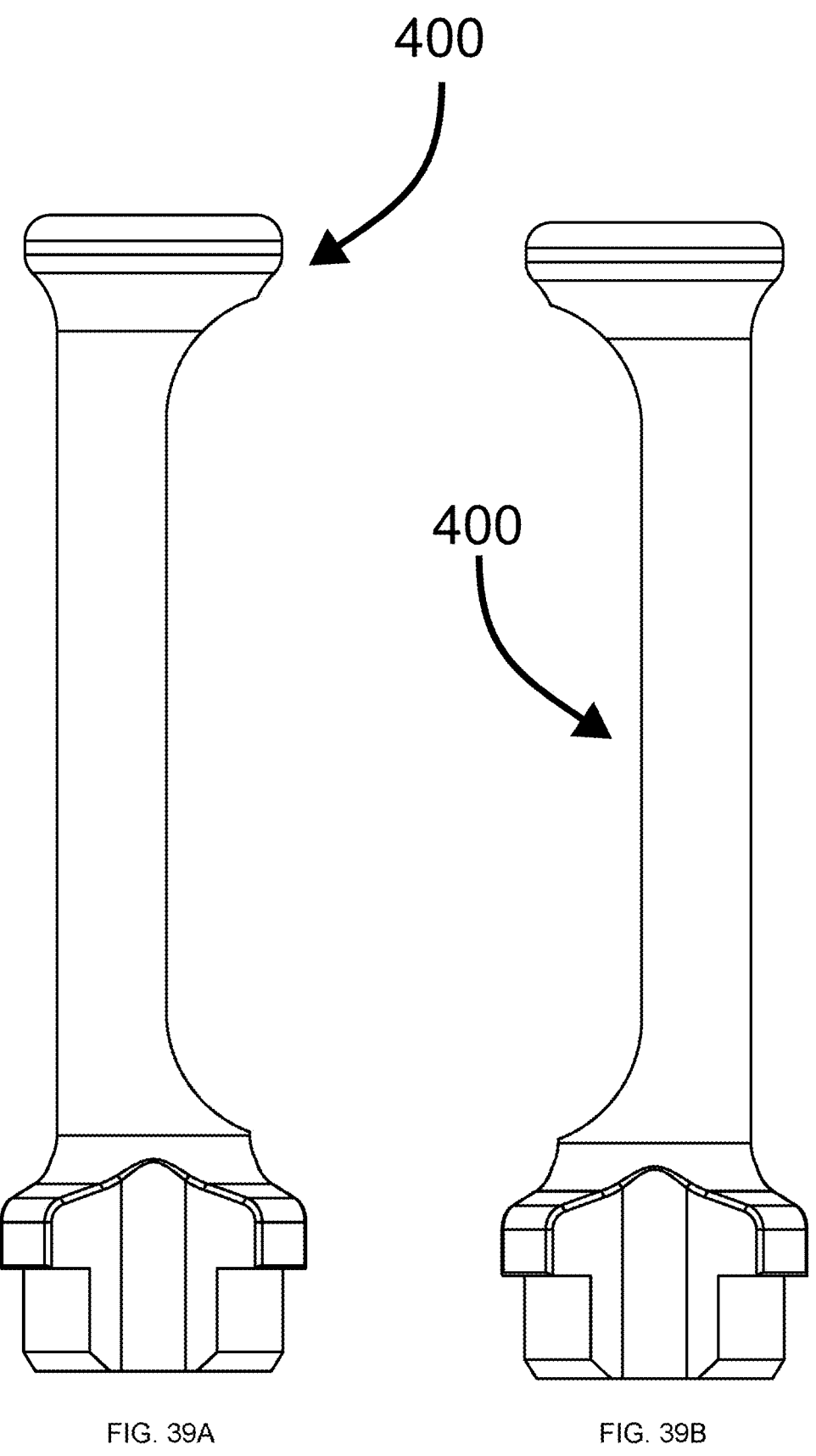
FIG. 39A                    FIG. 39B

400

400

10

400          300

400                    300

B

101

30
40
50
60
35
45
55

306

DETAIL B
SCALE 2 : 1

2

3

10

400     300

400

300

B

101

30

35

40

45

50

55

60

306

DETAIL B
SCALE 2 : 1

2

3

305

500

500

500

505

B

DETAIL A
SCALE 5 : 1

DETAIL B
SCALE 5 : 1

500

500

500

501

SECTION C-C

500

101

C

305

500

101

DETAIL C
SCALE 2 : 1

450

450

450

450

450

450

450

450

450

450

A

450

450

A

SECTION A-A
SCALE 3 : 1

450

450

D

450

DETAIL D
SCALE 2 : 1

450

450

450

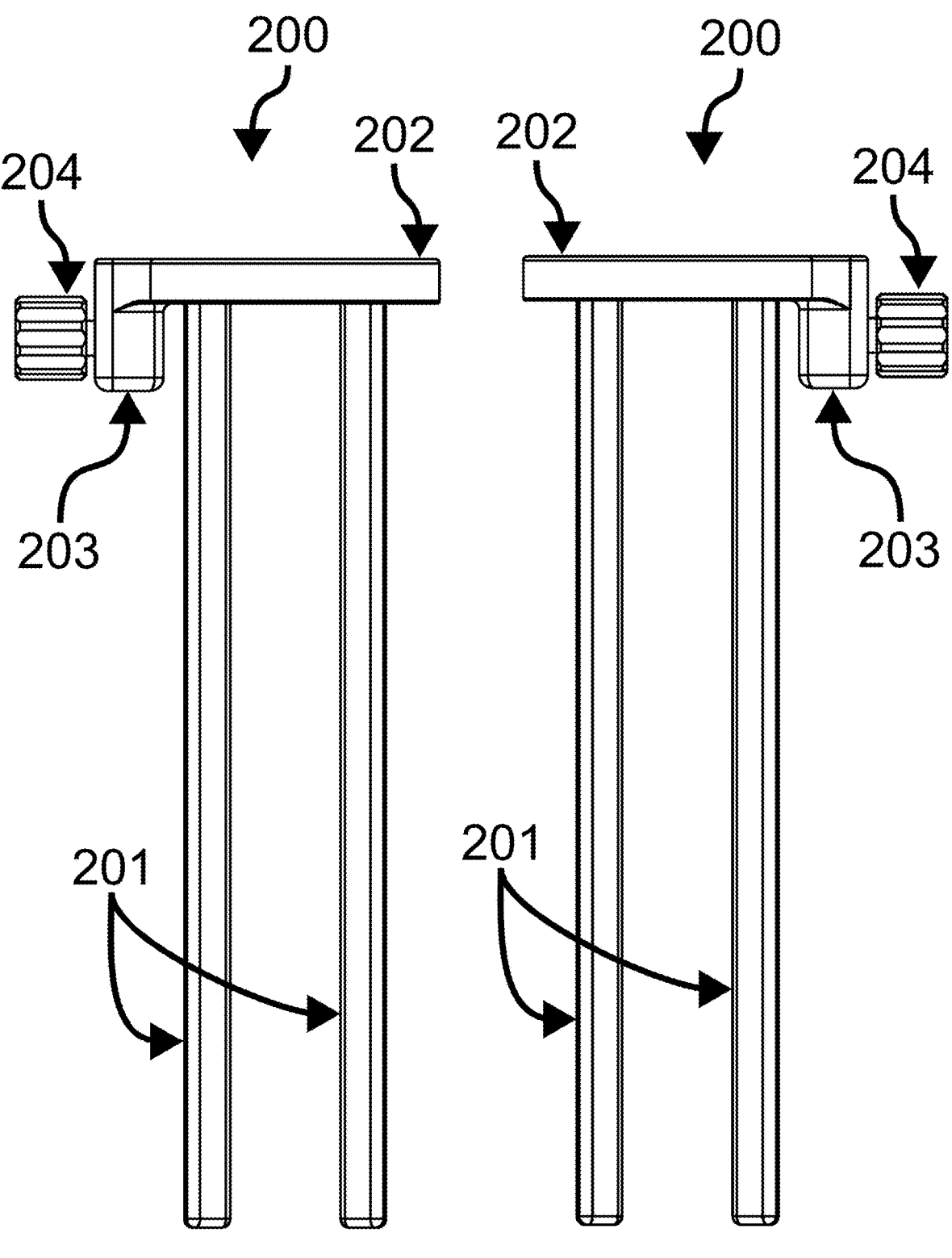
FIG. 62A                    FIG. 62B

200

202

204

203

201

600

603

605

600

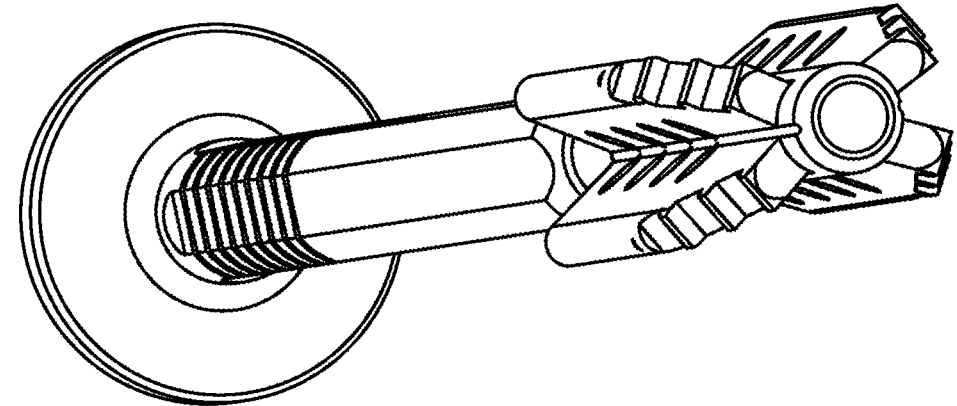
FIG. 74A
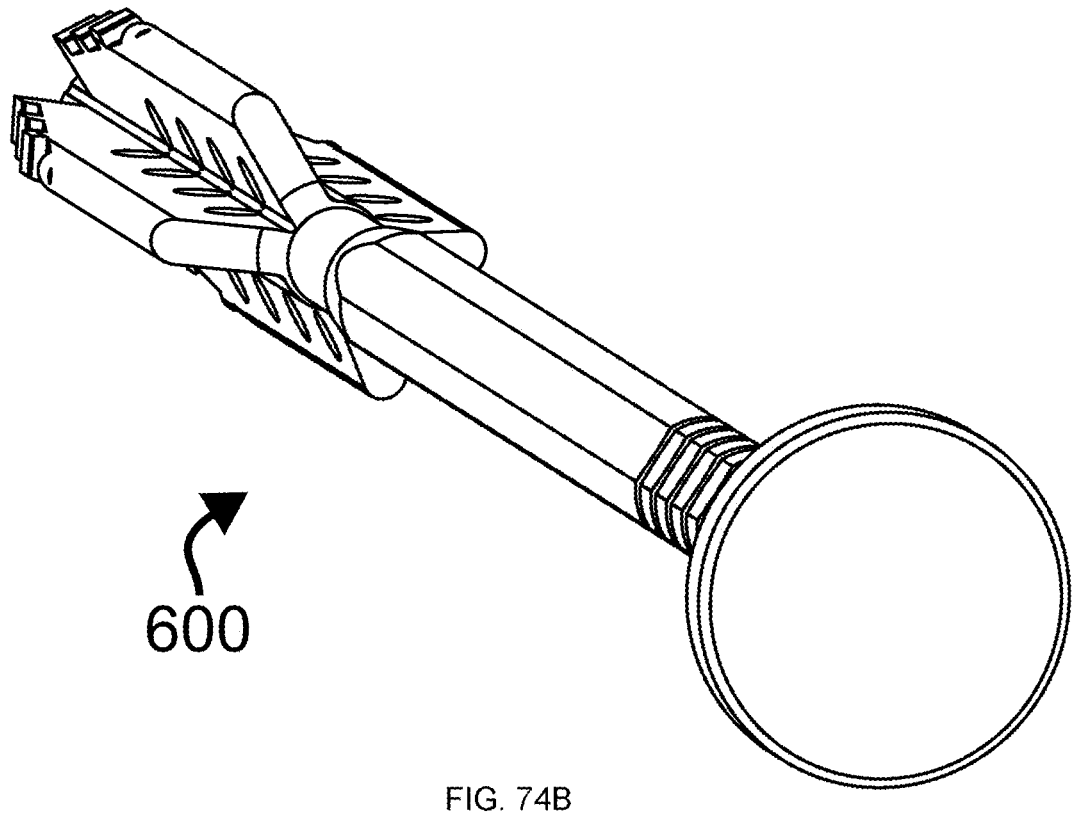
FIG. 74B

600

600

A

B

600

600

DETAIL A
SCALE 2 : 1

DETAIL B
SCALE 2 : 1

600

600

600

300

600

600

600

600

600

A

600

B

600

DETAIL A
SCALE 2 : 1

600

DETAIL B
SCALE 2 : 1

D

600

D

600

SECTION D-D

600

600

600

10

700

703

700

700

702

700

700

703

700

SECTION A-A

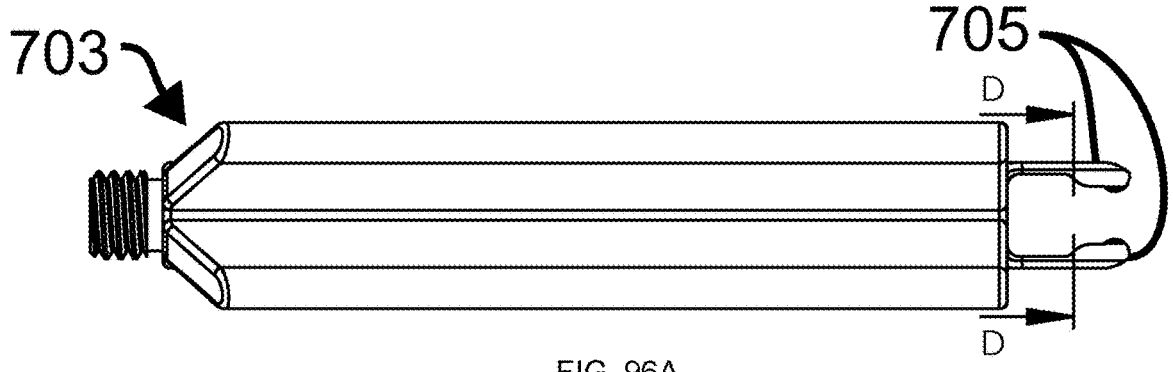
703    705    D    D
FIG. 96A
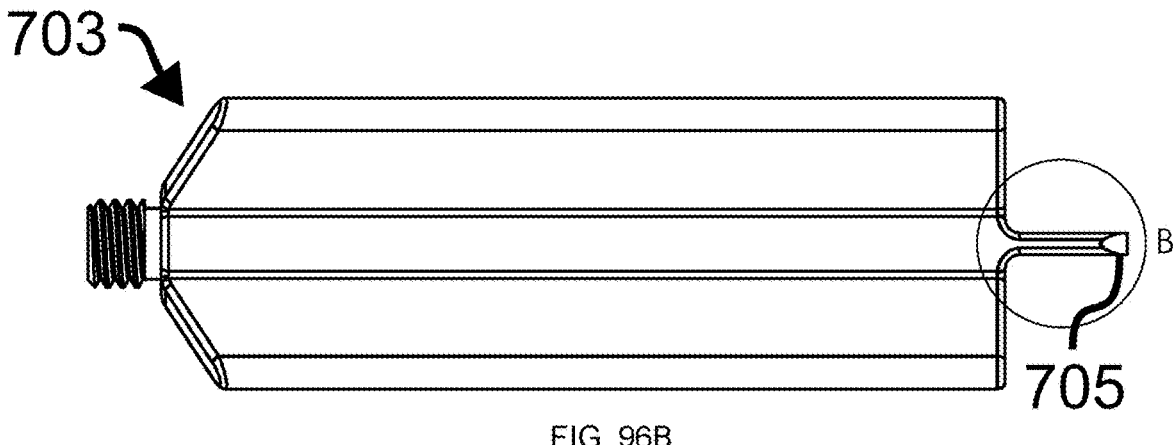
703    B    705
FIG. 96B
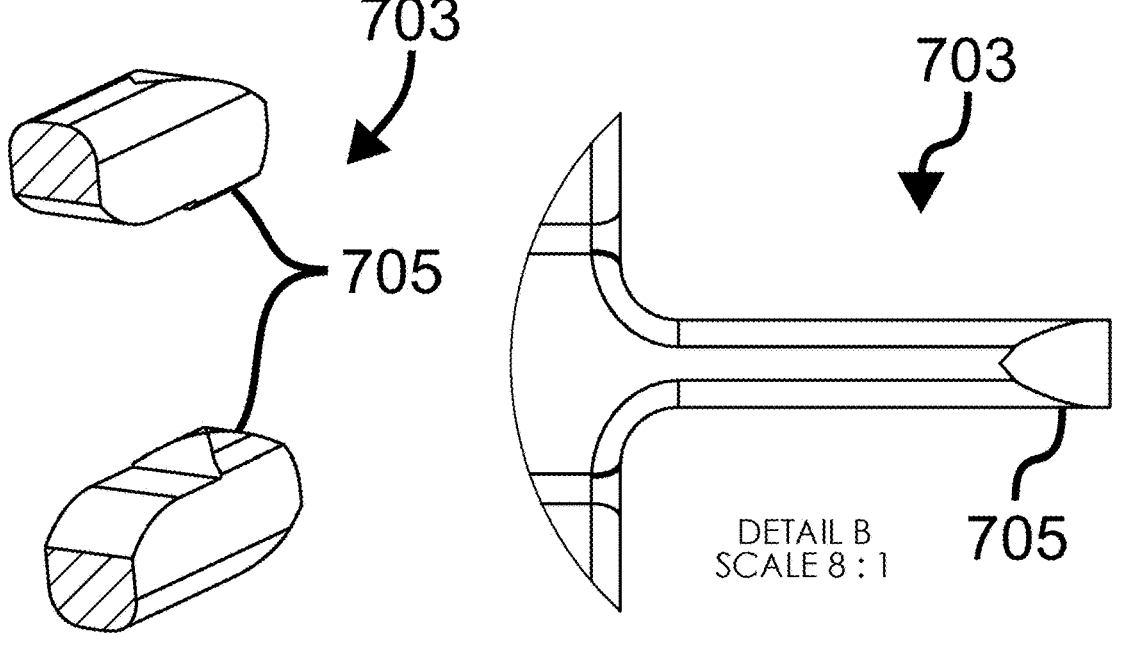
703    705
703    705
SECTION D-D
SCALE 10 : 1
FIG. 96C
DETAIL B
SCALE 8 : 1
FIG. 96D

703

705

SECTION F-F
SCALE 10 : 1

DETAIL E
SCALE 8 : 1

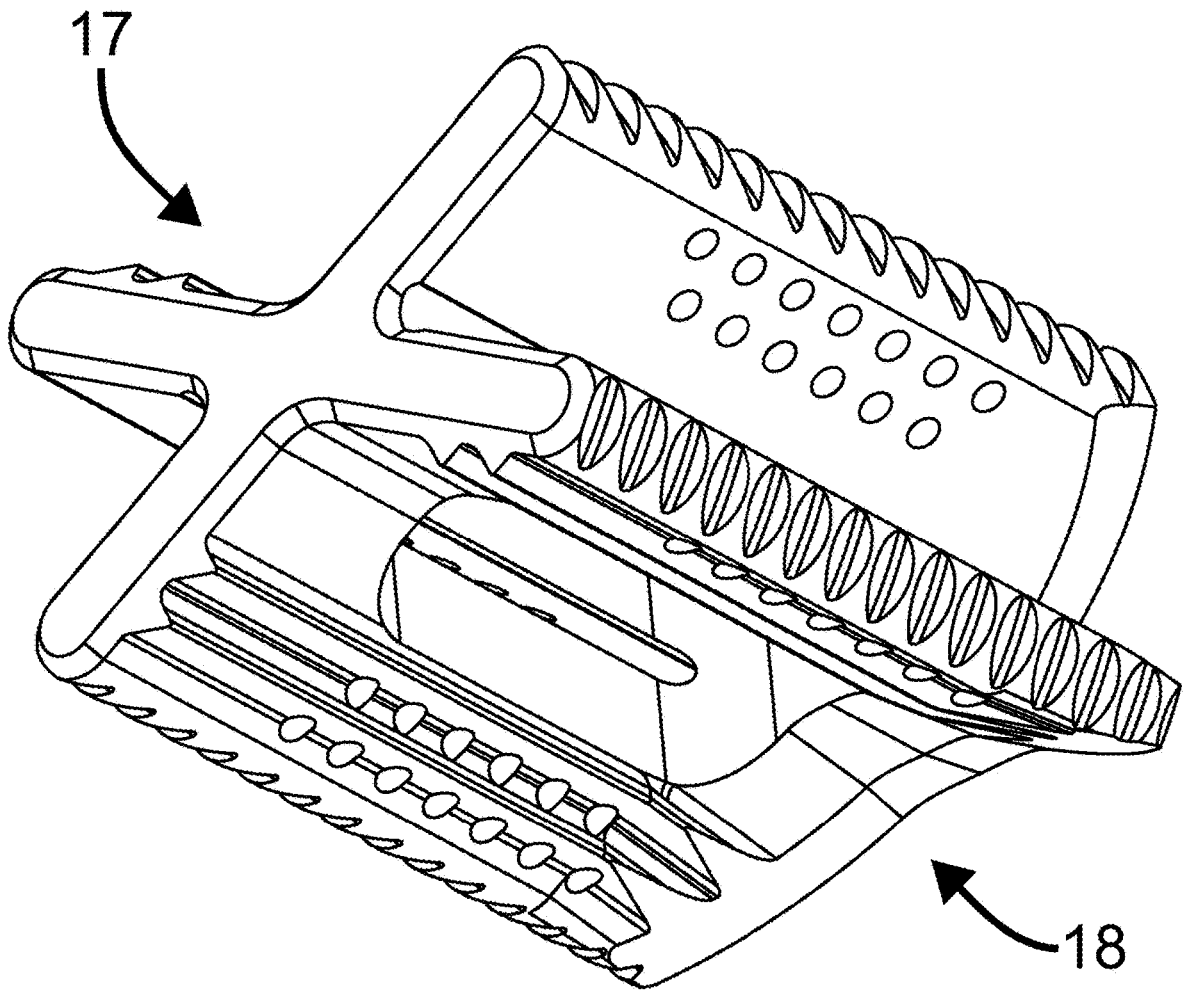
FIG. 100

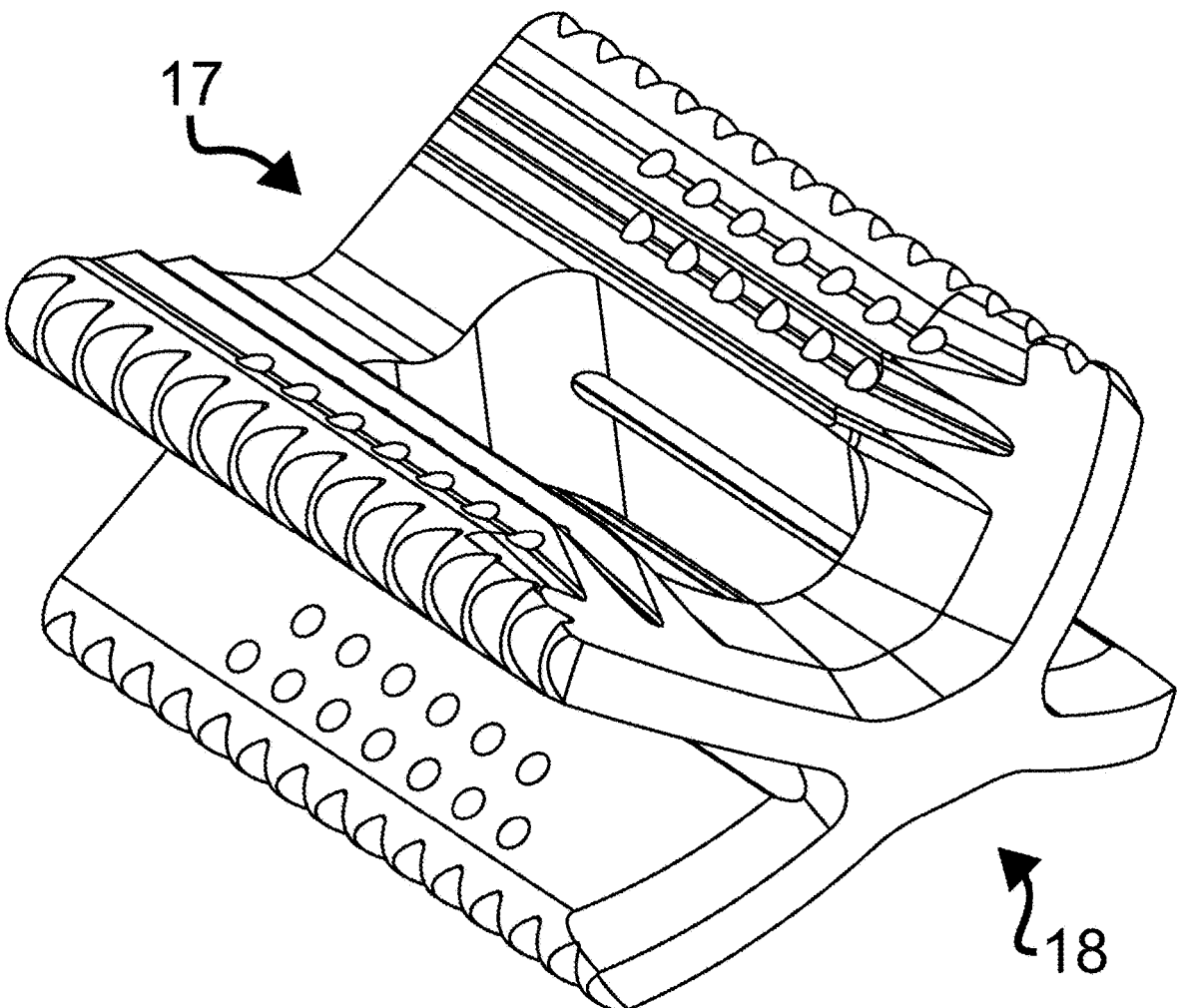
FIG. 101

12

18

17

12

700

700

704

702

DETAIL A
SCALE 5 : 1

A

700

700

700

704

702

SECTION D-D
SCALE 1.25 : 1

DETAIL J
SCALE 3.5 : 1

700

700

700

700

704

702

704

DETAIL I
SCALE 2.5 : 1

DETAIL H
SCALE 2.5 : 1

SECTION E-E
SCALE 1.25 : 1

DETAIL G
SCALE 3 : 1

700

704

MINIMALLY INVASIVE SYSTEMS FOR AND METHODS OF PREPARING AND FUSING A SACROILIAC JOINT DURING INTERVENTIONAL PROCEDURES

CROSS-REFERENCE TO RELATED APPLICATIONS

The present application is a continuation of U.S. application Ser. No. 17/149,821 filed Jan. 15, 2021, which application is a continuation-in-part of U.S. application Ser. No. 16/822,997 filed Mar. 18, 2020, now U.S. Pat. No. 11,376,026, which application is a continuation of U.S. application Ser. No. 16/133,605 filed Sep. 17, 2018, now U.S. Pat. No. 10,603,055, which application claims priority under 35 U.S.C. § 119 to U.S. Provisional Patent Application Nos. 62/559,386 filed Sep. 15, 2017; 62/608,476 filed Dec. 20, 2017; 62/609,095 filed Dec. 21, 2017; 62/632,635 filed Feb. 20, 2018; and 62/640,026 filed Mar. 8, 2018. All the aforementioned applications are hereby incorporated by reference in their entireties into the present application.

U.S. application Ser. No. 17/149,821 also claims the benefit of and priority to U.S. Provisional Application Nos. 62/938,344 filed Nov. 21, 2019, and 63/134,971 filed Jan. 8, 2021.

The present application incorporates by reference the following patent applications in their entireties: U.S. patent application Ser. No. 16/544,193 filed Aug. 19, 2019; U.S. patent application Ser. No. 16/455,308 filed on Jun. 27, 2019; U.S. patent application Ser. No. 16/431,301 filed on Jun. 4, 2019; U.S. provisional patent application Ser. No. 62/854,041 filed May 29, 2019; U.S. patent application Ser. No. 16/282,114 filed Feb. 21, 2019; U.S. patent application Ser. No. 16/133,605 filed Sep. 18, 2018, which claims priority under 35 U.S.C. § 119 to U.S. Provisional Patent Application Nos. 62/559,386 filed Sep. 15, 2017; 62/608,476 filed Dec. 20, 2017; 62/609,095 filed Dec. 21, 2017; 62/632,635 filed Feb. 20, 2018; and 62/640,026 filed Mar. 8, 2018. All the aforementioned U.S. Patent Applications are hereby incorporated by reference in their entireties into the present application.

TECHNICAL FIELD

Aspects of the present disclosure relate to medical apparatus and methods. More specifically, the present disclosure relates to devices and methods for preparing and fusing a sacroiliac joint for fusion.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint may be that the surgeon must make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using an anterior approach can be damage to the L5 nerve root, which lies approximately two centimeters medial to the sacroiliac joint or damage to the major blood vessels. Additionally, during a conventional fusion procedure (immobilization of the articular surfaces of the sacroiliac joint in relation to one another) on a sacroiliac joint, one or more screws or implants are implanted transversely across the articular surfaces and through the sacrum and the ilium bones. That is, the joint is immobilized by placement of a fusion device transverse to or across a plane defined by articular surfaces of the sacroiliac joint space.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to malplacement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension, and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

Improvements to sacroiliac joint fusion involve systems and methods for non-transverse delivery of an implant into the sacroiliac joint are described in U.S. patent application Ser. No. 12/998,712, filed May 23, 2011 entitled SACRO-ILIAC JOINT FIXATION FUSION SYSTEM; Ser. No. 13/236,411, filed Sep. 19, 2011 entitled SYSTEMS FOR AND METHODS OF FUSING A SACROILIAC JOINT; and Ser. No. 13/475,695, filed May 18, 2012, entitled SYSTEMS FOR AND METHODS OF FUSING A SAC-ROILIAC JOINT; and Ser. No. 13/945,053, filed Jul. 18, 2013, entitled SYSTEMS FOR AND METHODS OF FUS-ING A SACROILIAC JOINT; and Ser. No. 13/946,790, filed Jul. 19, 2013, entitled SYSTEMS FOR AND METHODS OF FUSING A SACROILIAC JOINT; and Ser. No. 14/216,975, filed Mar. 17, 2014, entitled SYSTEMS AND METH-ODS FOR FUSING A SACROILIAC JOINT AND ANCHORING AN ORTHOPEDIC APPLIANCE; and Ser. No. 14/447,612, filed Jul. 31, 2014, entitled SYSTEMS FOR AND METHODS OF FUSING A SACROILIAC JOINT. All of applications Ser. Nos. 12/998,712, 13/236,411, 13/475,695, 13/945,053, 13/946,790, 14/216,975, and 14/447,612 are herein incorporated by reference in their entirety. In certain instances, it may be desirable to prepare the surfaces of the sacroiliac joint prior to implantation of the fusion device, e.g., the intra-articular or extra-articular surfaces. While surgical preparation tools may exist for procedures in other areas of the body, tools for preparing the sacroiliac joint for fusion are lacking. Thus, the systems and methods discussed herein address the challenges in preparing the sacroiliac joint for fixation and fusion.

SUMMARY

One implementation of the present disclosure may take the form of a surgical preparation tool for preparing a sacroiliac joint having a sacrum and an ilium for a surgical procedure.

Aspects of the present disclosure may include a system 10 for performing a fusion procedure on a sacroiliac joint 1 defined between a sacrum 2 and an ilium 3. In certain instances, the system 10 may include a working cannula 101 that may include a proximal end 102, a distal end 103, a tubular body 104 extending between the proximal 102 and distal ends 103, a cannula passageway 105 defined within the tubular body 104 and having a cannula axis 106 extending there through. In certain aspects, the tubular body 104 may have a generally circular cross section perpendicular to the cannula axis 106. In other aspects, the tubular body 104 may have a generally ovular cross section perpendicular to the cannula axis 106. In yet further aspects, the tubular body 104 may have a generally slot shaped or even rectangular cross section perpendicular to the cannula axis 106. Irrigation, suction, lighting, electrocautery, bone engaging features, visual or radiographic markers, or electrophysiologic monitoring electrodes and electrical insulation may be incorporated into the working cannula 101 or other tools or implants of the system 10.

In certain instances, the tubular body 104 may include an inner surface 107 that defines the cannula passageway 105, the inner surface 107 may receive a portion of a guide rail assembly 200 including a pair of guide rails 201 extending inward from opposite sides of the inner surface and along the cannula axis 106. Another portion of the guide rail assembly including a ring structure 202 may be seated at the proximal end of the working cannula 101. The guide rail assembly 200 may further include a fastening portion 203 coupled with the ring structure 202 and configured to receive a fastener 204 in order to lock a position and or orientation and or arrangement between the guide rail assembly 200 and the working cannula 101. The fastening portion 203 may be connected with the ring structure 202 such that the fastening portion 203 may engage the tubular body 104 and, for example, may be positioned up against an outer surface 108 of the tubular body 104 when the ring structure 202 is seated at the proximal end 102 of the working cannula. In certain instances, the guide rail assembly 200 may be configured to be rotatable in relationship to the working cannula 101 with an infinite resolution of rotational position. In other aspects the guide rail assembly 200 may be configured to be rotatable in relationship to the working cannula 101 with a finite resolution of indexable rotational positions.

In certain instances, the system 10 may include a joint finder 300 that may include a proximal end 301, a distal end 302, a tubular body 303 extending between the proximal and distal ends, a joint finder passageway 304 defined within the tubular body 303 and having a joint finder axis 311 extending there through, the passageway 304 configured to receive a needle 99 (e.g., a 20, 18 or 16 gauge needle with the hub removed), a head 305 at the distal end 302, a radial laser marking 306 near the proximal end 301 and a handle quick connect interface 307 at the proximal end 301. The head 305 may have a tapered shape and may include a height perpendicular to the joint finder axis which is substantially greater than a diameter of the outer diameter of the tubular body configured to act as a stop to prevent over drilling or over broaching during certain steps of the procedure.

In certain instances, the system 10 may include a depth gauge 400 configured to go over the joint finder 300 and further configured to seat within the working cannula 101 congruently in order to maintain concentricity with the tubular body 104 of the working cannula 101 and still further configured to seat up against the proximal end 102 of the working cannula 101 in order to register correctly with a working cannula length.

In certain instances, the system 10 may include a cannulated drill bit 500 configured to be placed over the joint finder 300. The cannulated drill bit 500 may include a pattern of radial grooves 505 configured to couple with an adjustable depth stop 450. In certain aspects, the cannulated drill bit 500 may be only partially cannulated with a plugged proximal end 501 which is configured to abut the proximal end 301 of the joint finder 300 in order to prevent over drilling. In certain aspects, a drill sleeve is provided having an outer diameter which is configured to seat closely within the working cannula 101 to assist in maintaining concentricity with the desired drilling trajectory and having an inner diameter which is sized close to the outer diameter of the drill bit in order to constrain the trajectory of the drill bit during use.

In certain instances, the system 10 may include a pilot broach and a finishing broach. Each broach may include a cannulated tubular body 603 configured to be placed over the joint finder 300. The cannulated tubular body 603 may include a pattern of radial grooves 605 configured to couple with further adjustable depth stops 450. In certain aspects, the cannulated tubular body 603 may be only partially cannulated with a plugged proximal end 601 which is configured to abut the proximal end 301 of the joint finder 300 in order to prevent over broaching.

In certain instances, the guide rail assembly 200 may be installed within the working cannula 101 prior to broaching, while the broach 600 is at least partially received in the working cannula 101, while the broach 600 is in the bone defining the sacroiliac joint 1, or after broaching. The guide rail assembly 200 may be configured to guide a broach 600 or series of broaches up to and into the bones defining the sacroiliac joint 1 by adjustably (or non-adjustably) constraining the trajectory and orientation of the broach 600 relative to the sacroiliac joint 1 of the patient. Following joint preparation (e.g., broaching) the guide rail assembly 200 may be maintained in the same position as was used for the joint preparation in order to accurately guide an implant 12 into the implant receiving space 11 created by the previous drilling and broaching steps. According to particular aspects, the pair of guide rails 201 may have a shape, size and arrangement which generally matches an outer profile of the implant body 13. For example, the shape, size and arrangement of the pair of guide rails 201 may be configured to constrain and guide an X-shaped implant 12 having four gaps 14*a-d* defined in between four arms 15*a-d* of the implant 12 by having a guide rail outer surface which closely approximates the shape, size and arrangement of the gap or more than one gap (e.g., opposing gaps) thereby preventing gross rotation of the implant 12 along the implant axis 16.

In certain instances, the system 10 further may include an inserter tool 700 having a distal end 702 with an implant-shape-matching portion 703 configured to deliver the implant 12 into the sacroiliac joint 1. The implant-shape-matching portion 703 may also be guided by the pair of rails 201. According to certain aspects, the inserter tool 700 may couple with the implant 12 using a collet mechanism 704 selectively actuated between a locked or unlocked condition. According to yet other aspects, the inserter tool 700 may couple with the implant 12 using a pair of opposing spring arms 705.

In certain instances, the system 10 further may include the joint implant 12.

In certain instances, the joint implant 12 may include an implant body 13 including at least one planar member 15*a* extending a length between a proximal end 17 and a distal end 18, and an opening extending 19 through the implant body 13.

In certain instances, the implant body 13 defines X-shaped cross-section.

In certain instances, the inner surface 107 of the tubular body 104 of the working cannula 101 may be keyed to a cross-sectional shape of a joint implant 12 to permit passage of the joint implant 12 therethrough.

In certain instances, the system 10 further may include the joint implant 12.

In certain instances, the tubular body 104 may include an inner surface 107 that defines the cannula passageway 105, the inner surface 107 defining a non-circular perimeter.

Aspects of the present disclosure may include a method of performing a fusion procedure on a sacroiliac joint 1 defined between a sacrum 2 and an ilium 3, where the sacroiliac joint 1 may include an articular region 4, and the ilium 3 may include a posterior superior iliac spine (PSIS) 5 and a posterior inferior iliac spine (PIIS) 6. In certain instances, the method may include: positioning a distal end 103 of a working cannula 101 up to the joint line 7 inferior to the PSIS 5 while aligning the cannula axis 106 to be generally located between the sacrum 2 and the ilium 3 via a posterior access.

In certain instances, the method further may include inserting a distal portion of a cutting tool through the cannula passageway 105 and into the sacroiliac joint 1 so as to prepare the sacrum 2 and the ilium 3 for insertion of the joint implant 12.

In certain instances, the cutting tool may include at least one tool from a group may include a rasp, a drill bit, a chisel, a broach, a paddle shaver, a curette, a bur, a saw blade, a mill bit, a router bit, a reciprocating saw, a sagittal saw, a box osteotome and an ultrasonic oscillating cutter. Additionally, the cutting tool (or as a separate tool used in conjunction therewith) may further include a surgical aspirator and may include an irrigation supply and suction supply to provide continuous irrigation and active suction in order to maintain a surgical site clear of liquids and debris which may also provide a clear field of view allowing for enhanced visualization.

In certain instances, the method further may include removing bone material from the PSIS 5 in order to place the bone material within the bone window 20 of the implant 12 and or adjacent the implant 12 prior to or after placement of the implant 12 at the sacroiliac joint 1.

In certain instances, the method further may include implanting the bone material into at least one or both of the joint implant 12 and the sacroiliac joint 1 using a tamp. A bone packing block may fixture the implant 12 to hold the implant 12 and to plug up at least one or more openings 19 of the bone window 20 when inserting bone material into the implant 12.

In certain instances, the joint implant 12 may be inserted at least partially into the articular region 4 of the sacroiliac joint 1 via a posterior access region 8 defined between the PSIS 5 and the PIIS 6.

According to particular embodiments, the working cannula 101 may have a transverse attachment point 150 for a handle 160 or other structure (e.g., to allow attachment to a surgical table either directly or via an (e.g., FISSO brand) articulating arm surgical tool holder).

In certain instances, the system 10 may comprise a lance 800 configure to go over the needle 99 such that once a distal tip 802 of the lance 800 touches the patient's skin, upon applying sufficient force, a cutting tip 803 and edges 804 of the lance 800 cut through the skin, through the soft tissue and up to the bones defining the sacroiliac joint 1. The lance 800 guided by the needle 400 provides an accurate and reliable means to create an appropriately sized and positioned incision in order to deliver the joint finder 300, a series of dilators 900 and, at about the maximum incision diameter provided by the lance 800, the working cannula 101.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 1 is a side view of a pelvic region.

FIG. 17 is a perspective view of a series of dilators in addition to a sectional view of the same.

FIGS. 38A-38B are respectively top and bottom views of the depth gauge.

FIGS. 39A-39B are opposite side views of the depth gauge.

FIGS. 49A-55 are different views of an adjustable depth stop.

FIGS. 56A-60 are different views of the adjustable depth stop joined with the cannulated drill bit.

FIGS. 62A-62B are opposite side views of the guide rail assembly.

FIGS. 73A-90 are different views of additional cutting tools guided by the guide rail assembly and joint finder and employed to create an implant receiving space.

FIGS. 92A-94 are different views of a first embodiment of an inserter tool including an implant-shape-matching portion at a distal end for implanting a sacroiliac joint implant into the implant receiving space.

FIGS. 95-96D are different views of a second embodiment of an inserter tool distal end with an implant-shape-matching portion and configured to couple with the implant using a pair of opposing spring arms.

FIGS. 97-98D are different views of a third embodiment of an inserter tool distal end with an implant-shape-matching portion and configured to couple with the implant using a pair of opposing spring arms.

FIGS. 99-106 are different views of an embodiment of an X-shaped implant.

FIGS. 116A-119 are different views of yet another embodiment of an inserter tool comprising a collet mechanism configured to be selectively actuated between a locked or unlocked condition.

DETAILED DESCRIPTION

Figure 1:
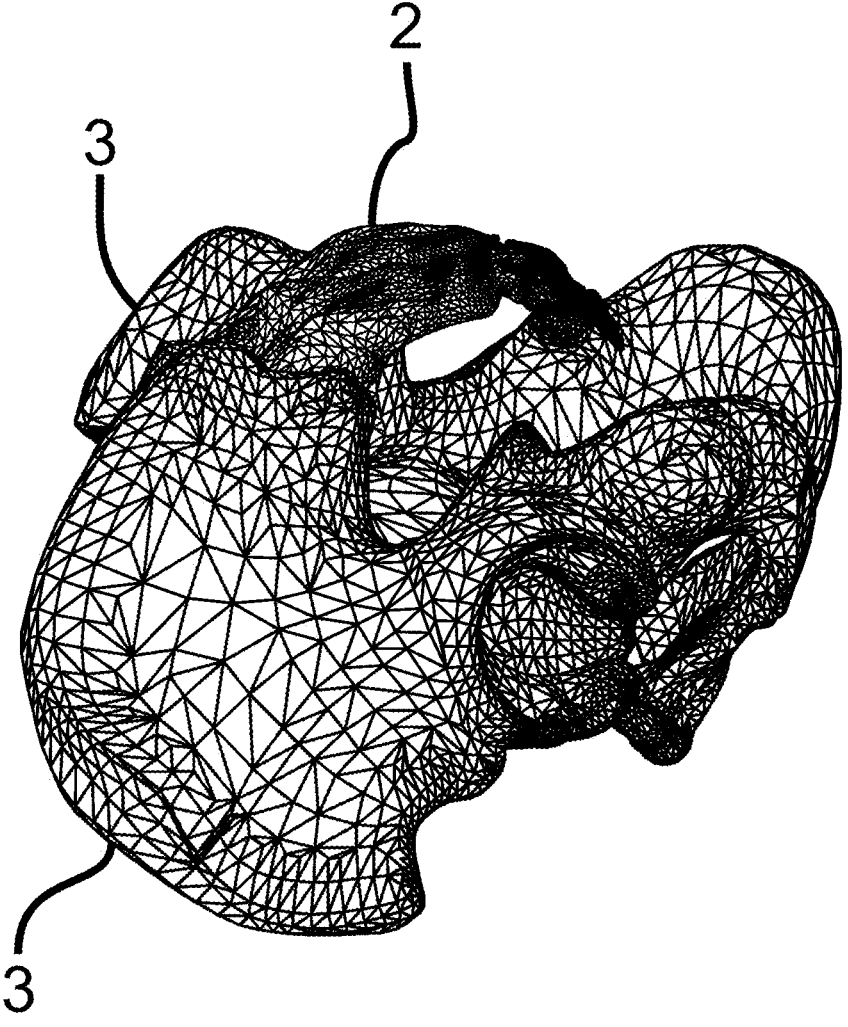
FIGS. 1-119 illustrate various tools and steps according to particular embodiments of systems and methods for preparing and treating a sacroiliac joint as can be understood by the description herein and also in the patent applications incorporated by reference.
Figure 2:
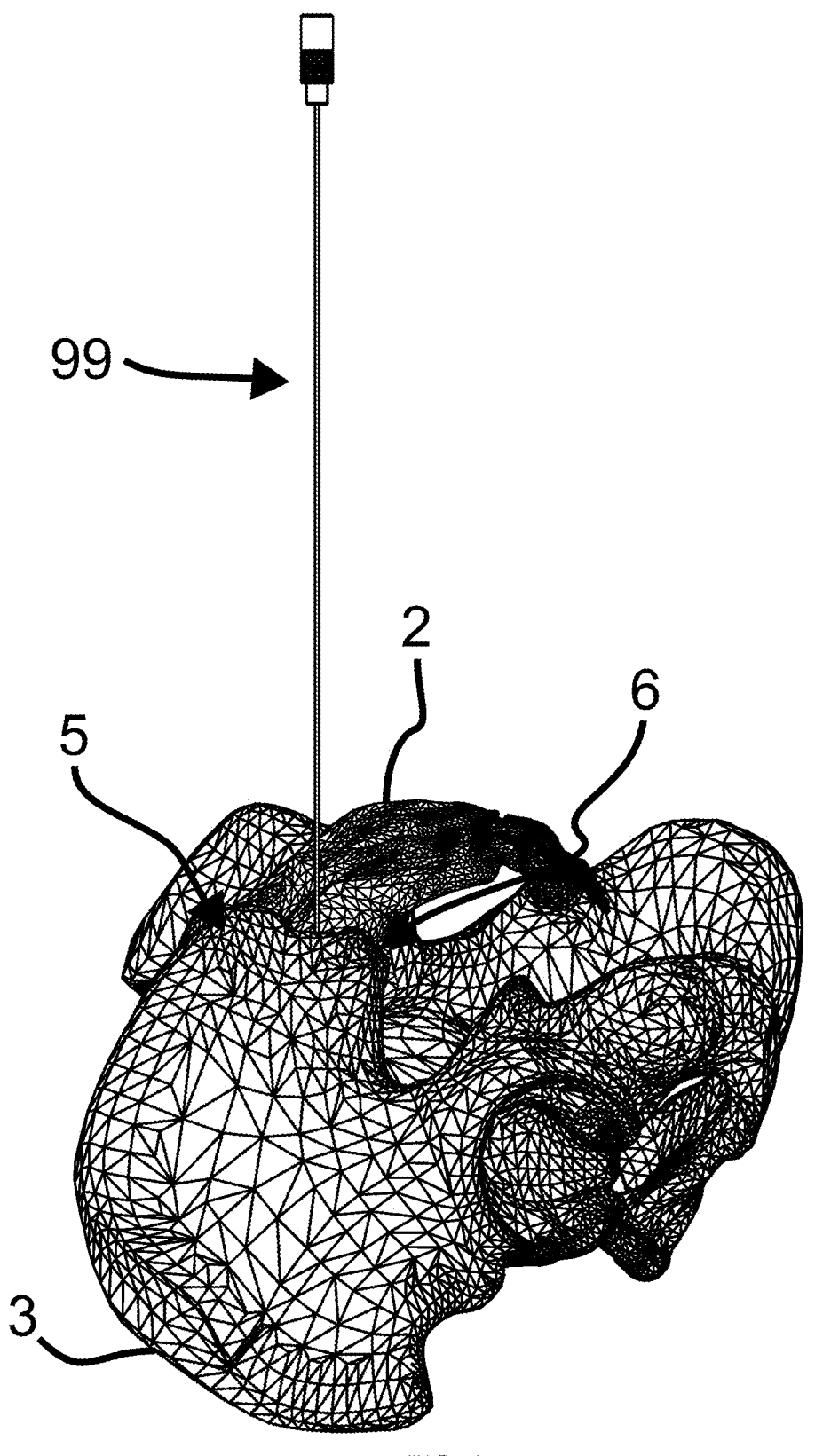
FIG. 2 is the view of FIG. 1 showing a needle positioned in the sacroiliac joint.
Figures 3A, 3B:
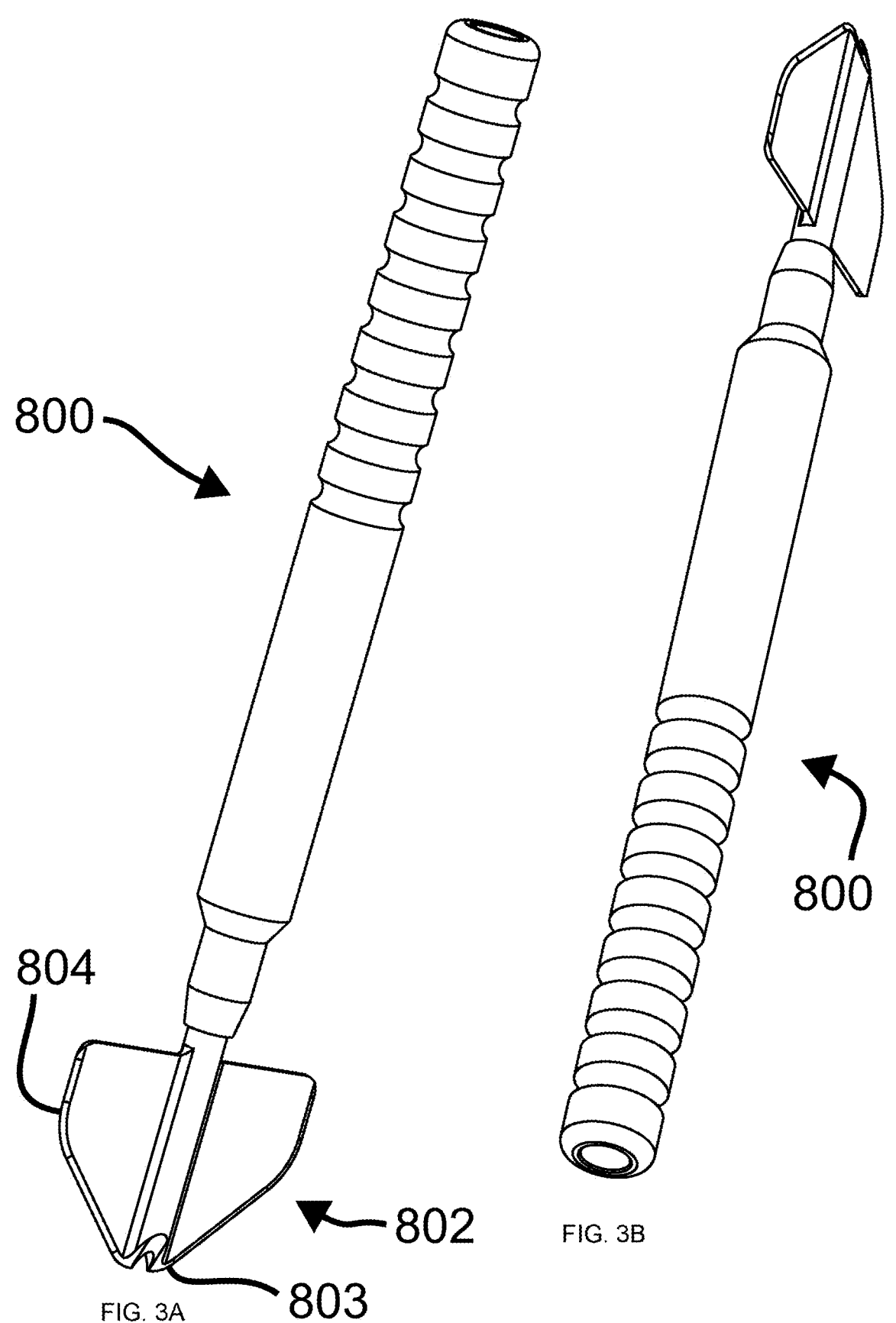
FIGS. 3A-3B are perspective views of a lance.
Figures 4A, 4B:
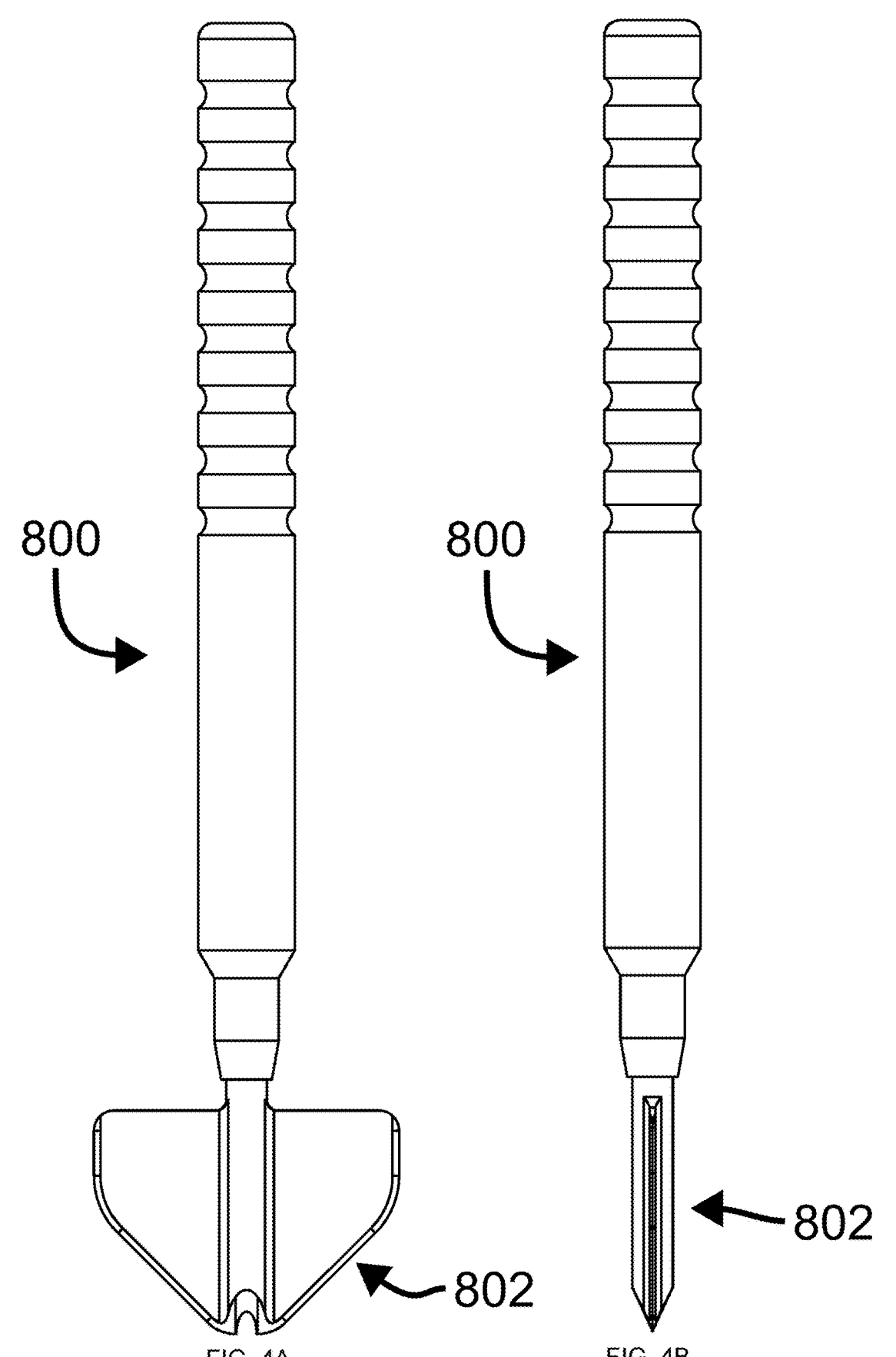
FIGS. 4A-4B are respectively top and side views of the lance.
Figure 5A:
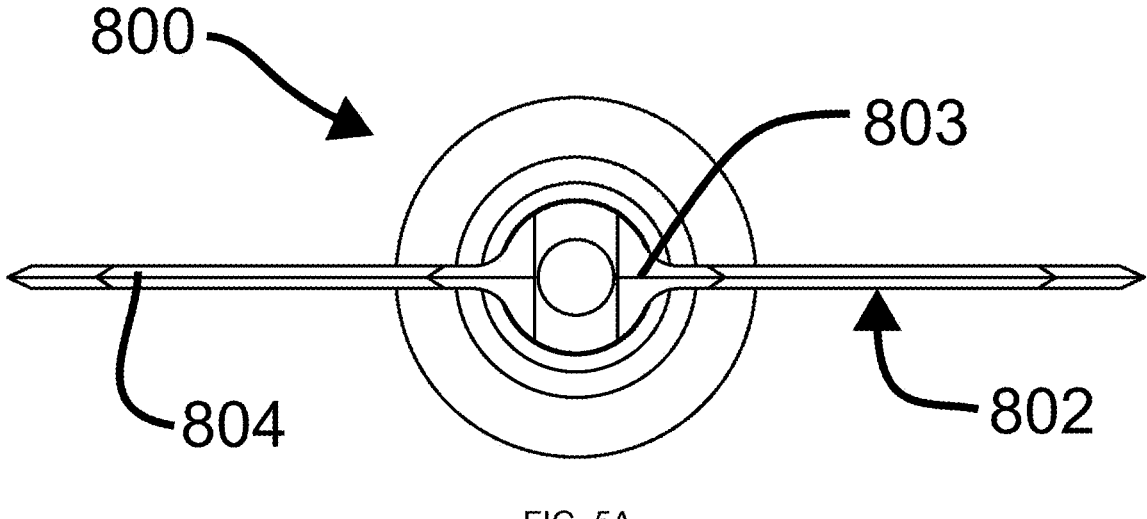
FIGS. 5A-5B are respectively distal and proximal end views of the lance.
Figure 5B:
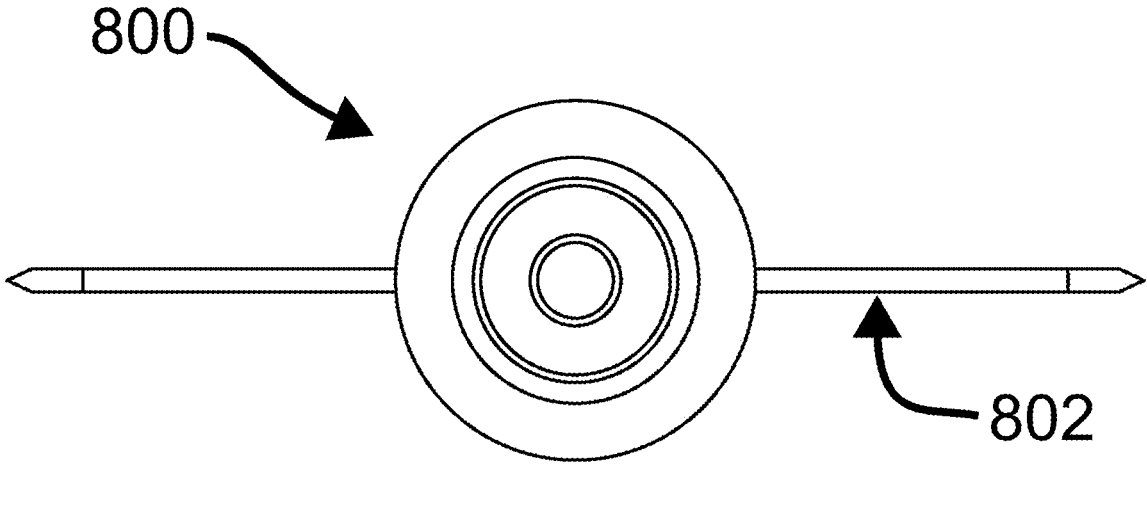
Figure 6:
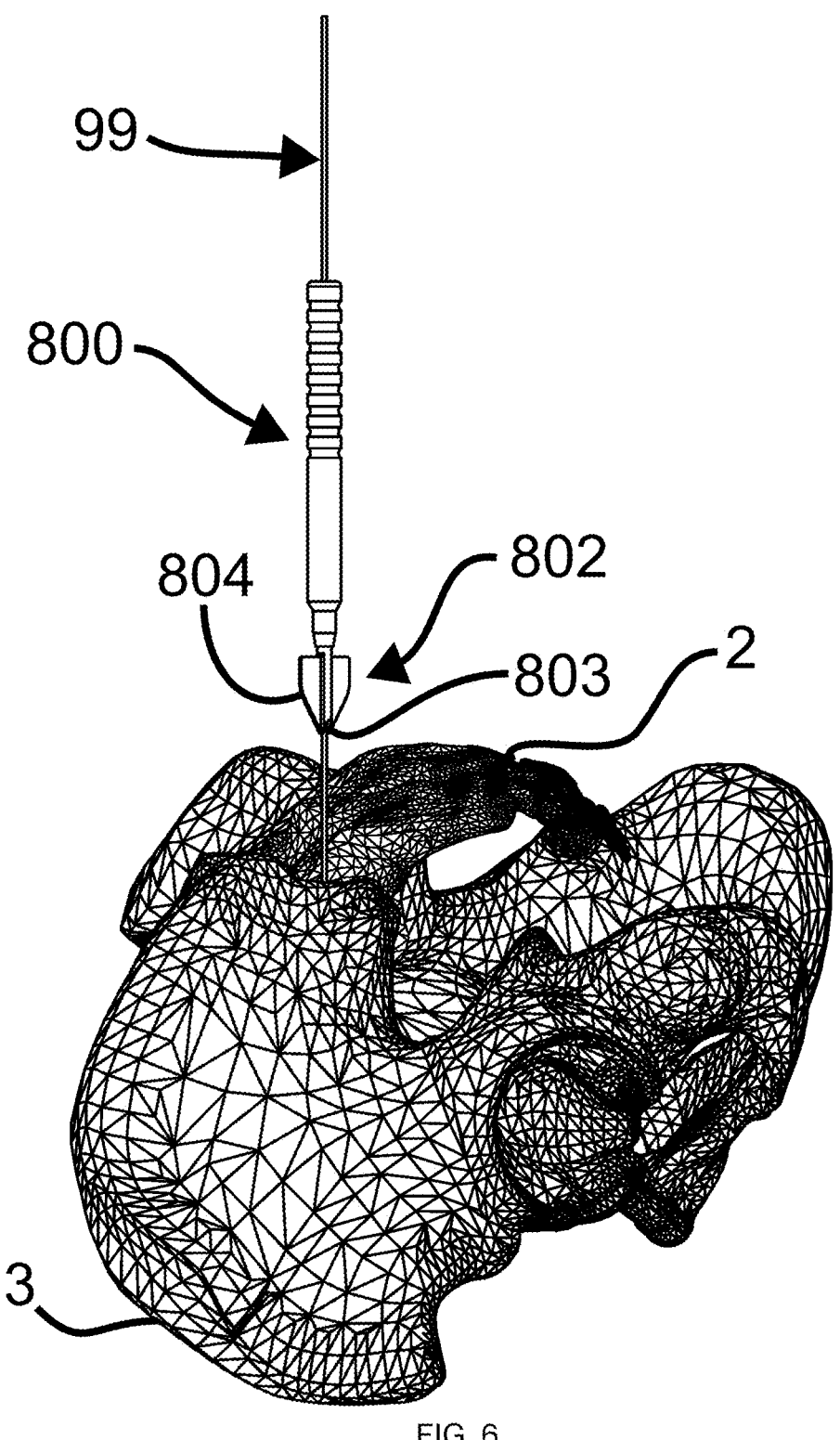
FIG. 6 is the view of FIG. 1 showing the lance over the needle.
Figure 7:
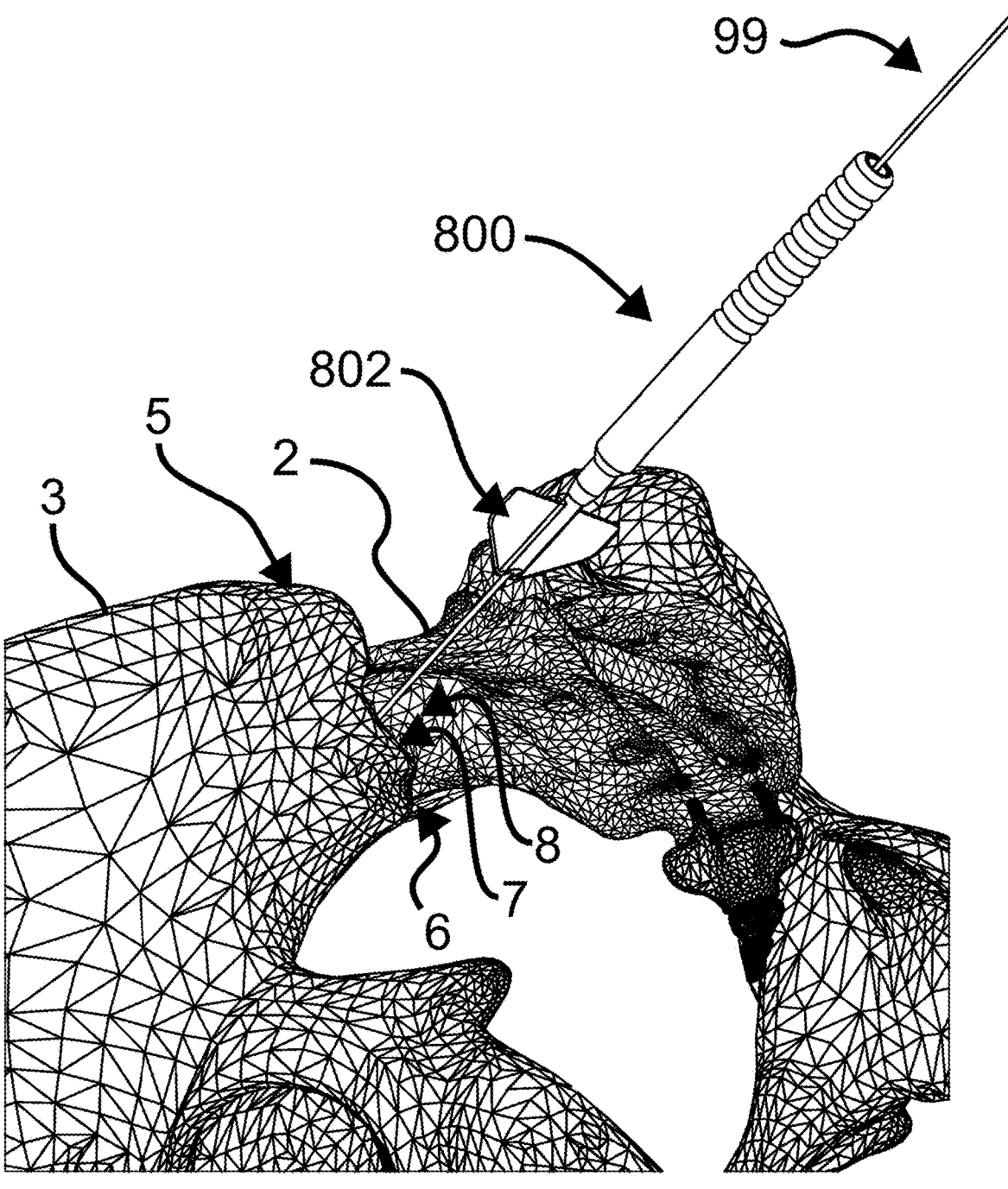
FIG. 7 is another view of the pelvic region showing the lance over the needle.
Figure 8:
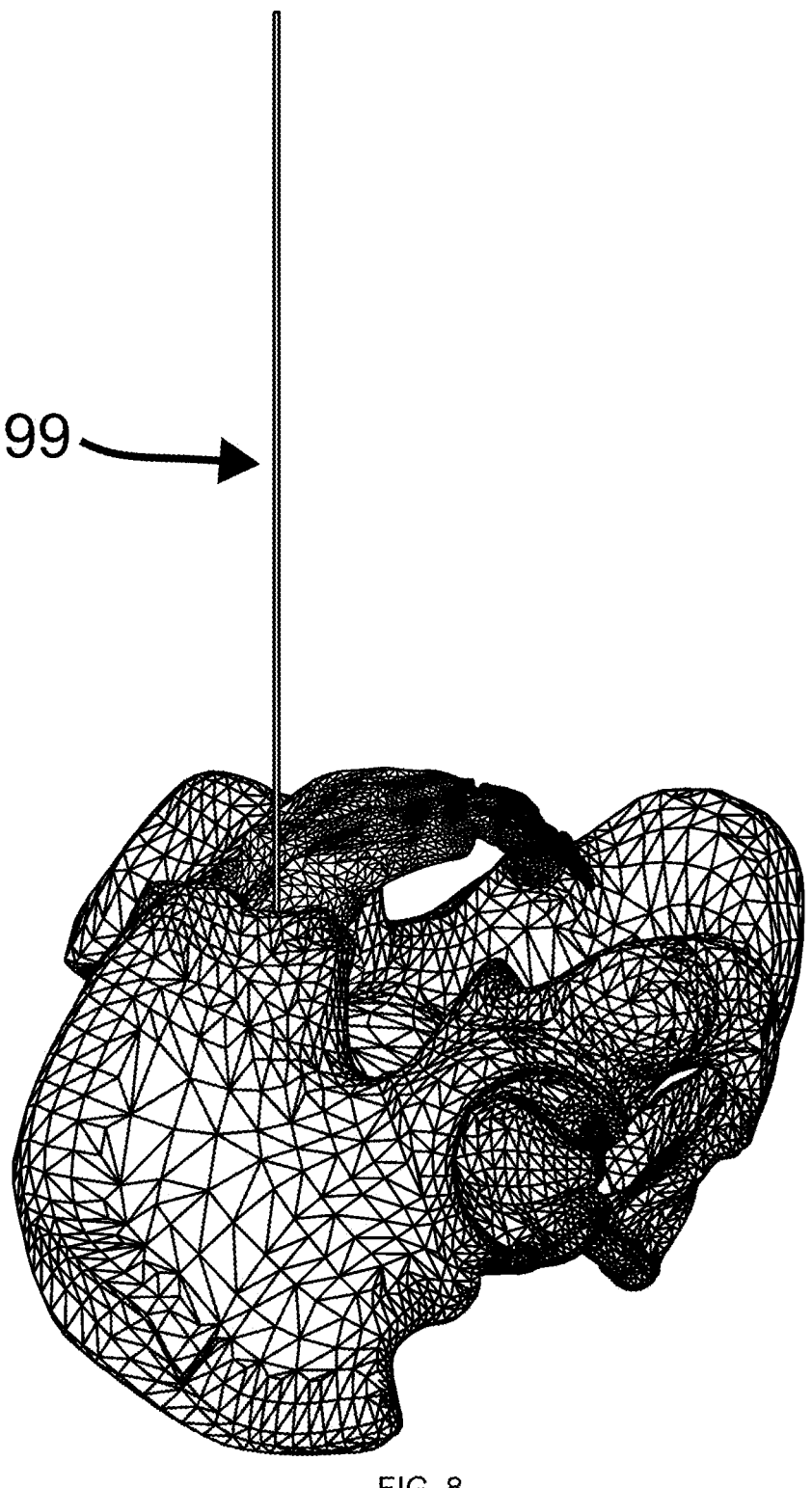
FIG. 8 is the view of FIG. 1 showing the needle in the sacroiliac joint with the lance removed.
Figures 9A, 9B, 9C, 9D:
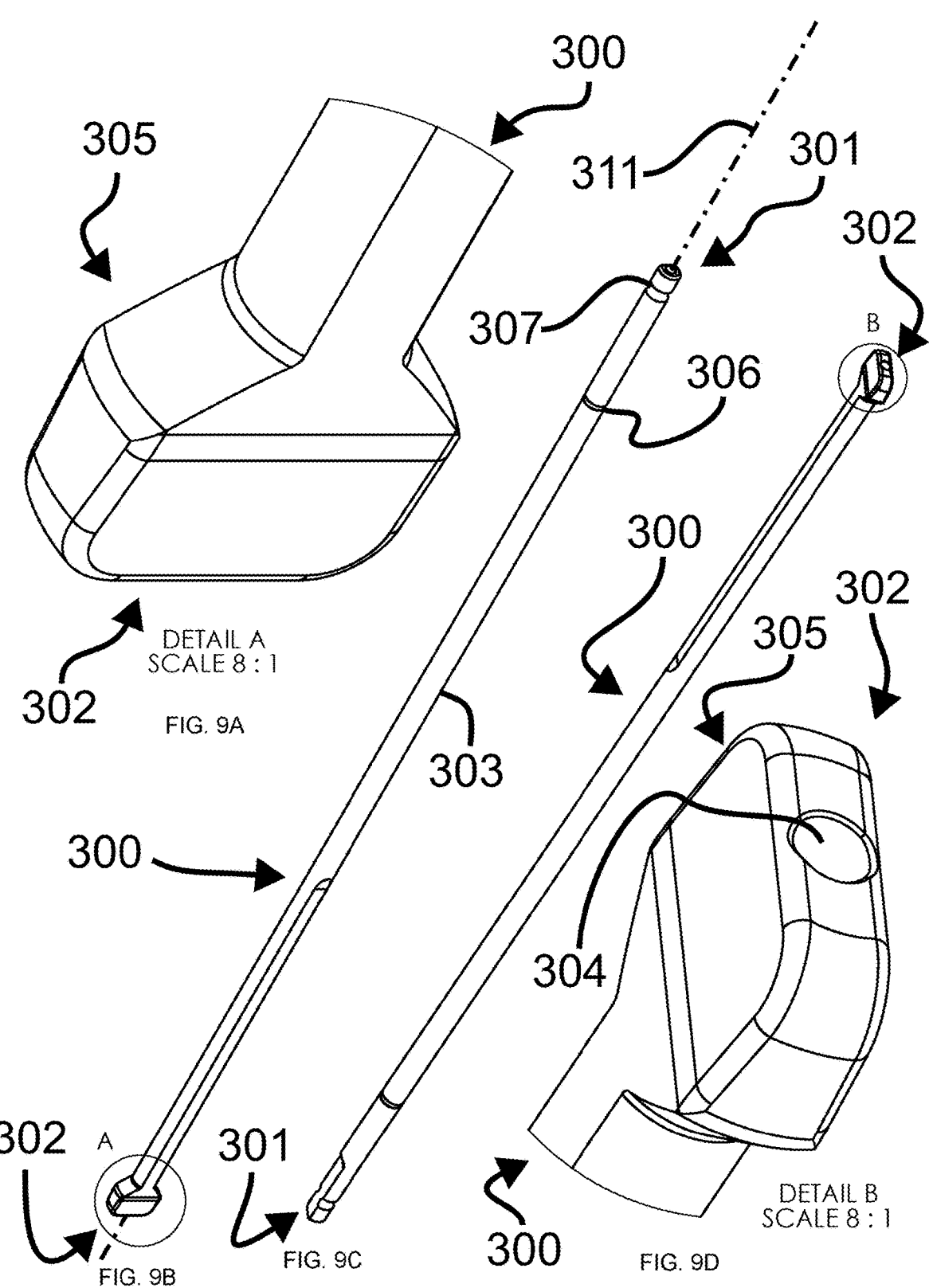
FIGS. 9A-9D are respectively a close-up perspective view of the distal end of the joint finder, a first perspective view of the joint finder, a second perspective view of the joint finder and a close-up perspective view of the distal end of the joint finder.
Figures 10A, 10B, 10C, 10D:
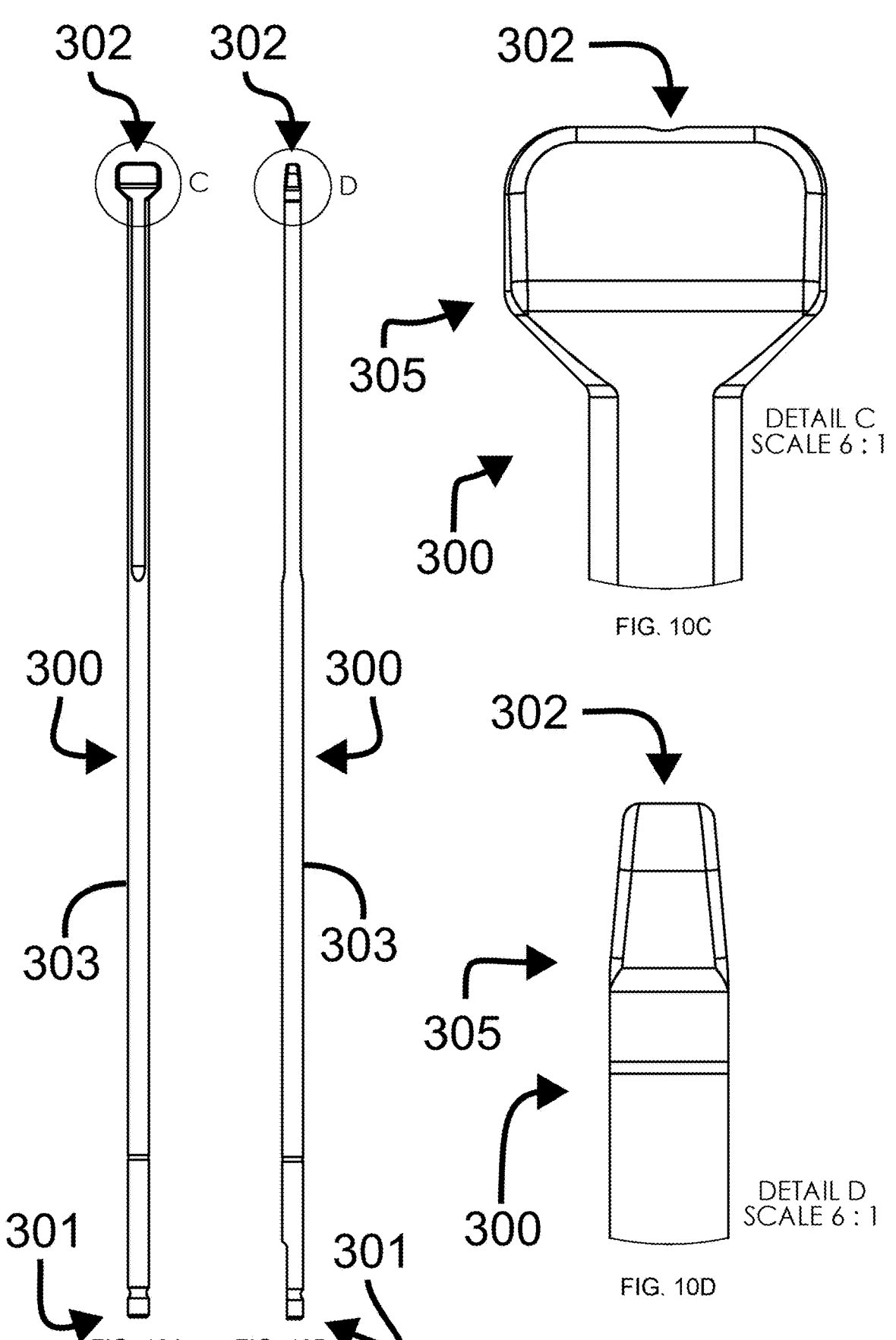
FIGS. 10A-10D are respectively a top view of the joint finder, a side view of the joint finder, a close-up top view of the distal end of the joint finder and a close-up side view of the distal end of the joint finder.
Figures 11A, 11B:
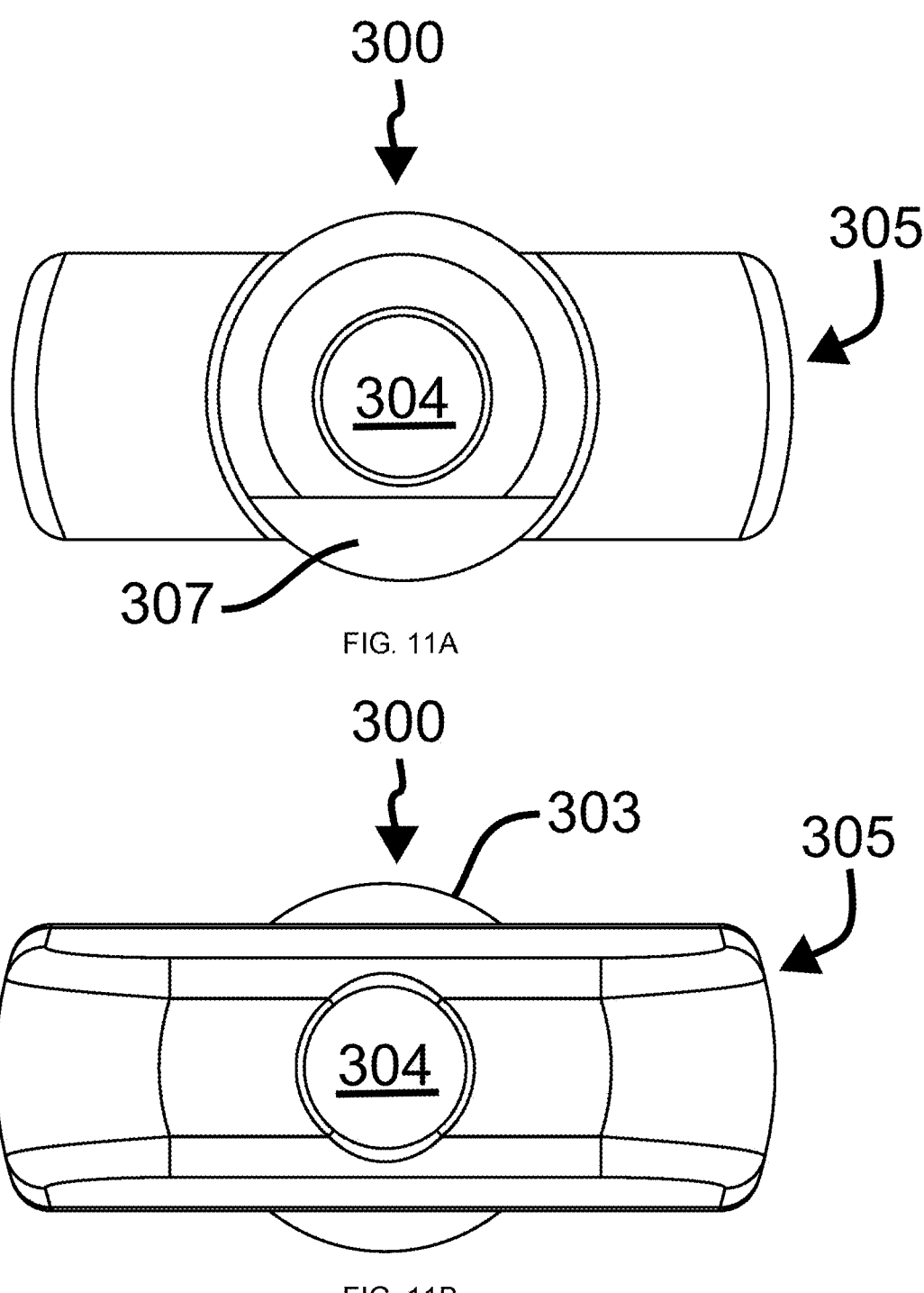
FIGS. 11A-11B are respectively a proximal end view and distal end view of the joint finder.
Figures 12A, 12B:
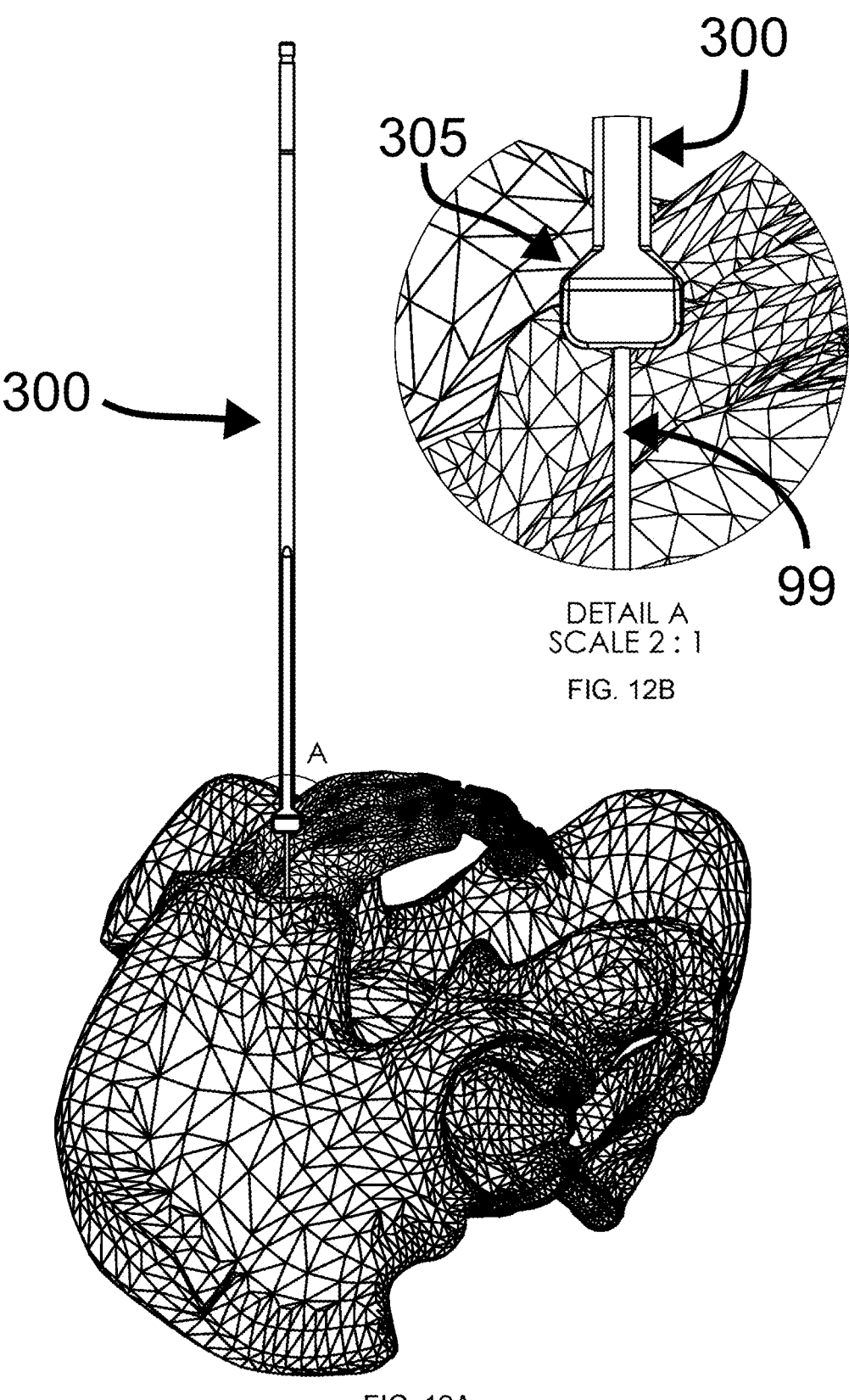
FIGS. 12A-12B are respectively the view of FIG. 1 with the joint finder over the needle and a close-up view of the same.
Figure 13:
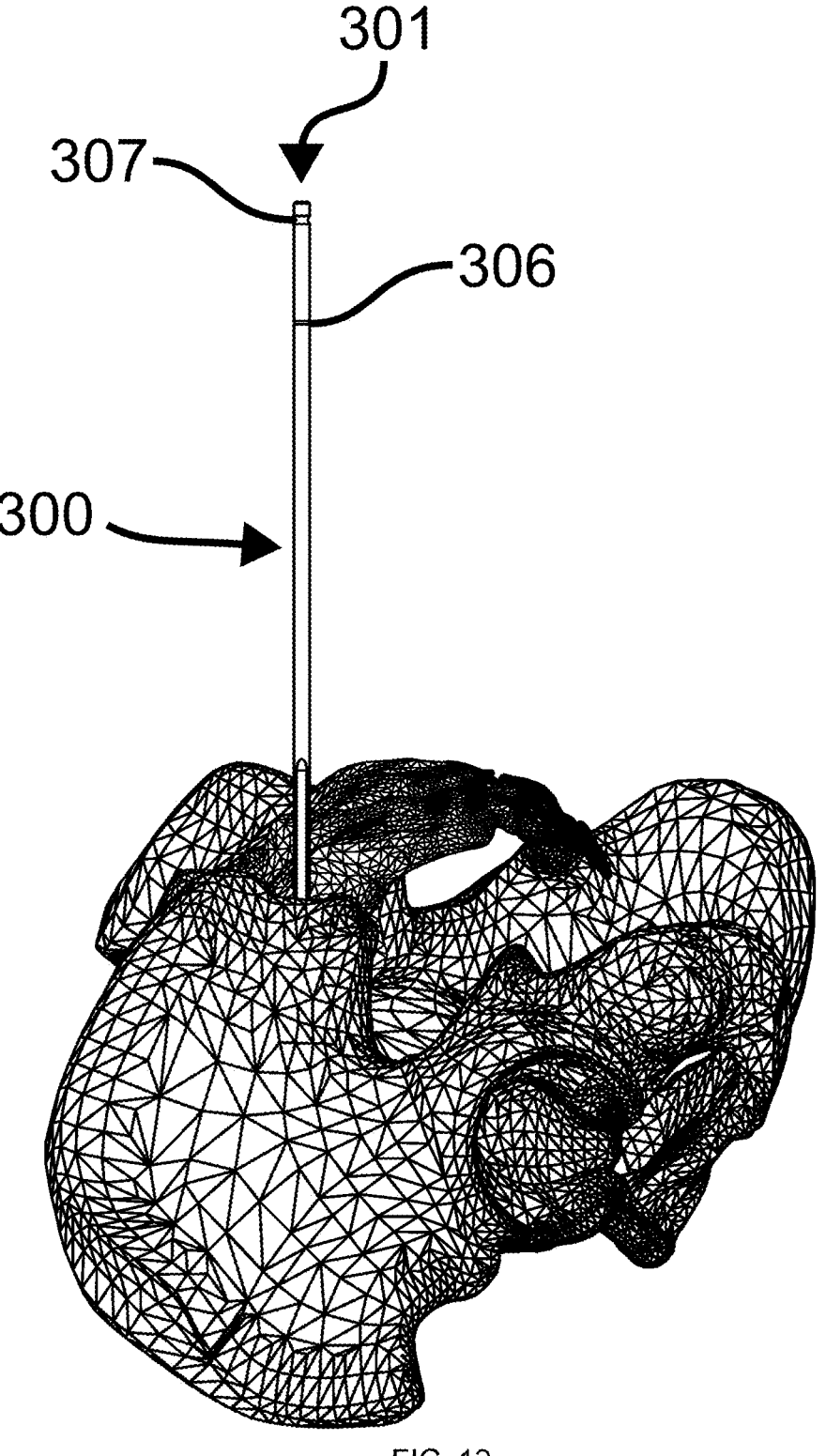
FIG. 13 is the view of FIG. 1 showing the distal end of the joint finder positioned within the sacroiliac joint.
Figure 14:
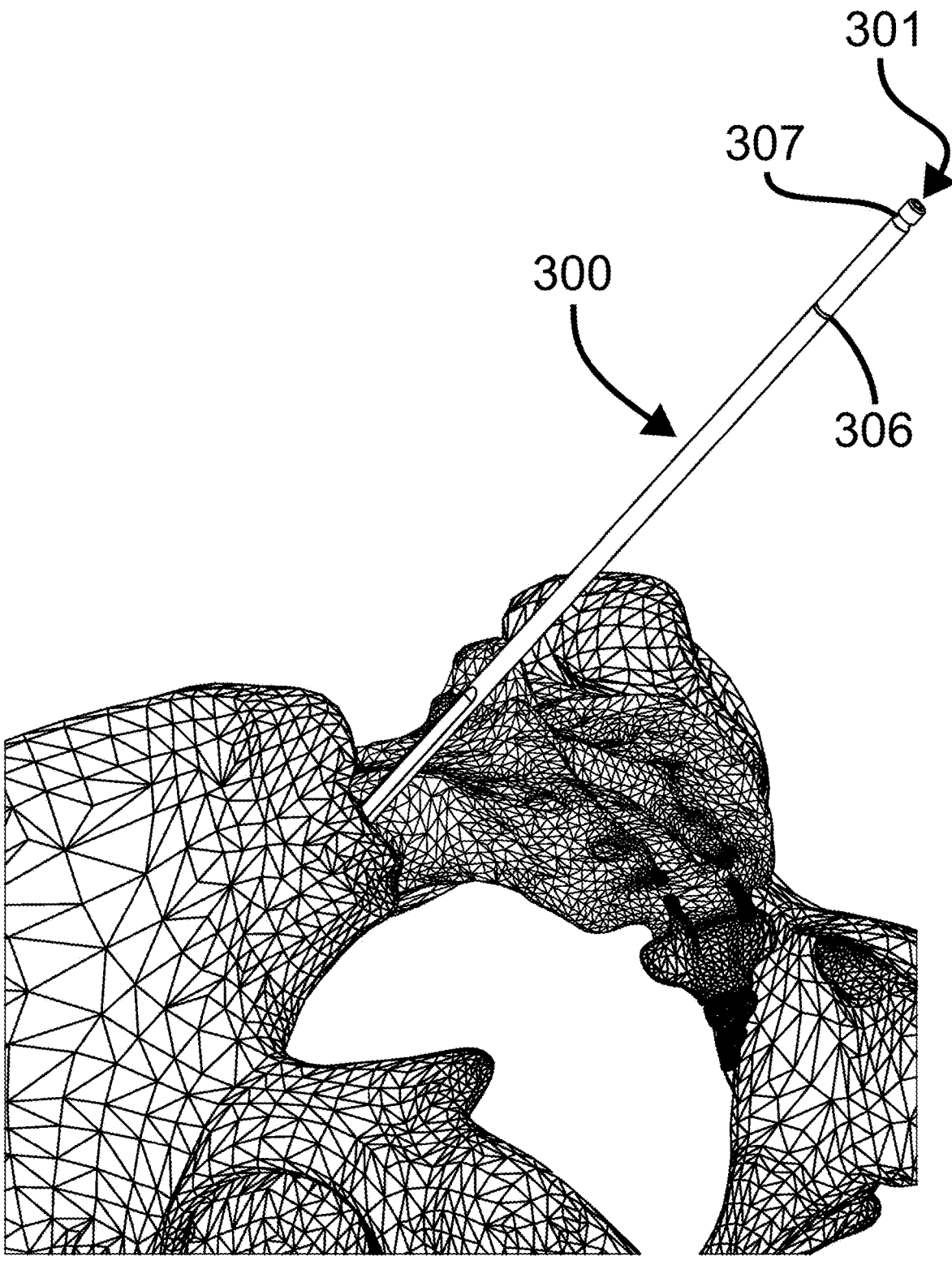
FIG. 14 is another view of the step shown in FIG. 13.
Figure 15:
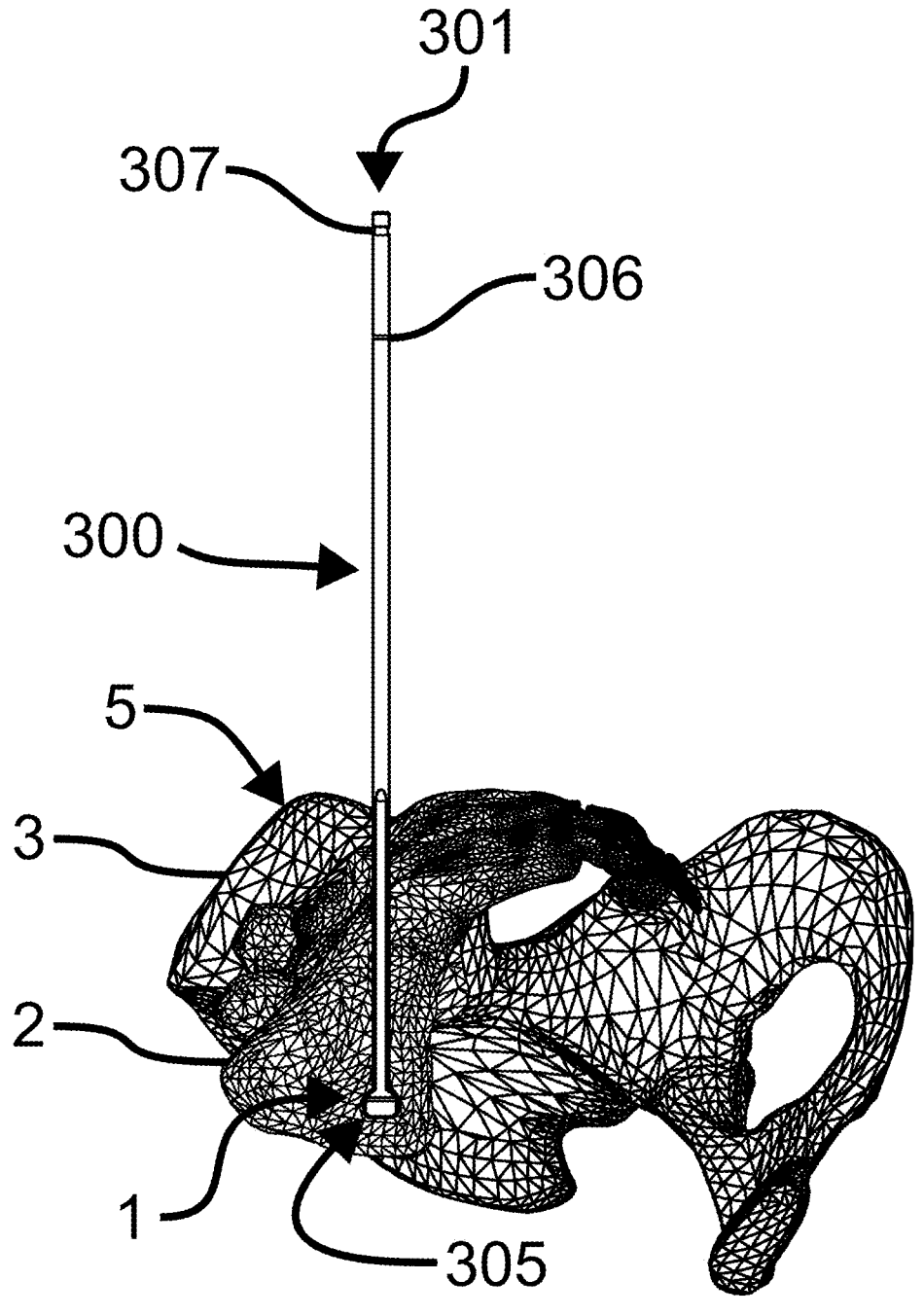
FIG. 15 is the view of FIG. 13 but with the left ilium removed to show the location of joint finder in greater detail.
Figure 16:
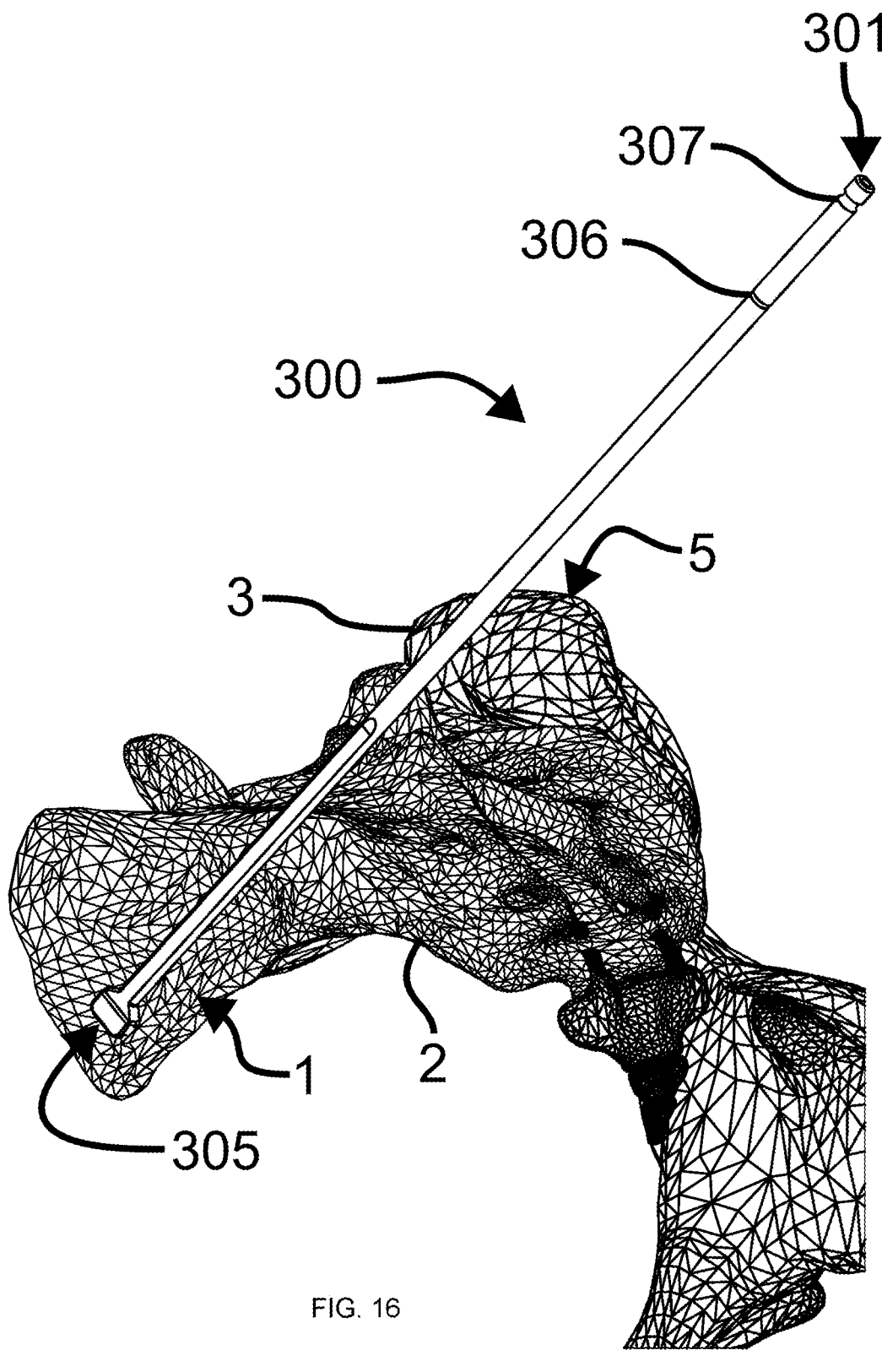
FIG. 16 is the view of FIG. 14 but with the left ilium removed to show the location of the joint finder in greater detail.
Figure 18:
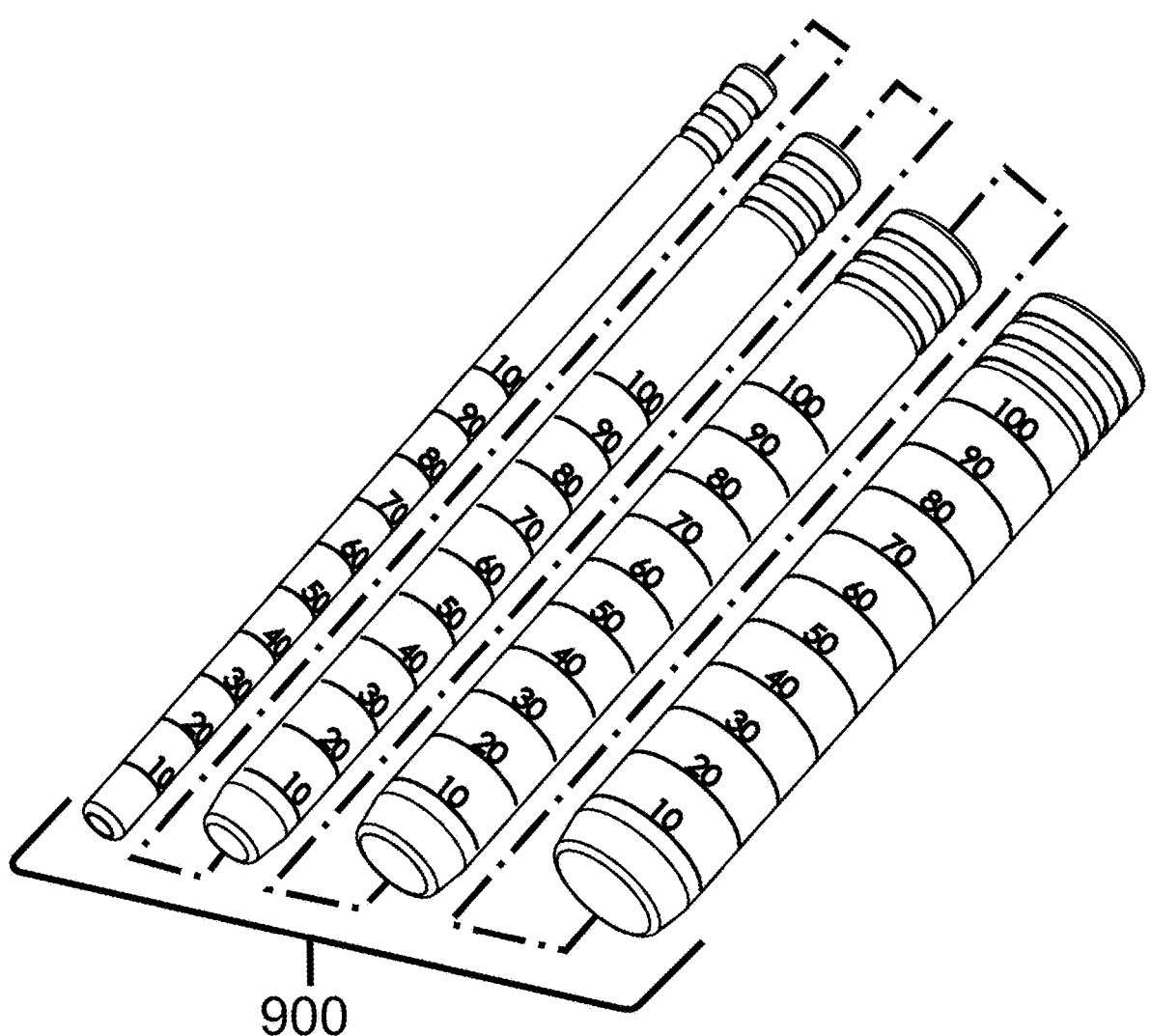
FIG. 18 is an exploded view of FIG. 17.
Figure 19:
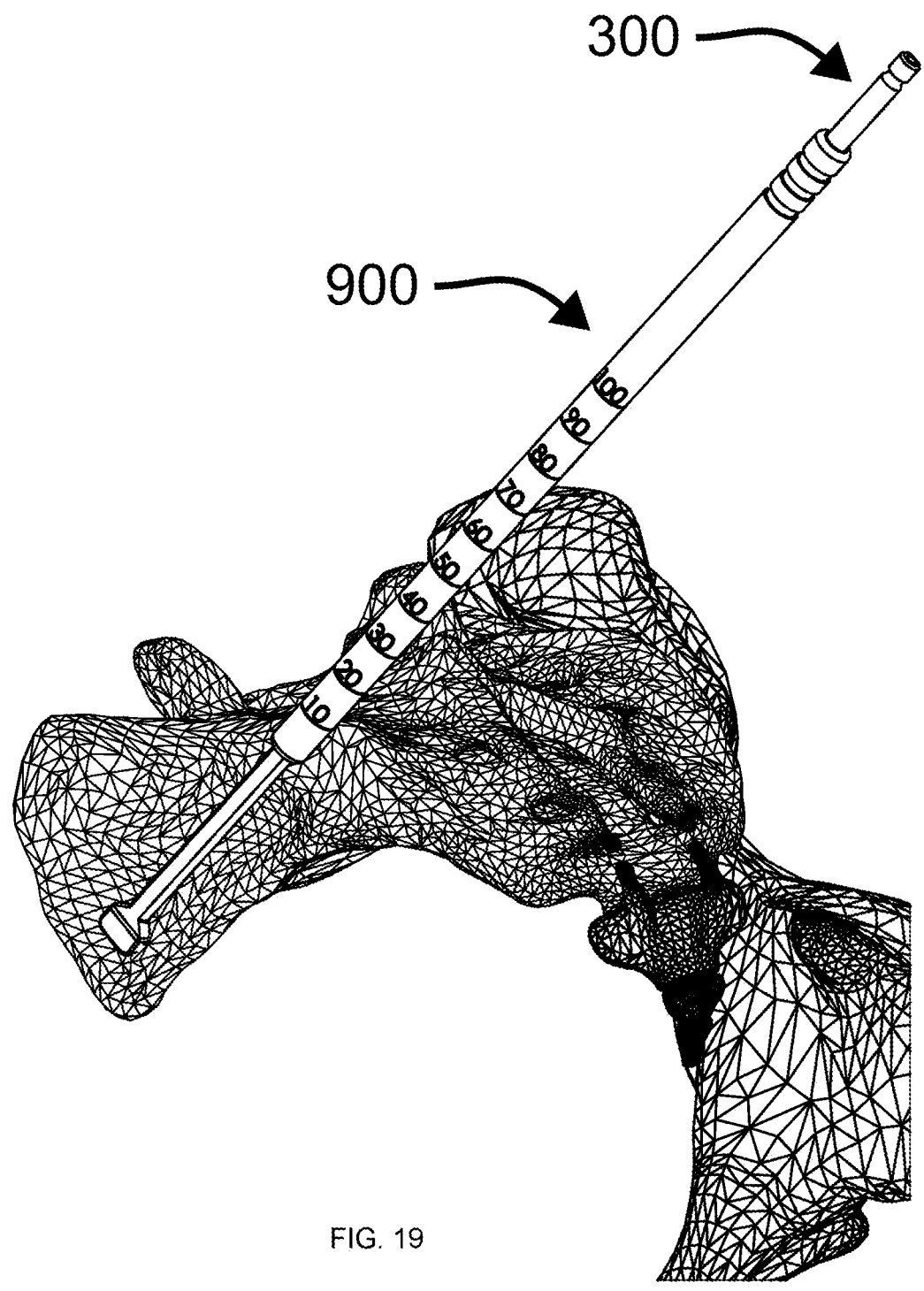
FIGS. 19-22 are the view of FIG. 16 respectively showing a first, second, third and fourth in the series of dilators positioned over the joint finder.
Figure 20:
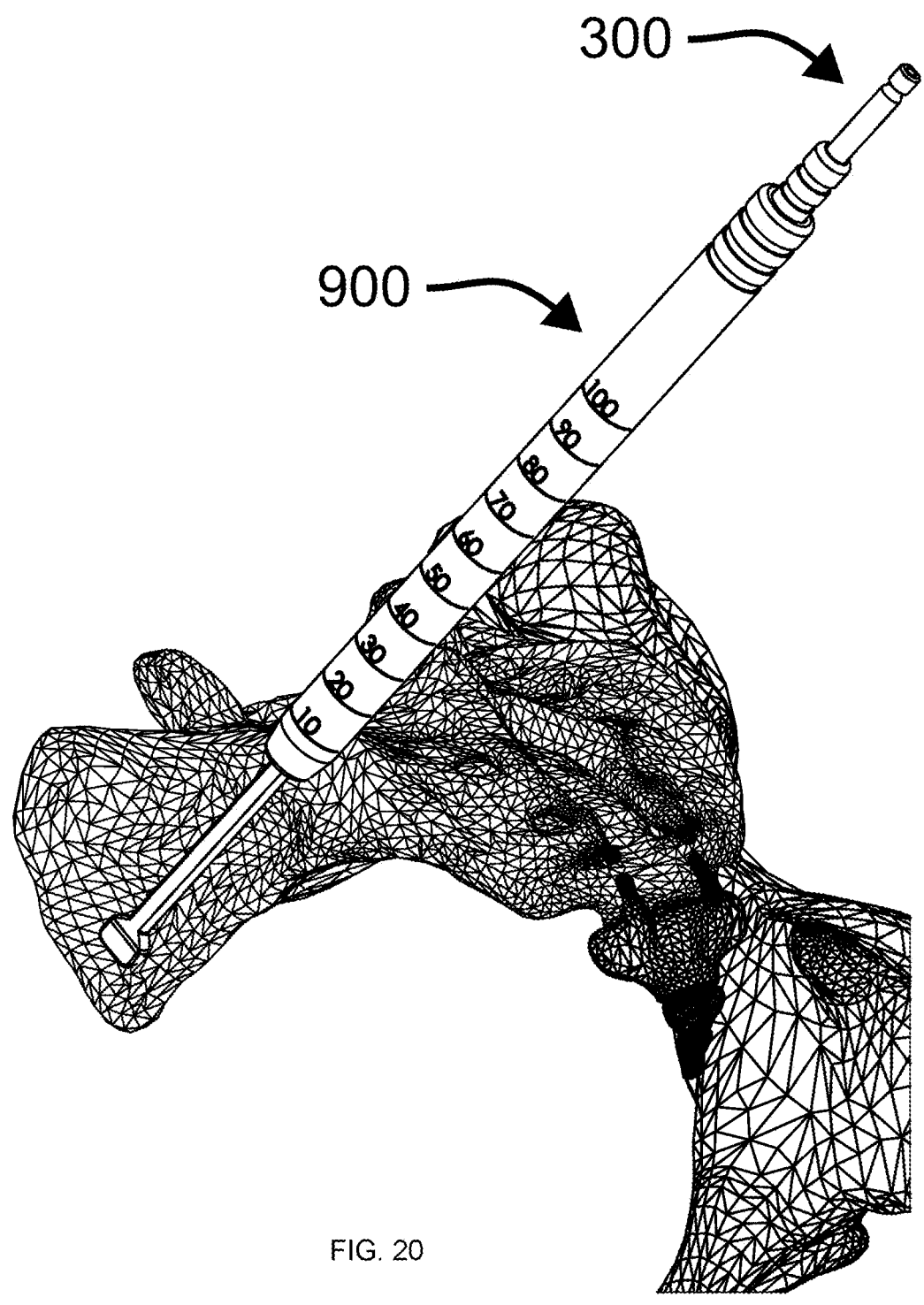
Figure 21:
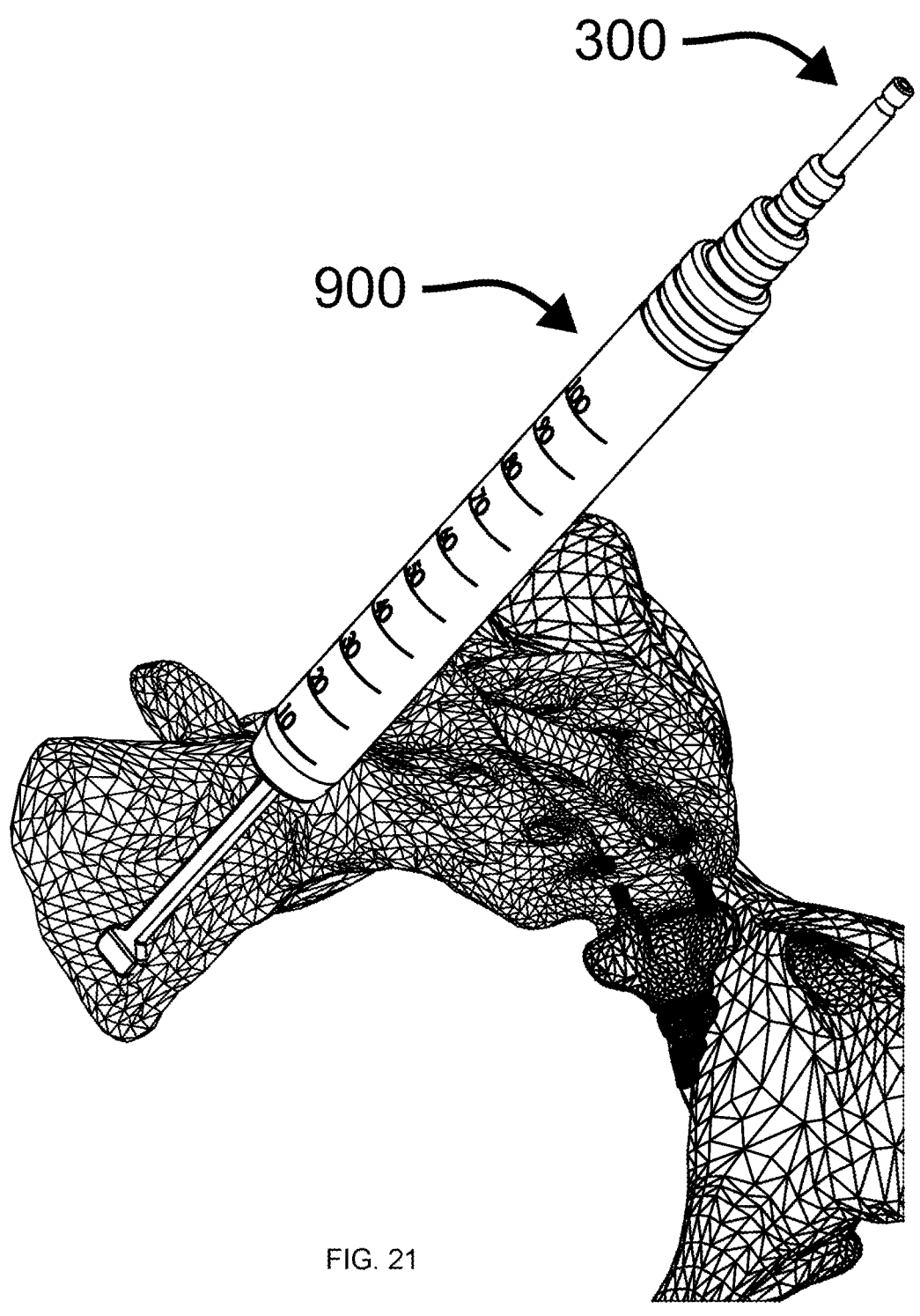
Figure 22:
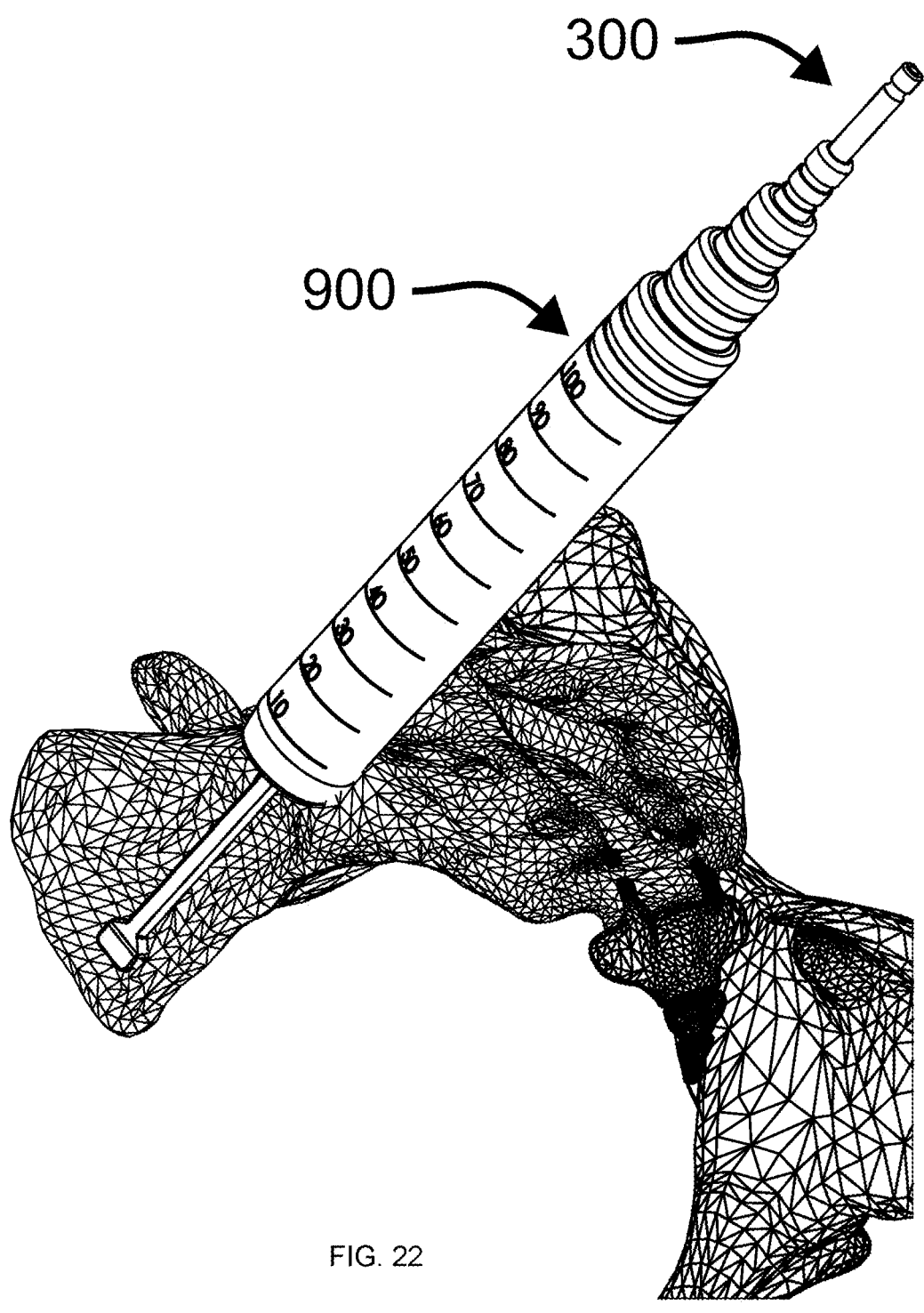
Figure 23:
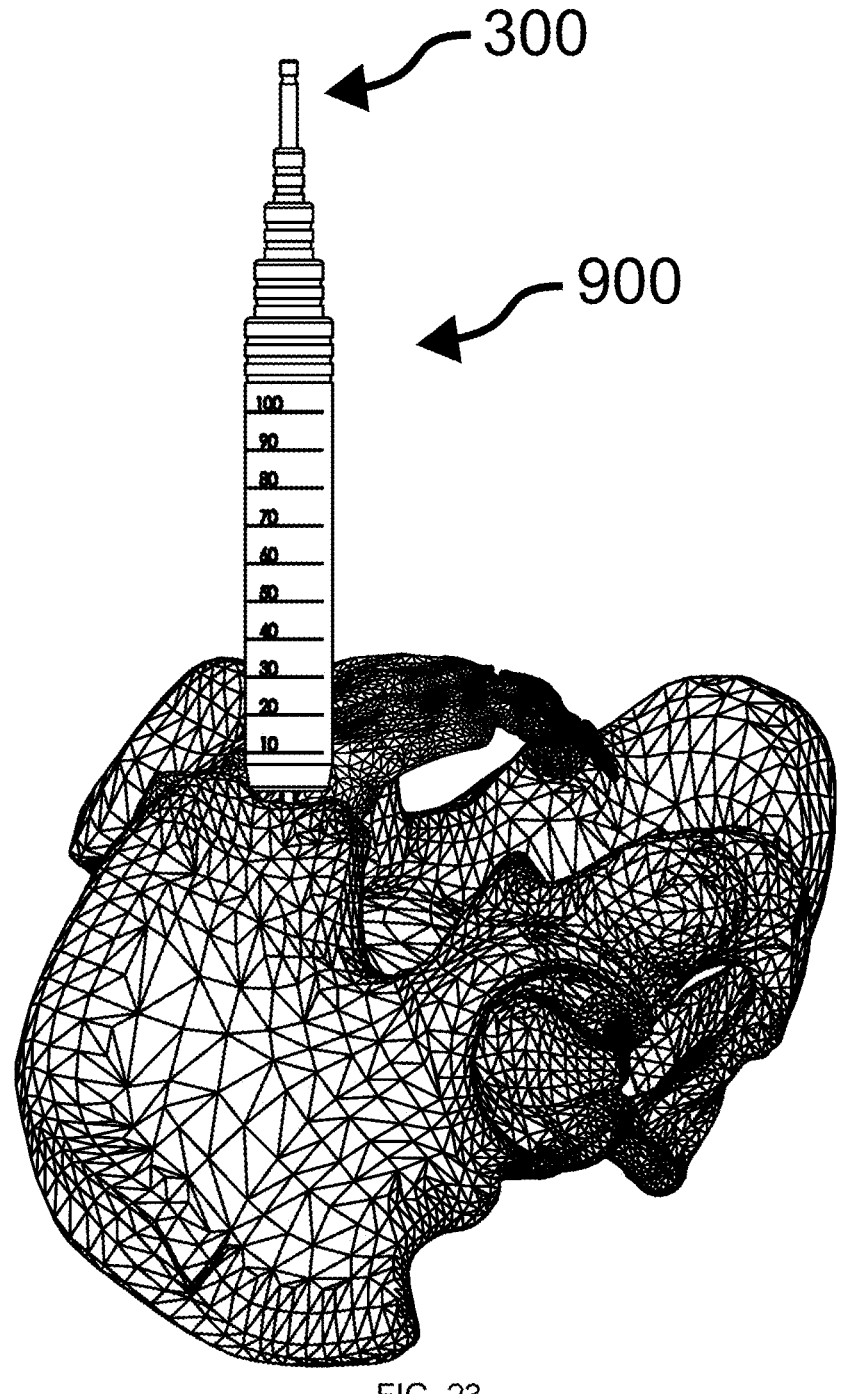
FIG. 23 is a view of the pelvic region showing the series of dilators positioned over the joint finder.
Figure 24:
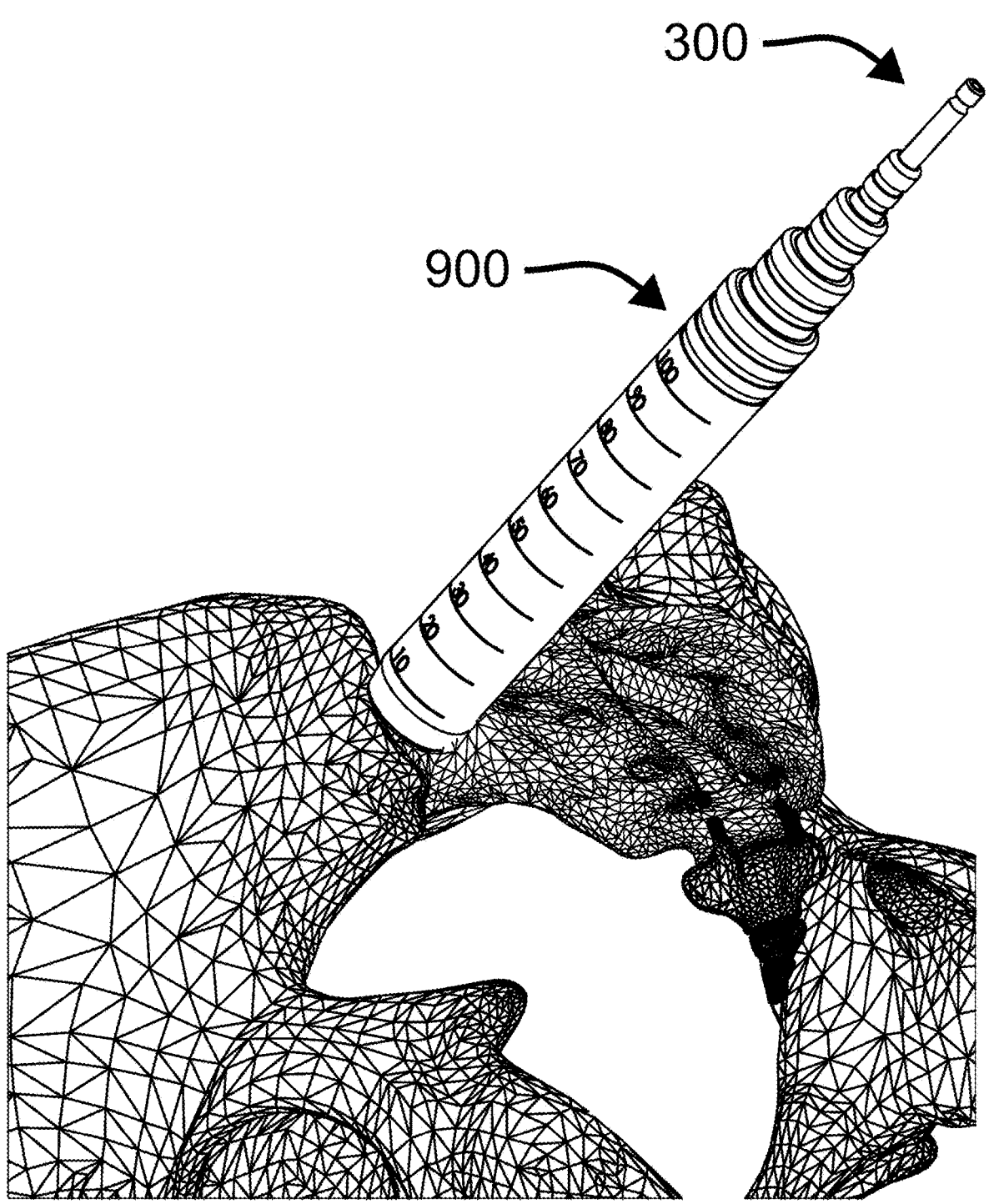
FIG. 24 is another view of the step shown in FIG. 23.
Figure 25:
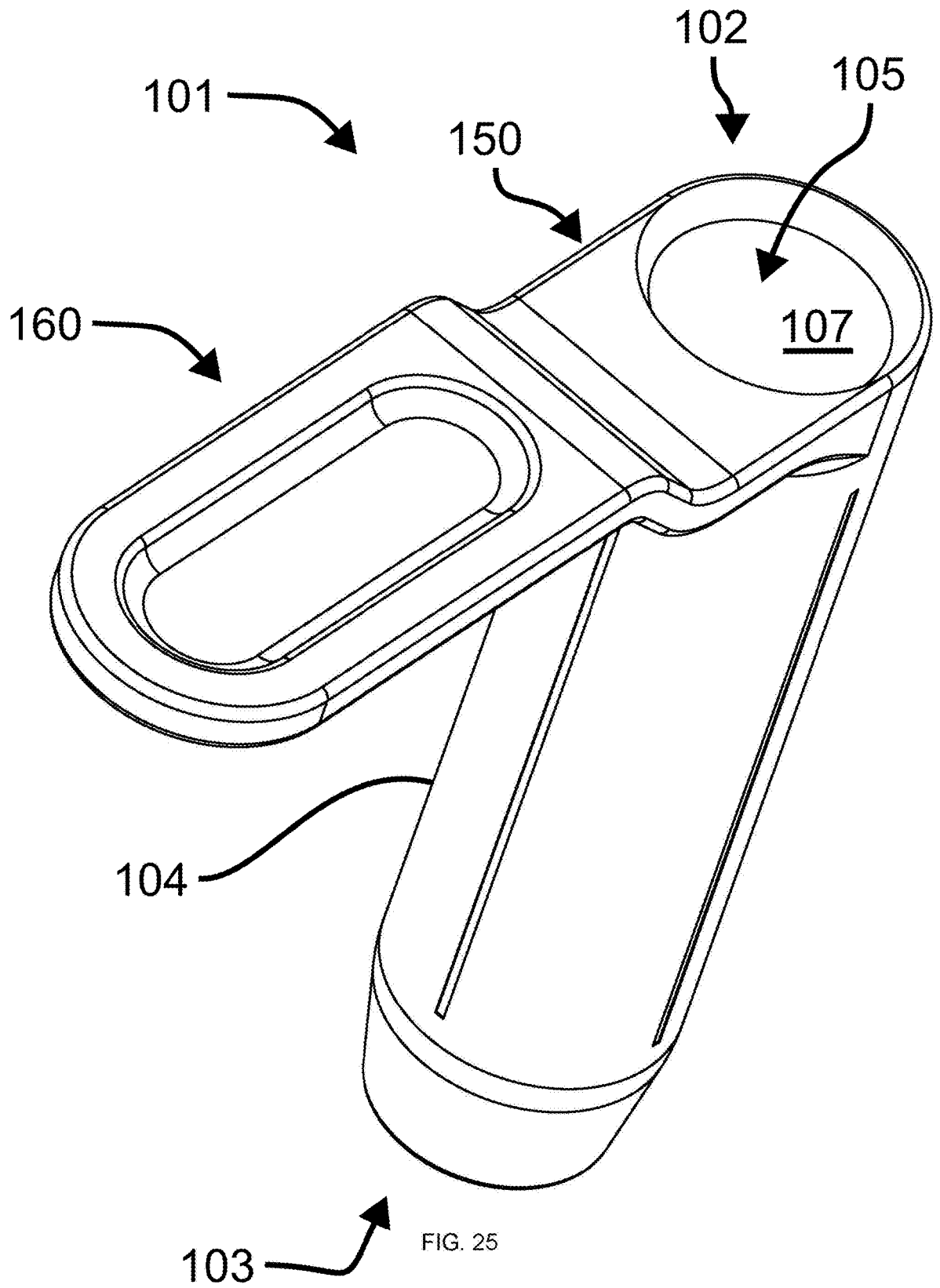
FIG. 25 is a proximal perspective view of a working cannula.
Figure 26:
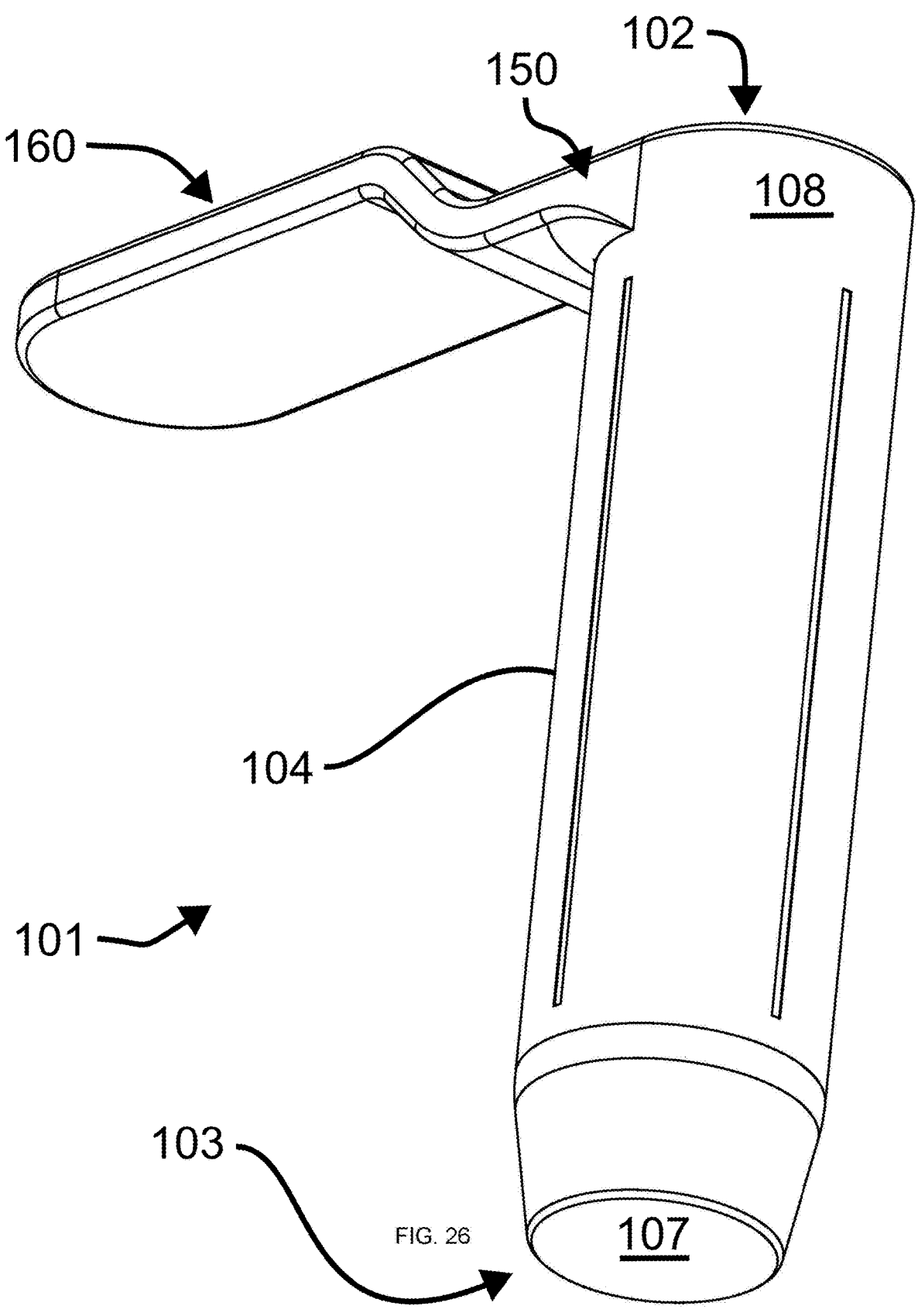
FIG. 26 is a distal perspective view of the working cannula.
Figure 27:
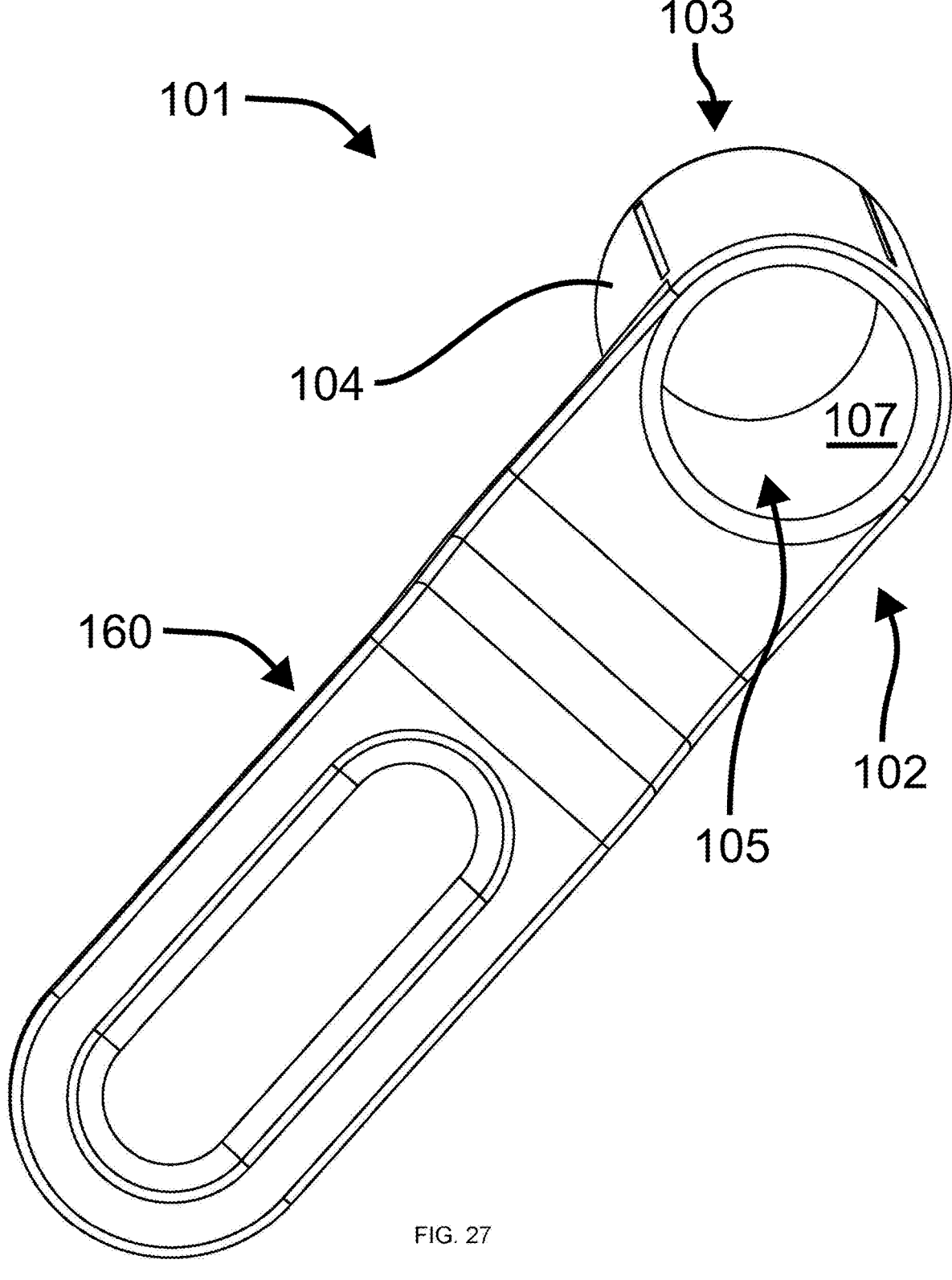
FIG. 27 is another proximal perspective view of the working cannula.
Figures 28A, 28B:
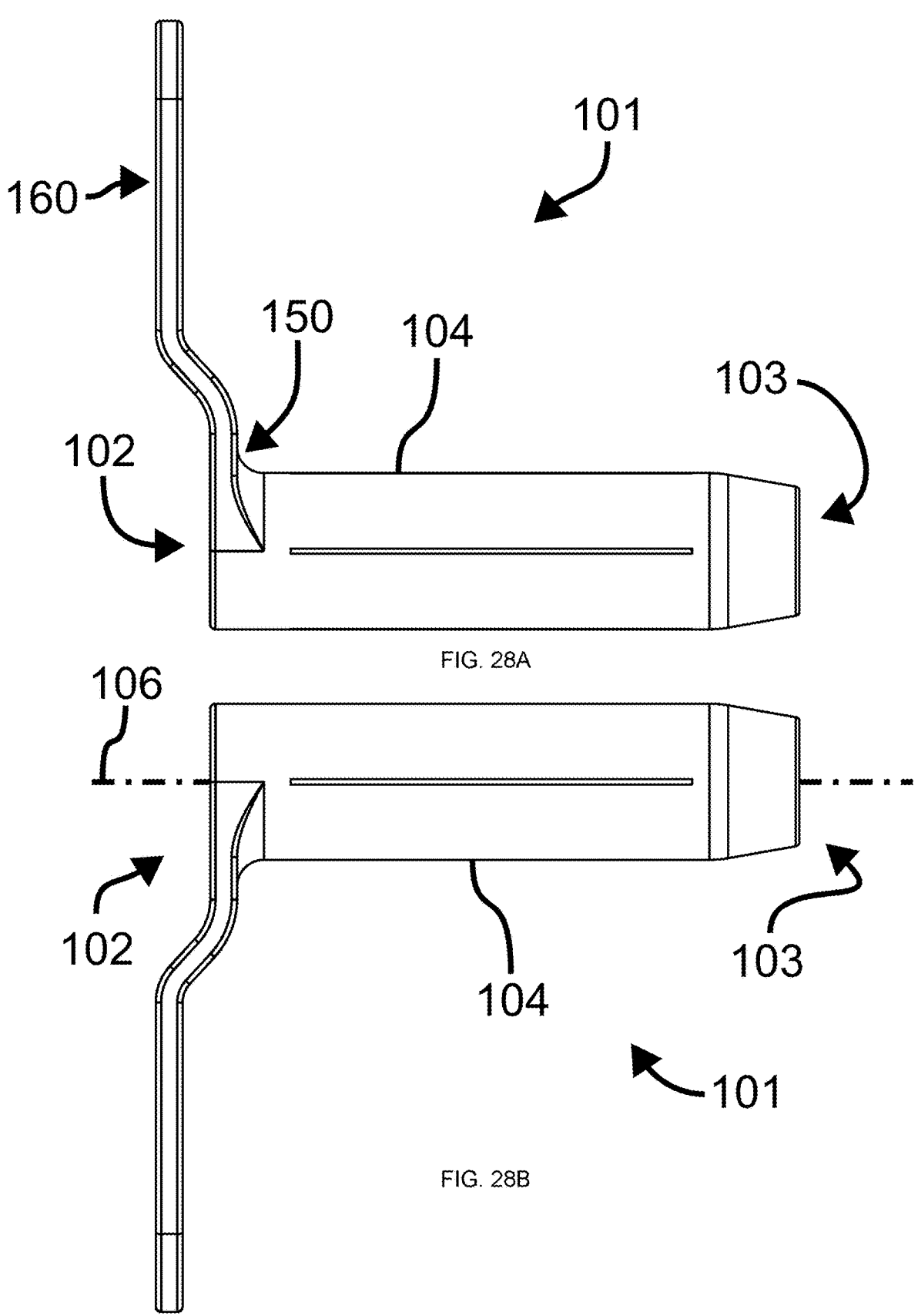
FIGS. 28A-28B are opposite side views of the working cannula.
Figures 29A, 29B:
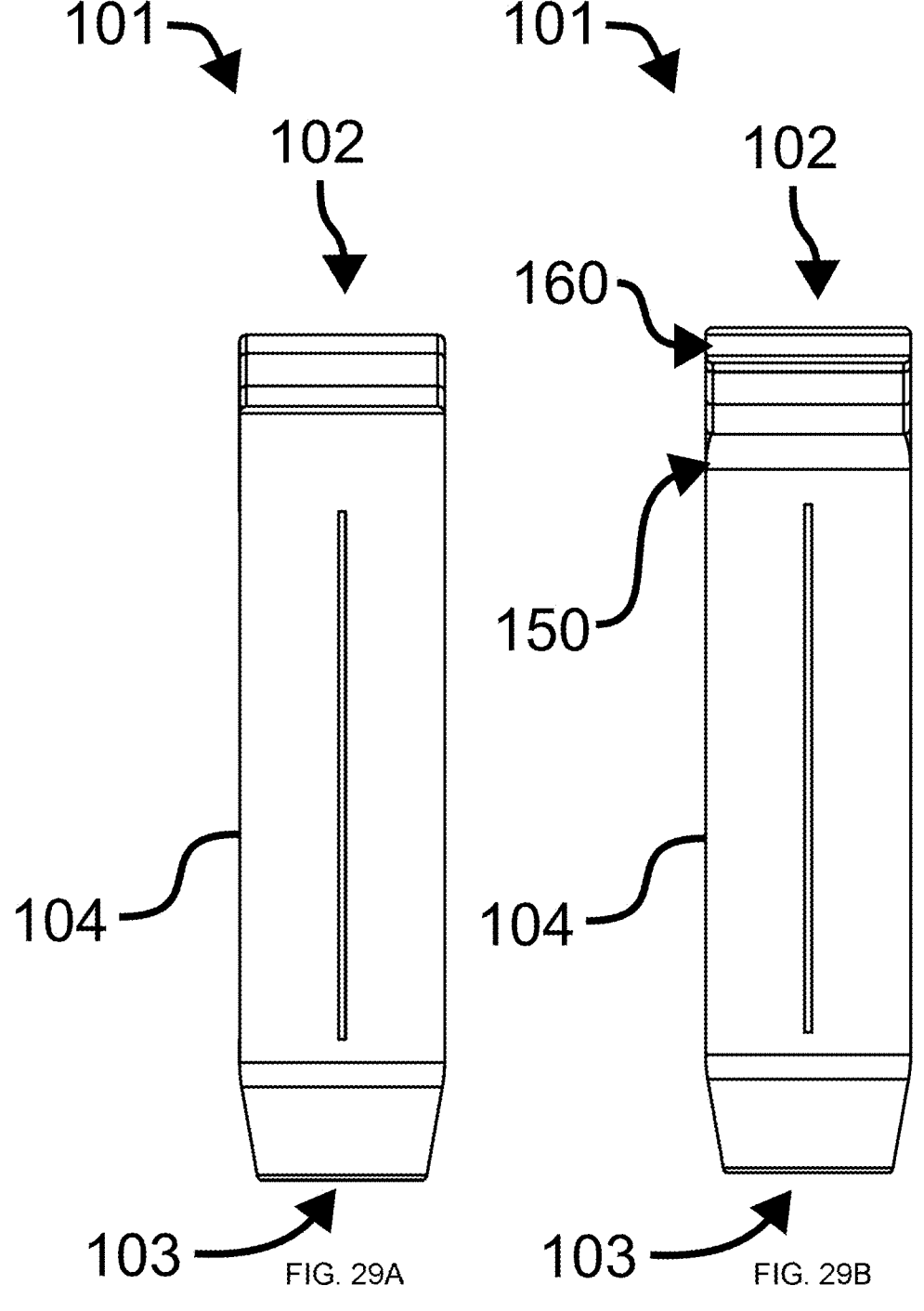
FIGS. 29A-29B are respectively bottom and top views of the working cannula.
Figures 30A, 30B:
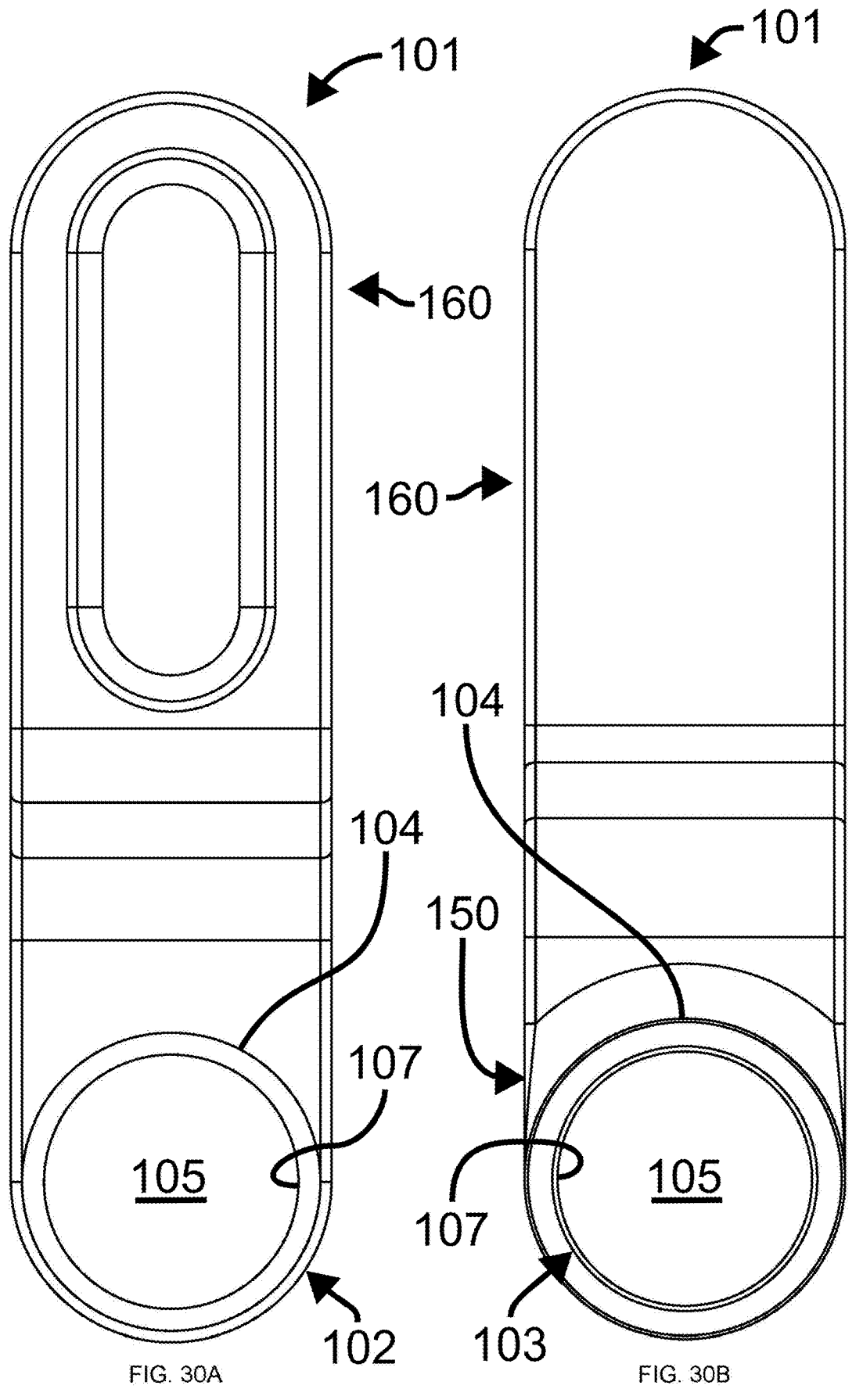
FIGS. 30A-30B are respectively proximal and distal end views of the working cannula.
Figure 31:
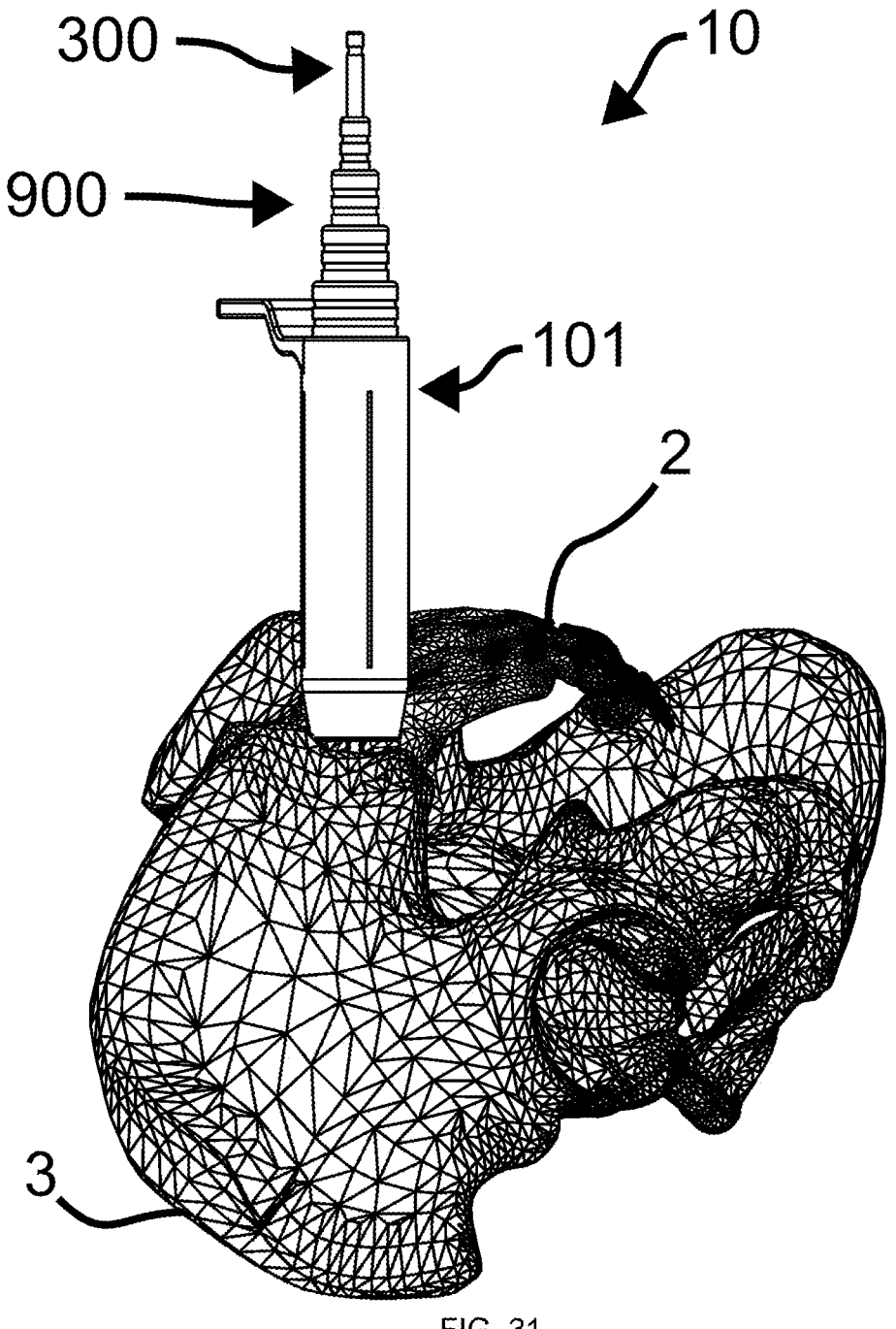
FIG. 31 is the view of FIG. 23 including the working cannula positioned over the series of dilators.
Figure 32:
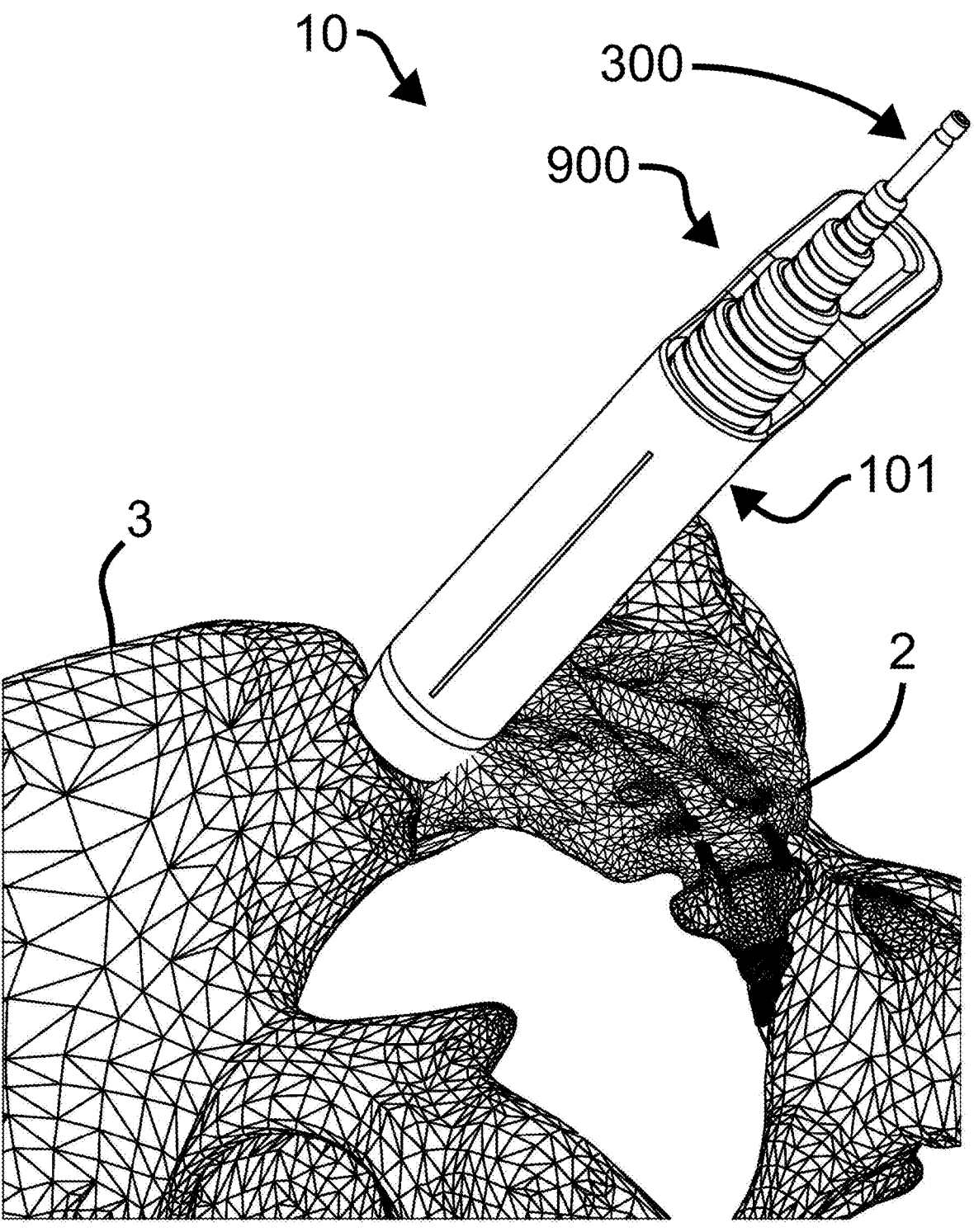
FIG. 32 is another view of the step shown in FIG. 31.
Figure 33:
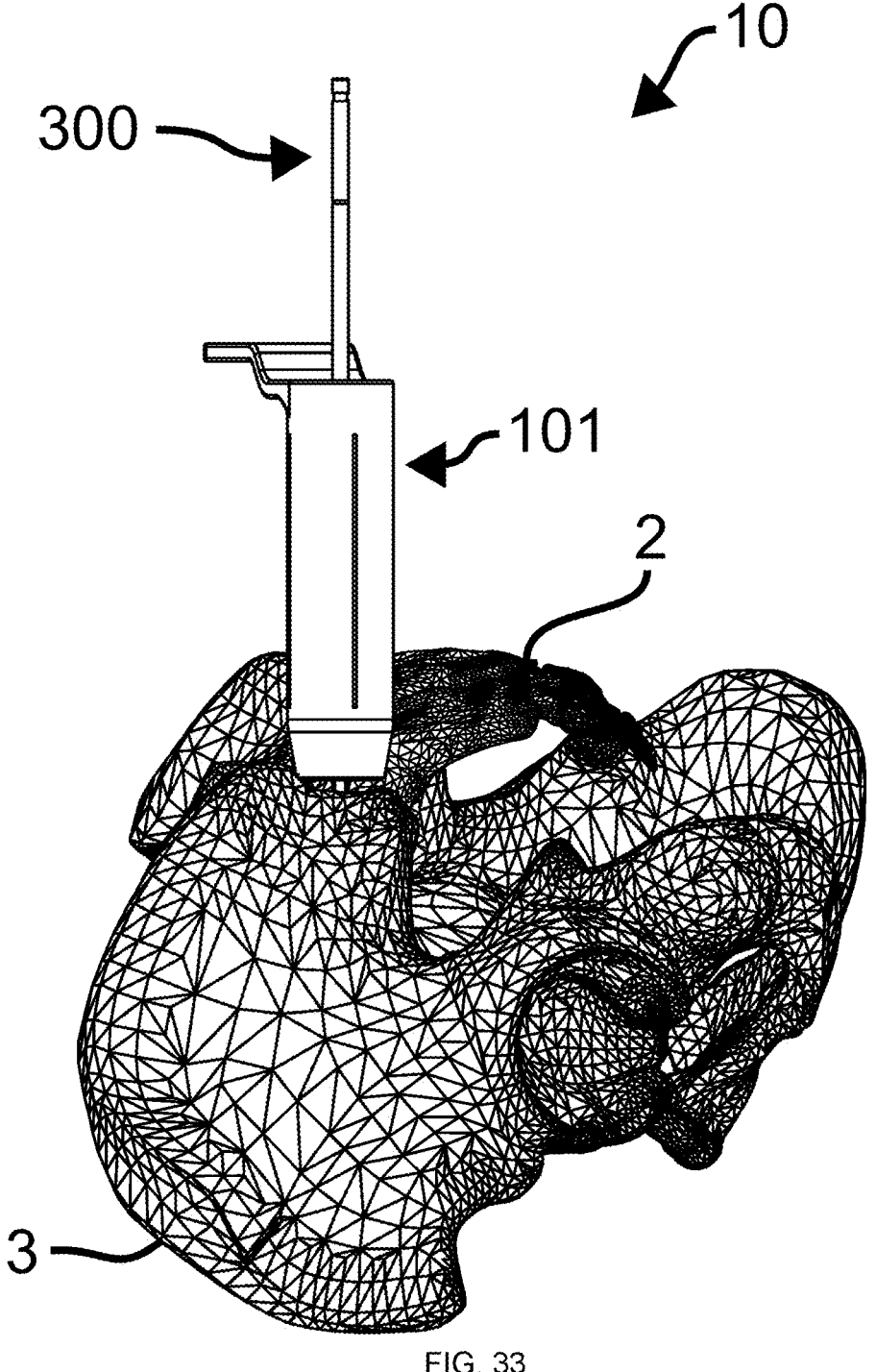
FIG. 33 is the view of the step shown in FIG. 31 but with the series of dilators removed from the working cannula.
Figure 34:
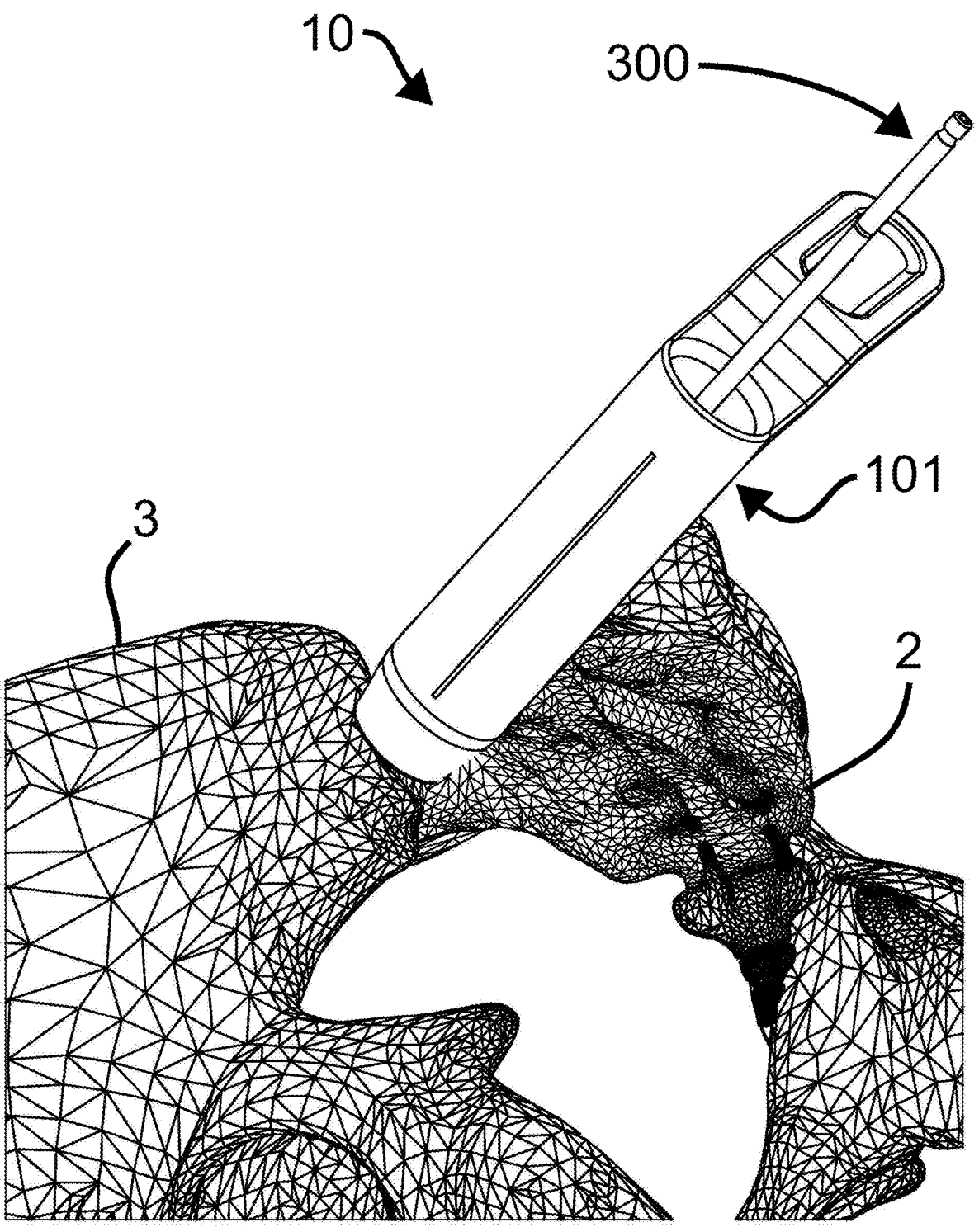
FIG. 34 is another view of the step shown in FIG. 33.
Figure 35:
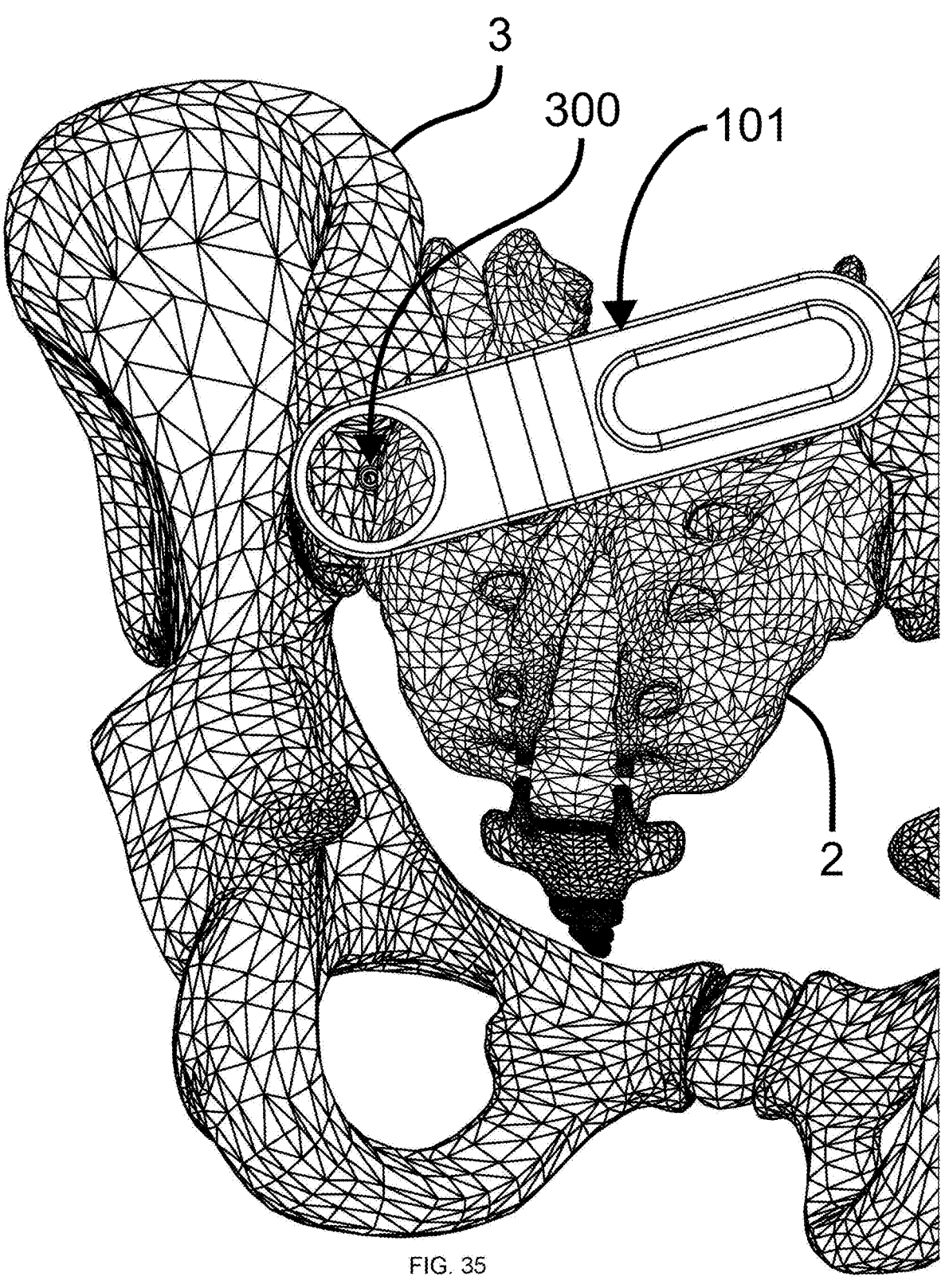
FIG. 35 is a proximal end view of the working cannula and joint finder of the step shown in FIGS. 33 and 34.
Figure 36:
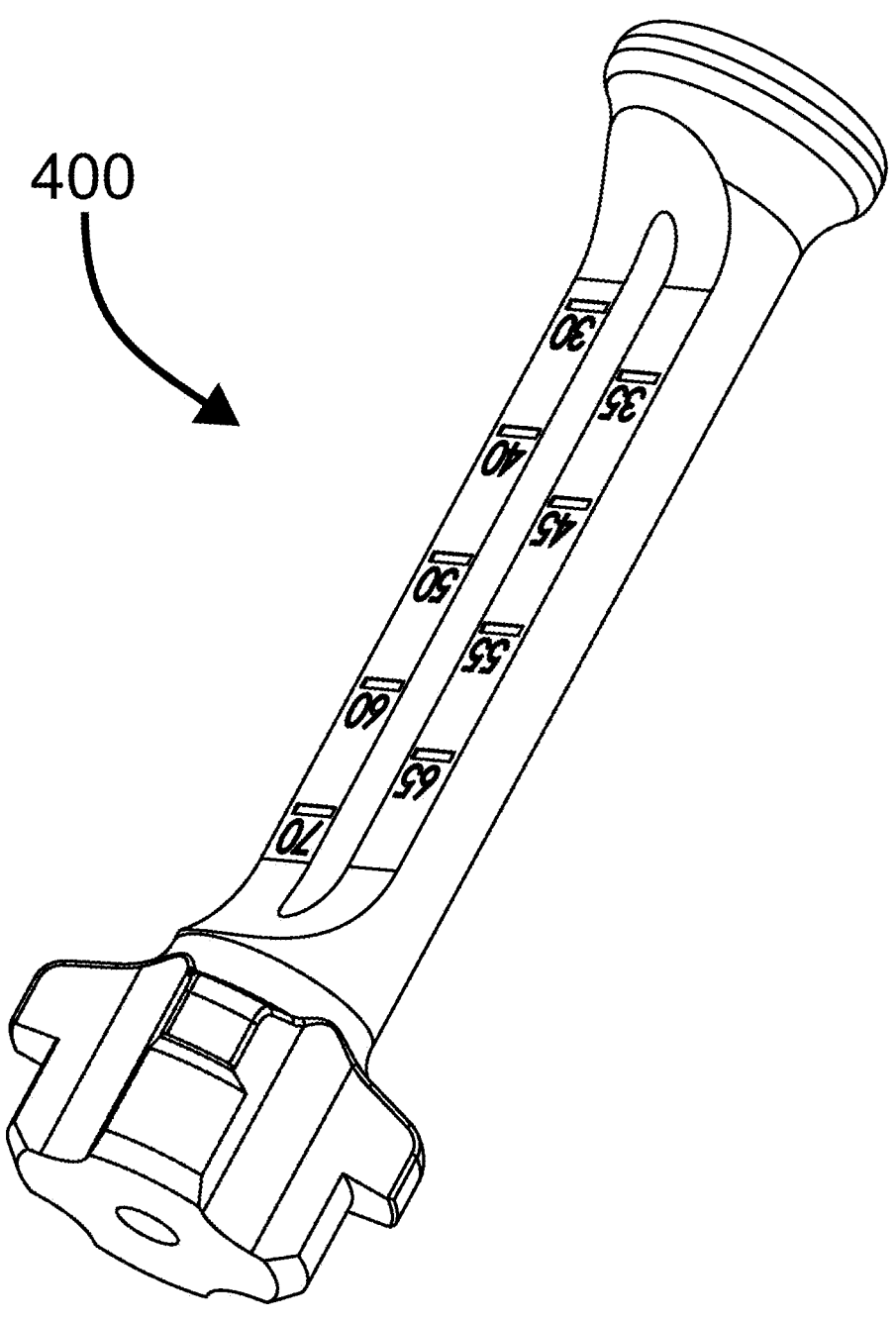
FIGS. 36 and 37 are perspective views of a depth gauge.
Figure 37:
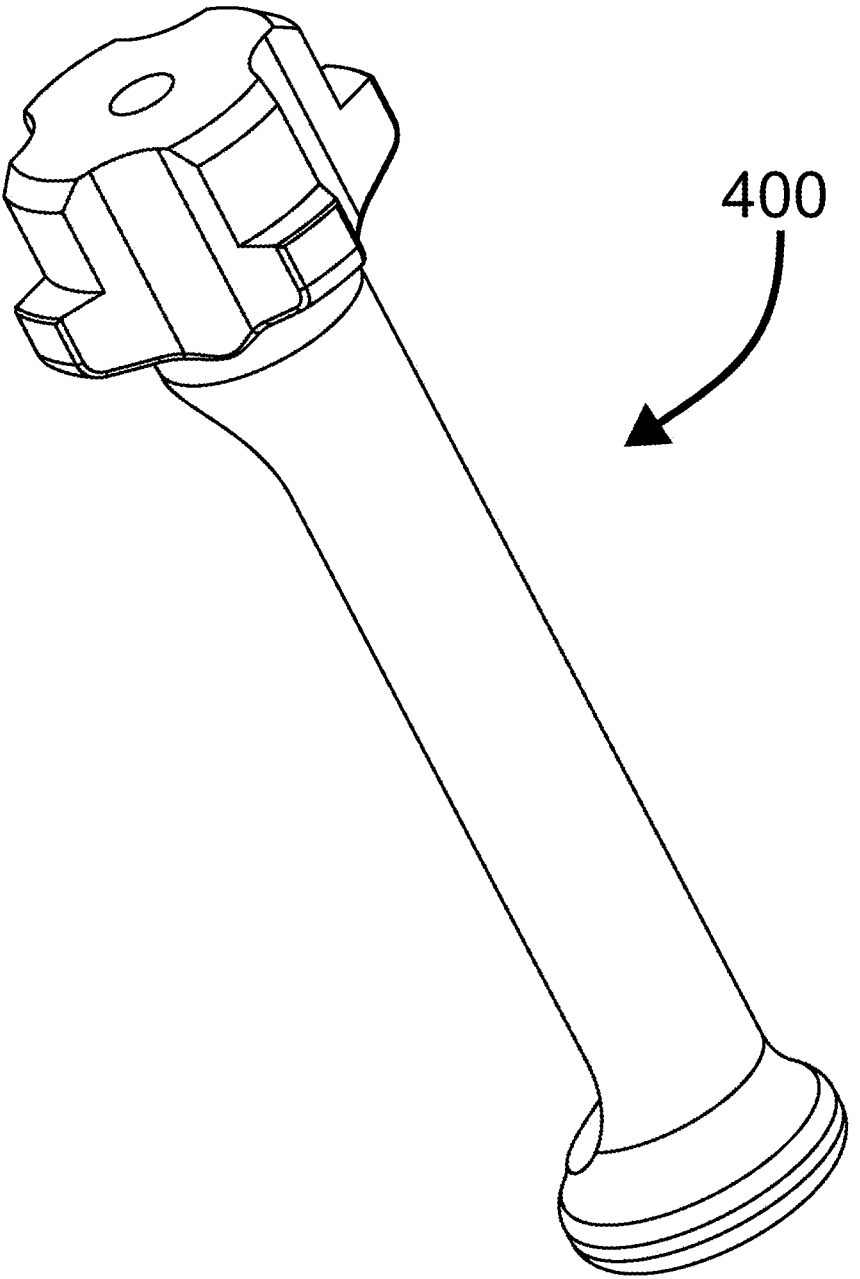
Figure 40A:
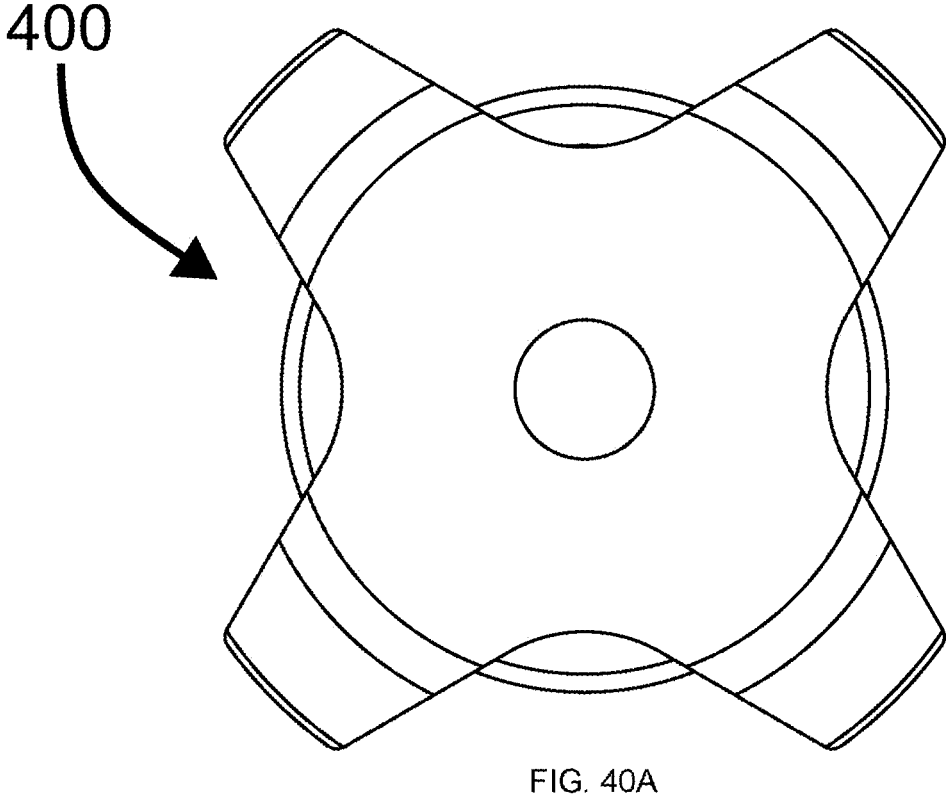
FIGS. 40A-40B are respectively proximal and distal end views of the depth gauge.
Figure 40B:
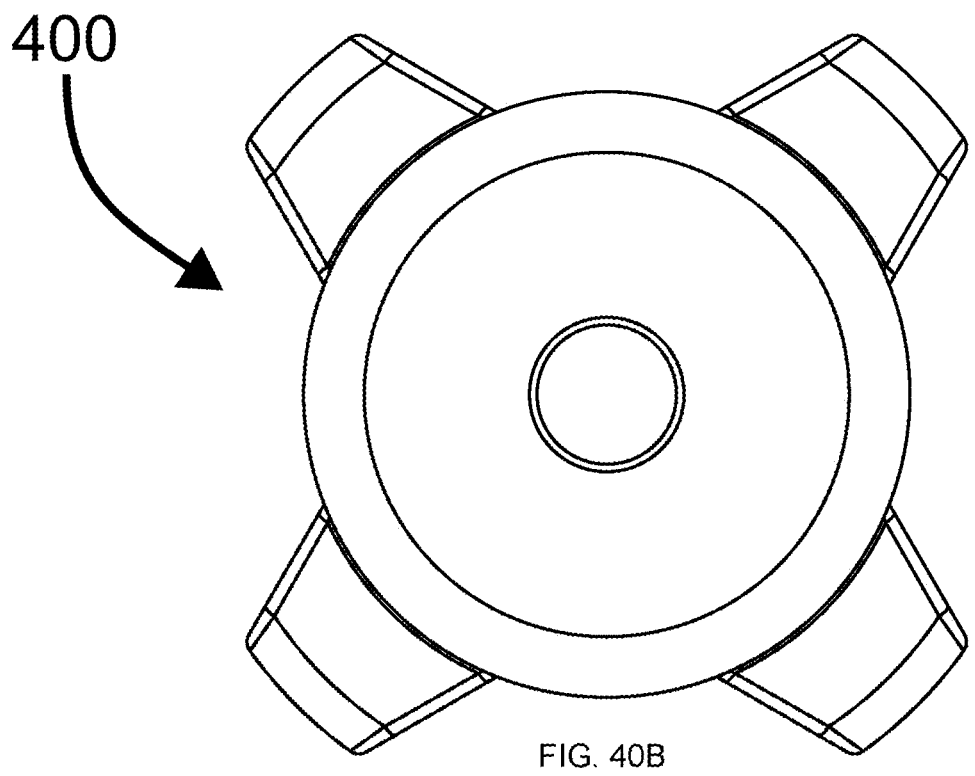
Figures 41A, 41B:
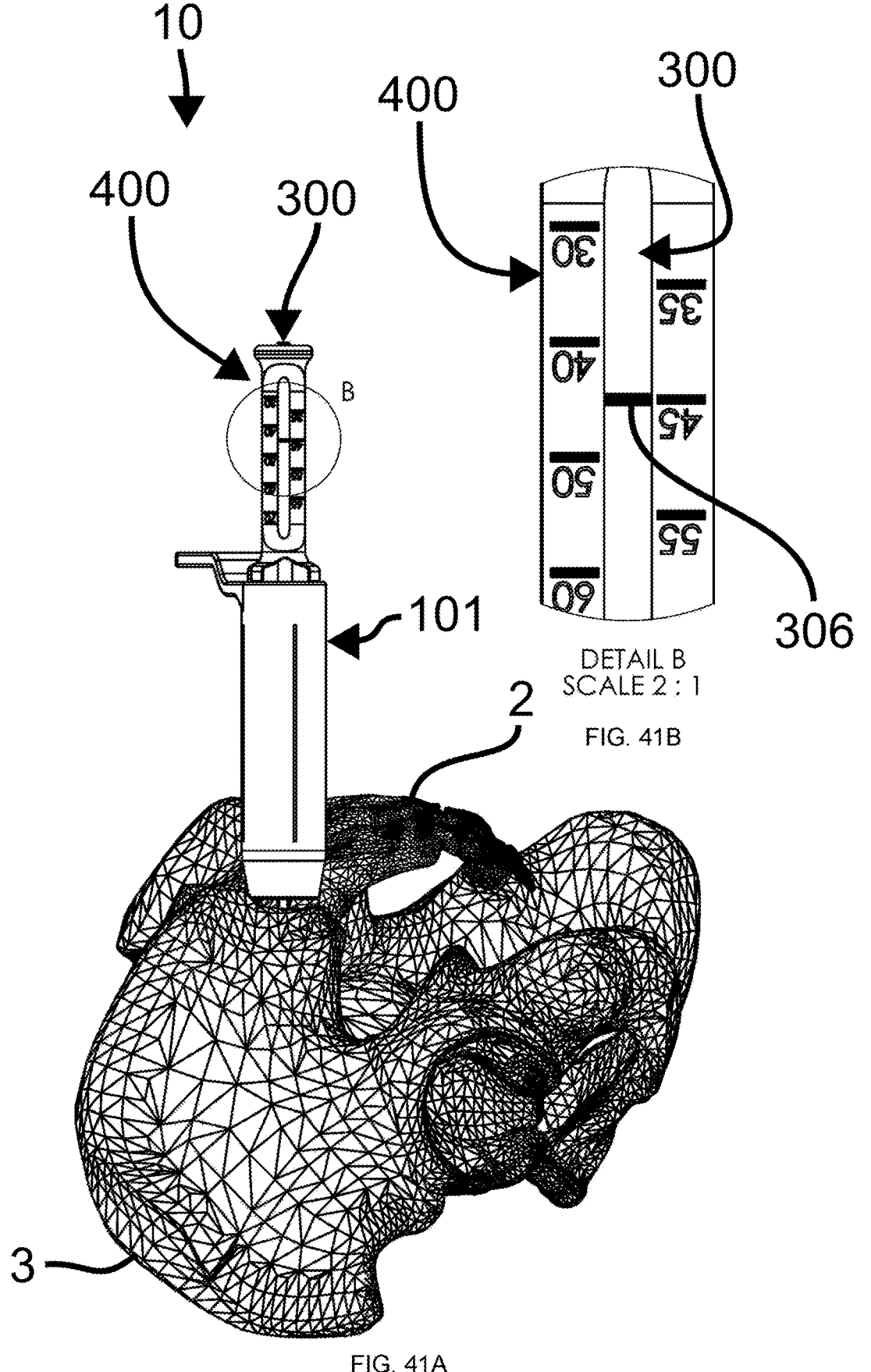
FIG. 41A shows the depth gauge seated within the working cannula and over the joint finder.
FIG. 41B is a close-up view of gradations marked on the depth gauge and a radial marking on the proximal end of the joint finder aligned with "45".
Figure 42:
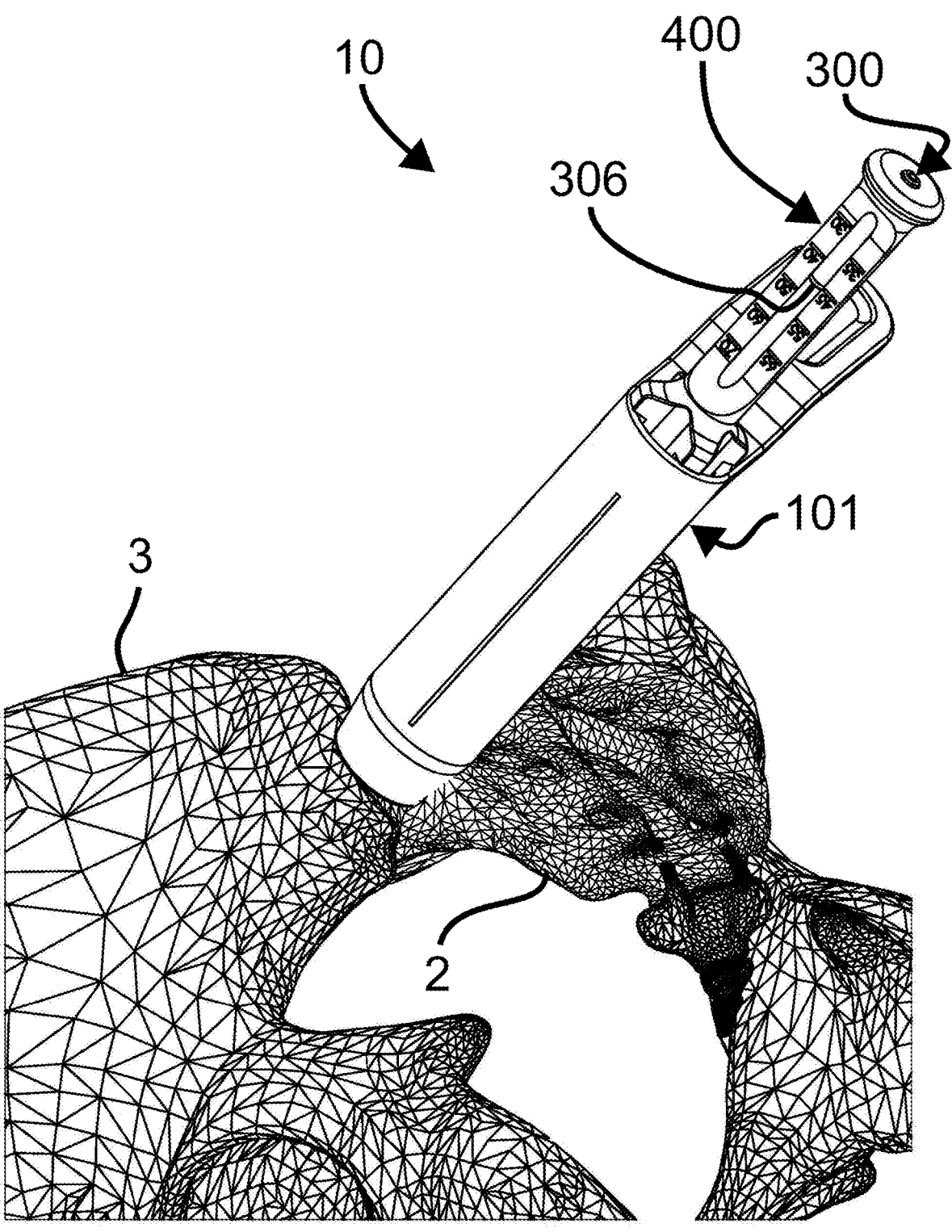
FIG. 42 is another view of the step shown in FIG. 41A.
Figures 43A, 43B:
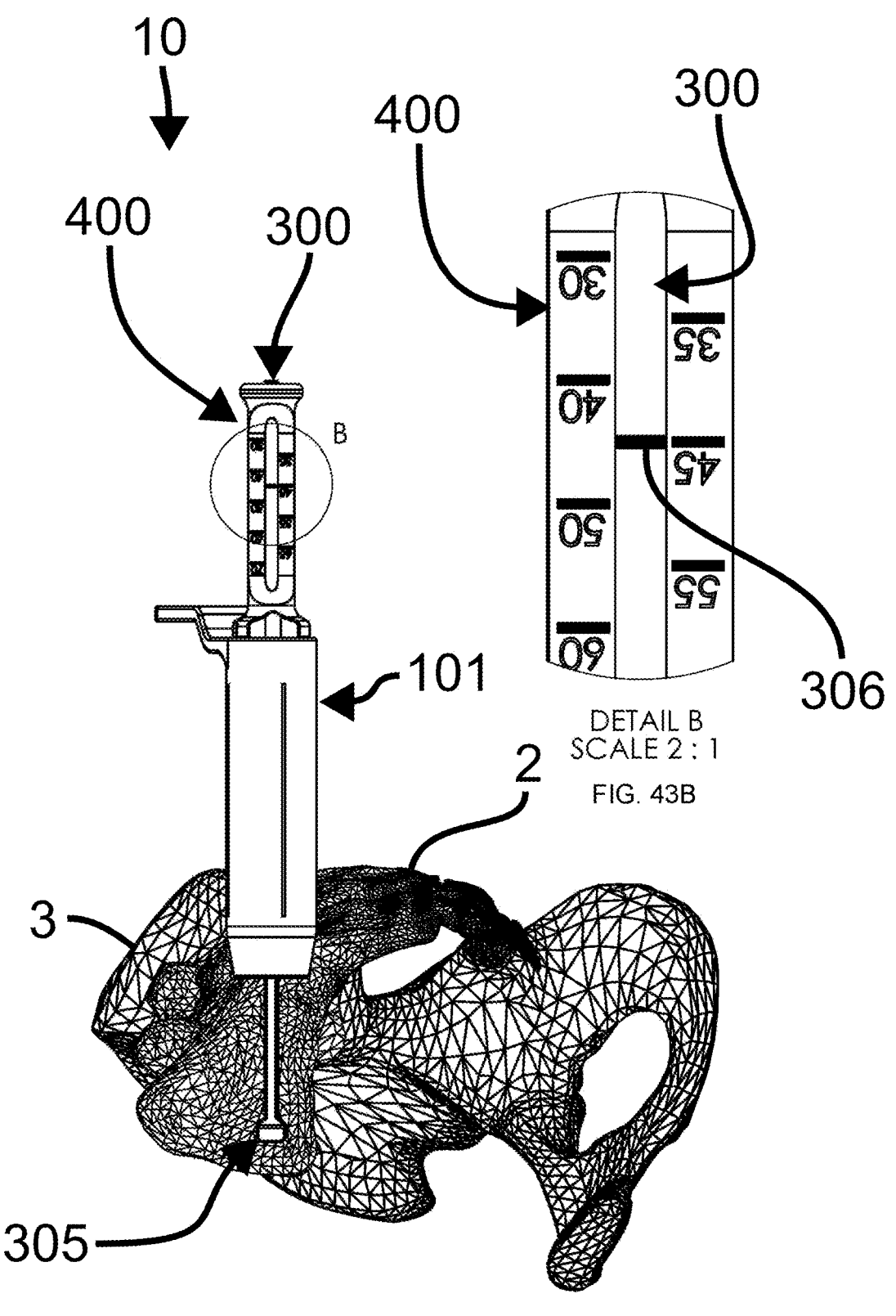
FIG. 43A is the view of FIG. 41A but with the left ilium removed to show the location of the joint finder in greater detail.
FIG. 43B is the same view of FIG. 41B.
Figures 44A, 44B, 44C:
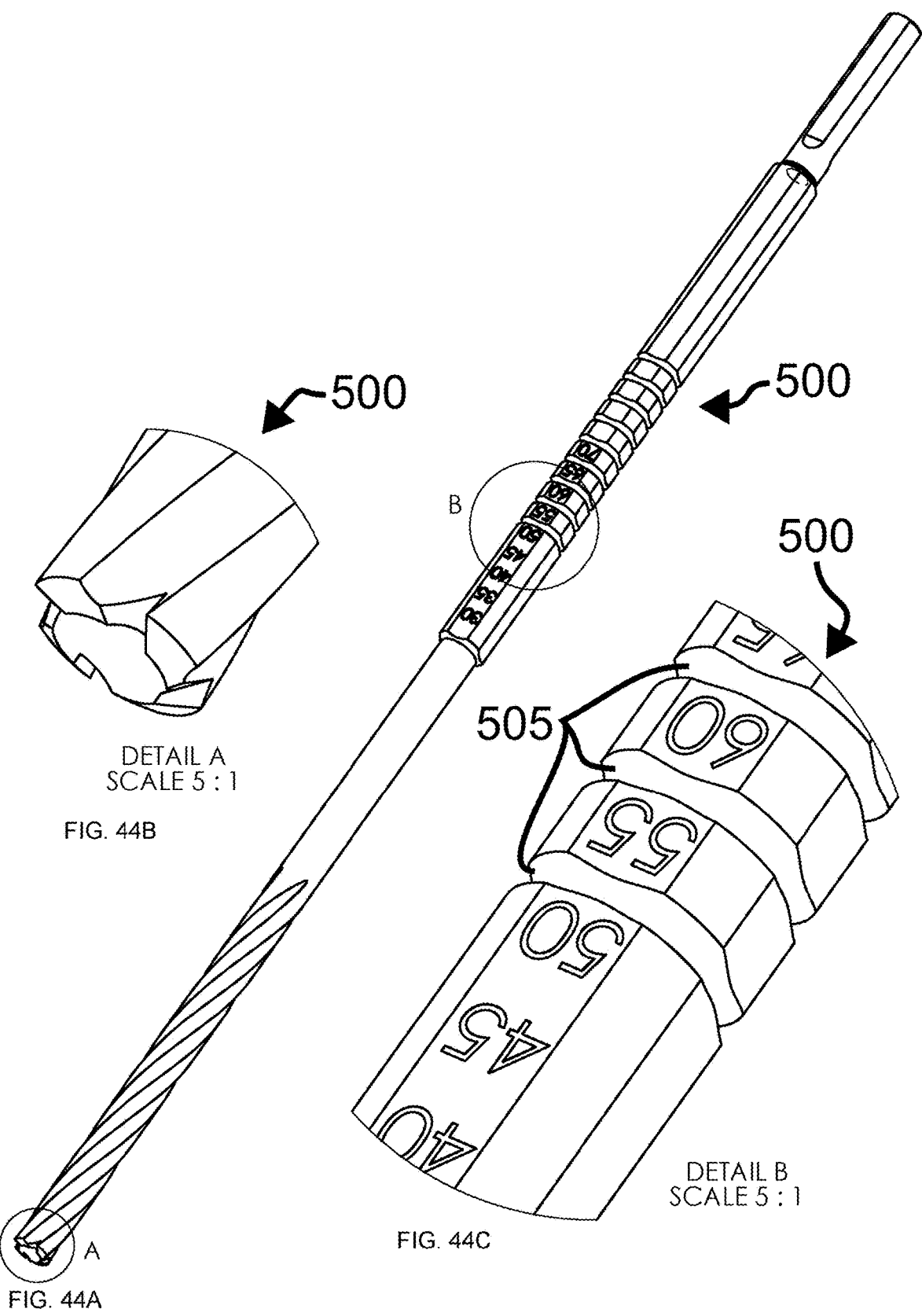
FIGS. 44A-44C are respectively a close-up view of the distal end of a cannulated drill bit, a perspective view of the cannulated drill bit and a close-up view of gradations and radial grooves on the shaft of the cannulated drill bit.
Figures 45A, 45B, 45C:
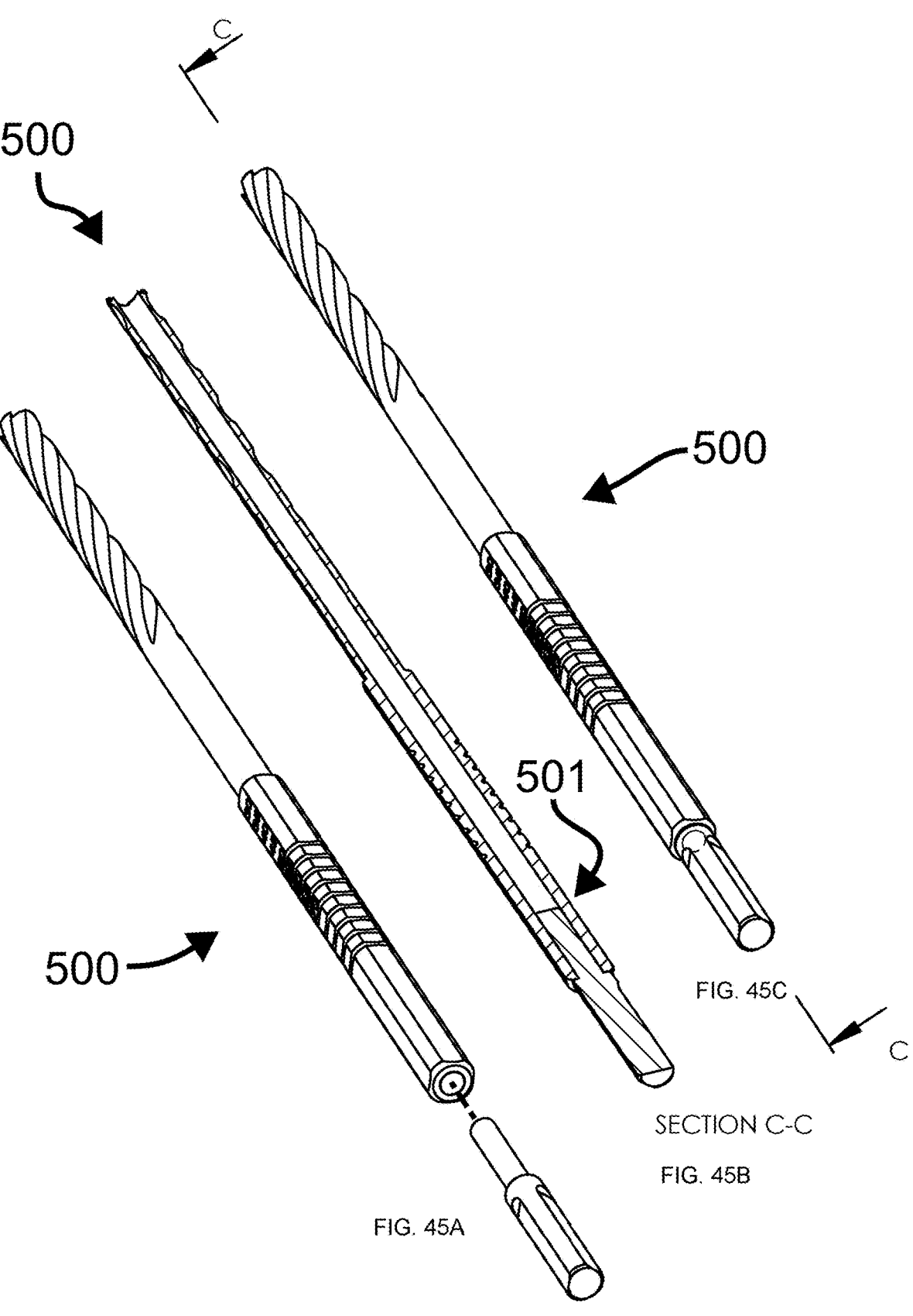
FIGS. 45A-45C are respectively a perspective exploded view of the cannulated drill bit showing the proximal end plug separated, a perspective longitudinal cross section of the cannulated drill bit as taken along section line C-C in FIG. 45C and a perspective assembled view of the cannulated drill bit.
Figures 46A, 46B:
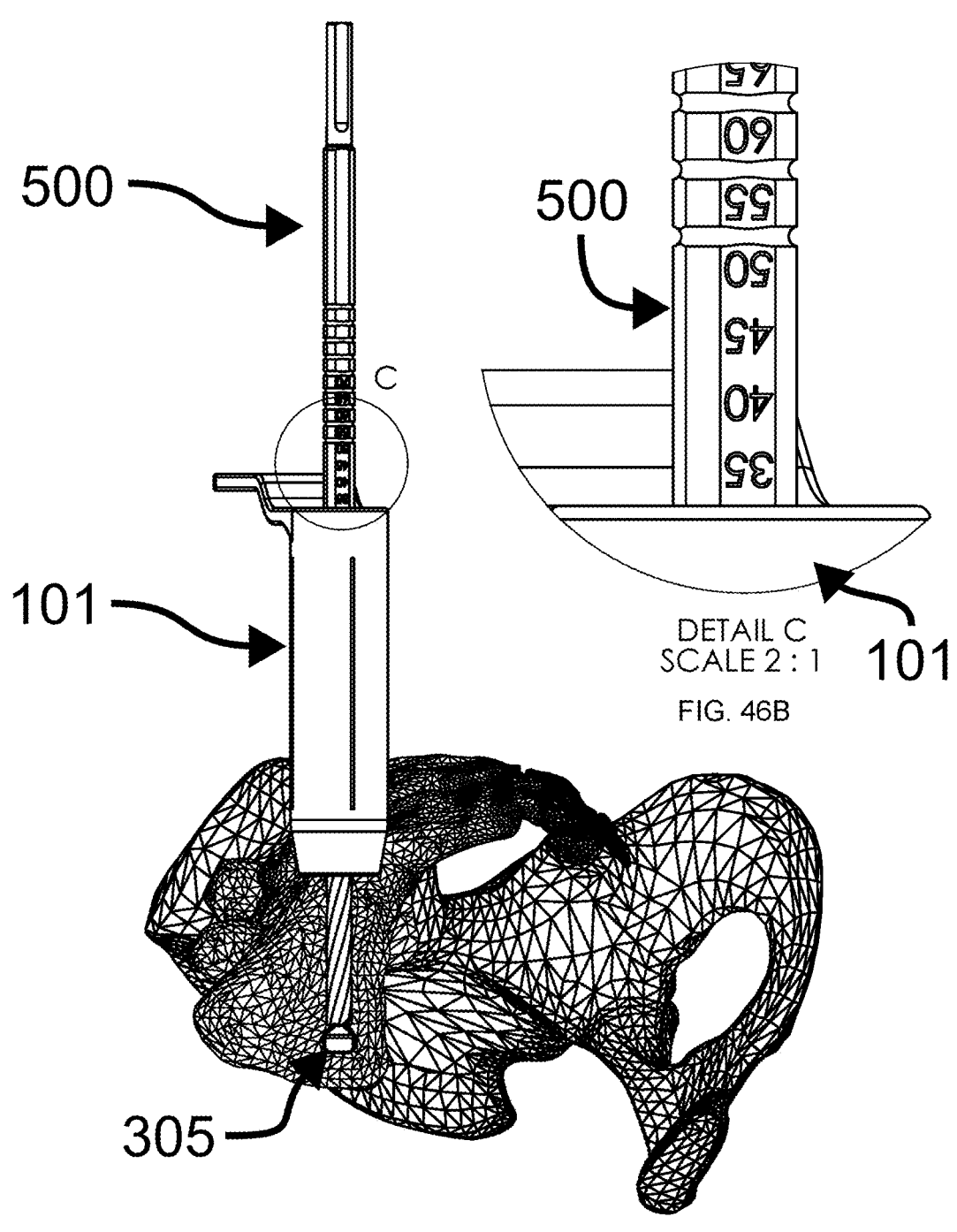
FIGS. 46A-46B are respectively a view of the cannulated drill bit over the joint finder, both located within the working cannula and positioned within the sacroiliac joint and a close-up view of the gradations on the cannulated drill bit.
Figure 47:
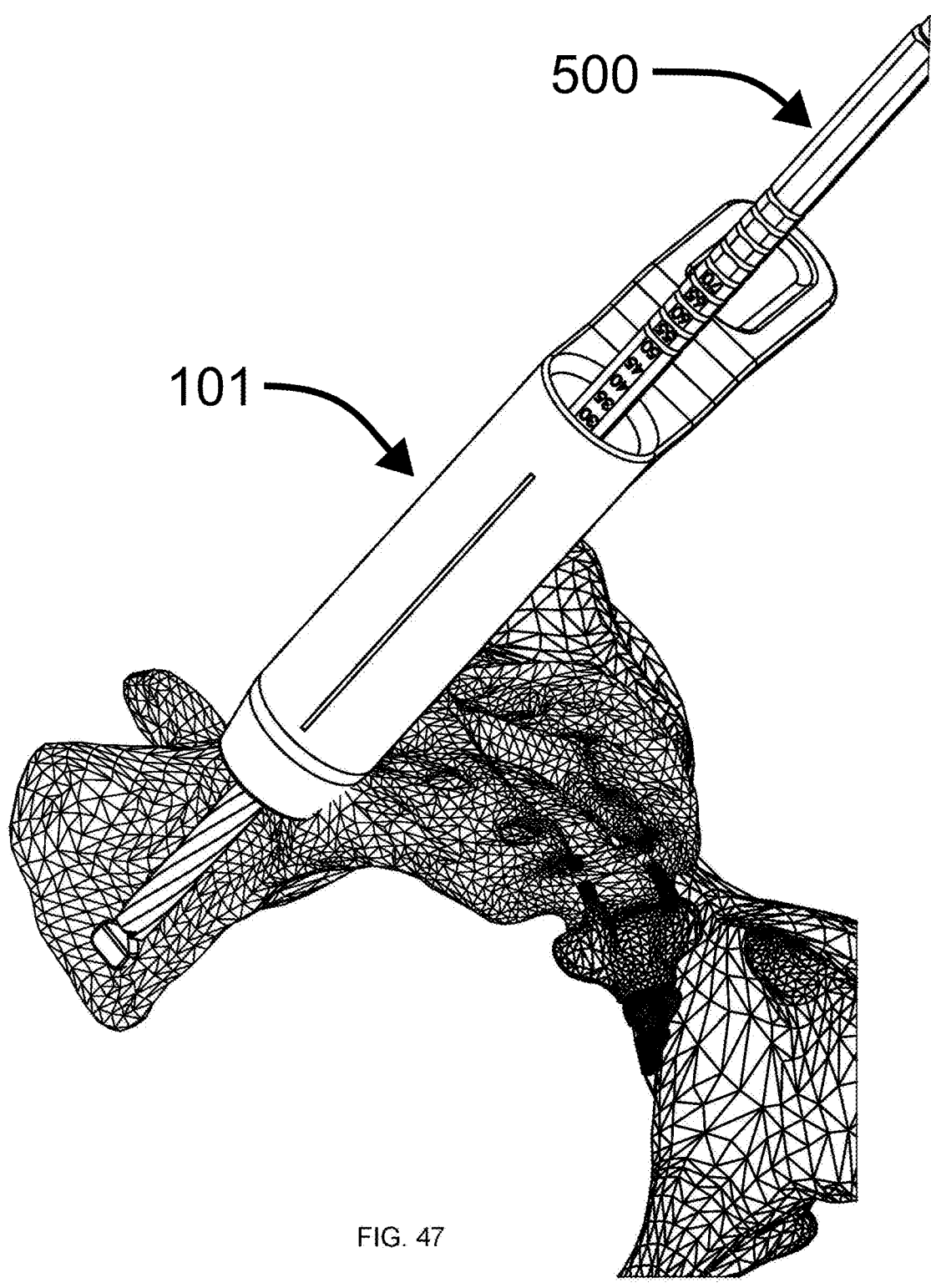
FIG. 47 is another view of the step shown in FIG. 46A.
Figure 48:
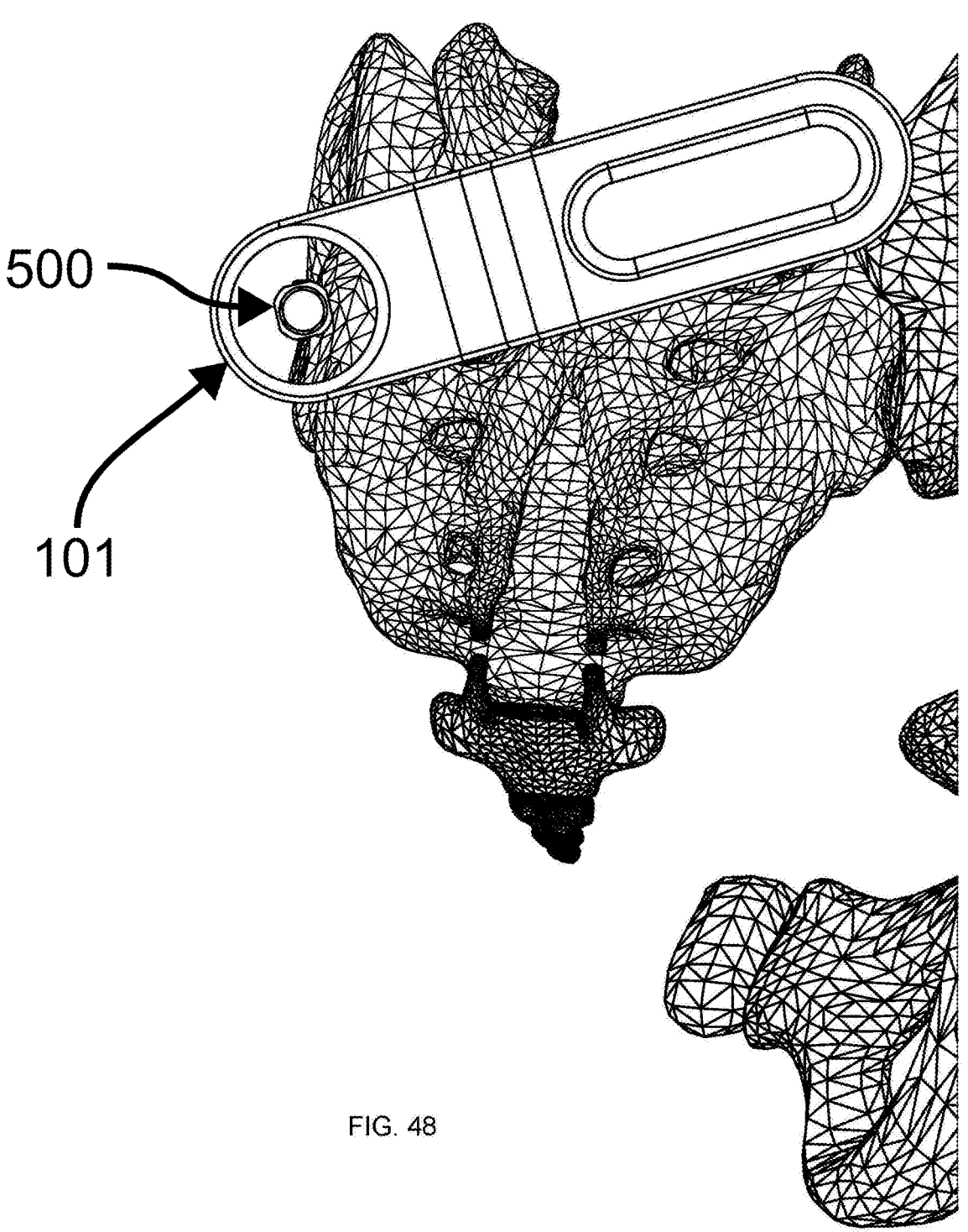
FIG. 48 is a proximal end view of the step shown in FIG. 46A but with the left ilium removed to show the location of the joint finder in greater detail.
Figures 49A, 49B:
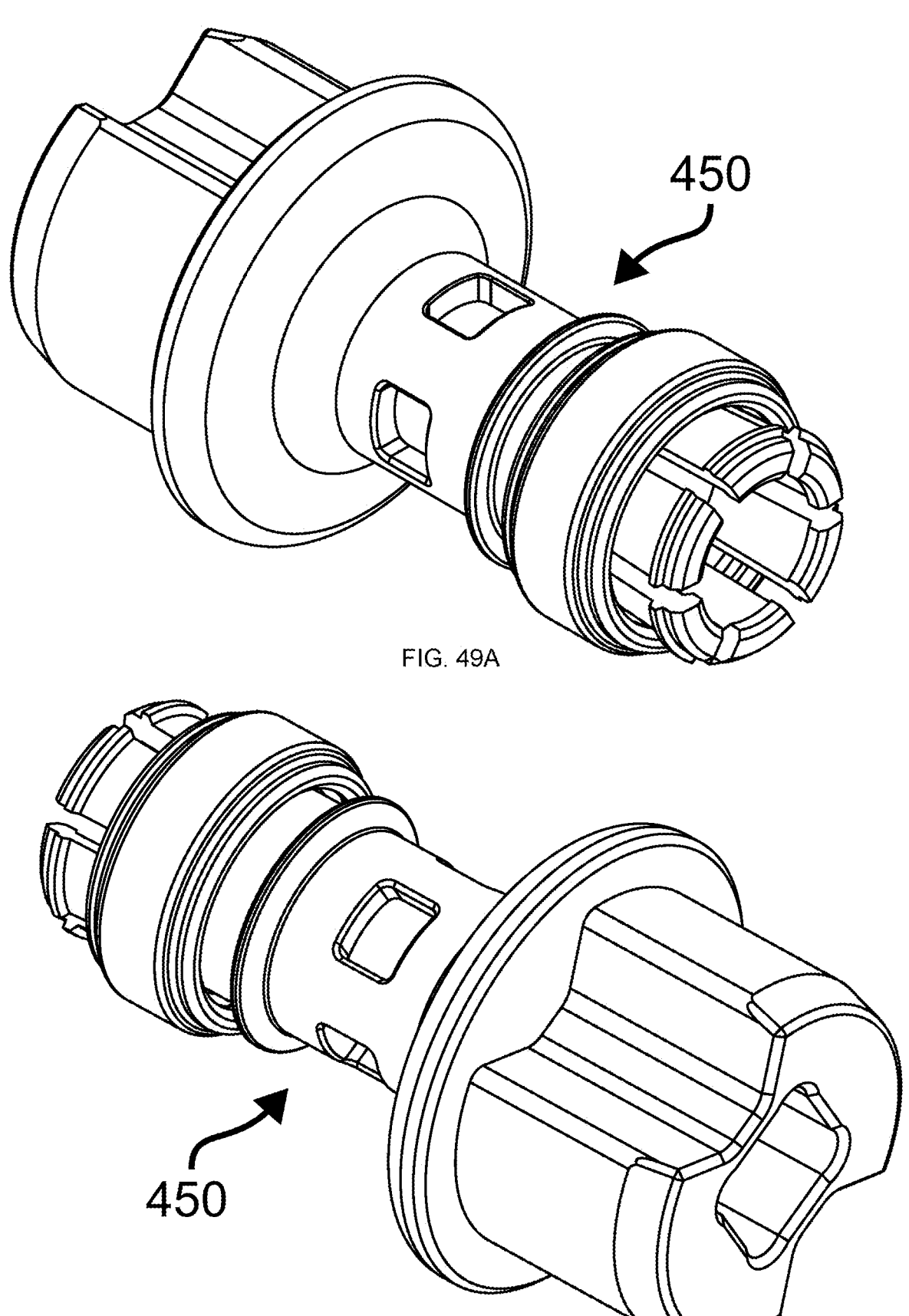
Figure 50A:
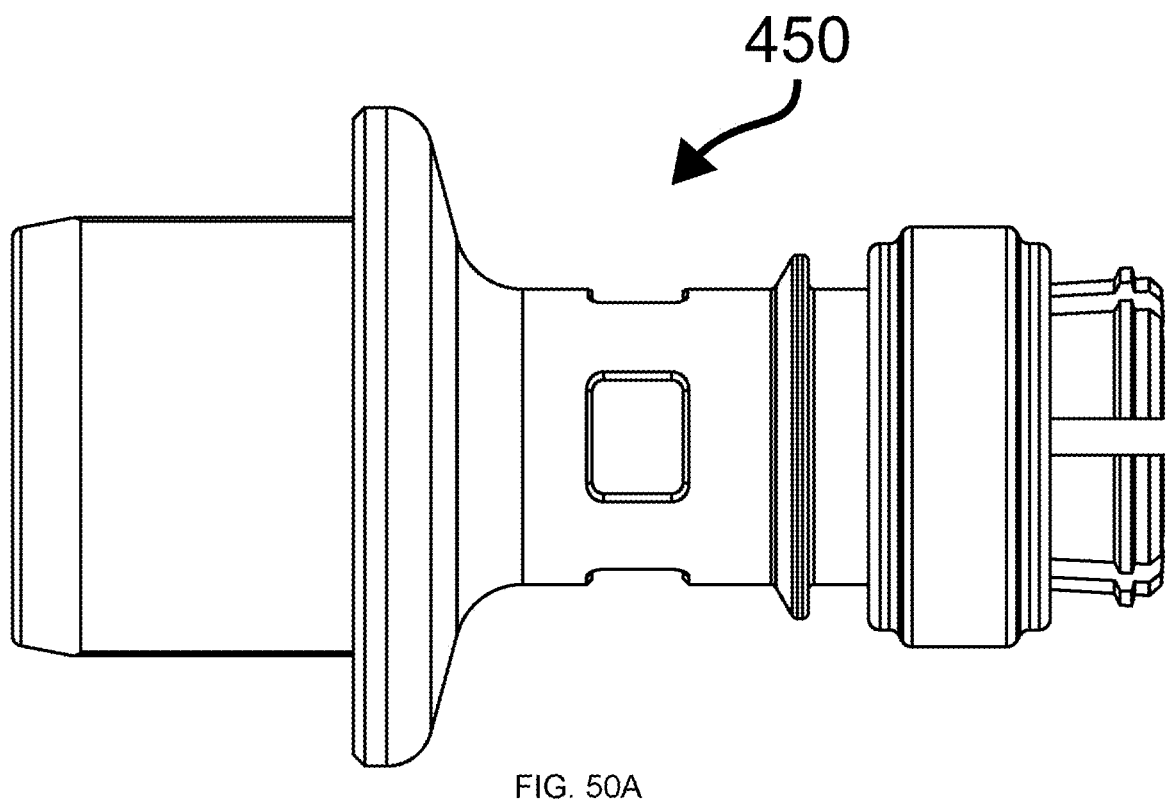
Figure 50B:
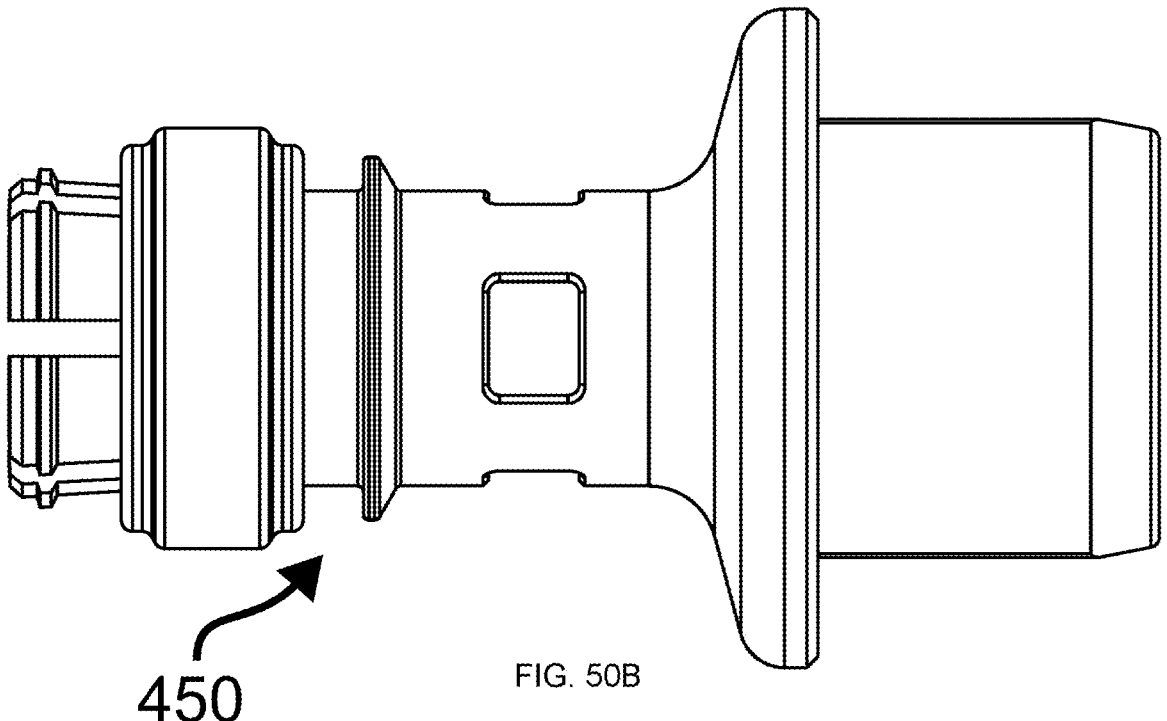
Figure 51A:
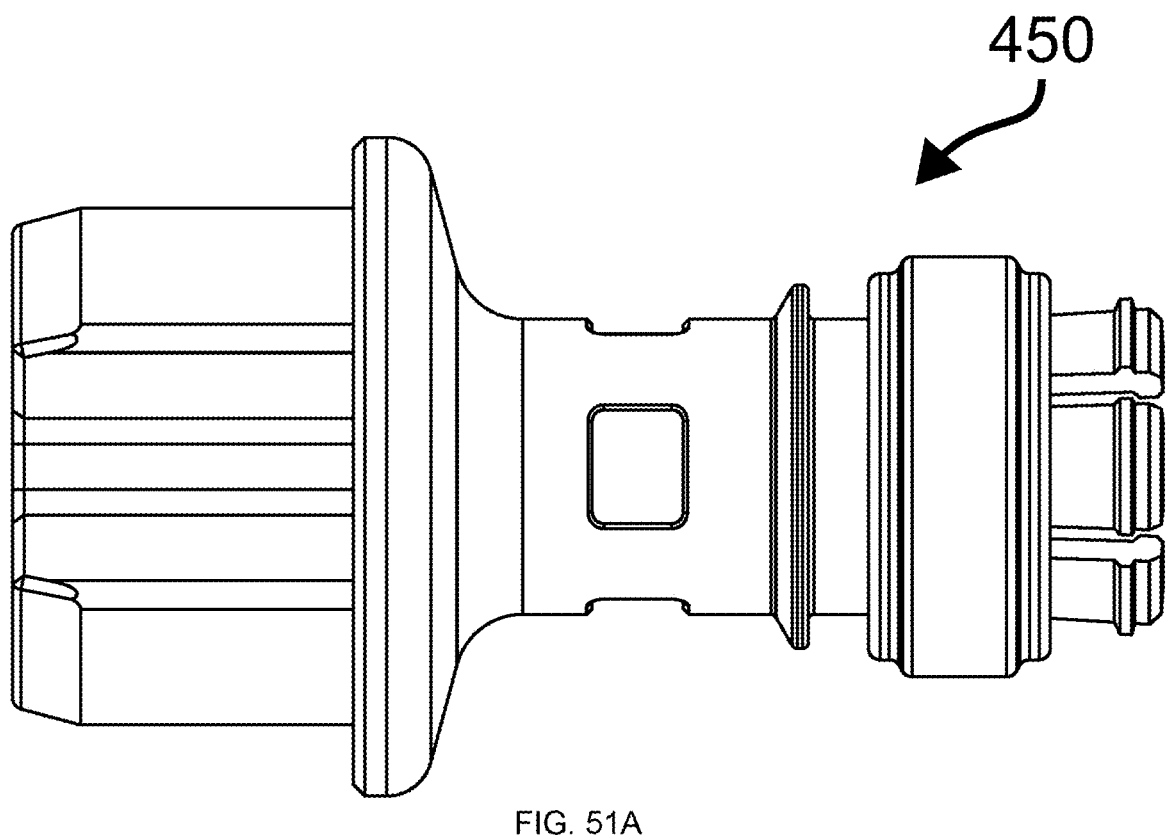
Figure 51B:
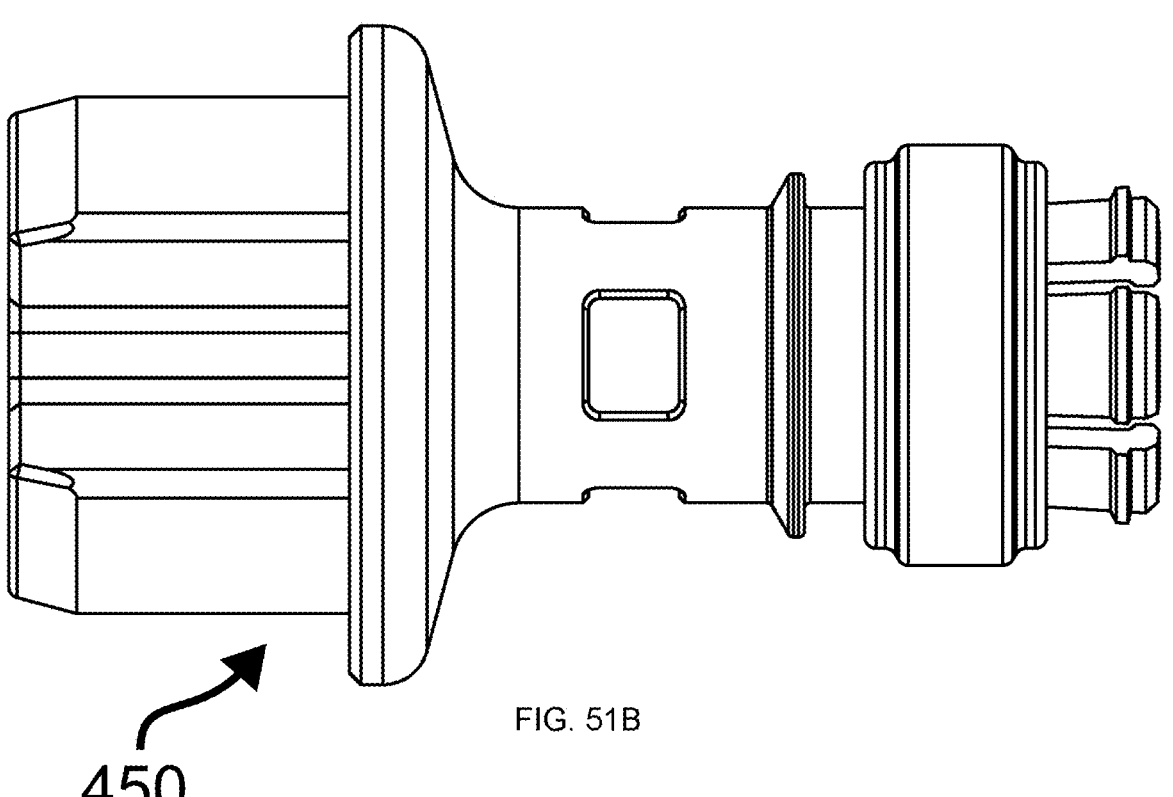
Figure 52A:
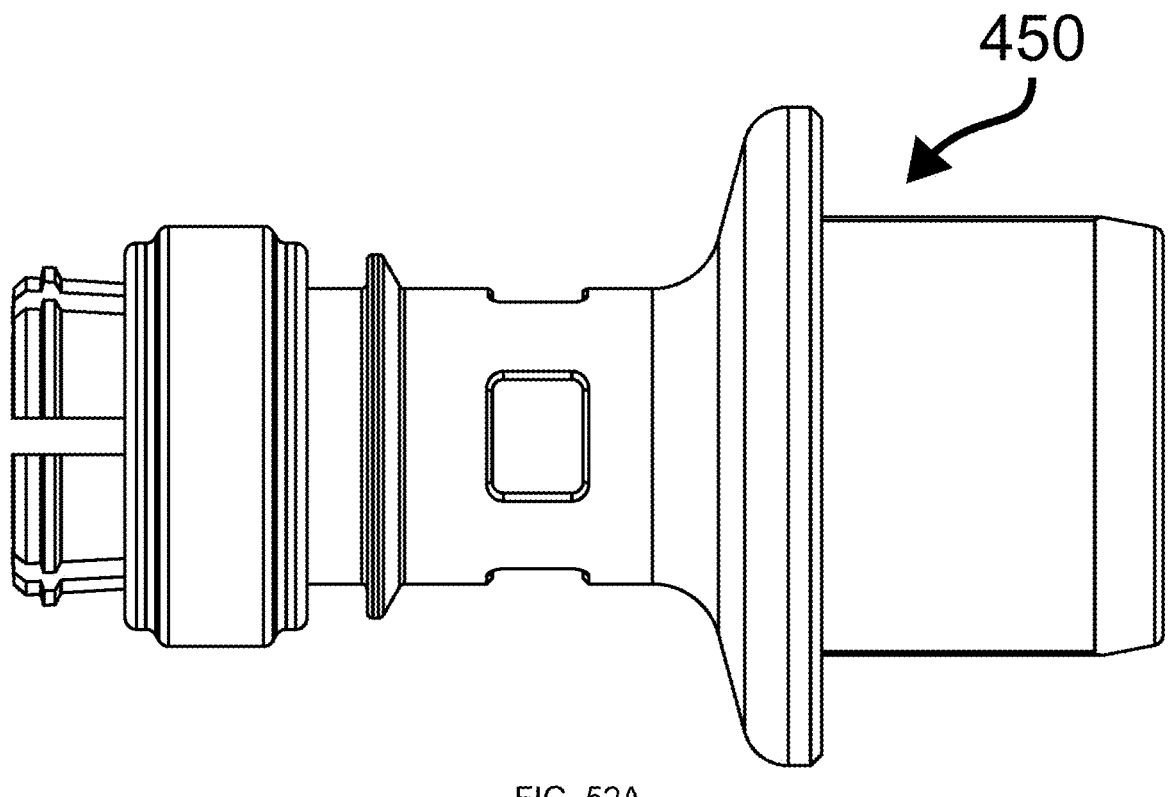
Figure 52B:
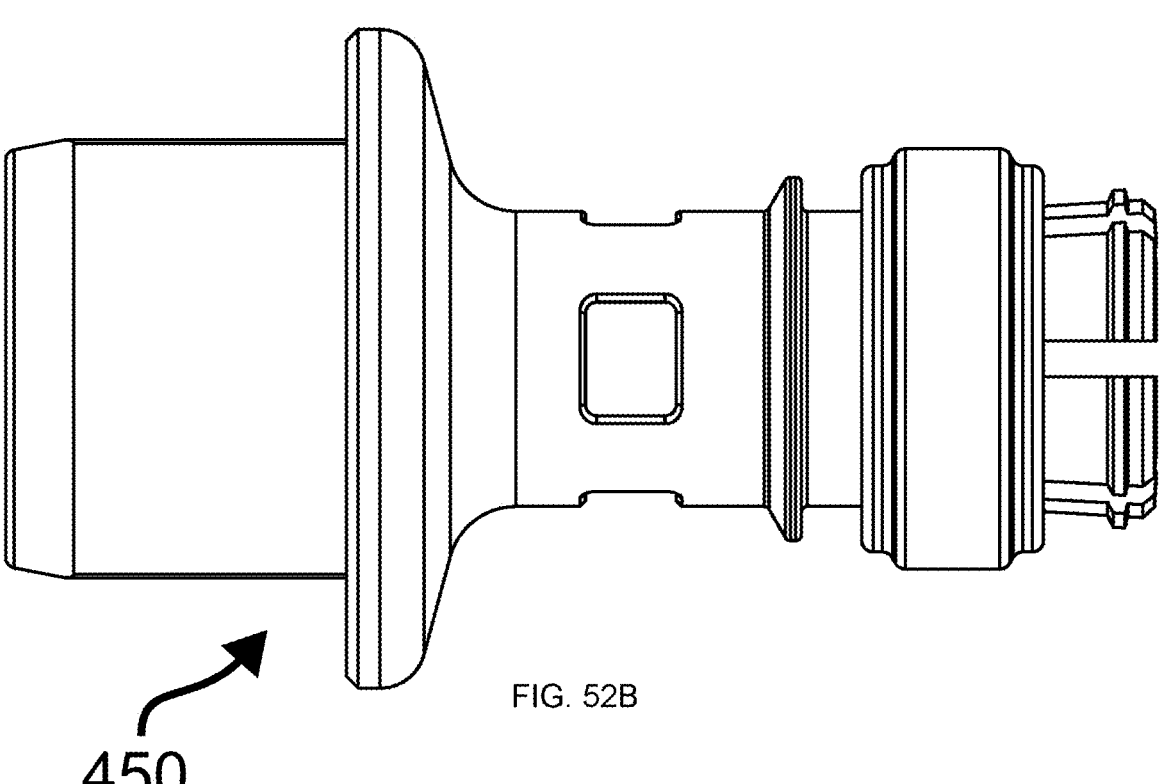
Figure 53A:
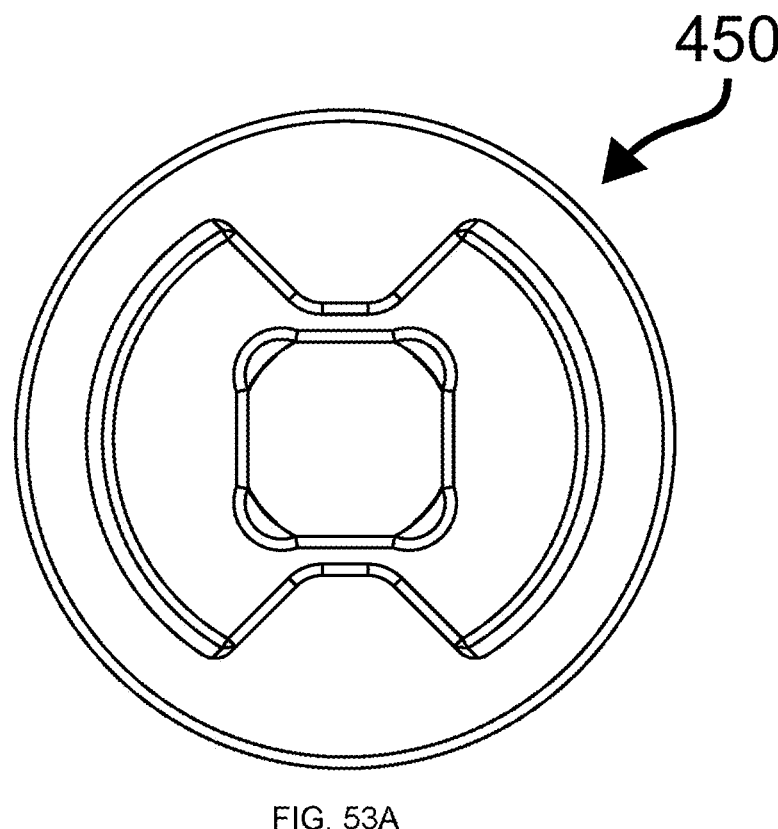
Figure 53B:
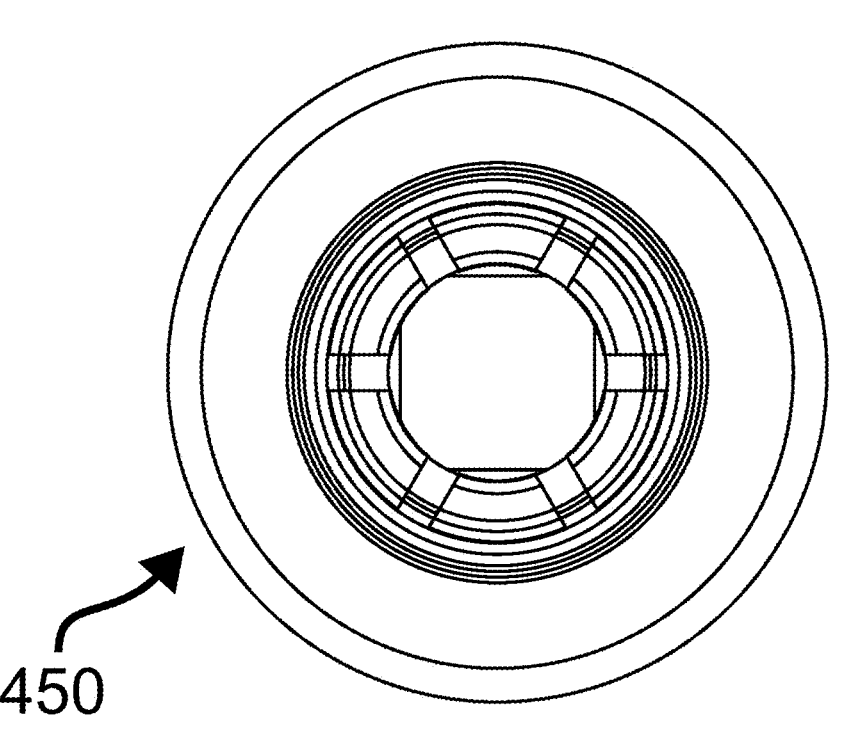
Figures 54A, 54B:
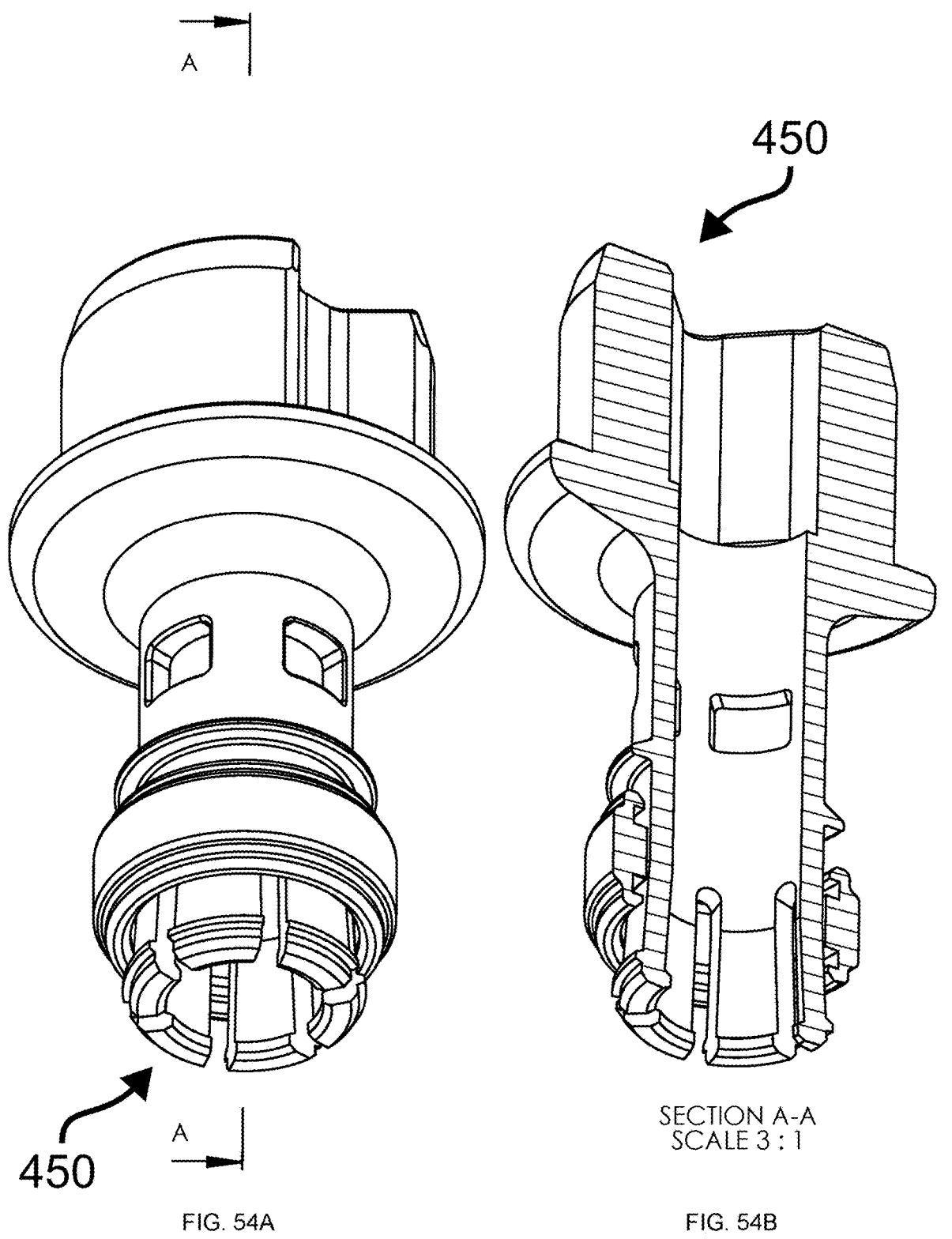
Figure 55:
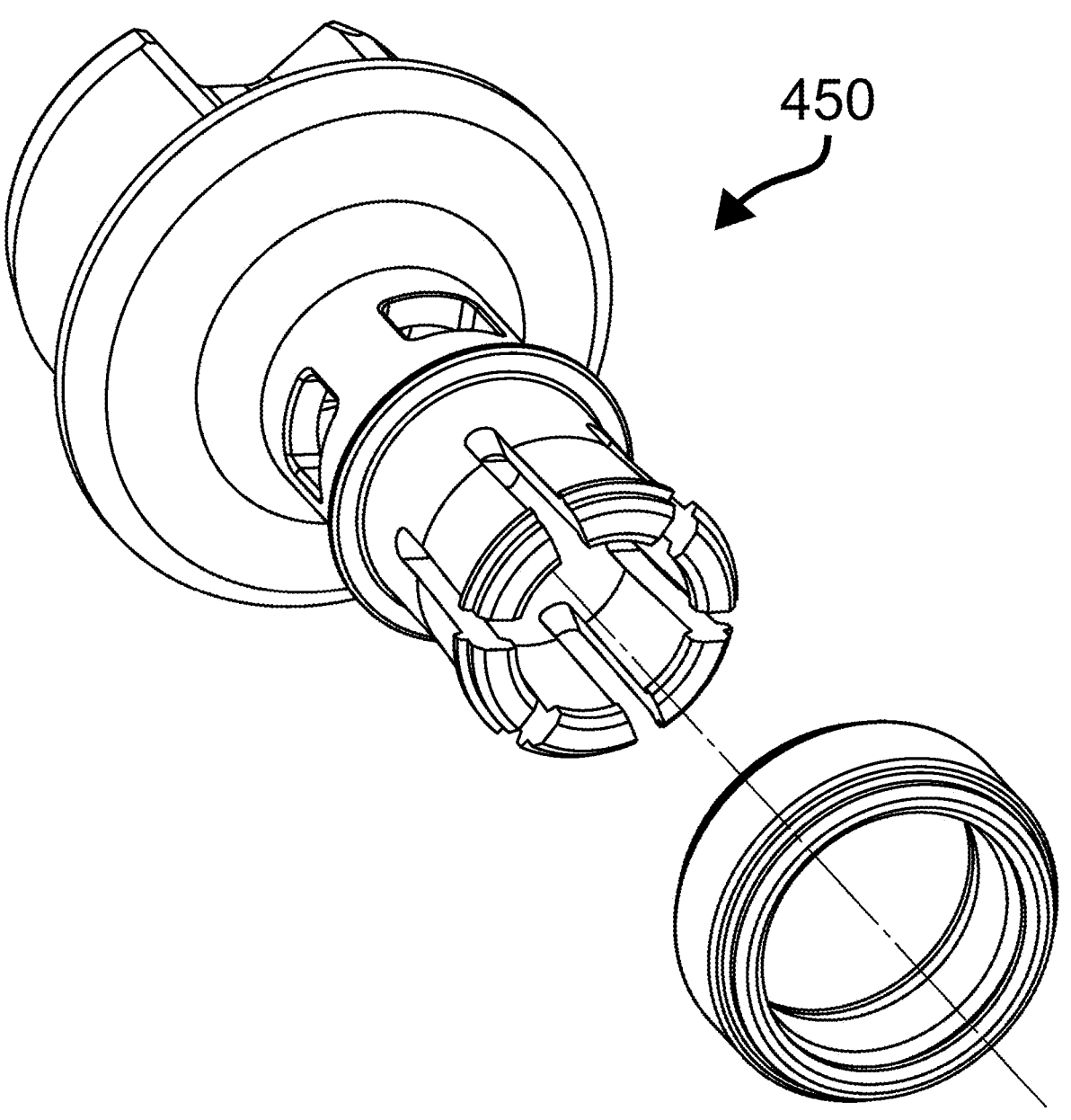
Figures 56A, 56B:
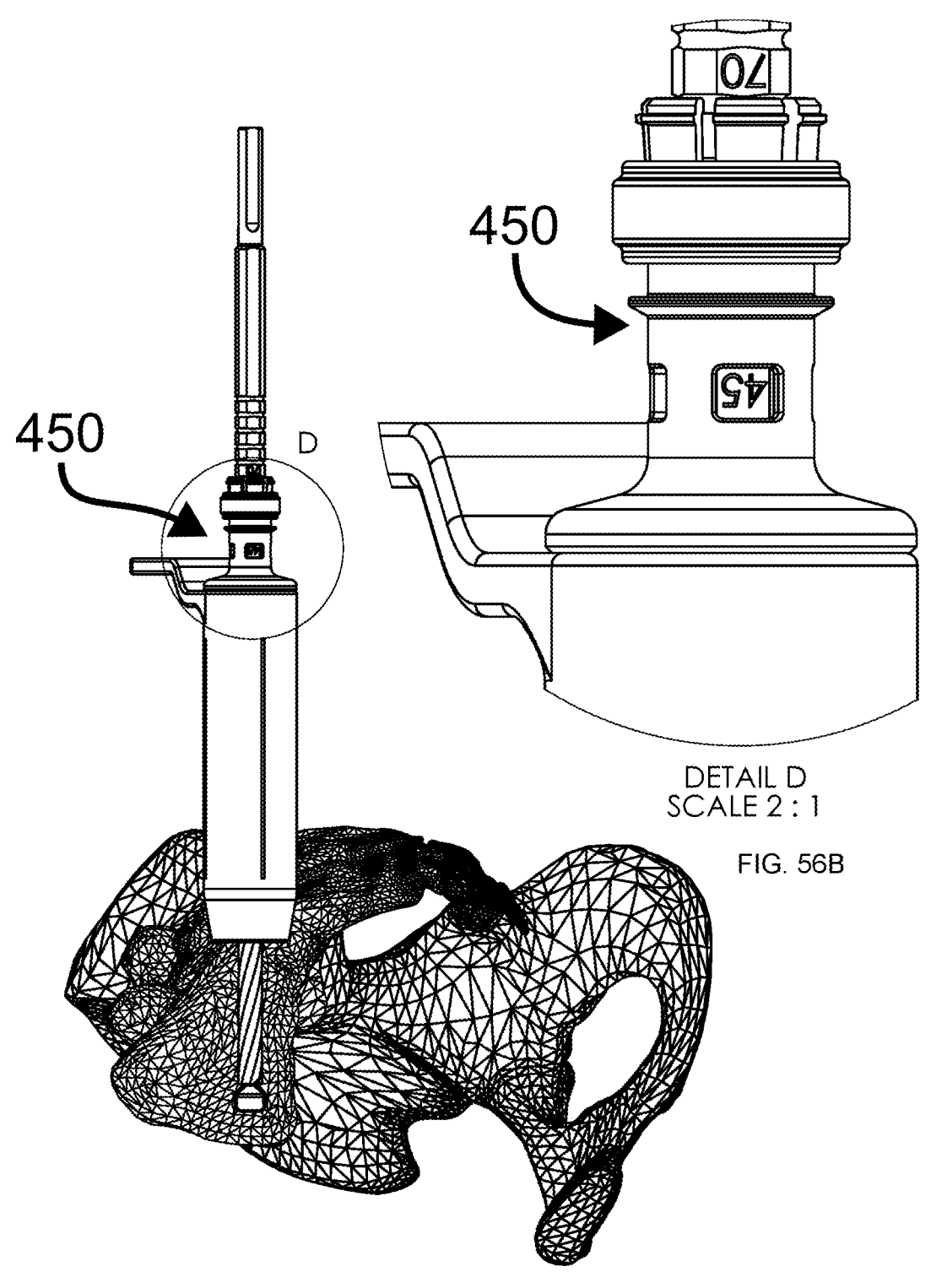
Figure 57:
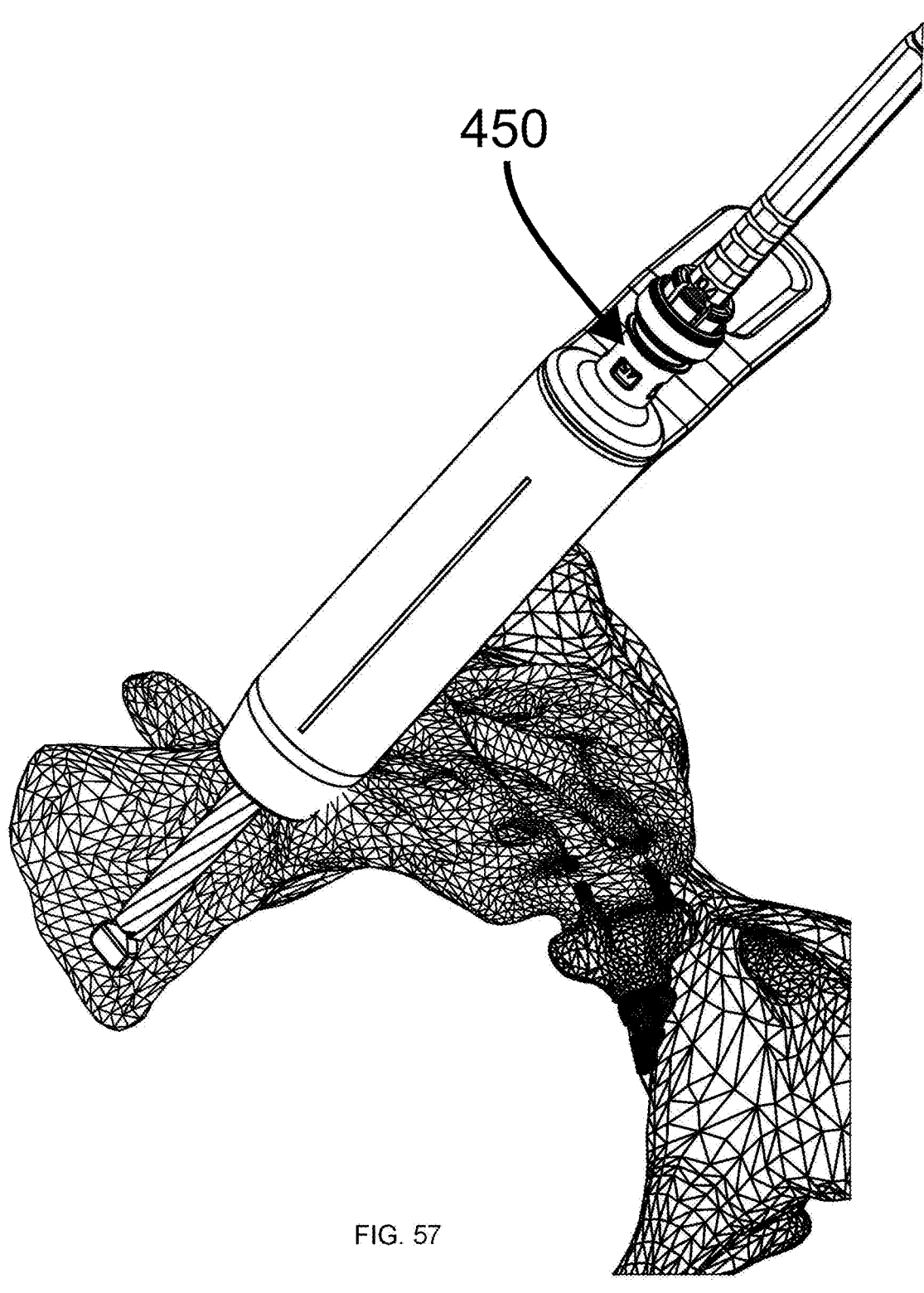
Figure 58:
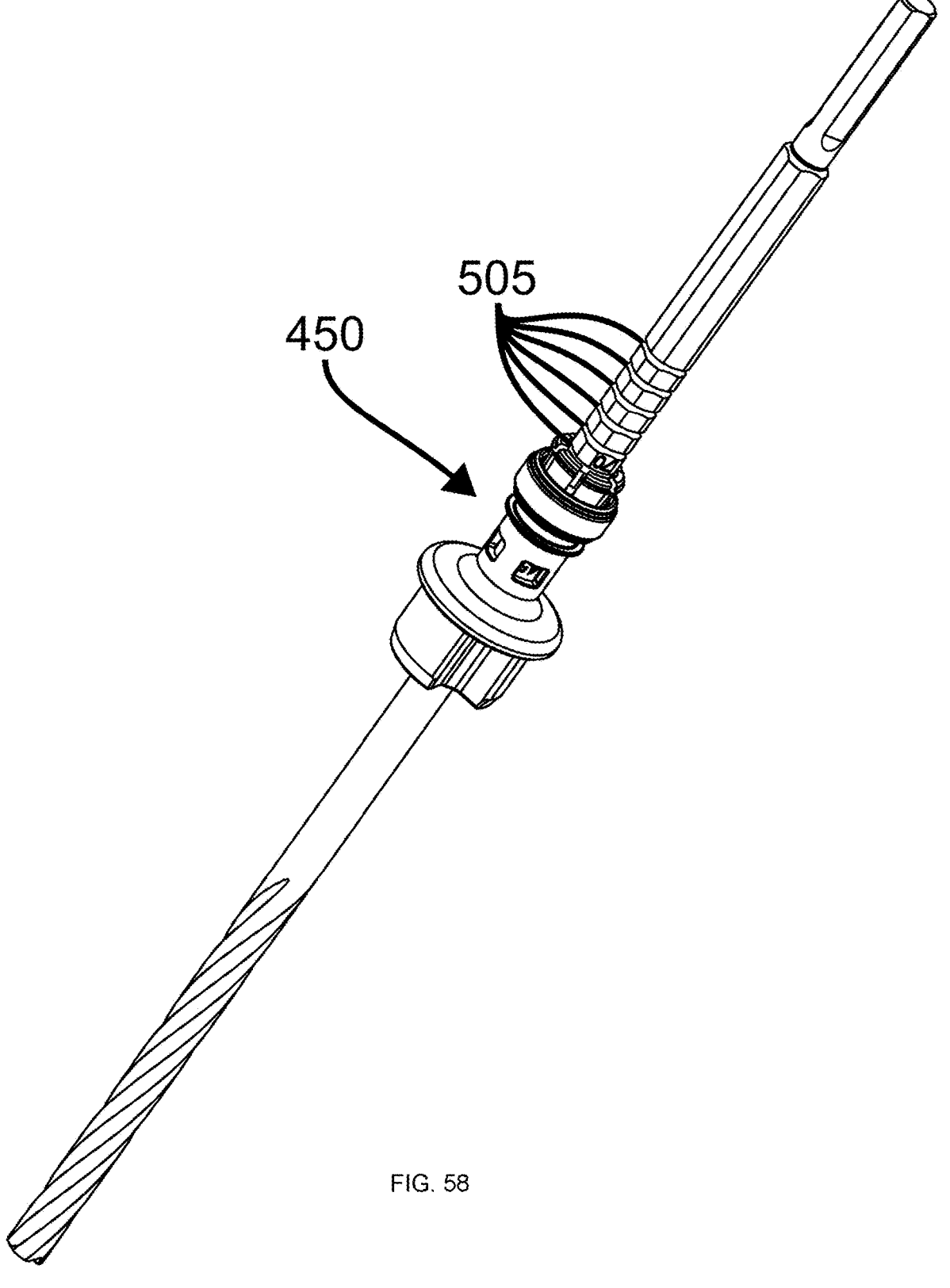
Figure 59:
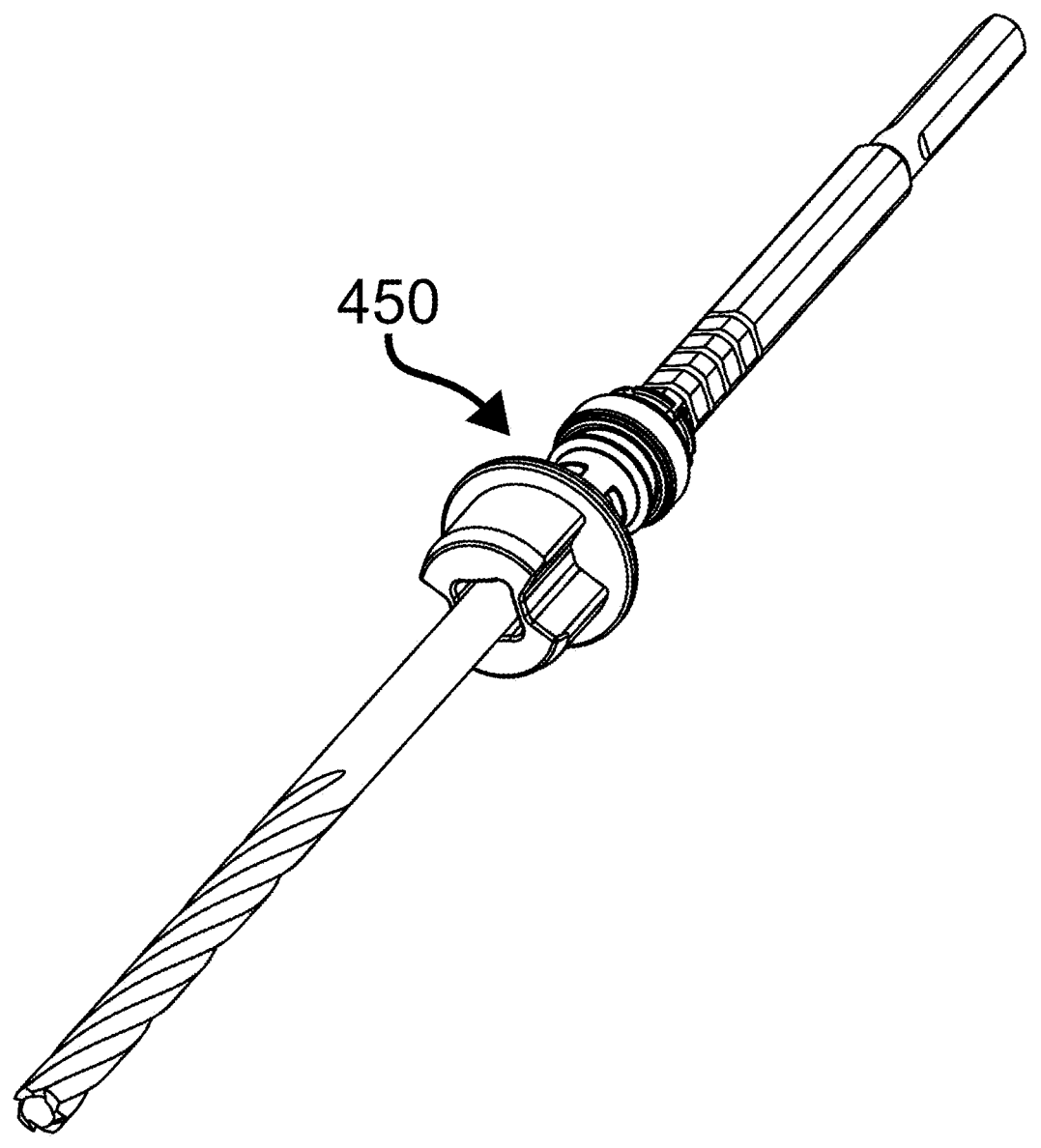
Figure 60:
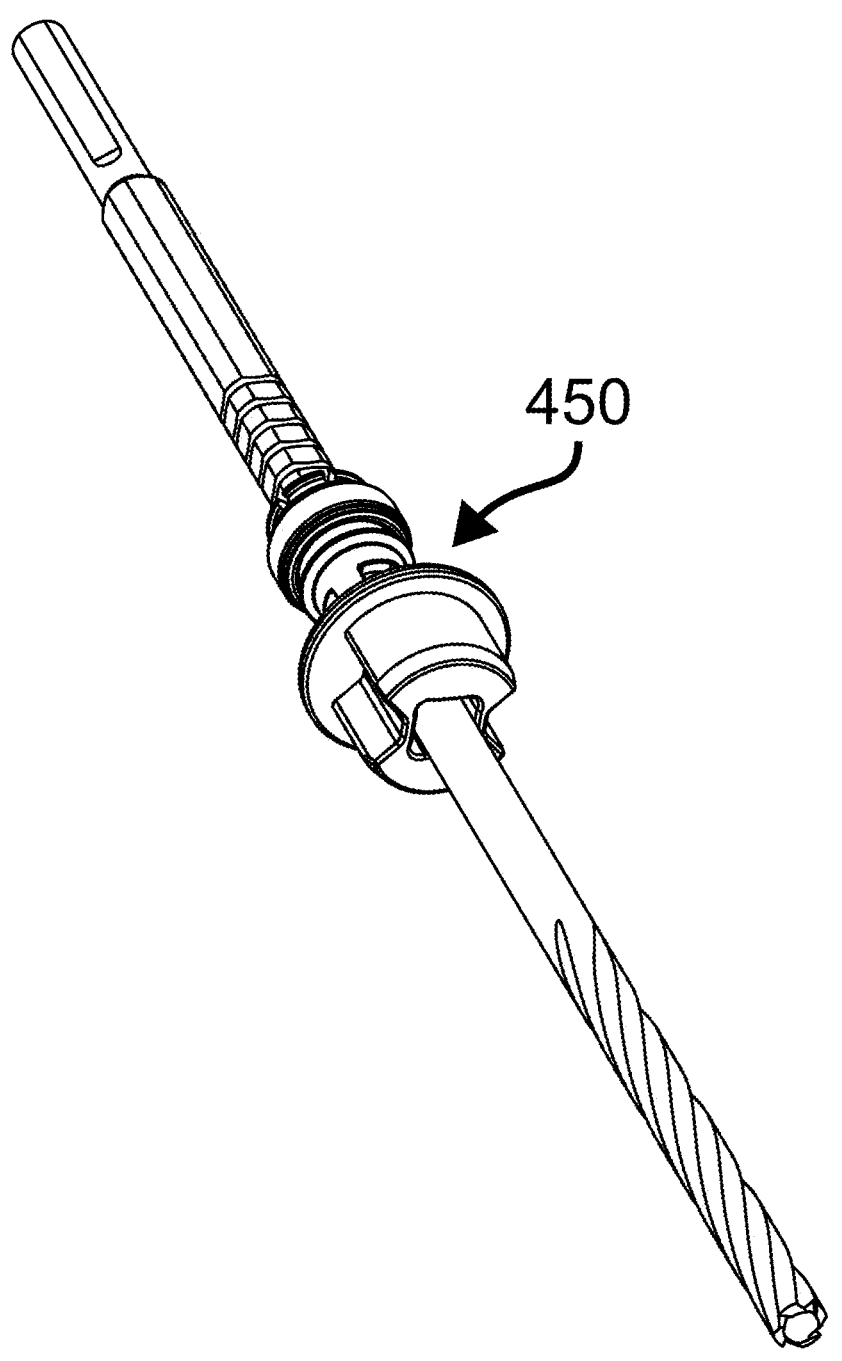
Figures 61A, 61B:
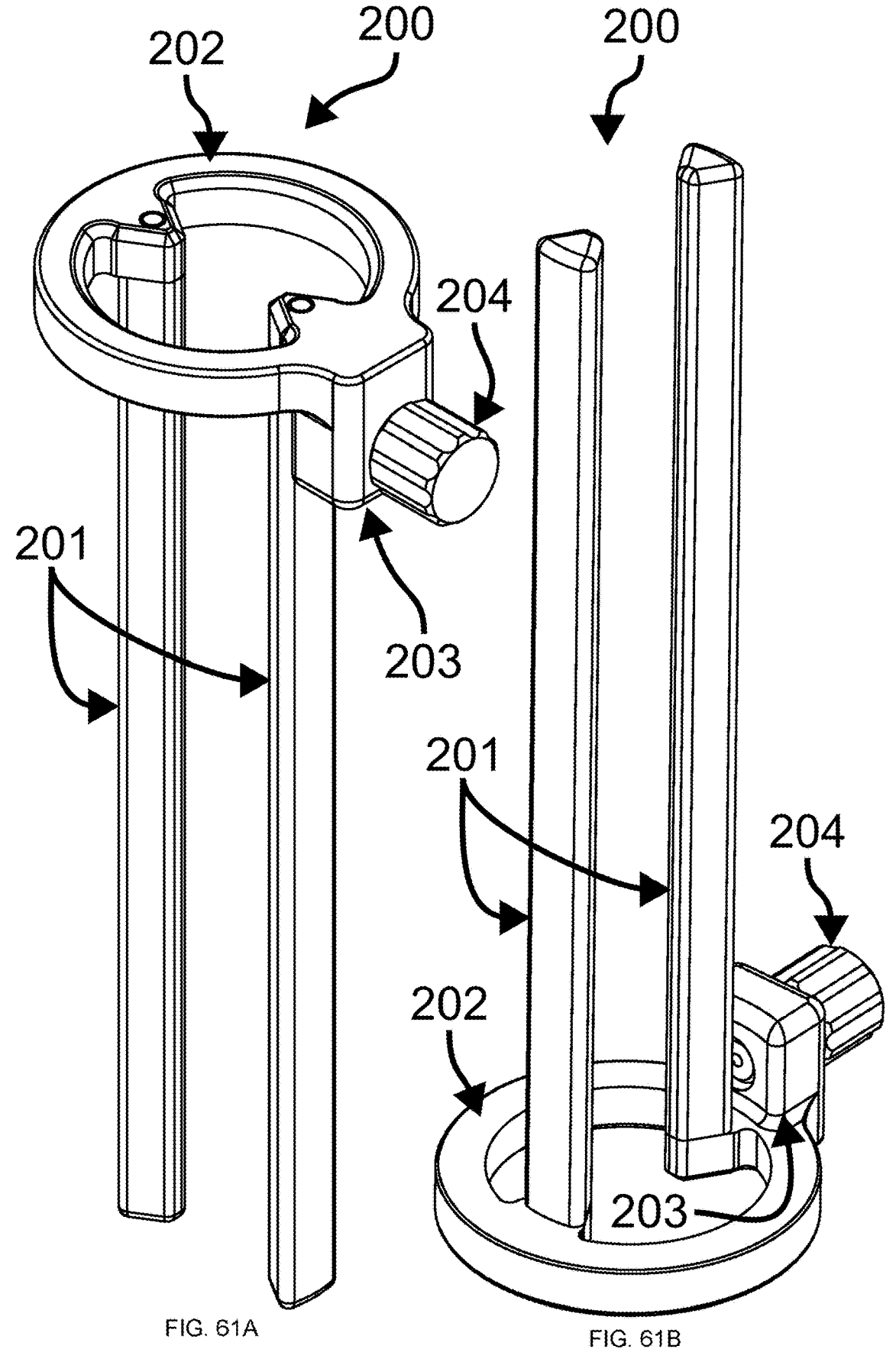
FIGS. 61A-61B are respectively proximal and distal perspective views of a guide rail assembly.
Figures 63A, 63B:
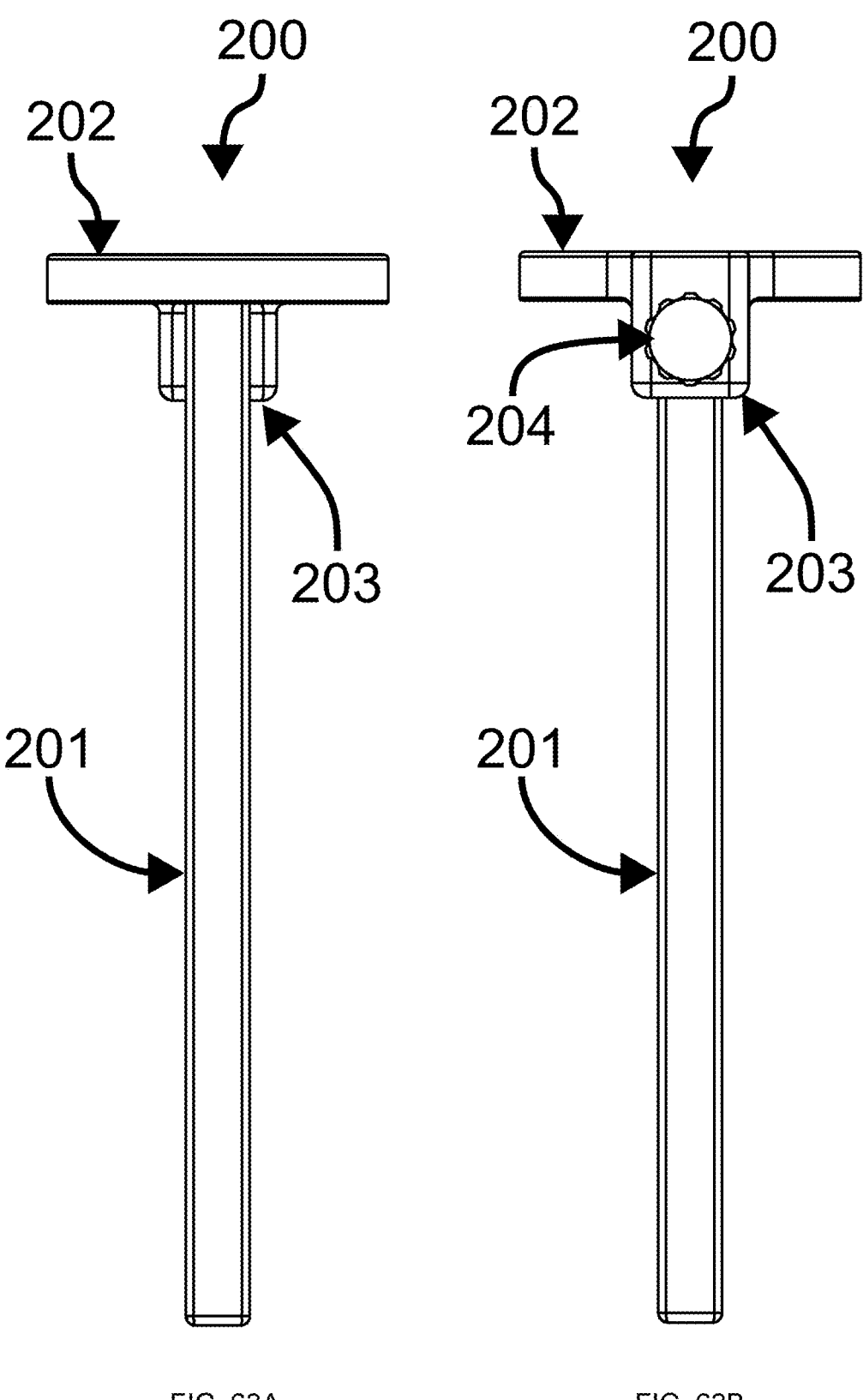
FIGS. 63A-63B are respectively bottom and top views of the guide rail assembly.
Figures 64A, 64B:
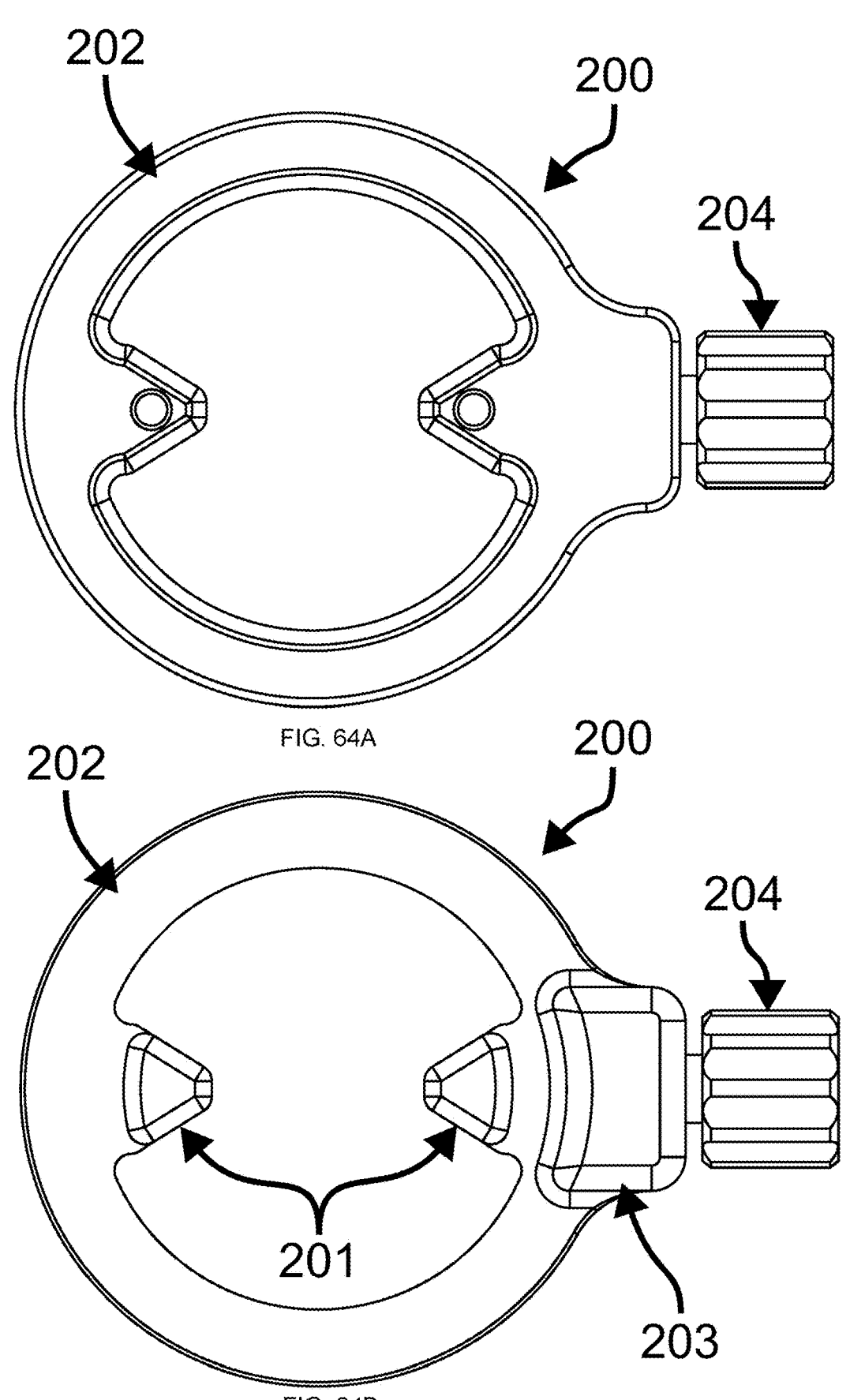
FIGS. 64A-64B are respectively proximal and distal end views of the guide rail assembly.
Figure 65:
FIG. 65 is the same view as FIG. 61A, except the guide rail assembly is shown exploded to better illustrate its components.
Figure 66:
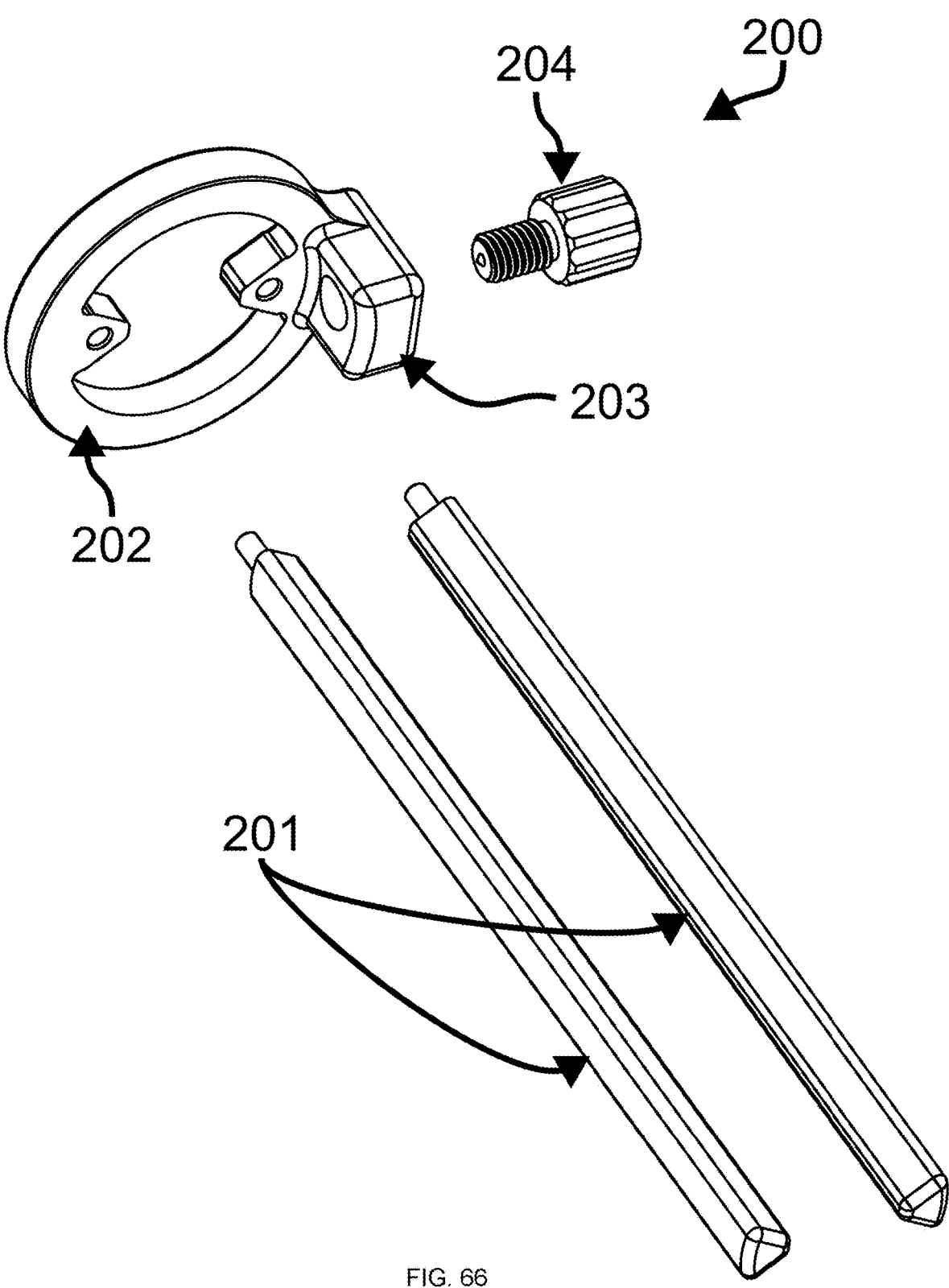
FIG. 66 is another exploded view of the guide rail assembly.
Figure 67:
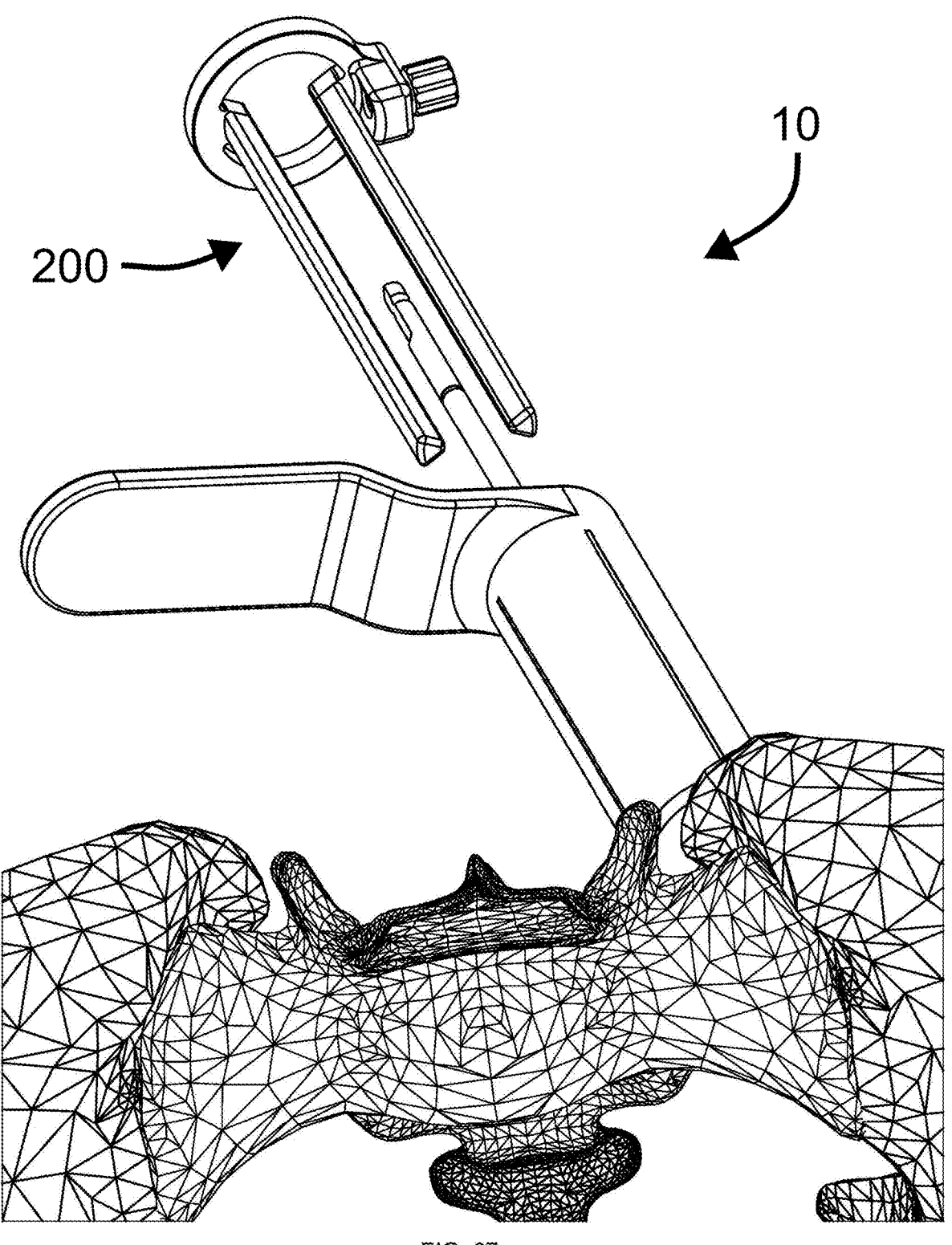
FIGS. 67-68 are different views of the pelvic region showing the step of installing the guide rail assembly within the working cannula with the joint finder still in place within the sacroiliac joint.
Figure 68:
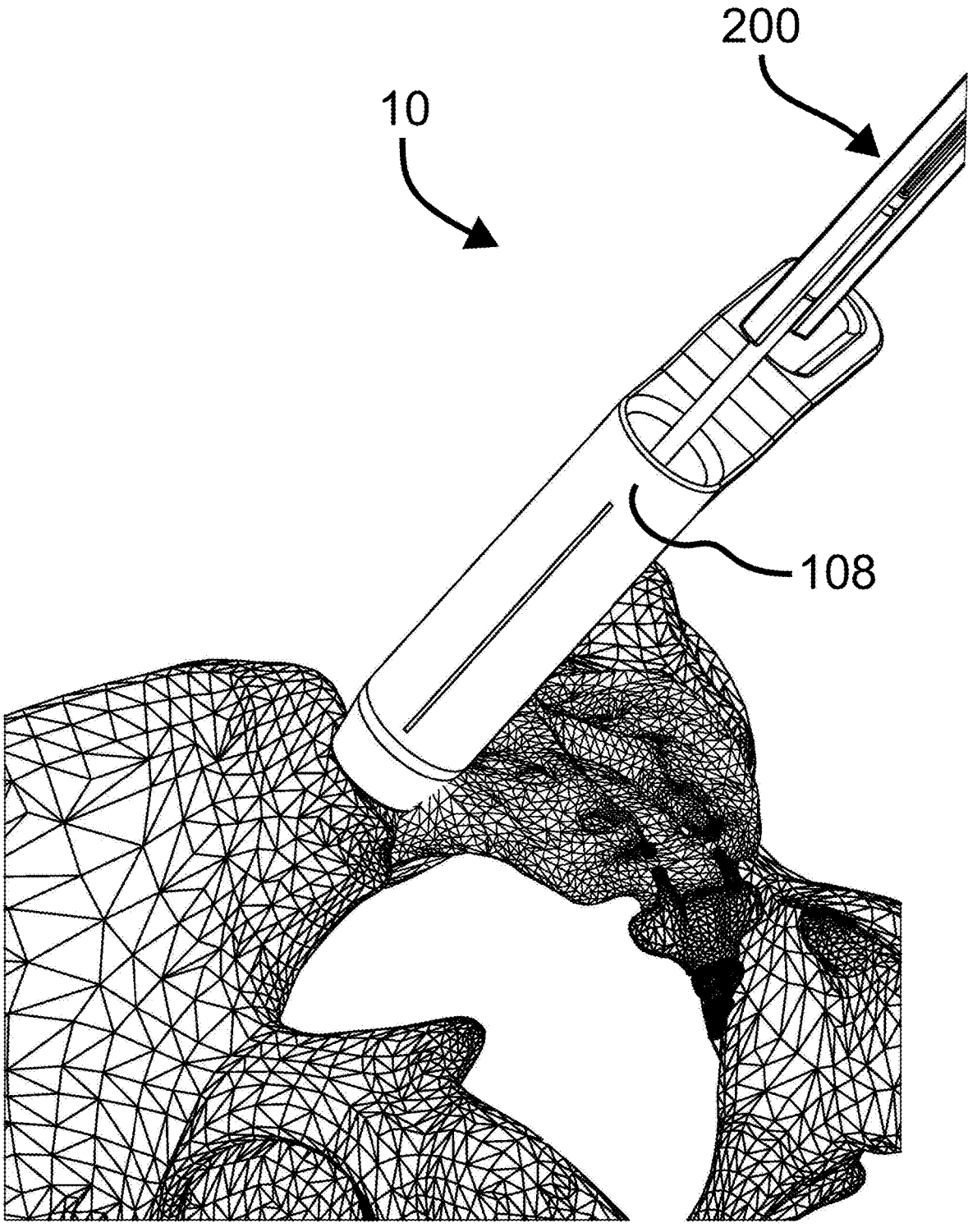
Figure 69:
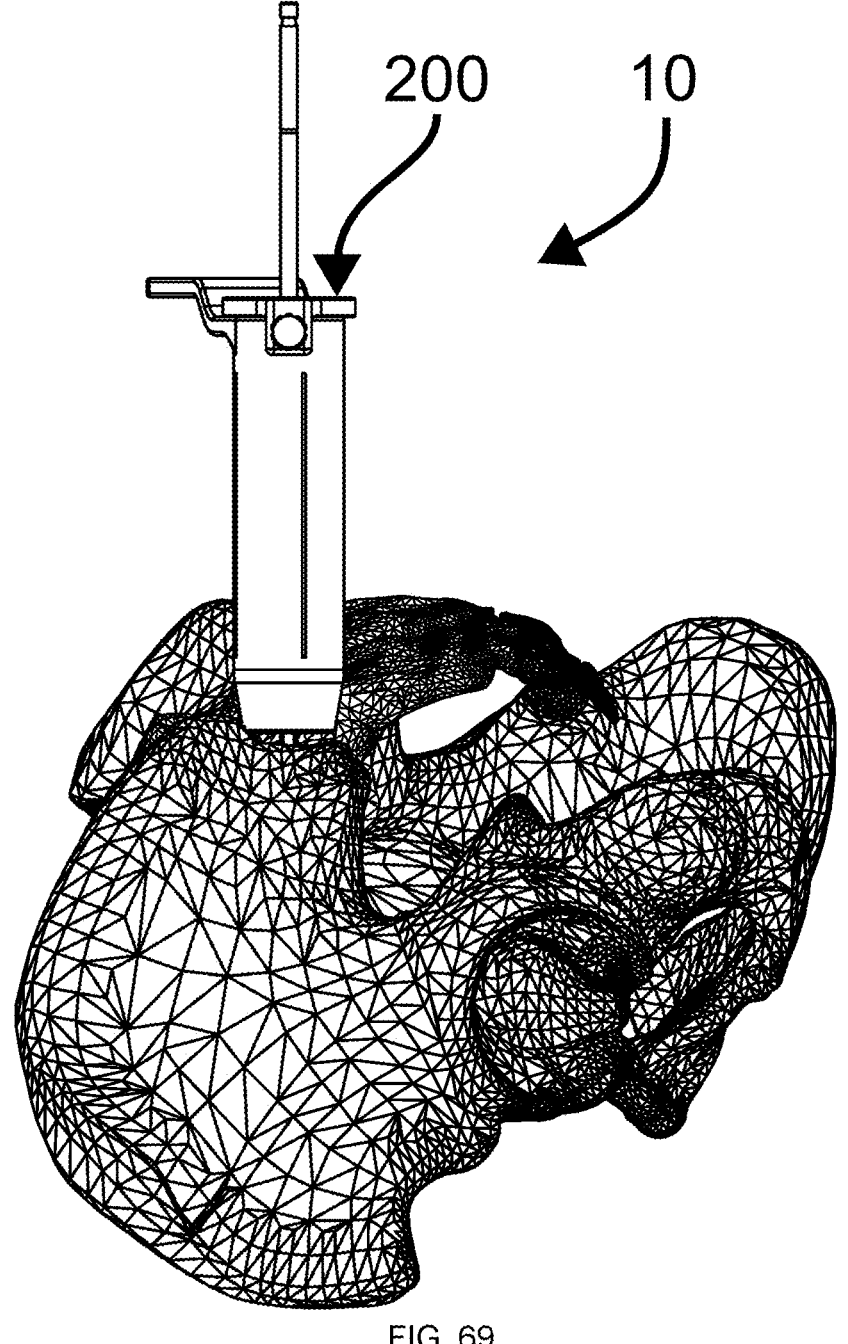
FIGS. 69-72 are different views of the pelvic region showing the guide rail assembly installed within the working cannula, wherein FIG. 71 further illustrates a void at the sacroiliac joint surrounding the joint finder created by the cannulated drill bit.
Figure 70:
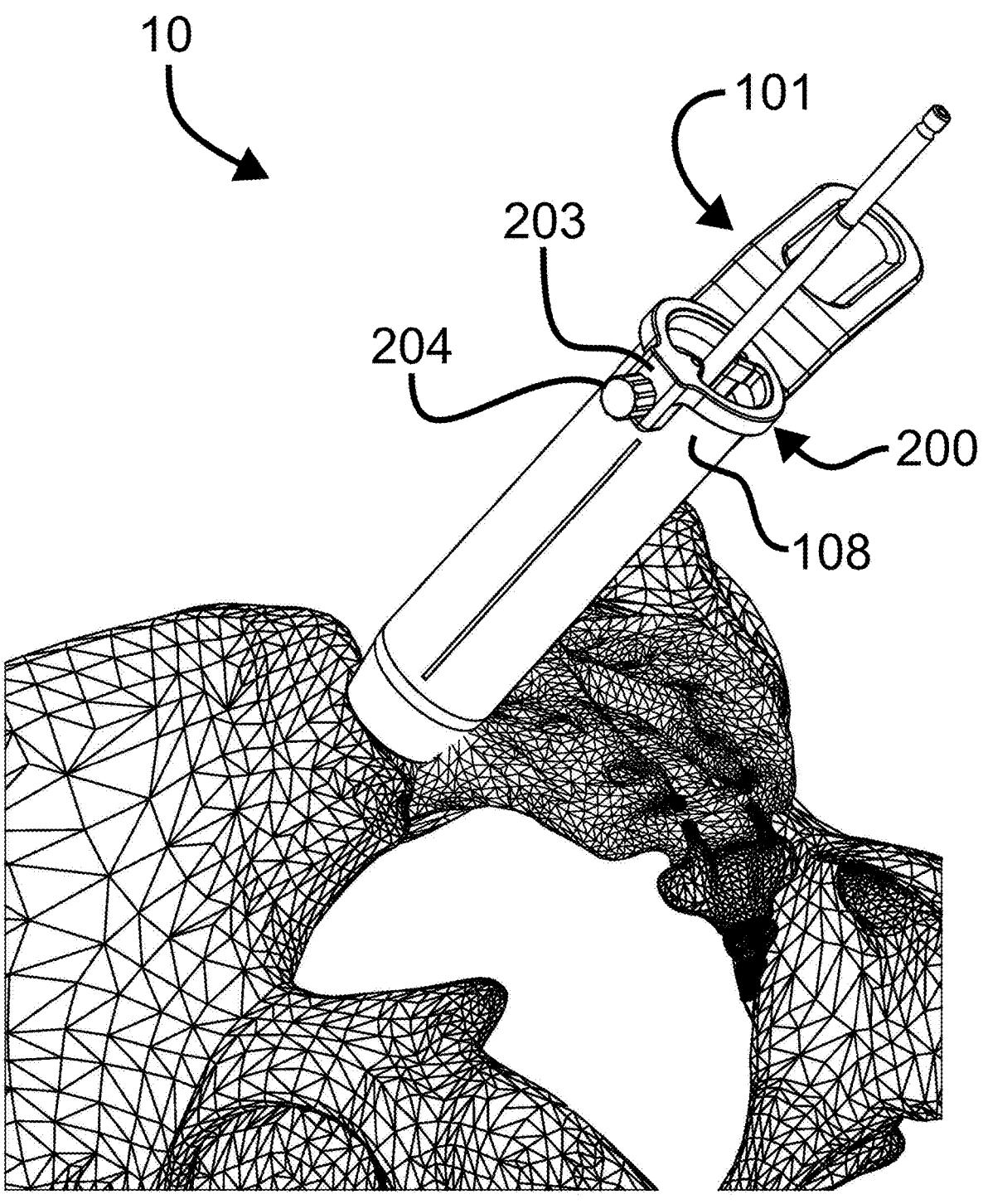
Figure 71:
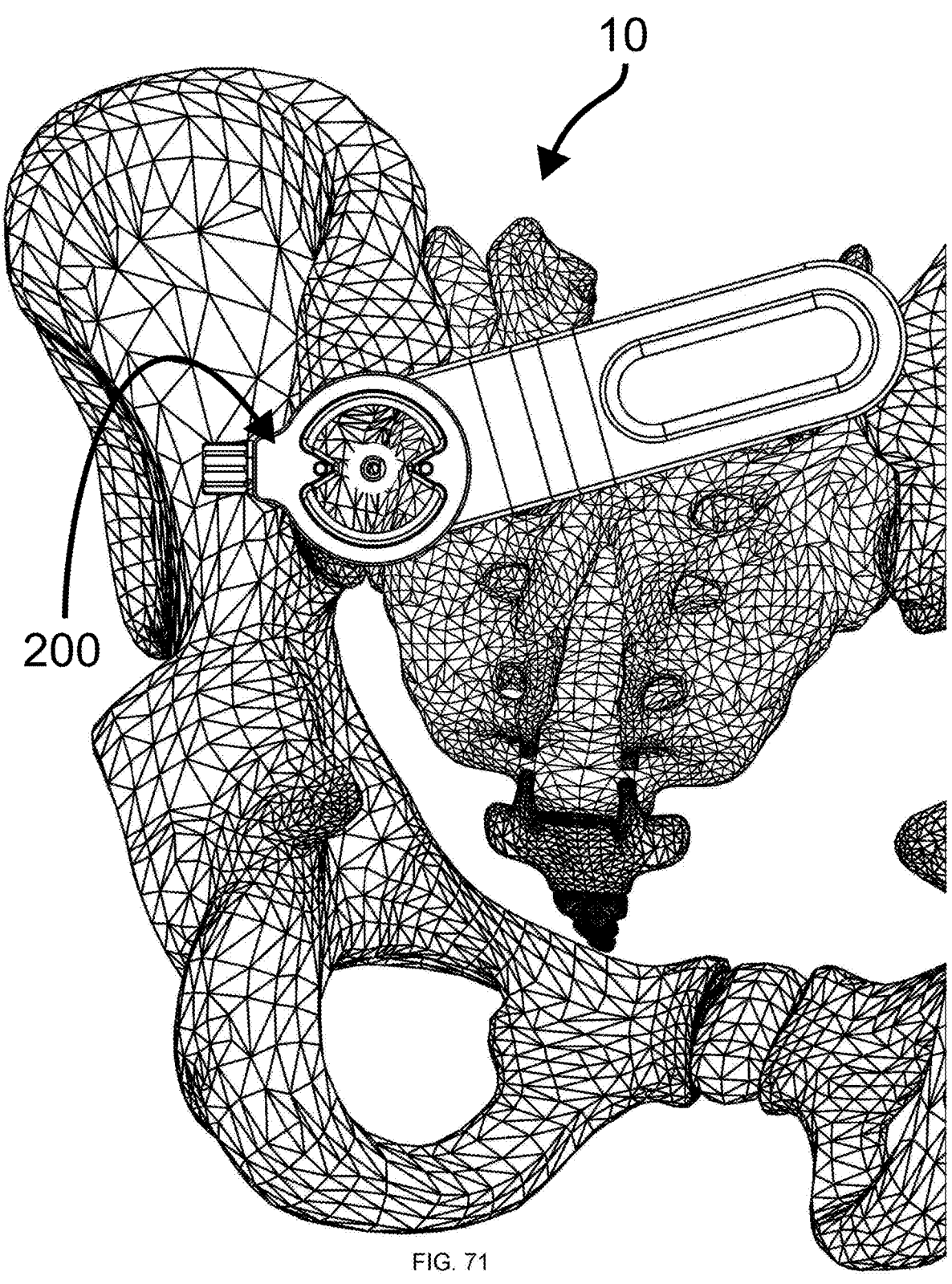
Figure 72:
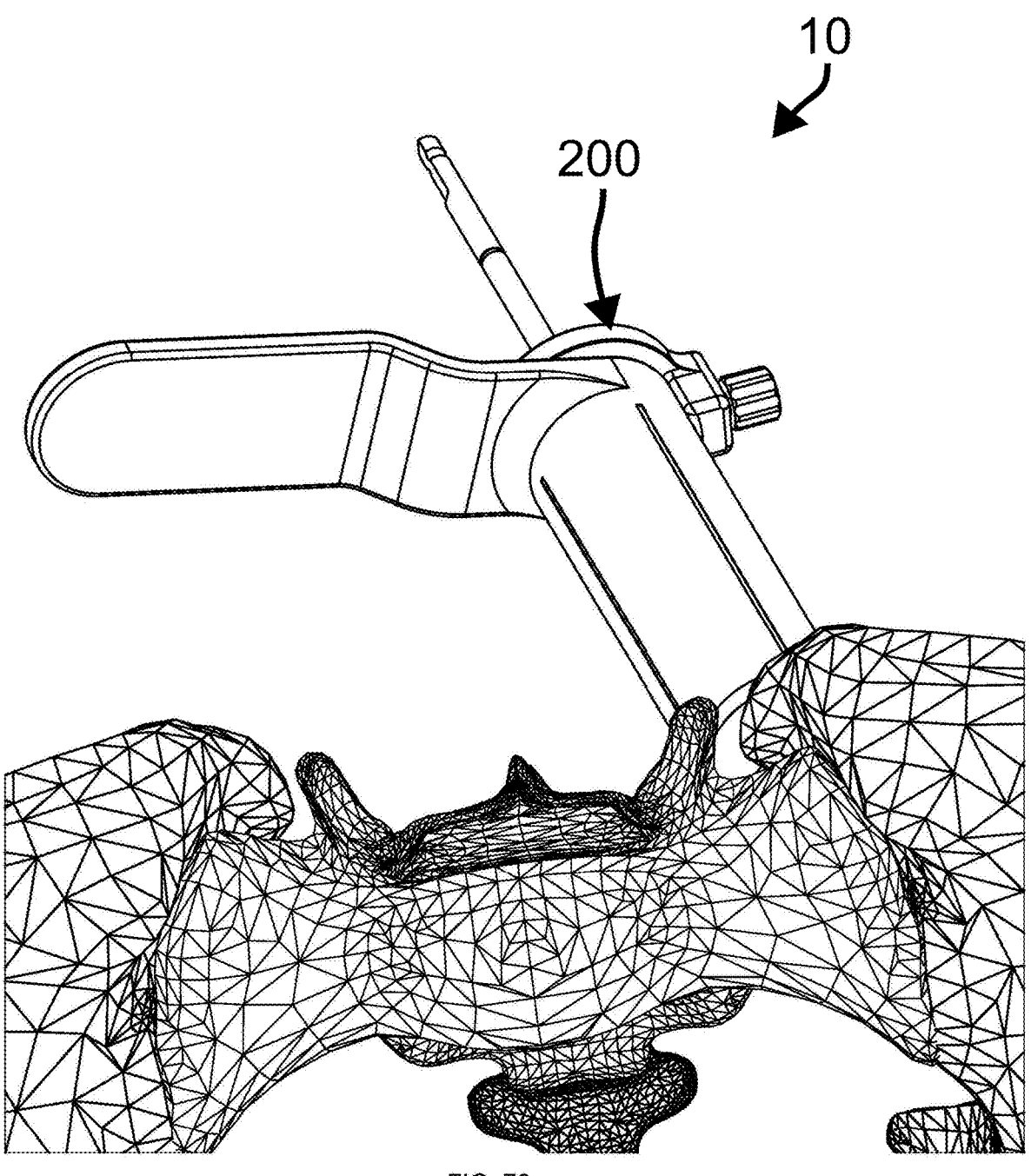
Figures 73A, 73B:
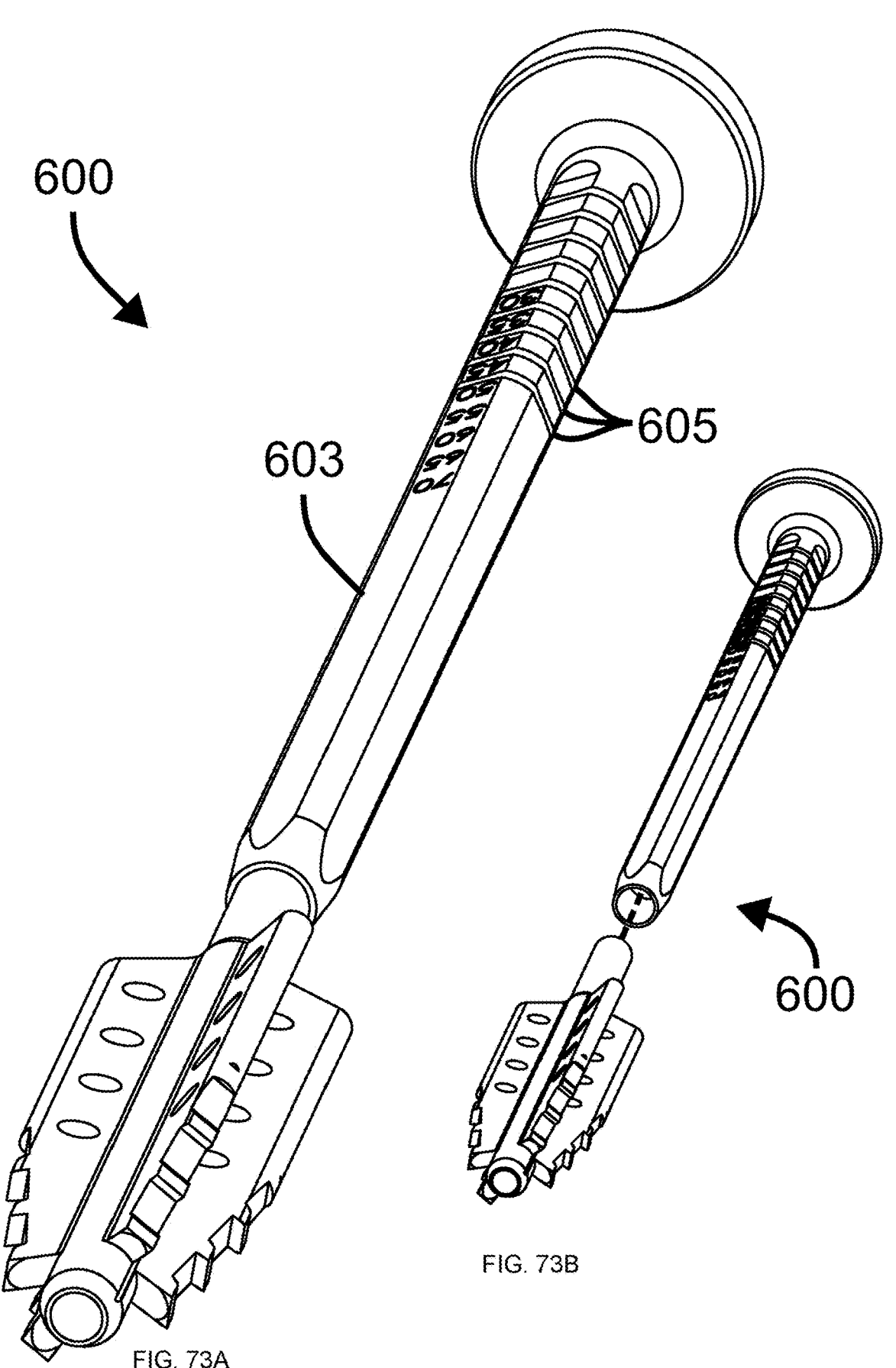
Figures 75A, 75B, 75C, 75D:
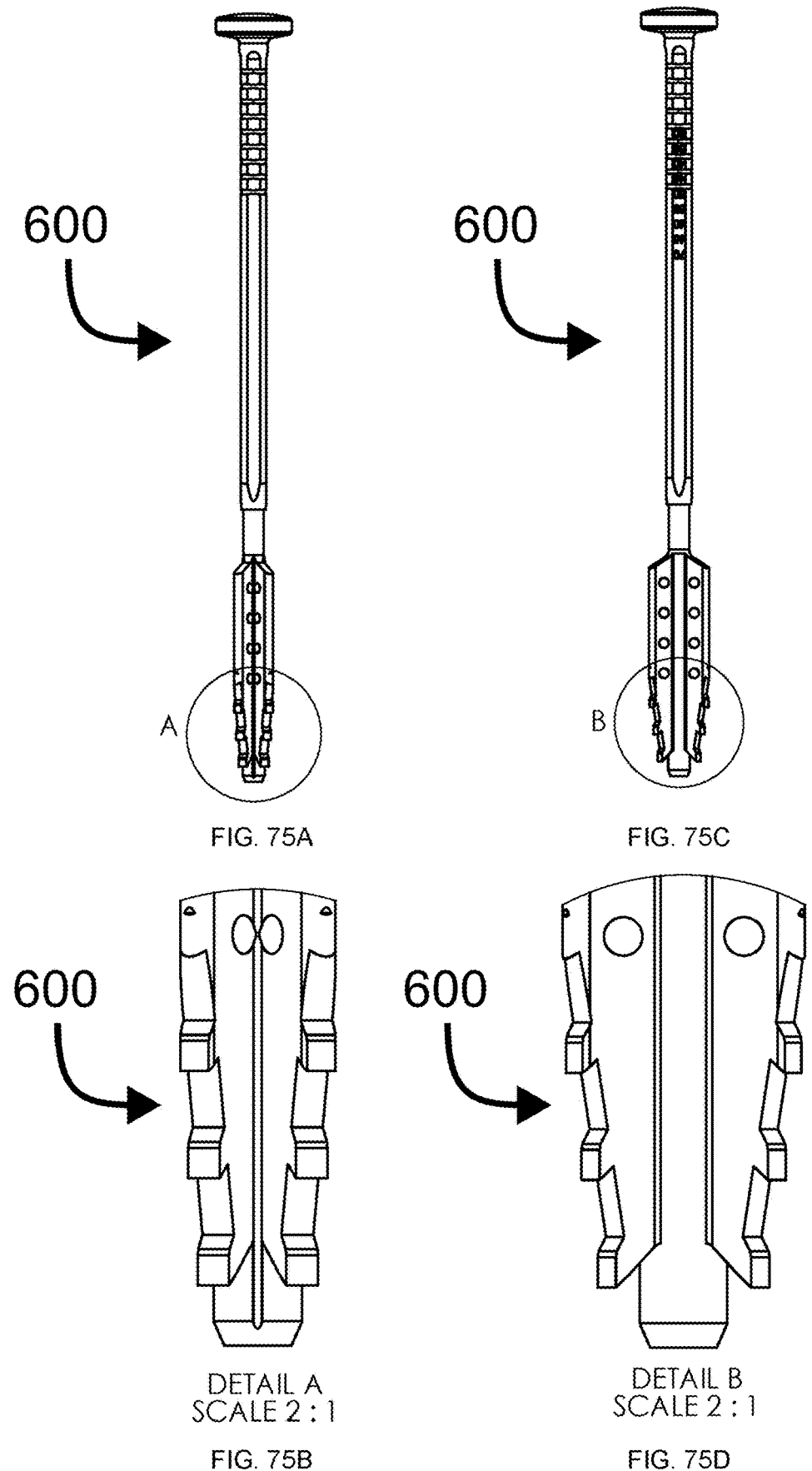
Figures 76A, 76B:
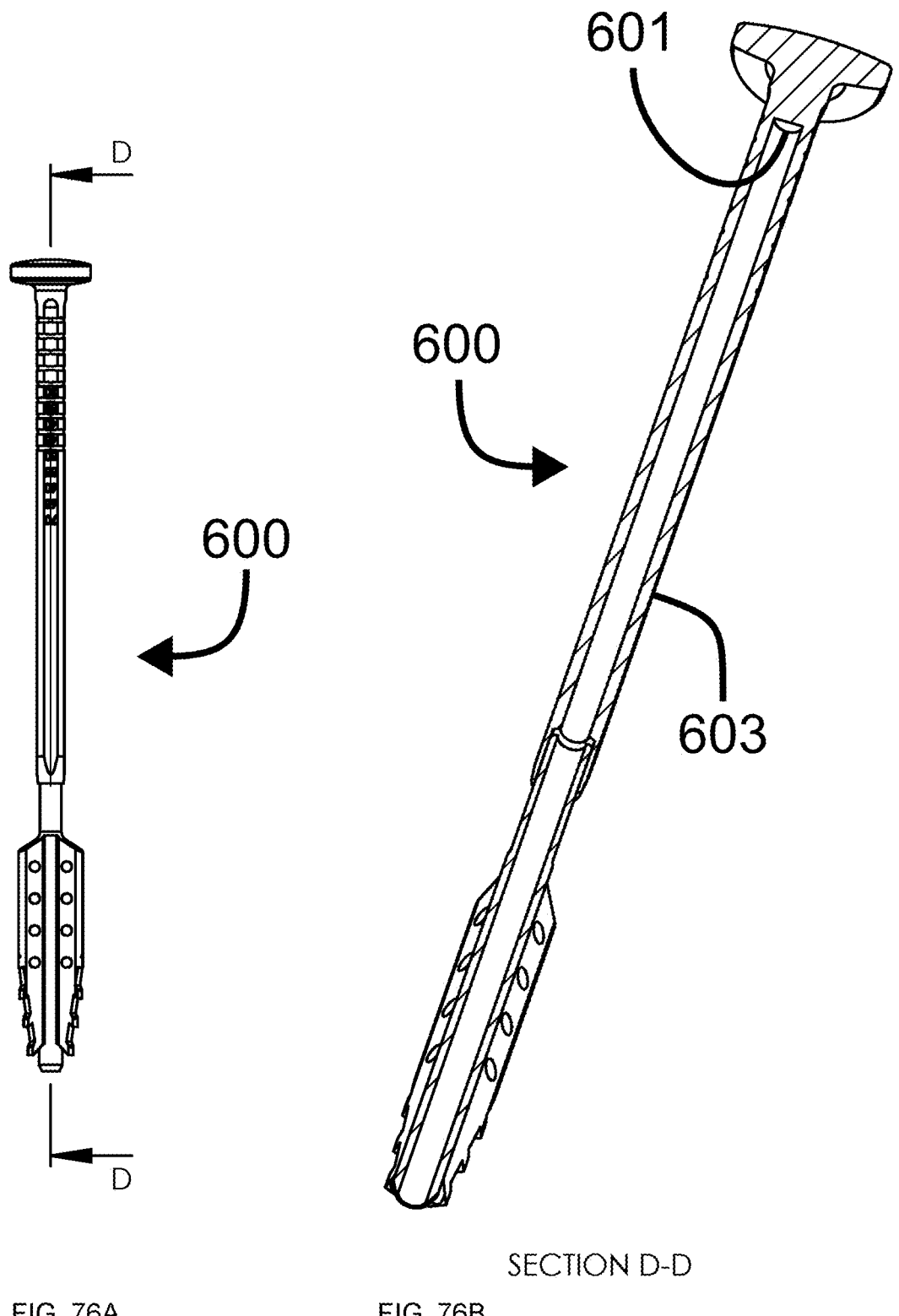
Figure 77A:
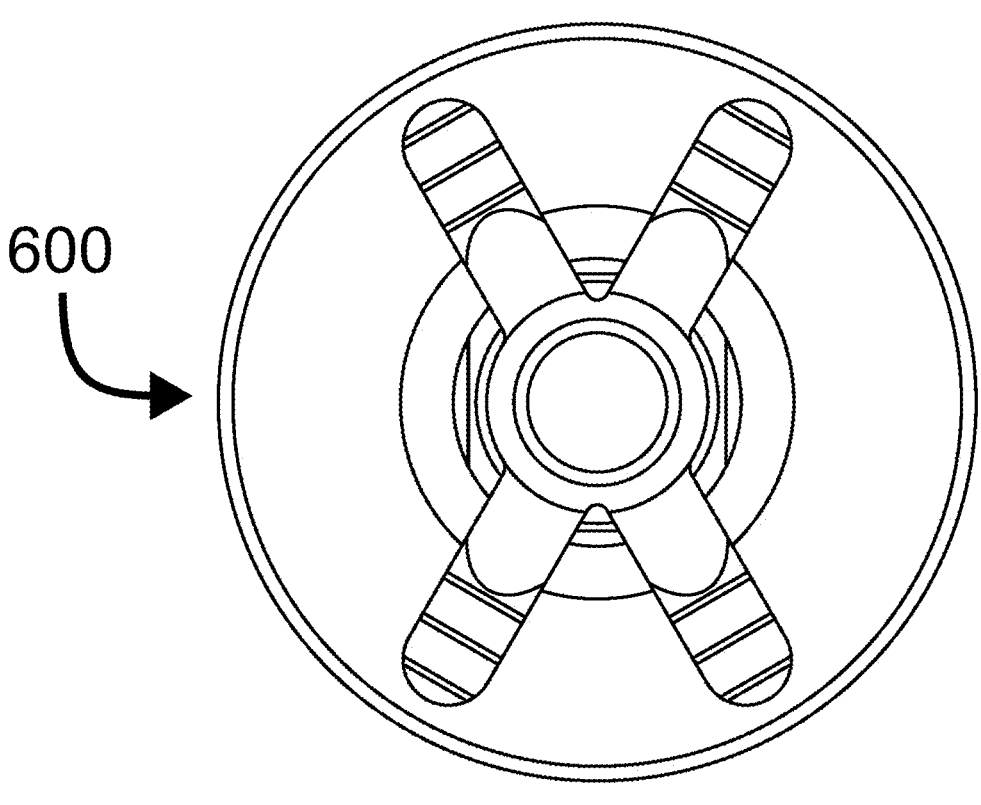
Figure 77B:
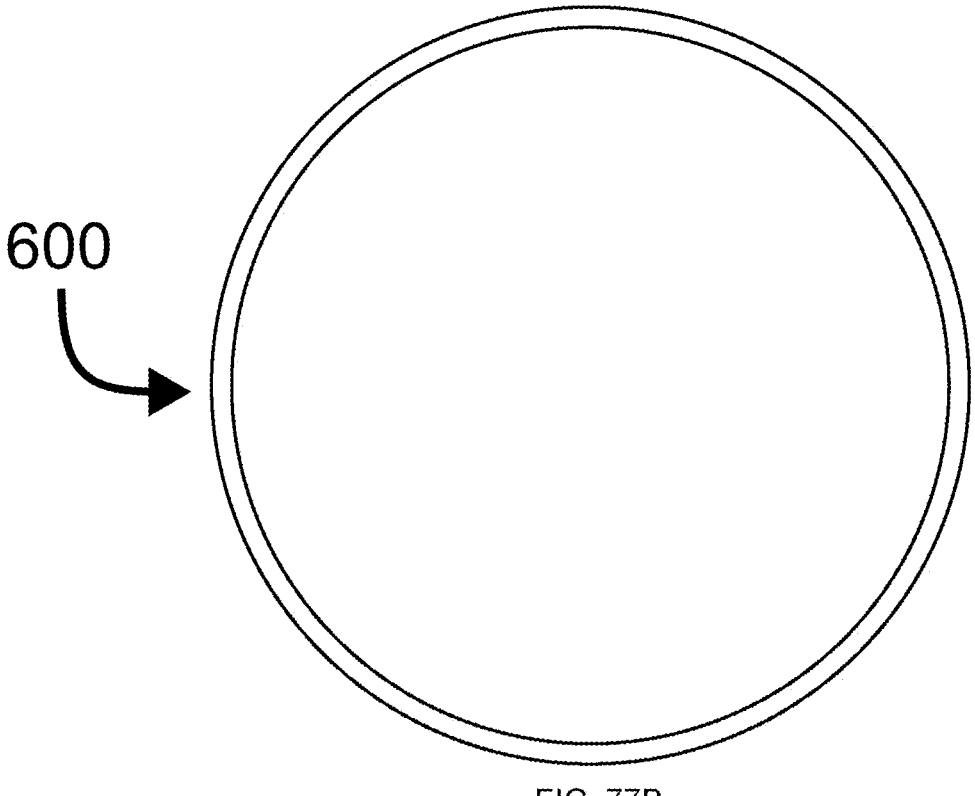
Figure 78:
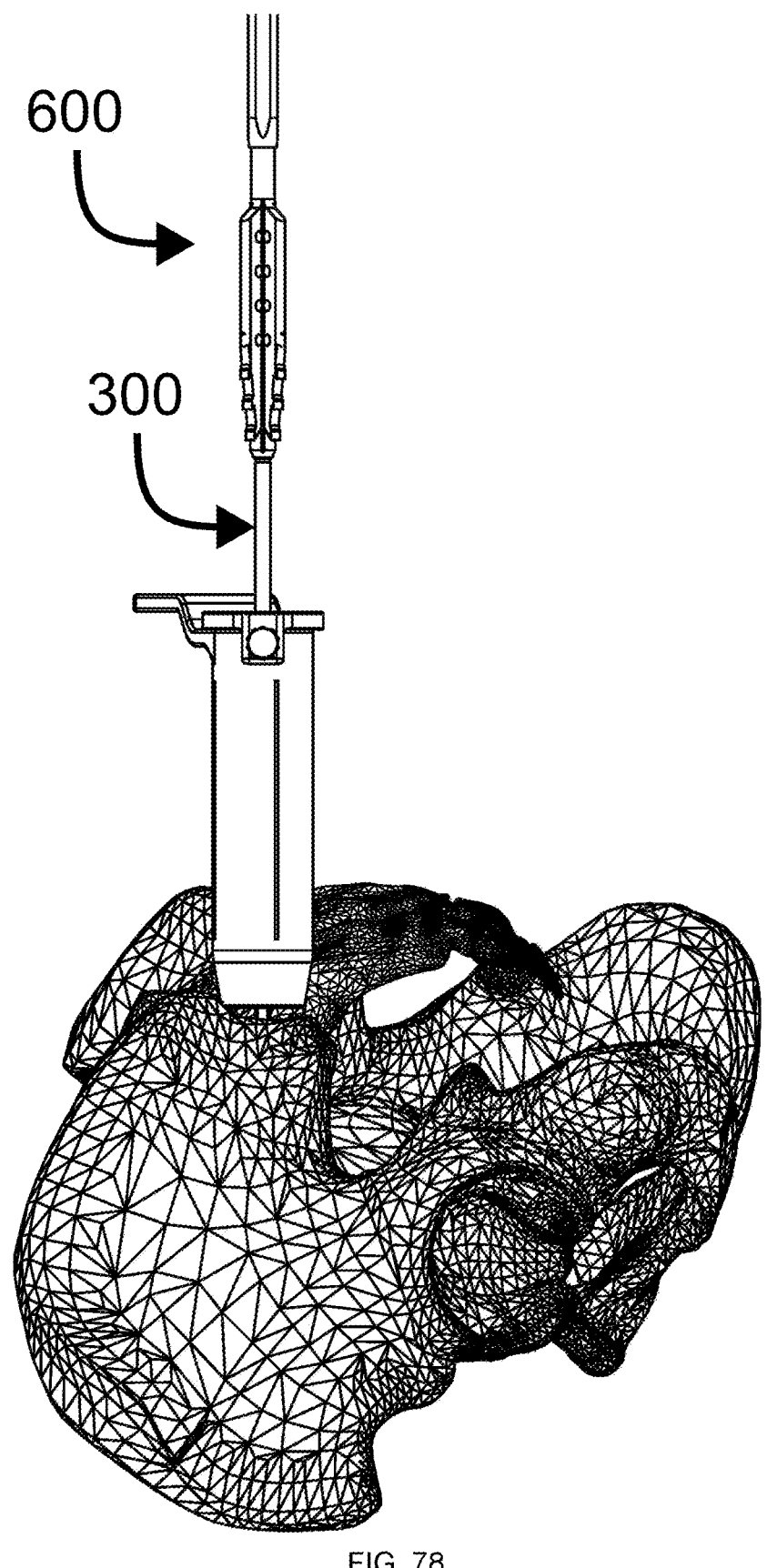
Figure 79:
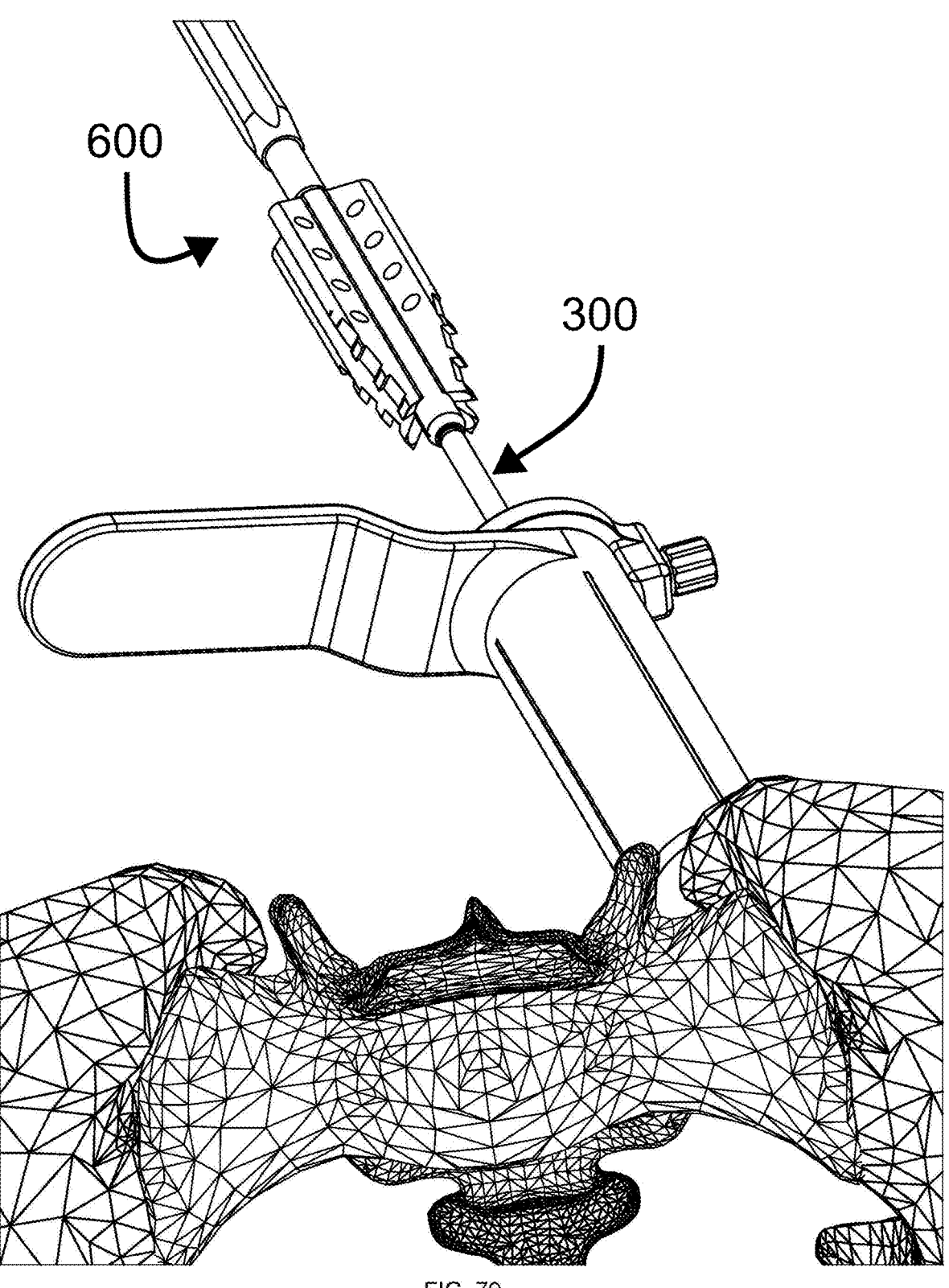
Figure 80:
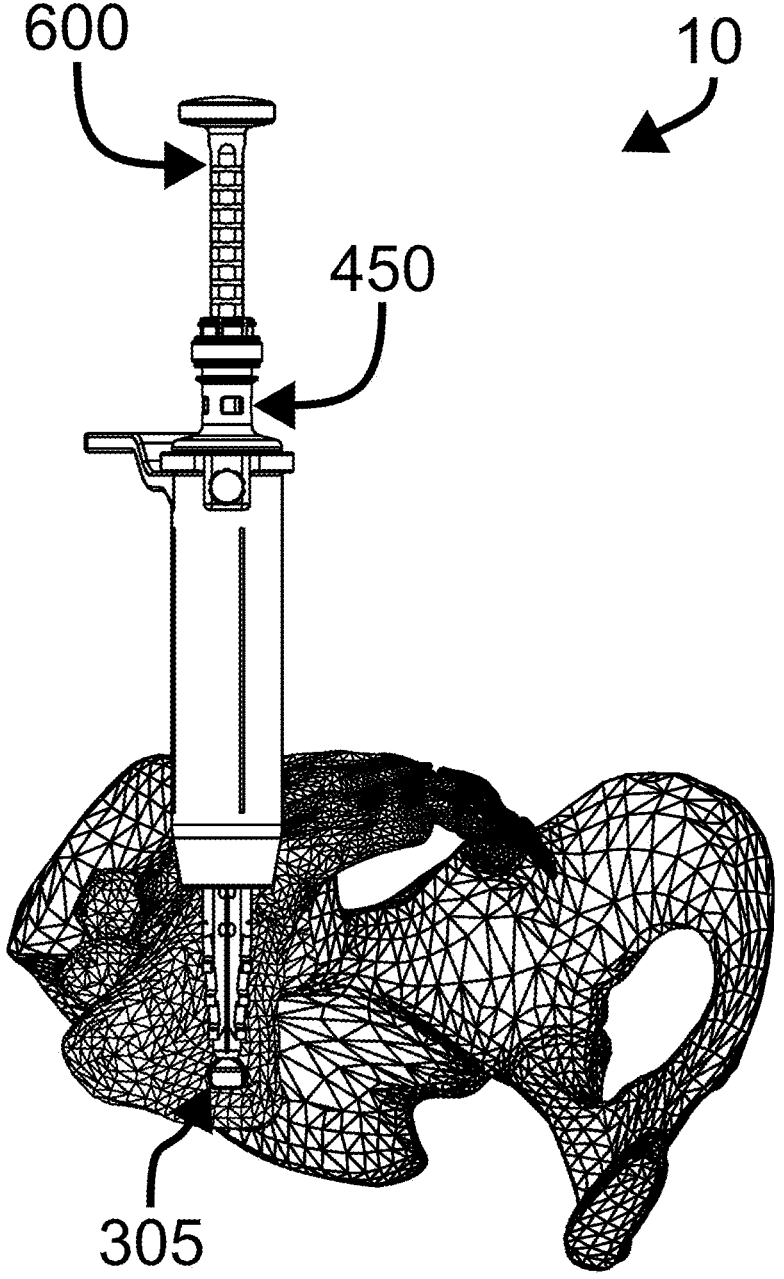
Figure 81:
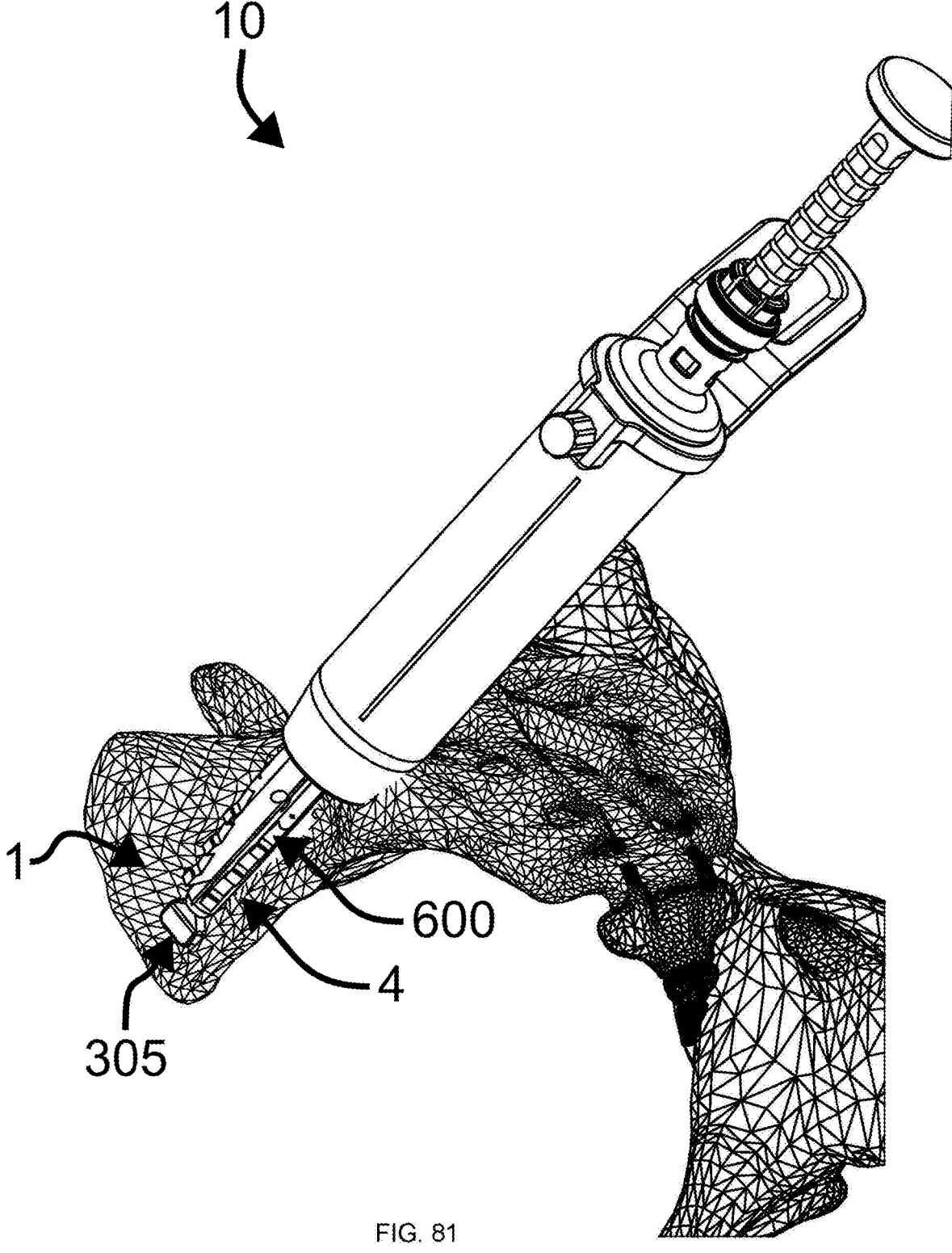
Figure 82:
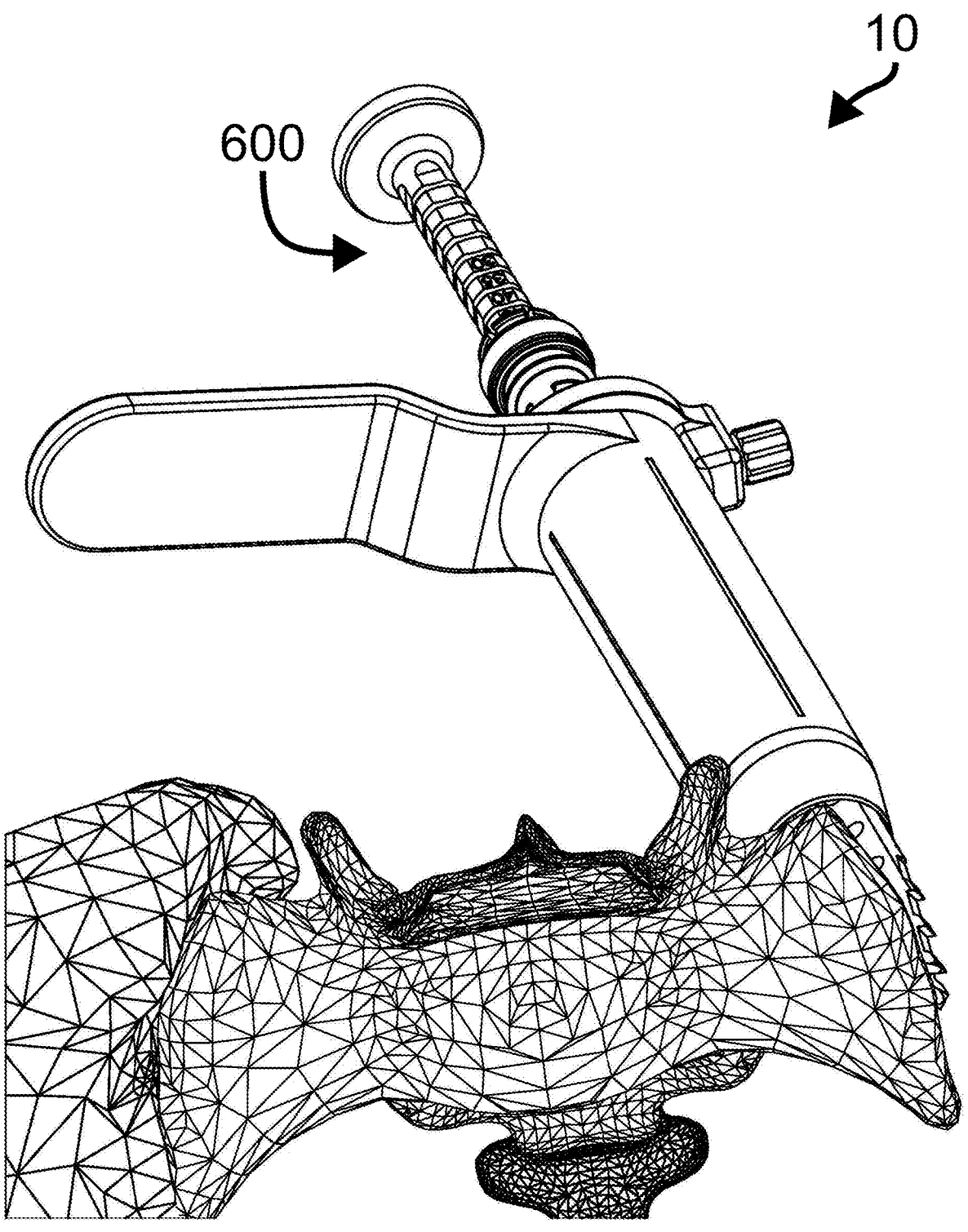
Figures 83A, 83B:
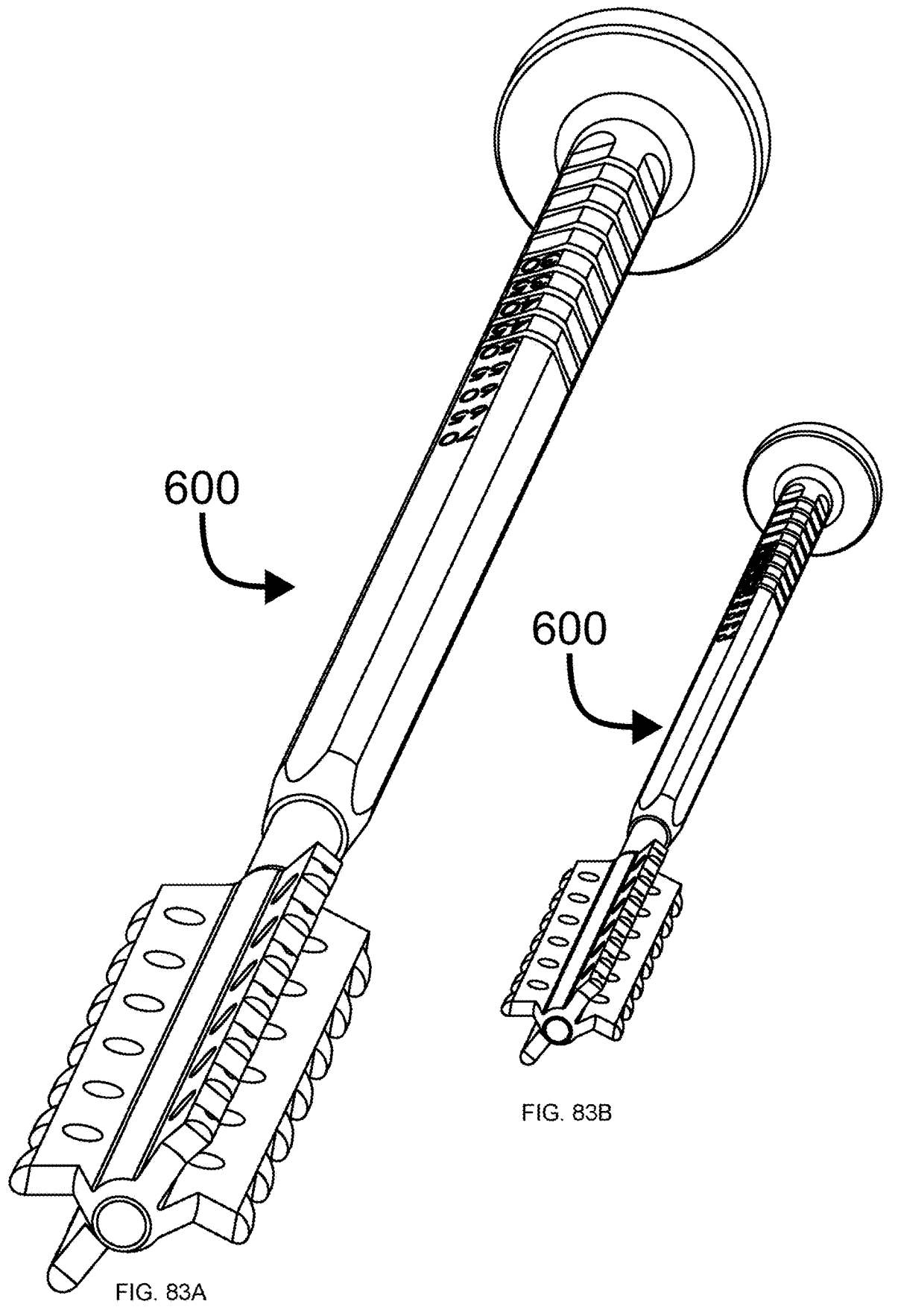
Figure 84A:
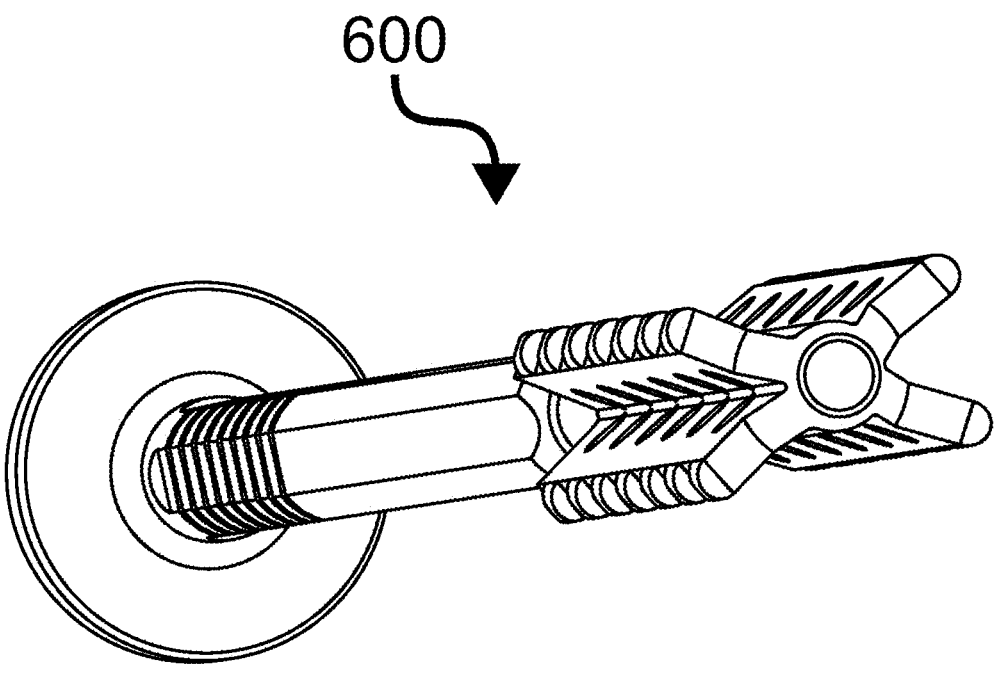
Figure 84B:
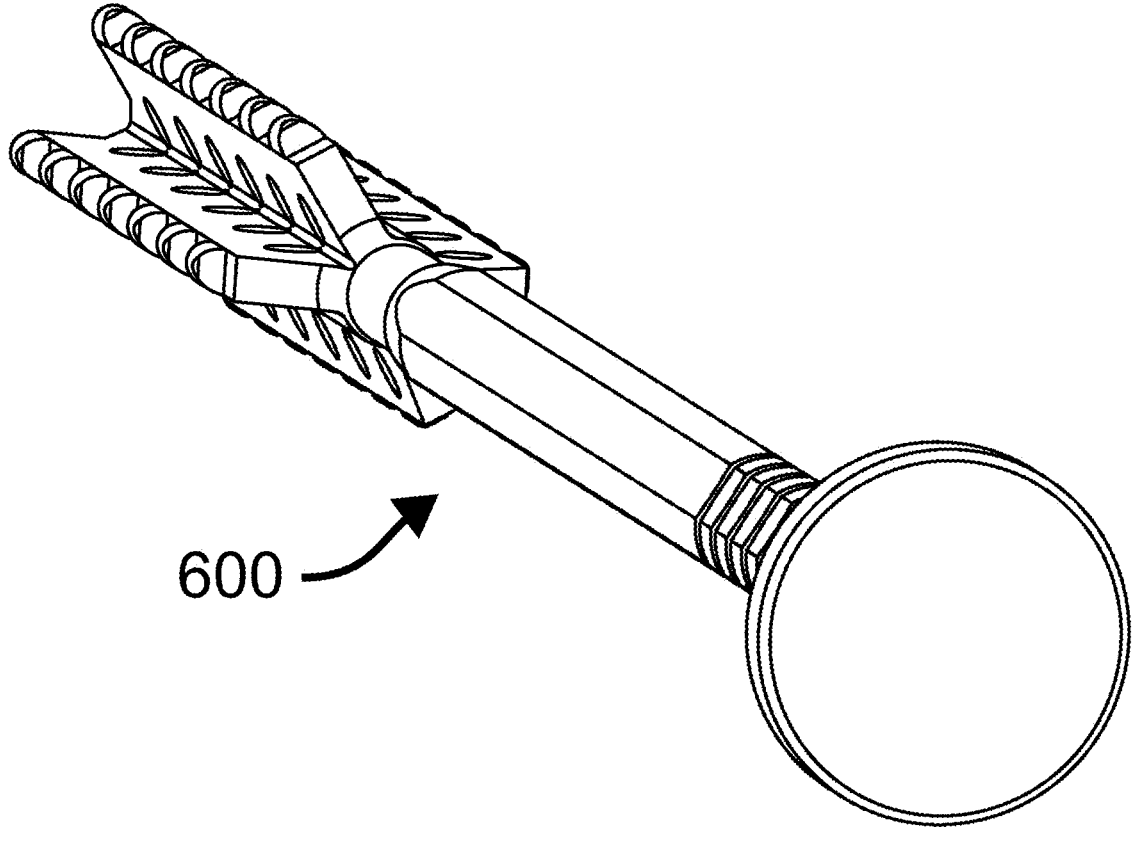
Figures 85A, 85B, 85C, 85D:
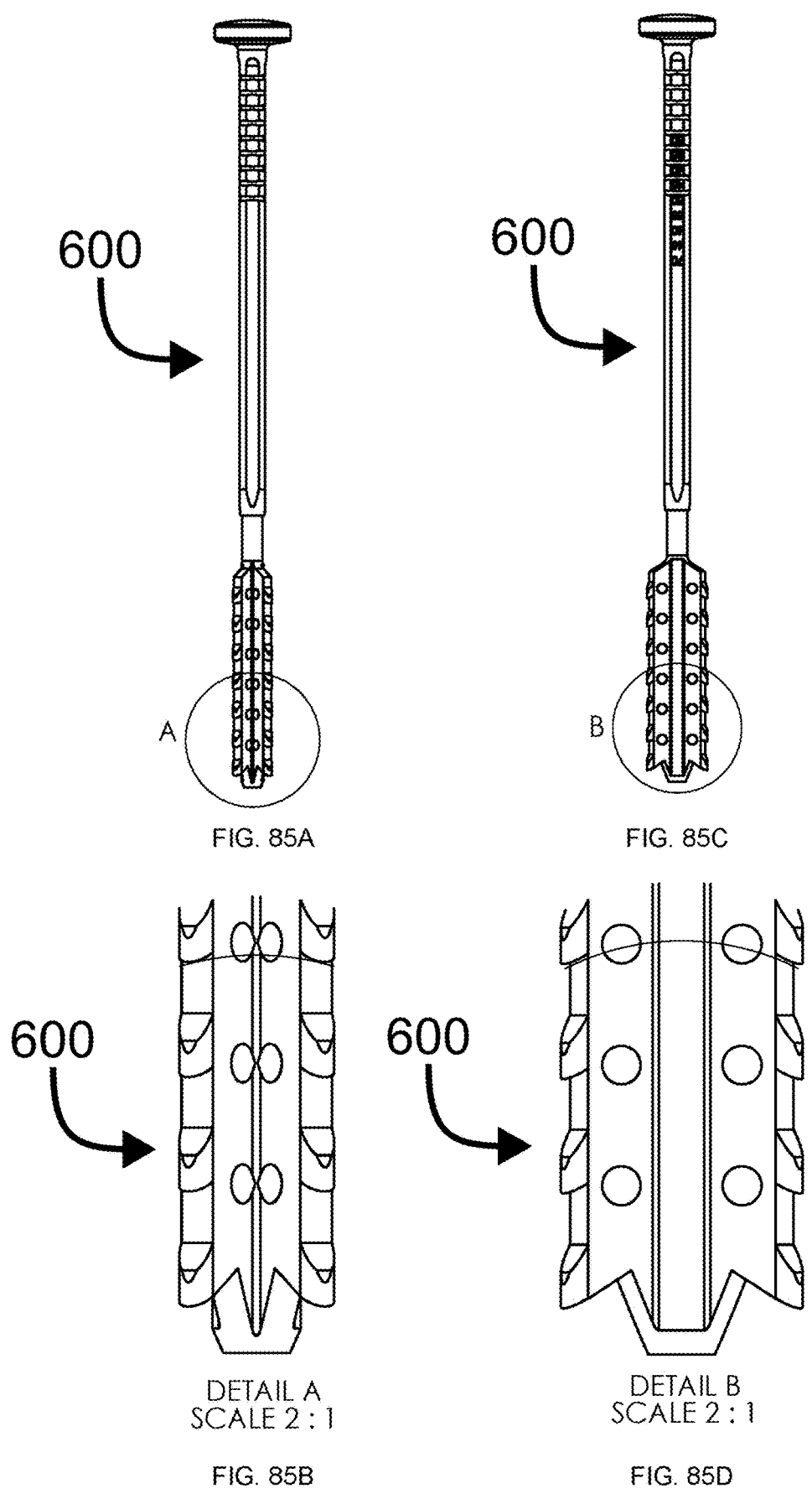
Figures 86A, 86B:
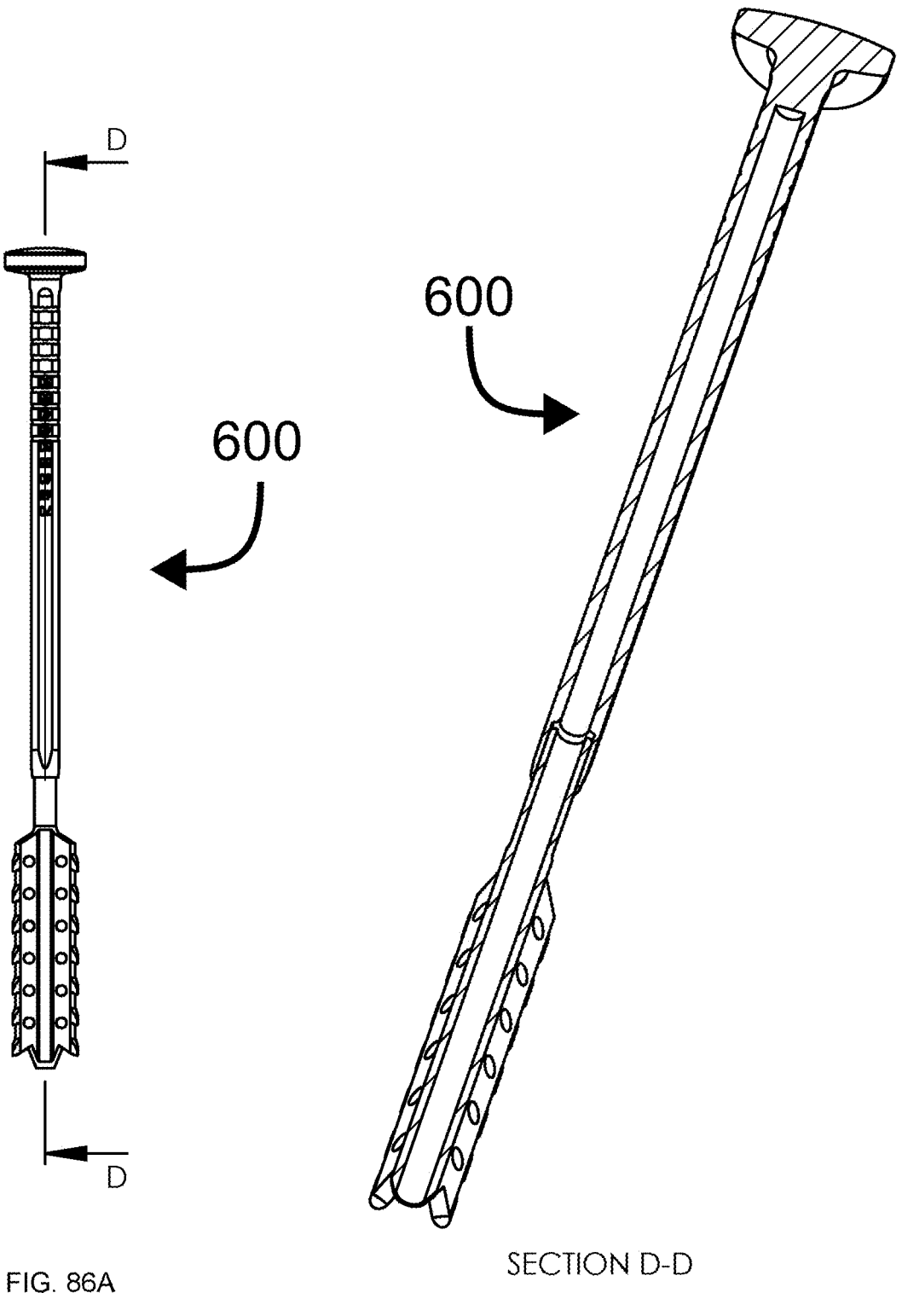
Figure 87A:
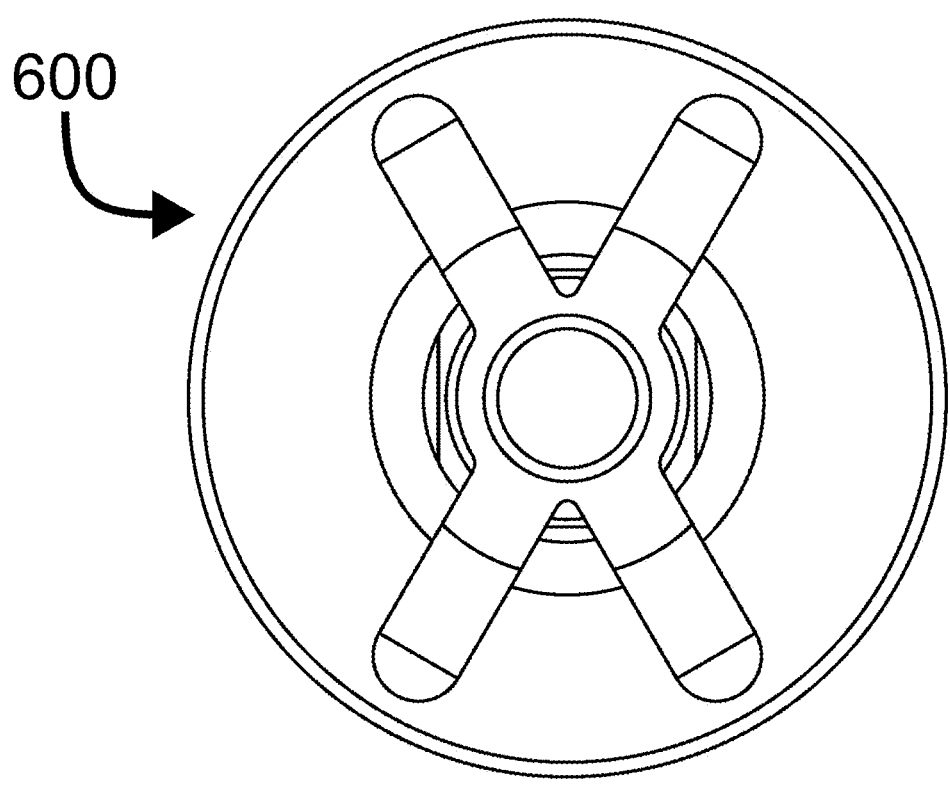
Figure 87B:
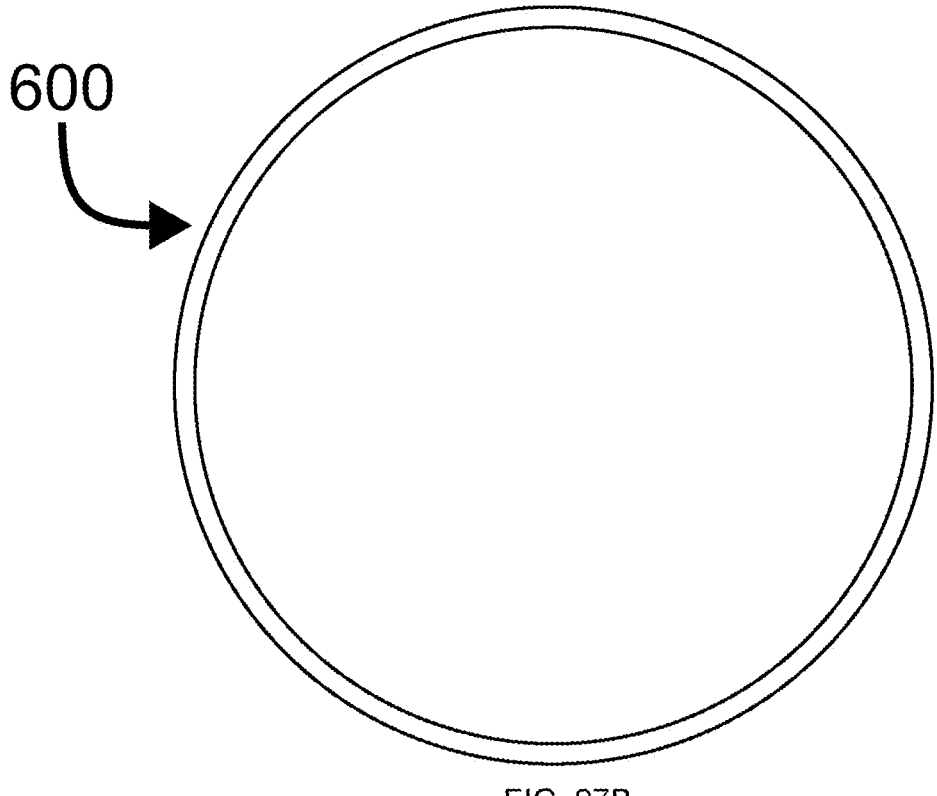
Figure 88:
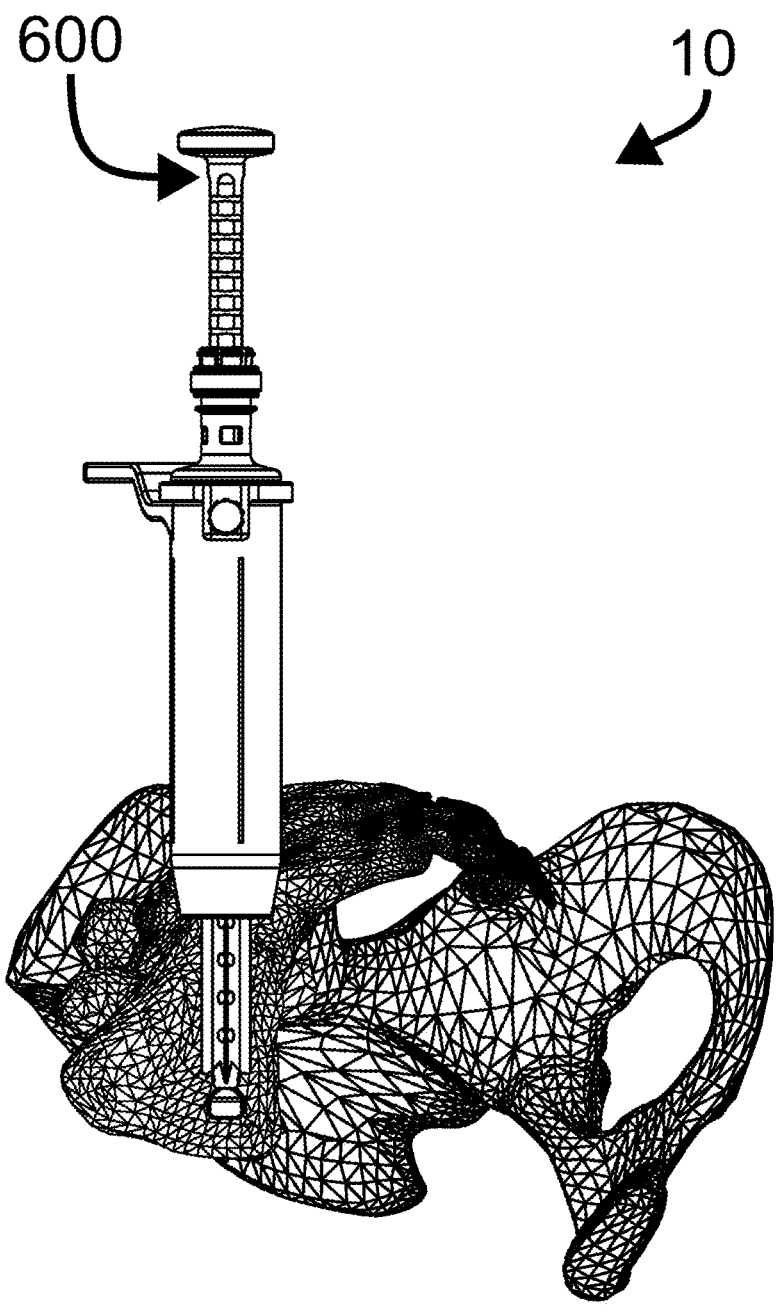
Figure 89:
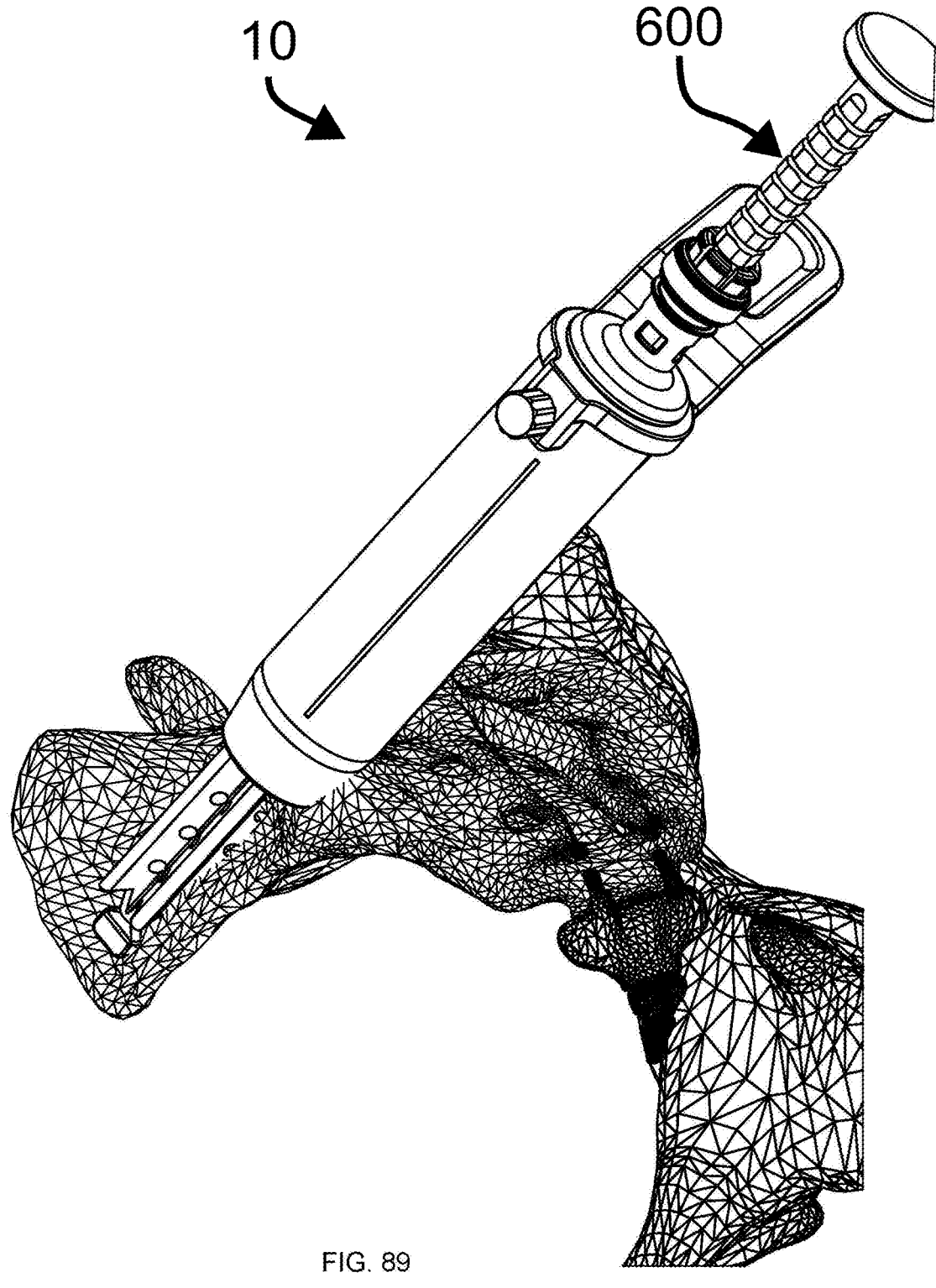
Figure 90:
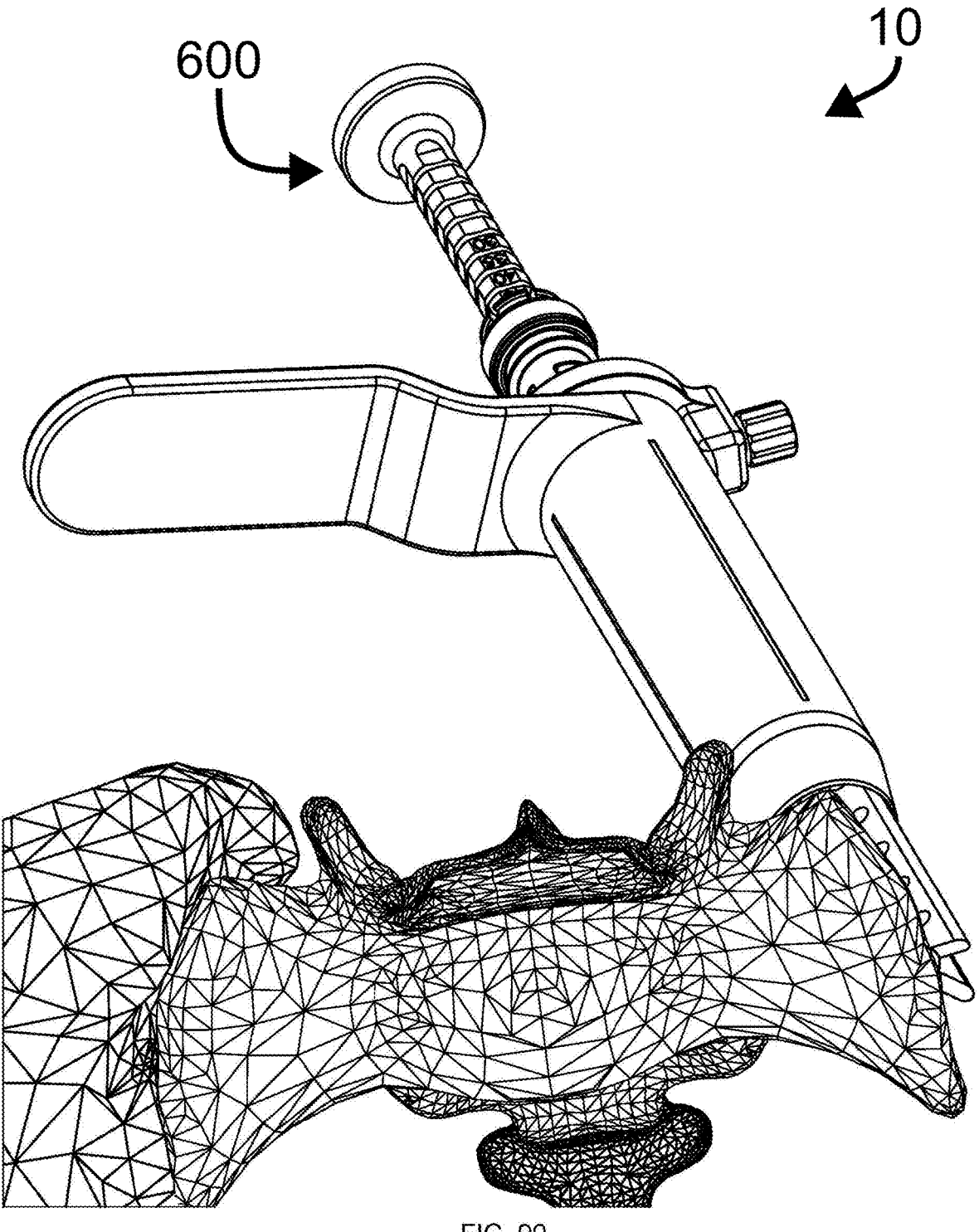
Figure 91:
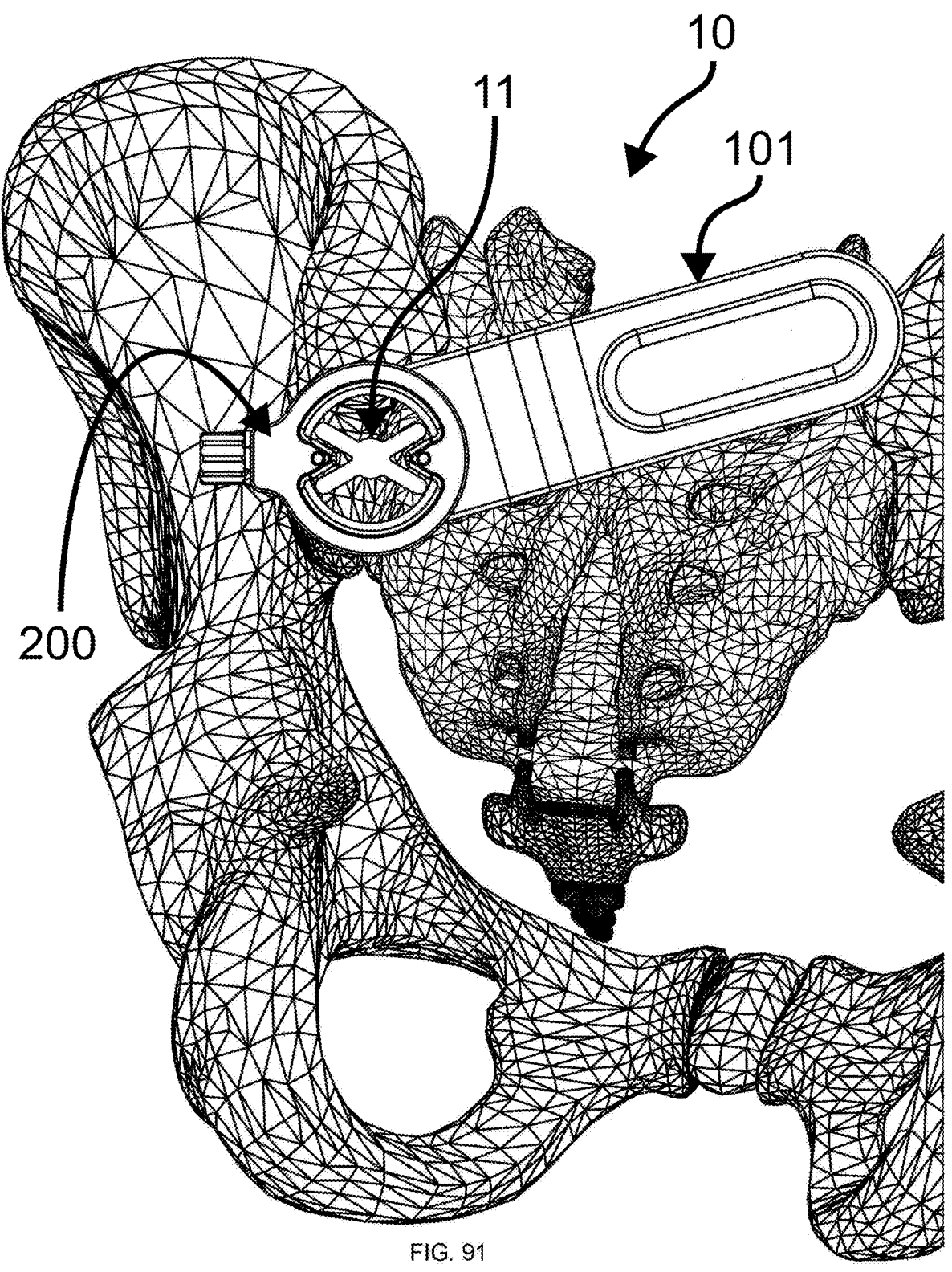
FIG. 91 is a view looking down through the working cannula showing the implant receiving space created by the aforementioned cutting tools.
Figures 92A, 92B:
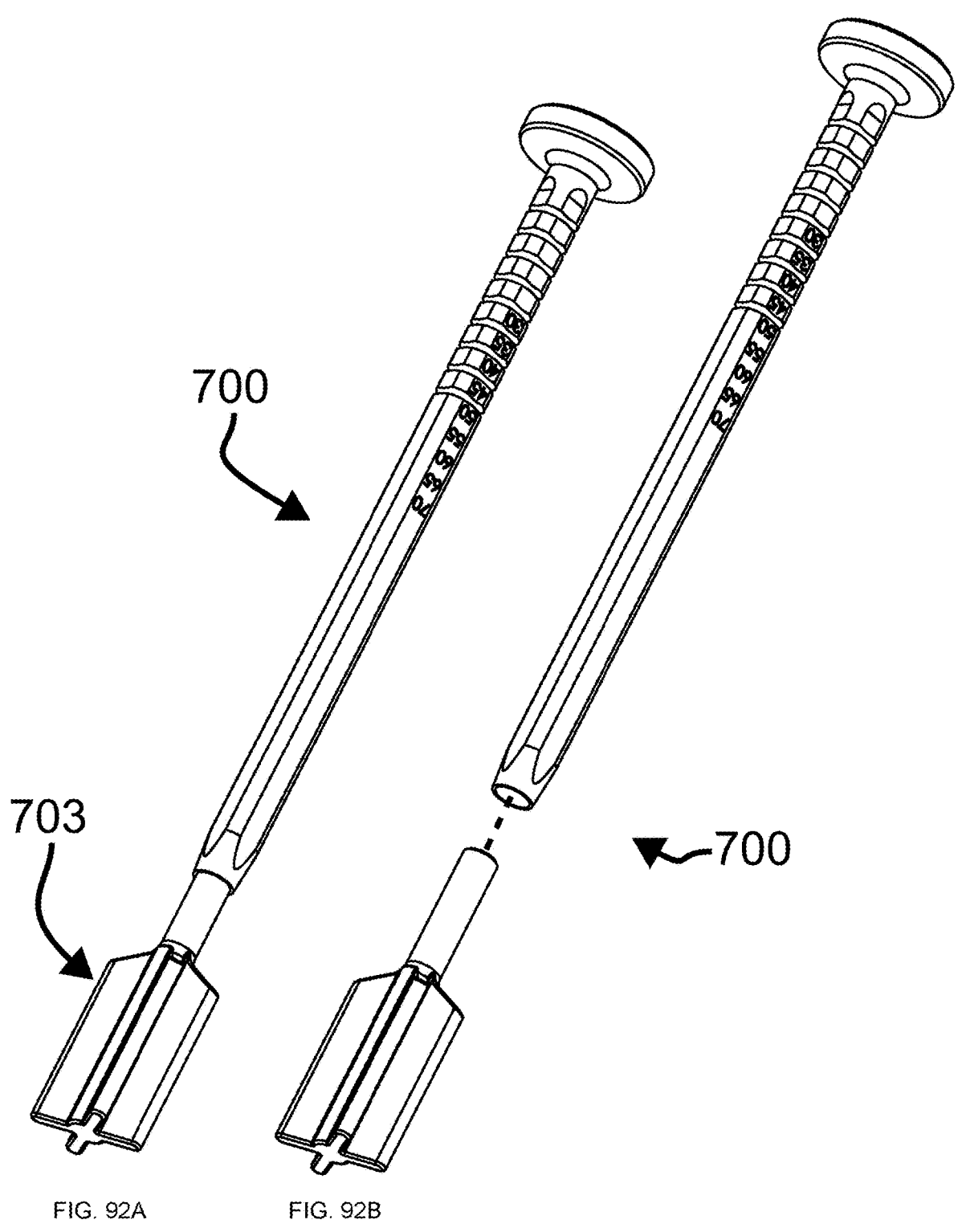
Figures 93A, 93B, 93C, 93D:
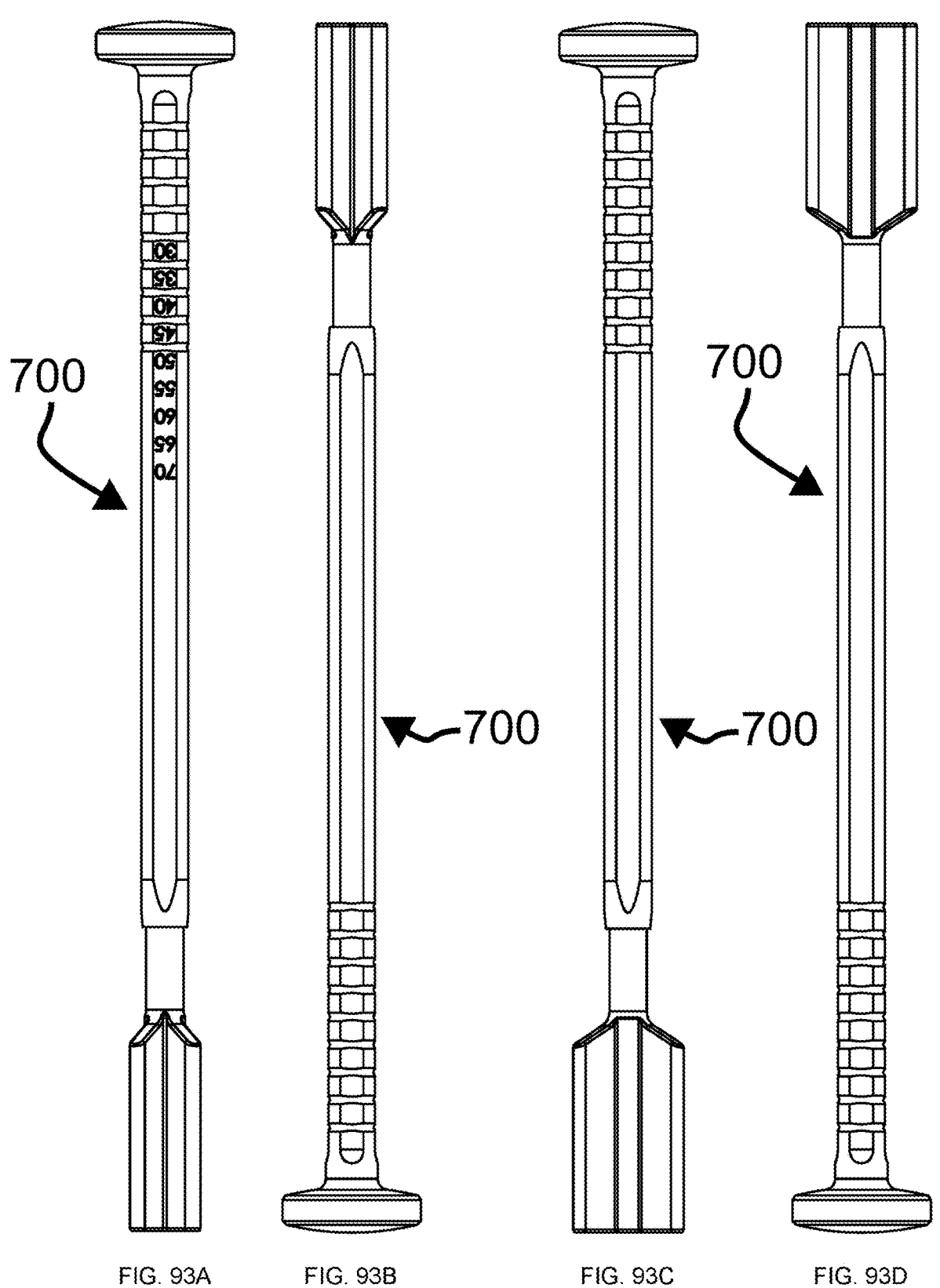
Figures 94A, 94B, 94C, 94D:
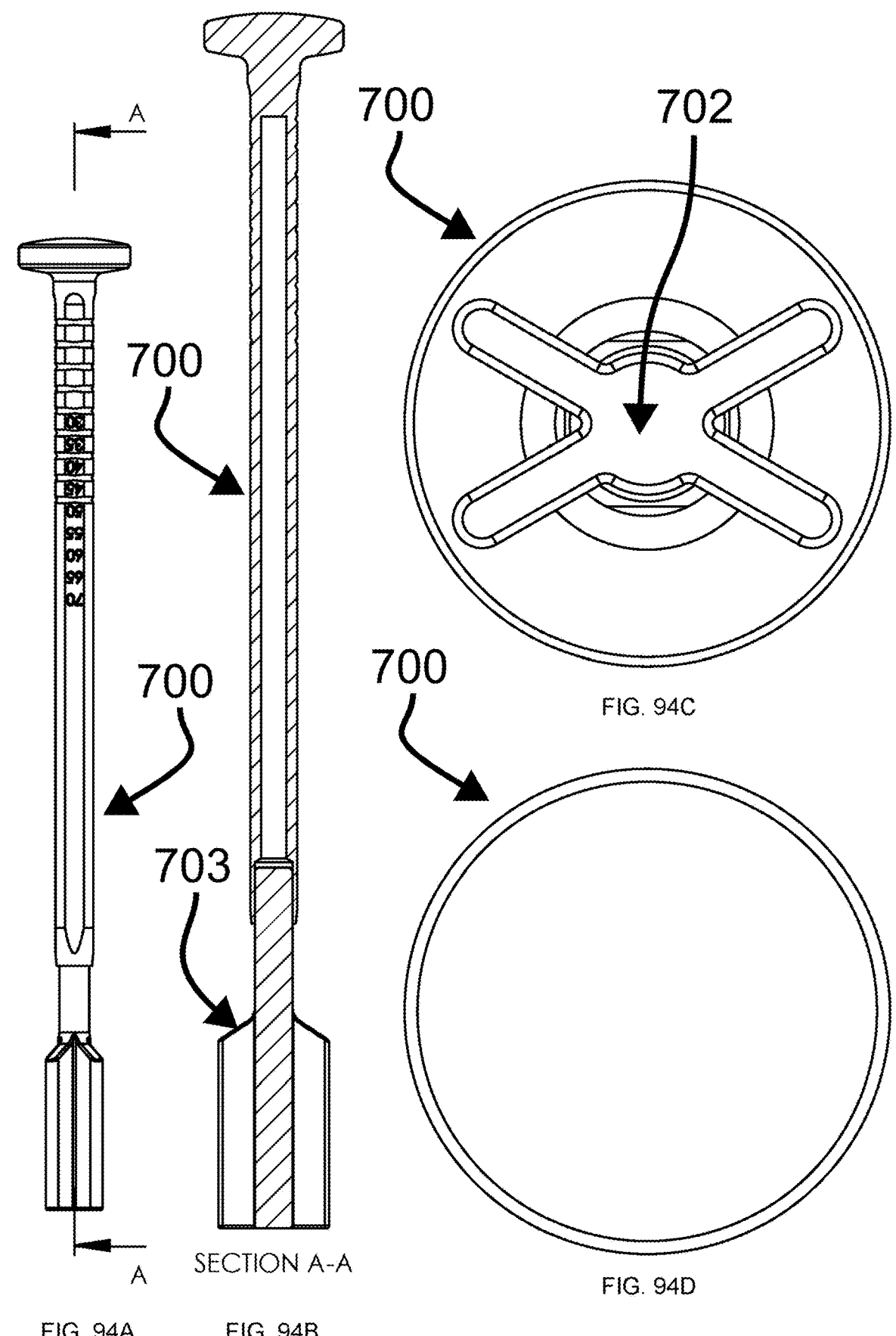
Figure 95:
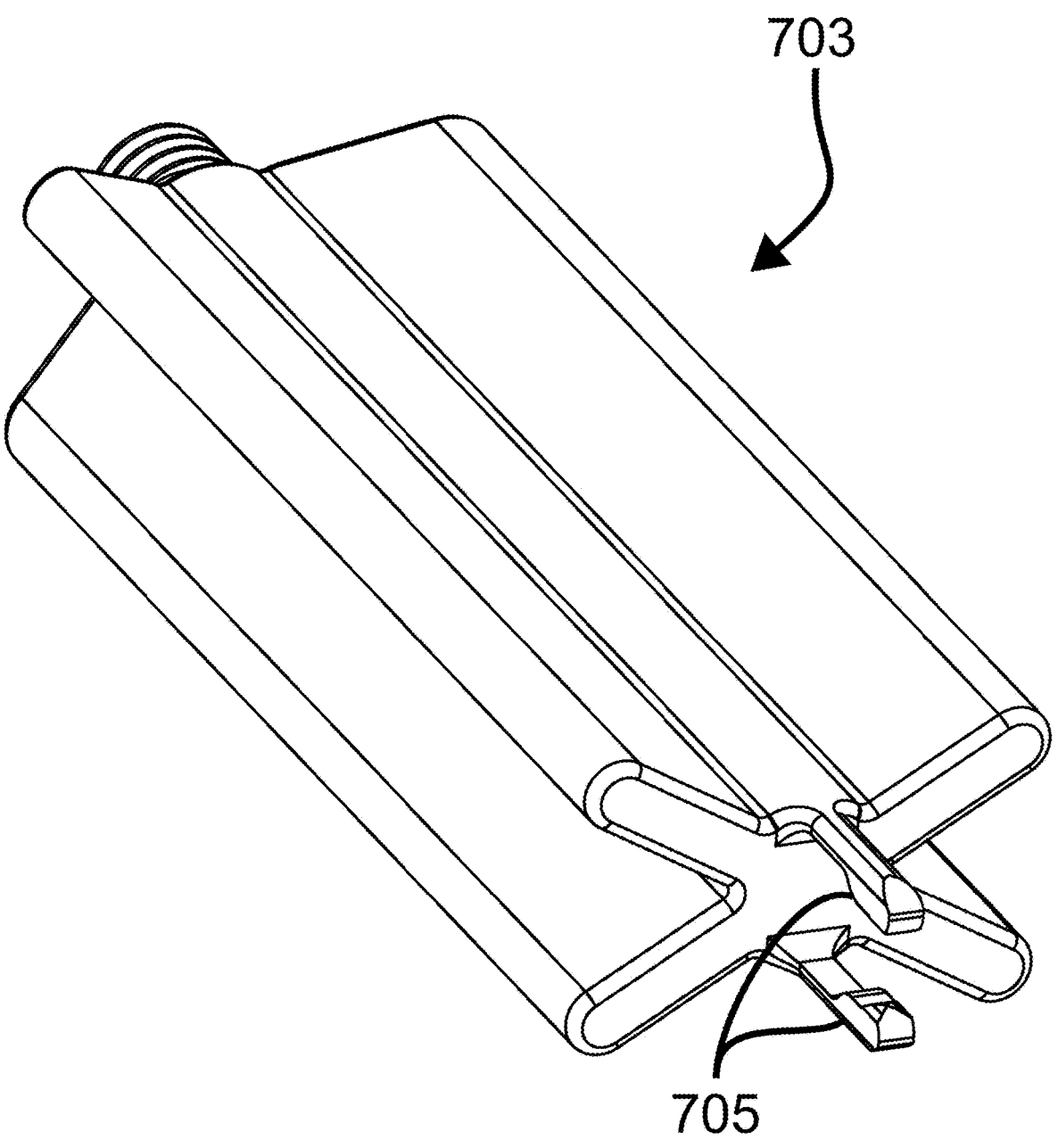
Figure 97:
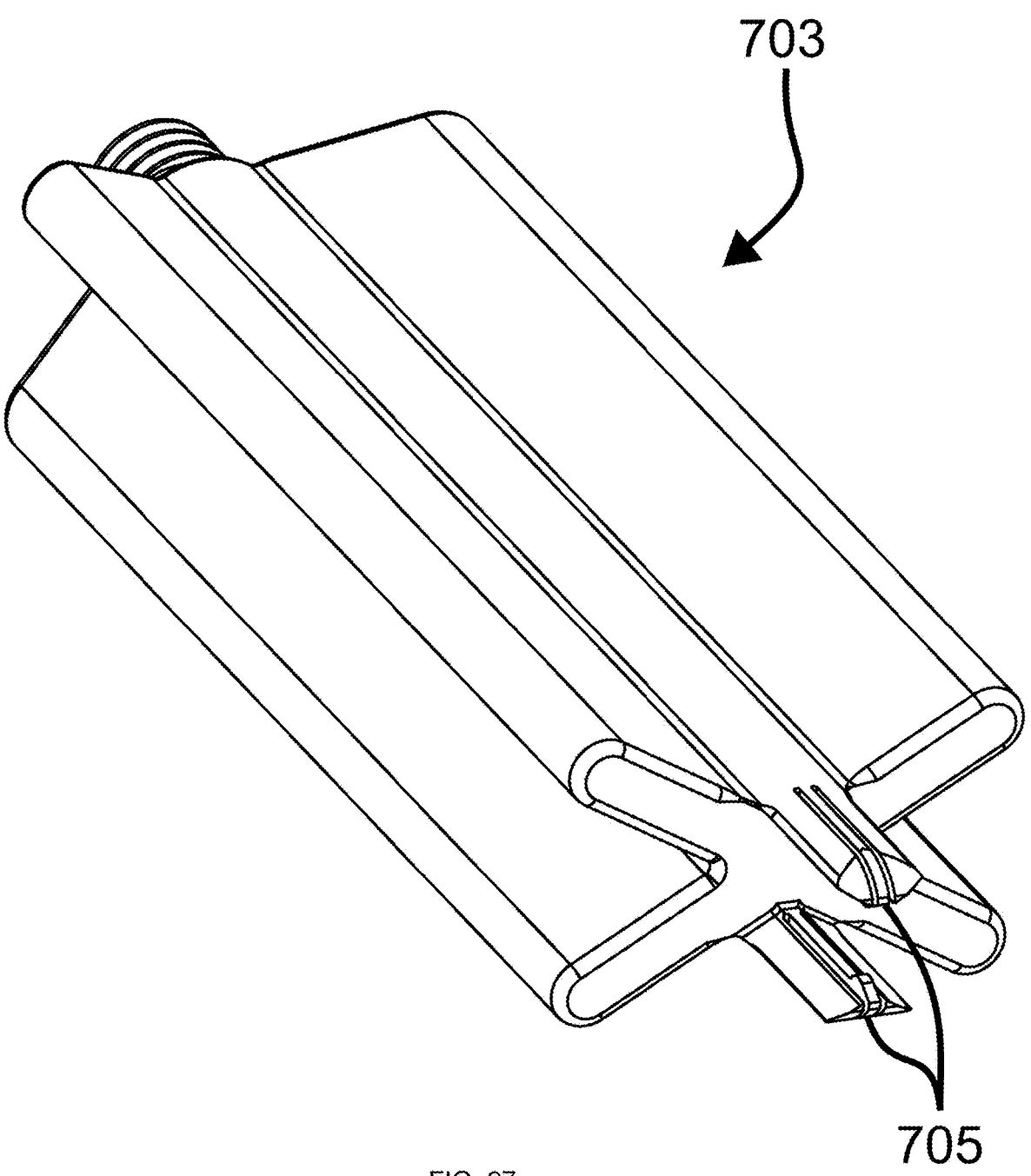
Figures 98A, 98B, 98C, 98D:
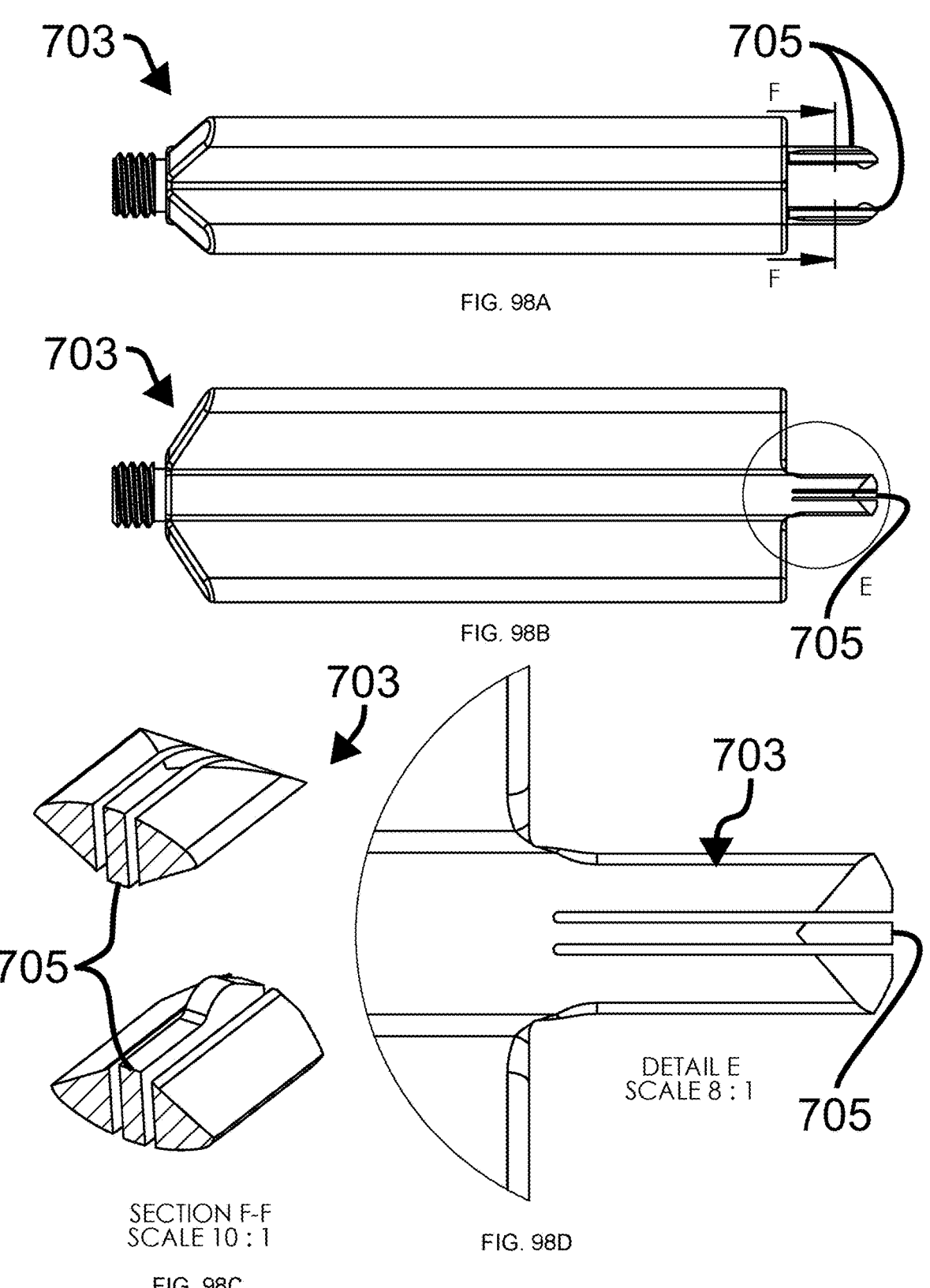
Figure 99:
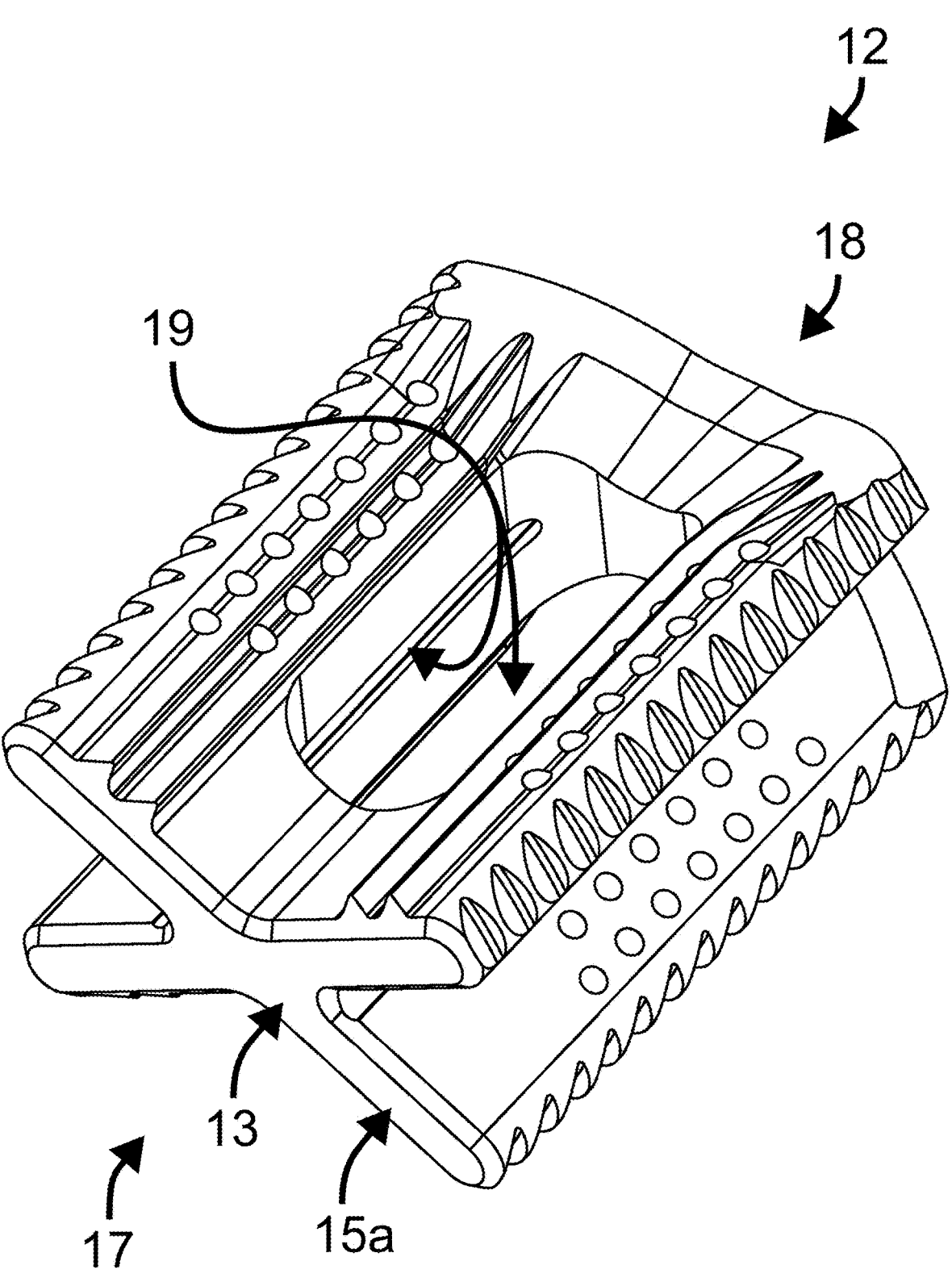
Figure 102:
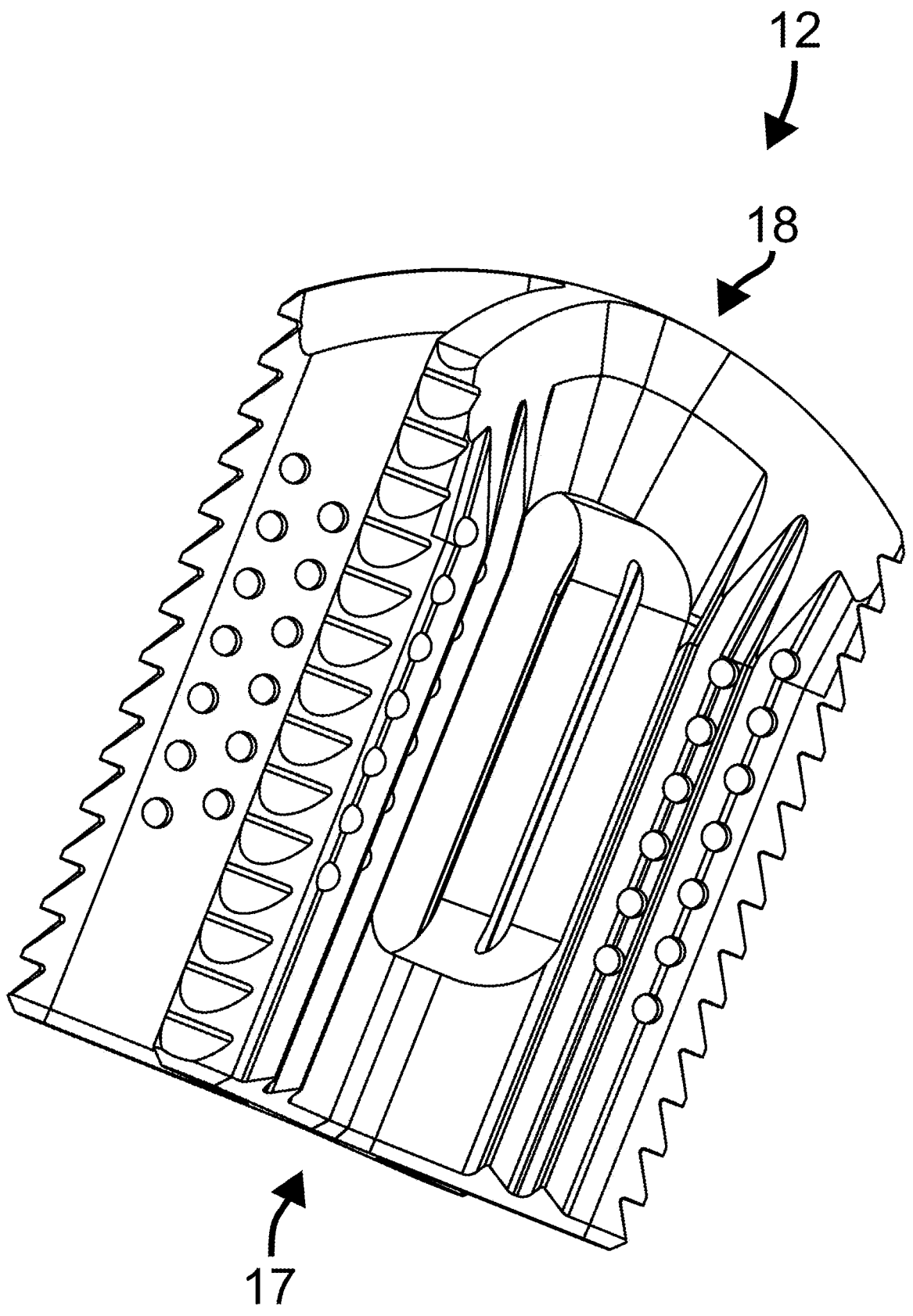
Figure 103:
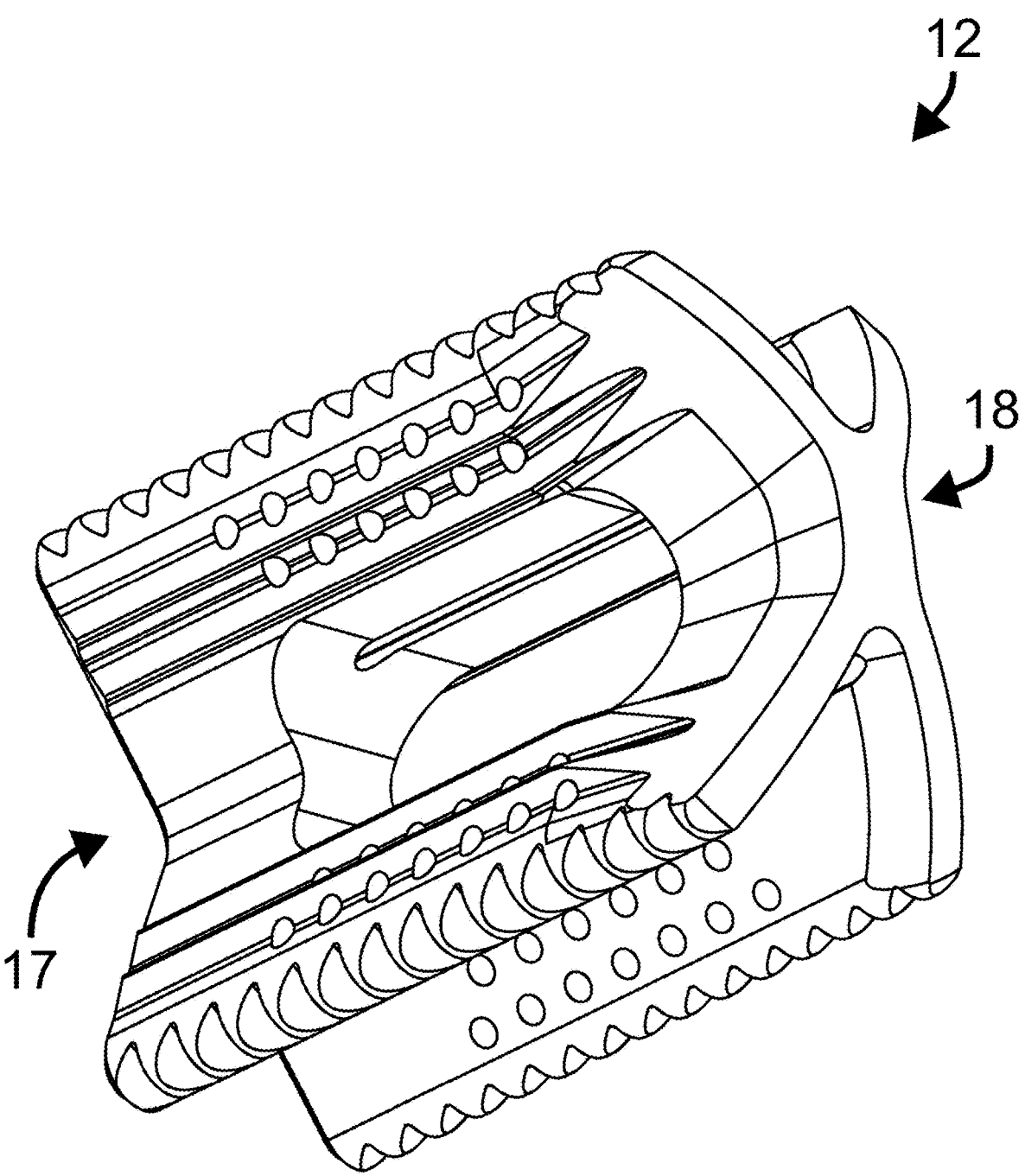
Figures 104A, 104B:
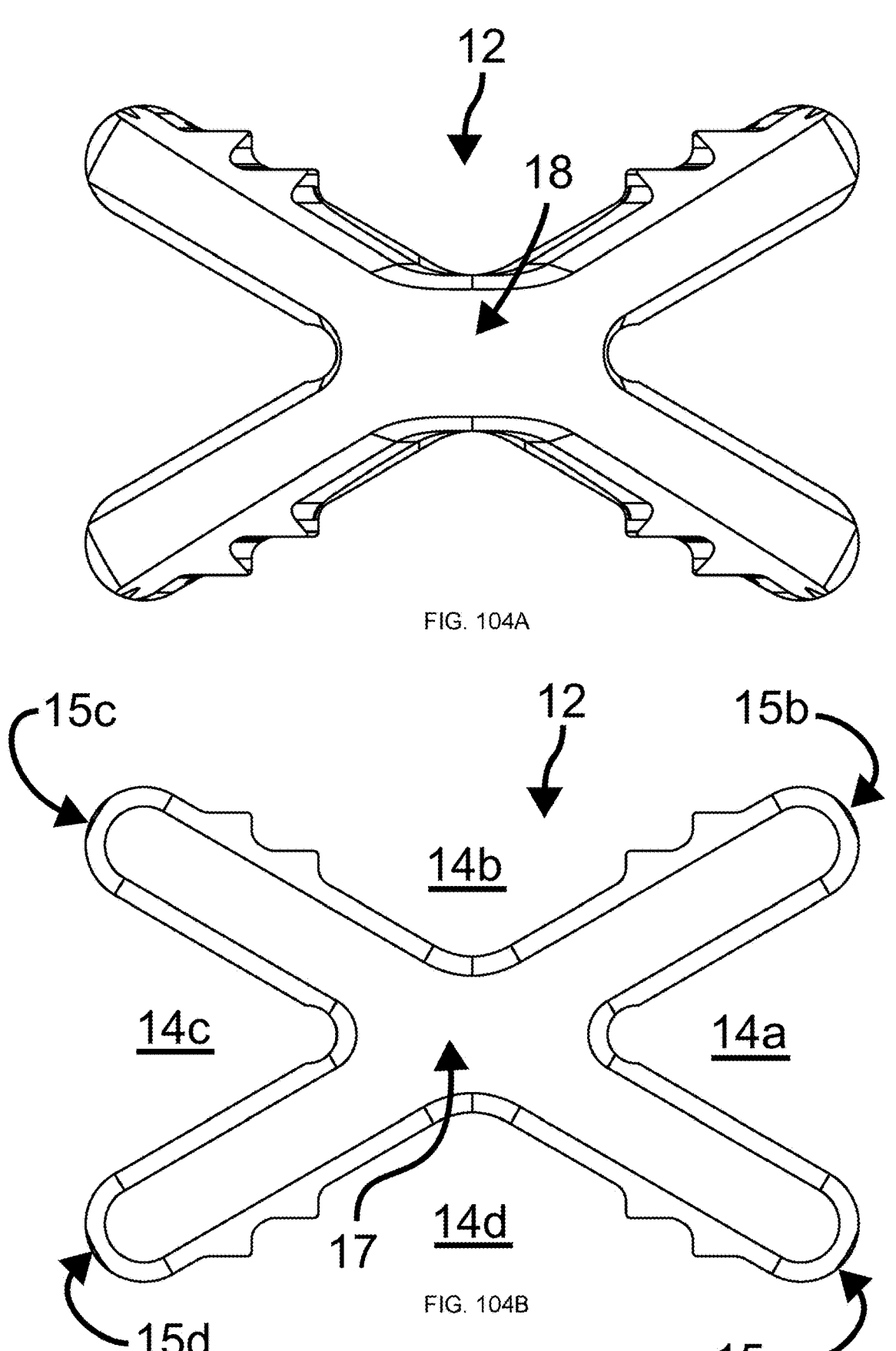
Figure 105A:
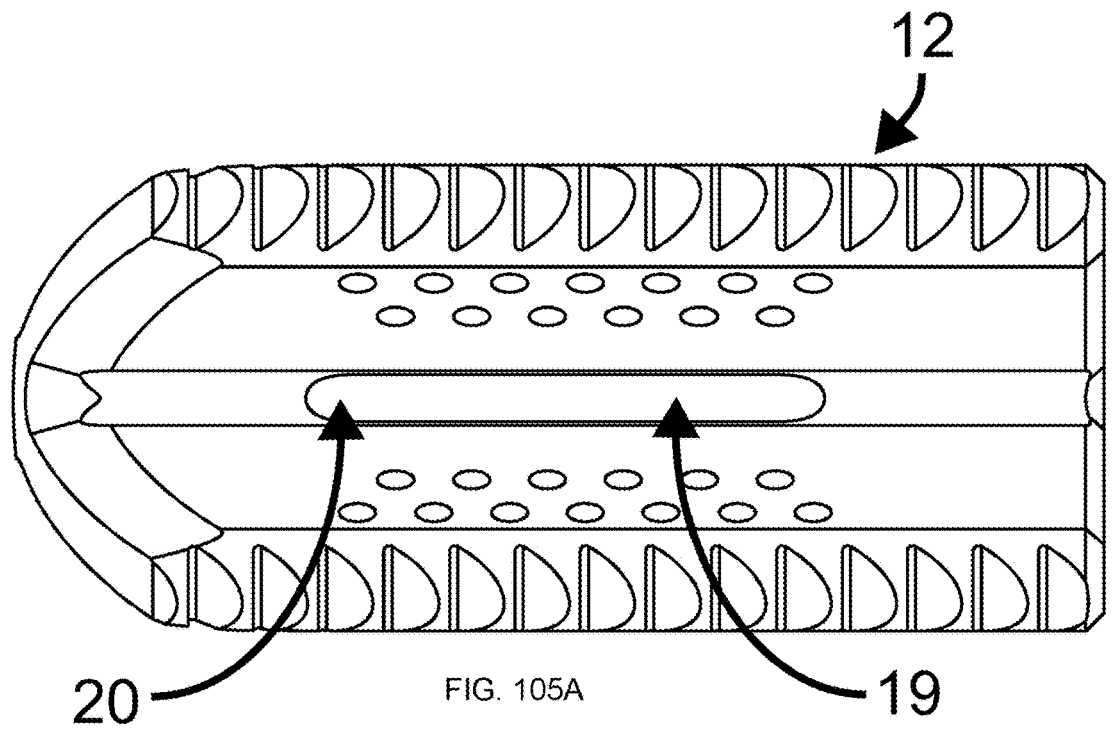
Figure 105B:
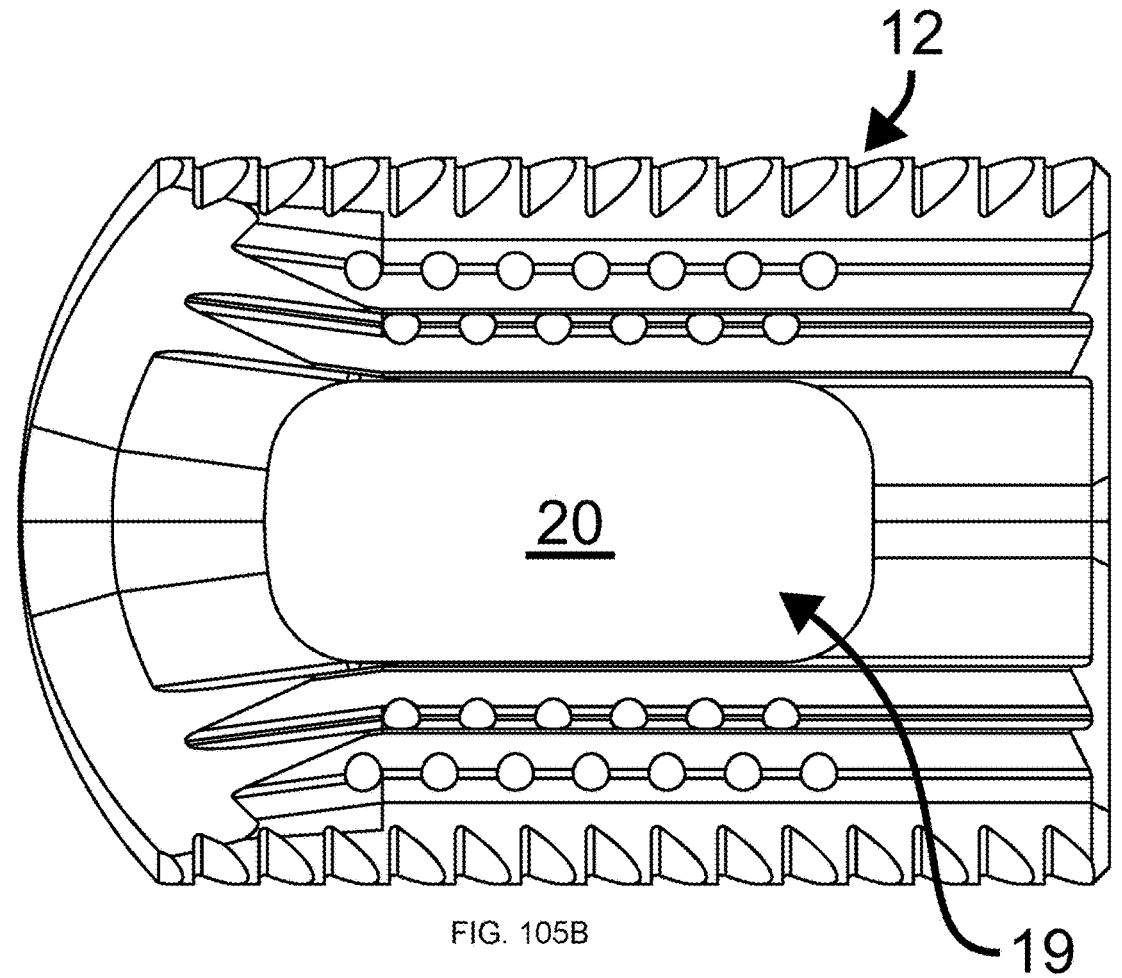
Figure 106:
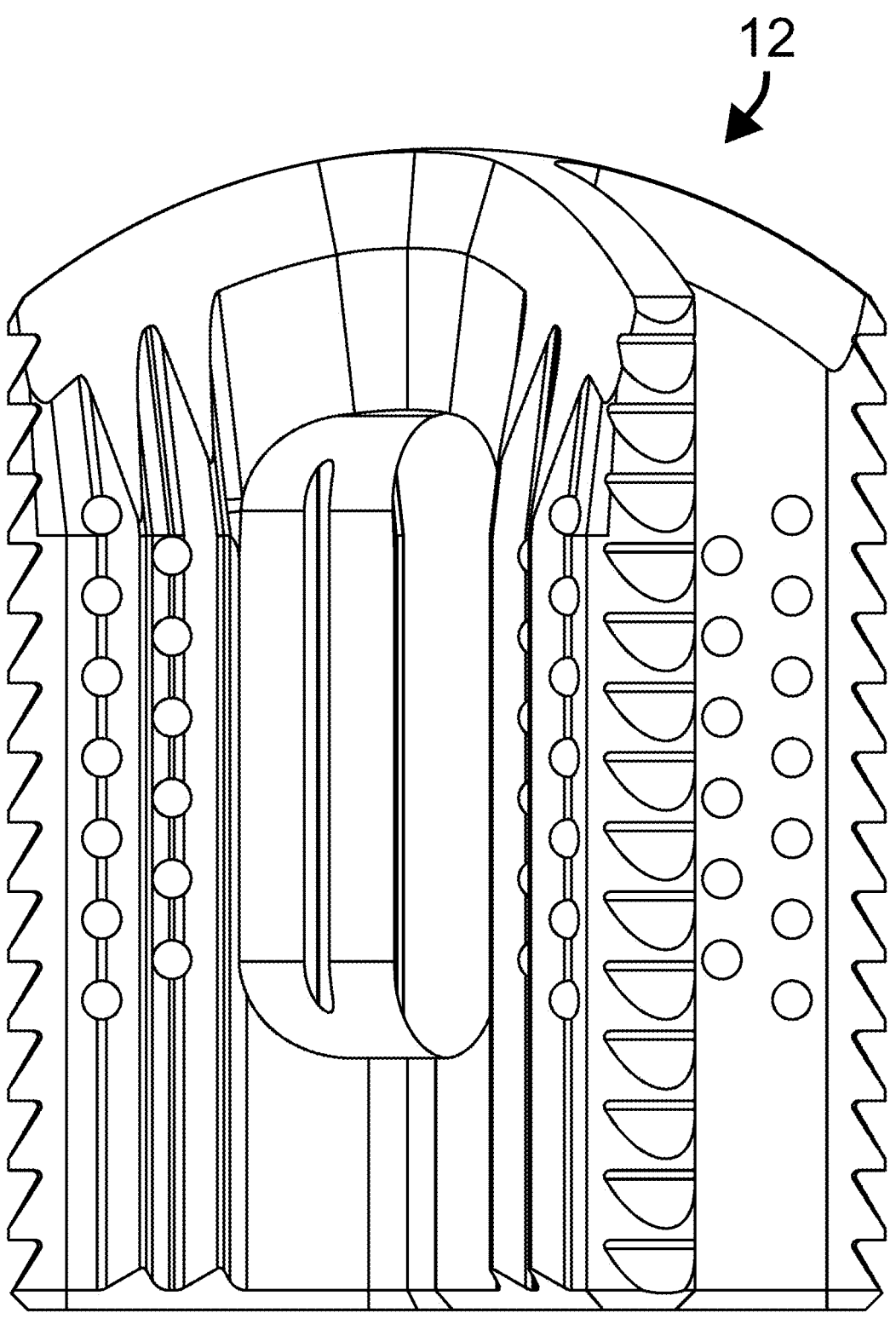
Figure 107:
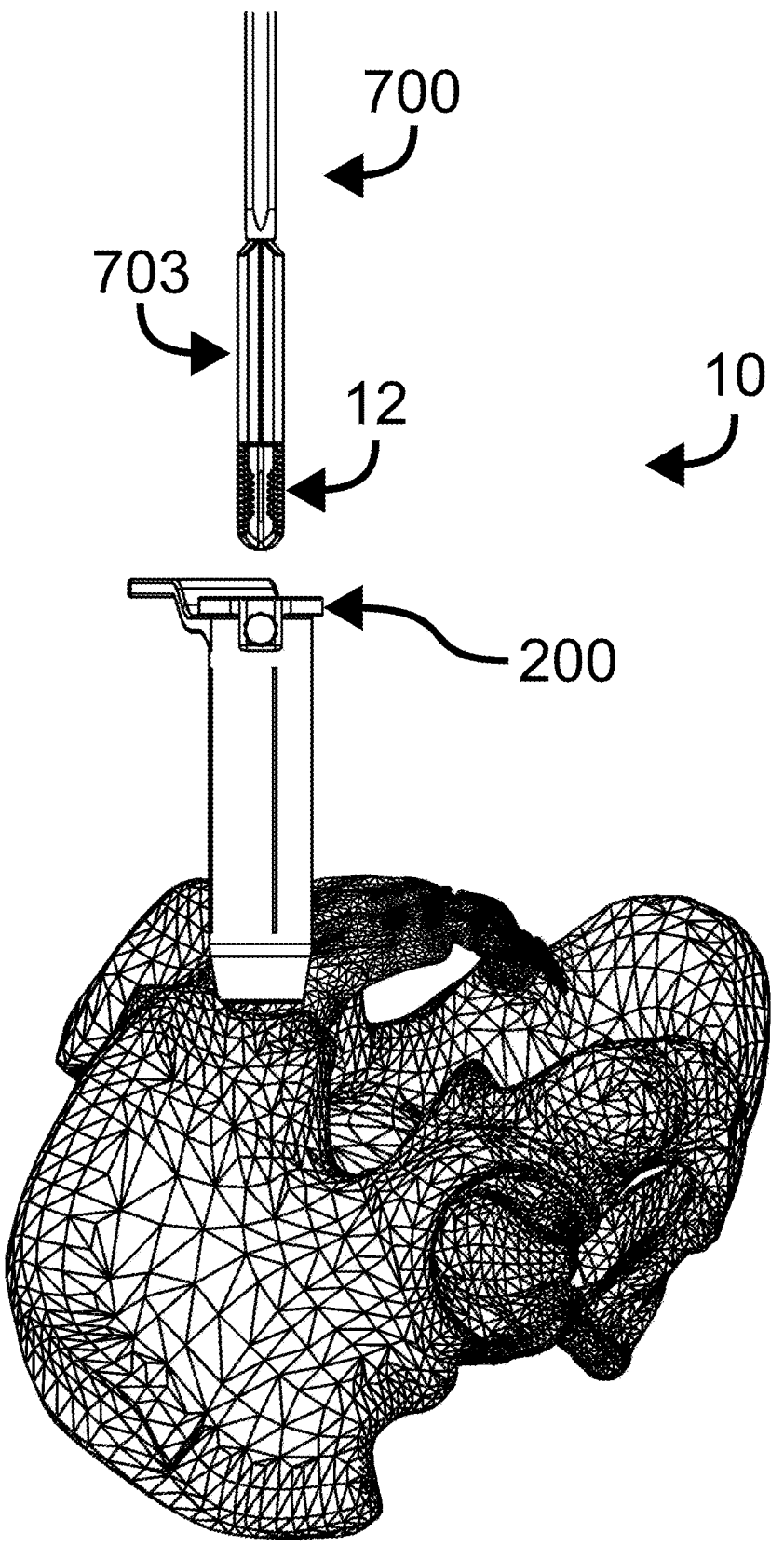
FIGS. 107-112 are different views of the X-shaped implant of FIGS. 99-106 coupled with the inserter tool of FIGS. 92A-94, except that the distal end is that of FIGS. 95-96D having the pair of opposing spring arms, and showing the step of implanting through the working cannula and guide rail assembly and into the sacroiliac joint via a posterior access region between the PSIS and PIIS.
Figure 108:
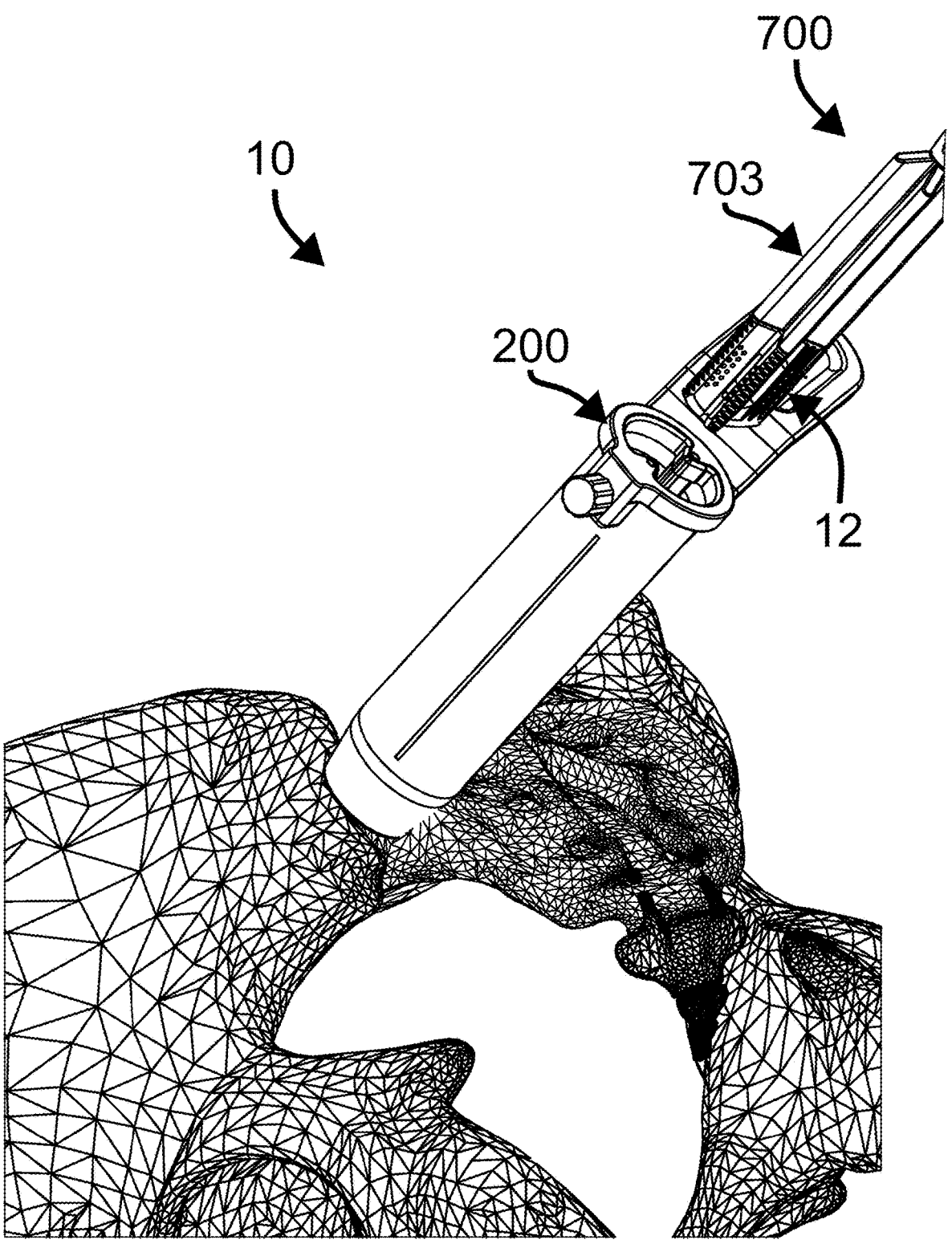
Figure 109:
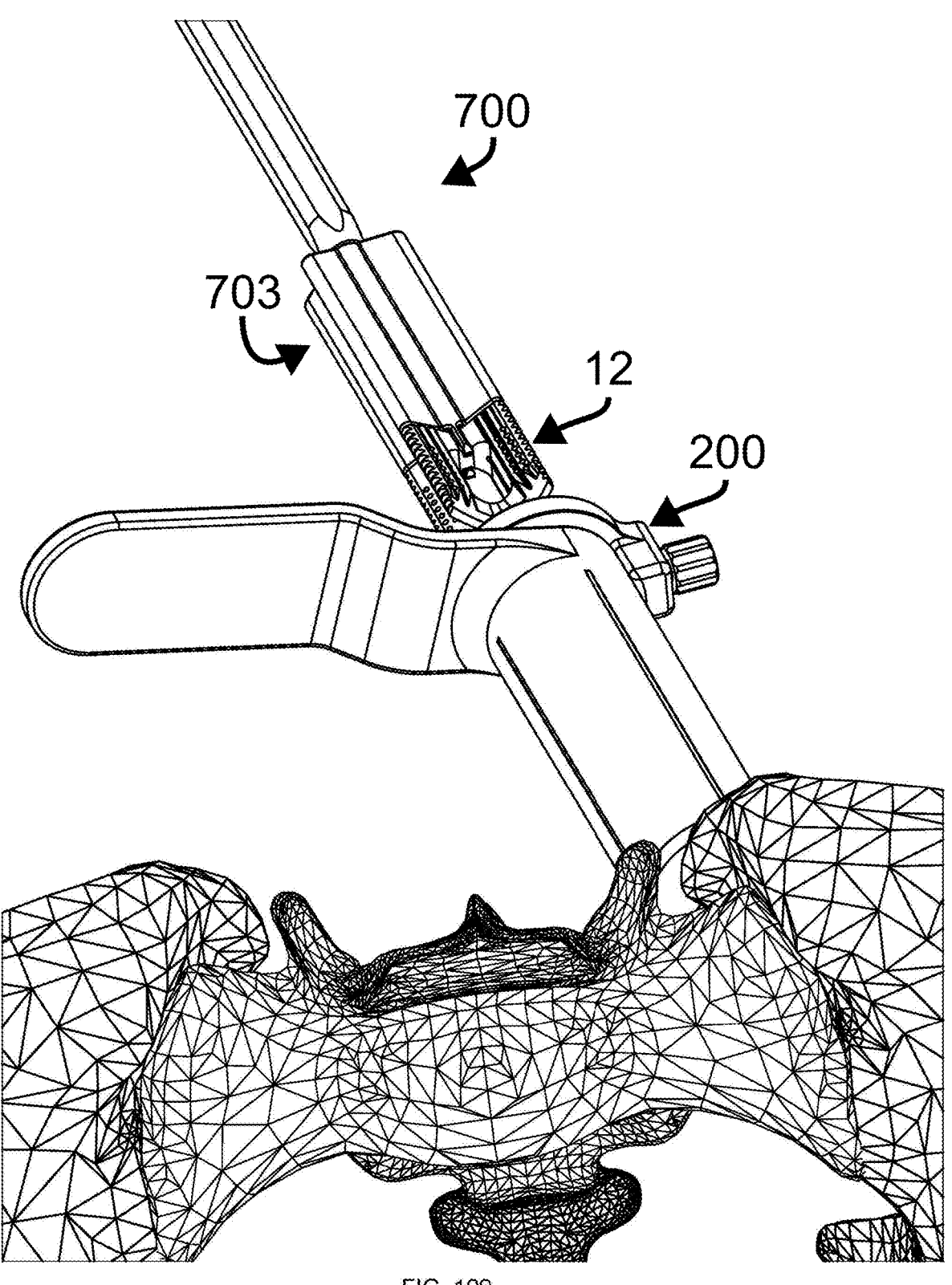
Figure 110:
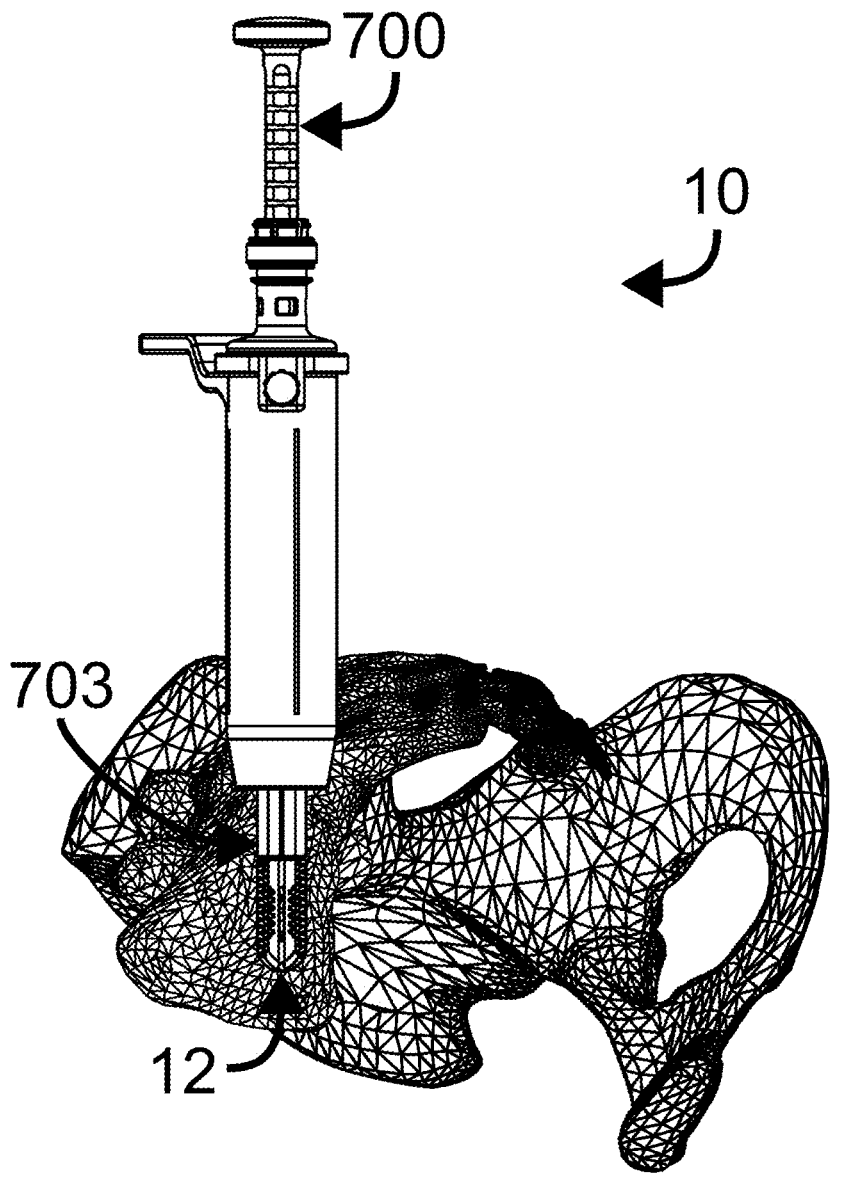
Figure 111:
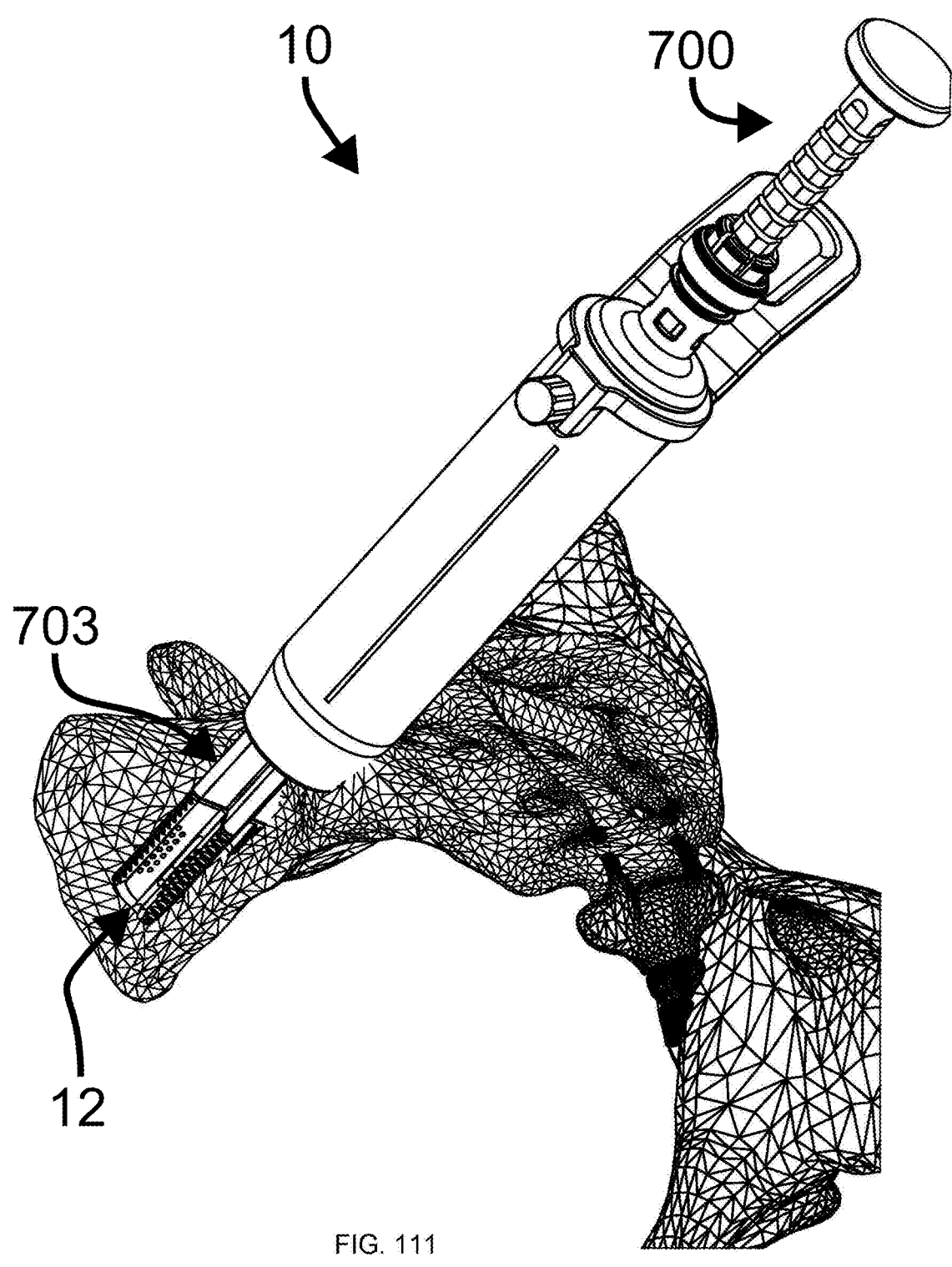
Figure 112:
Figure 113:
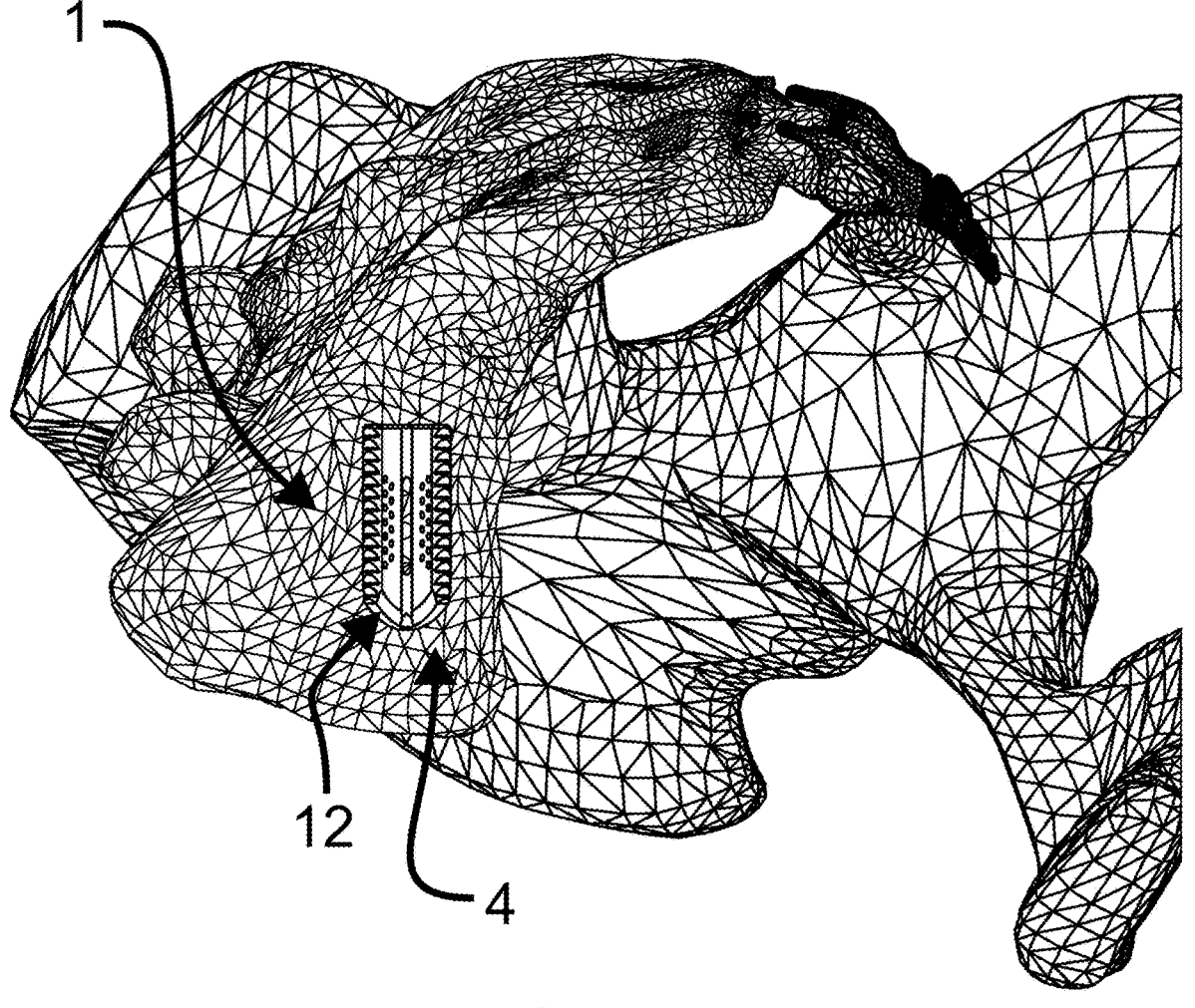
FIGS. 113-115 are different views showing the implanted sacroiliac joint implant but with the left ilium removed to show the location of the implant in greater detail.
Figure 114:
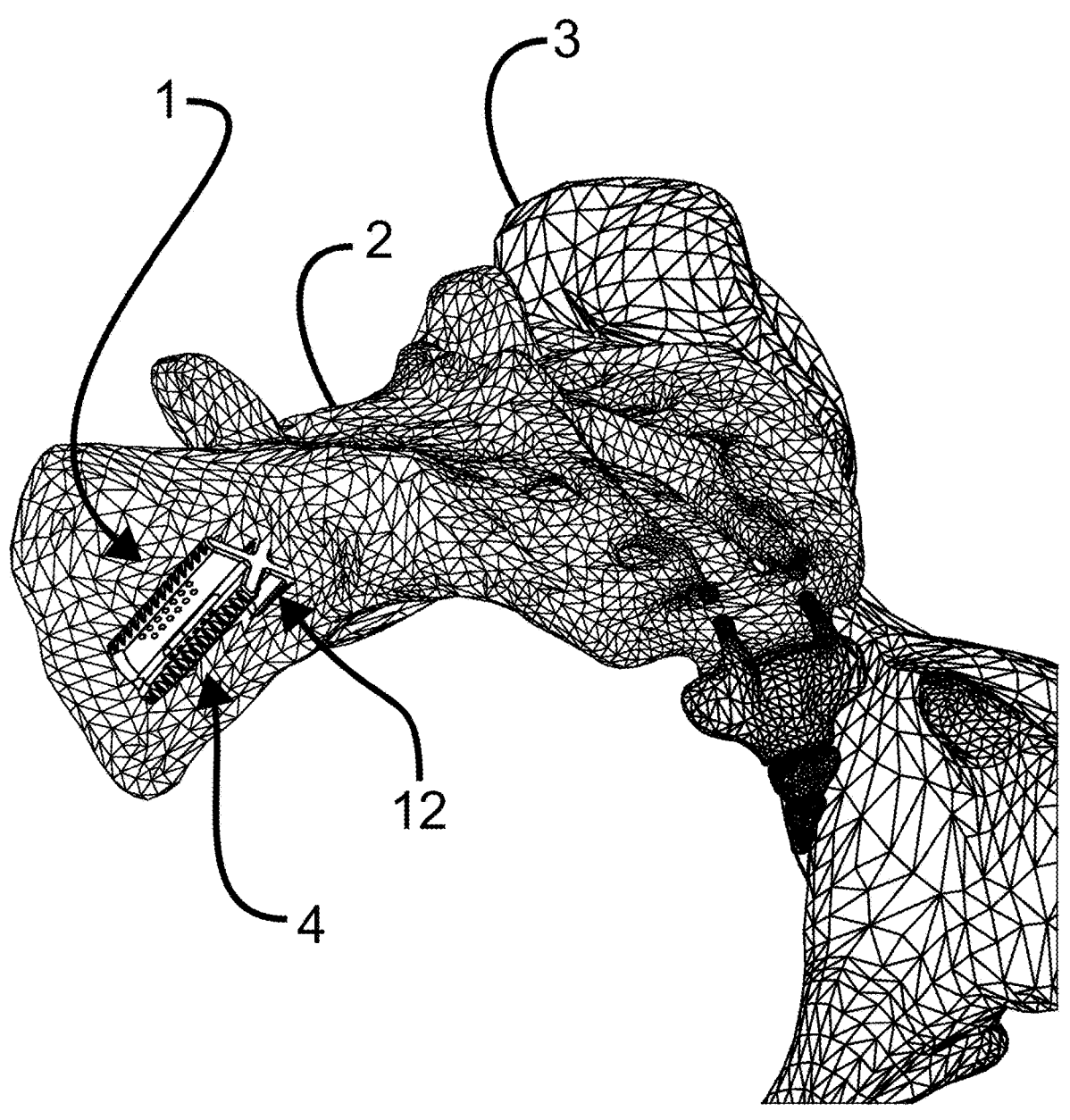
Figure 115:
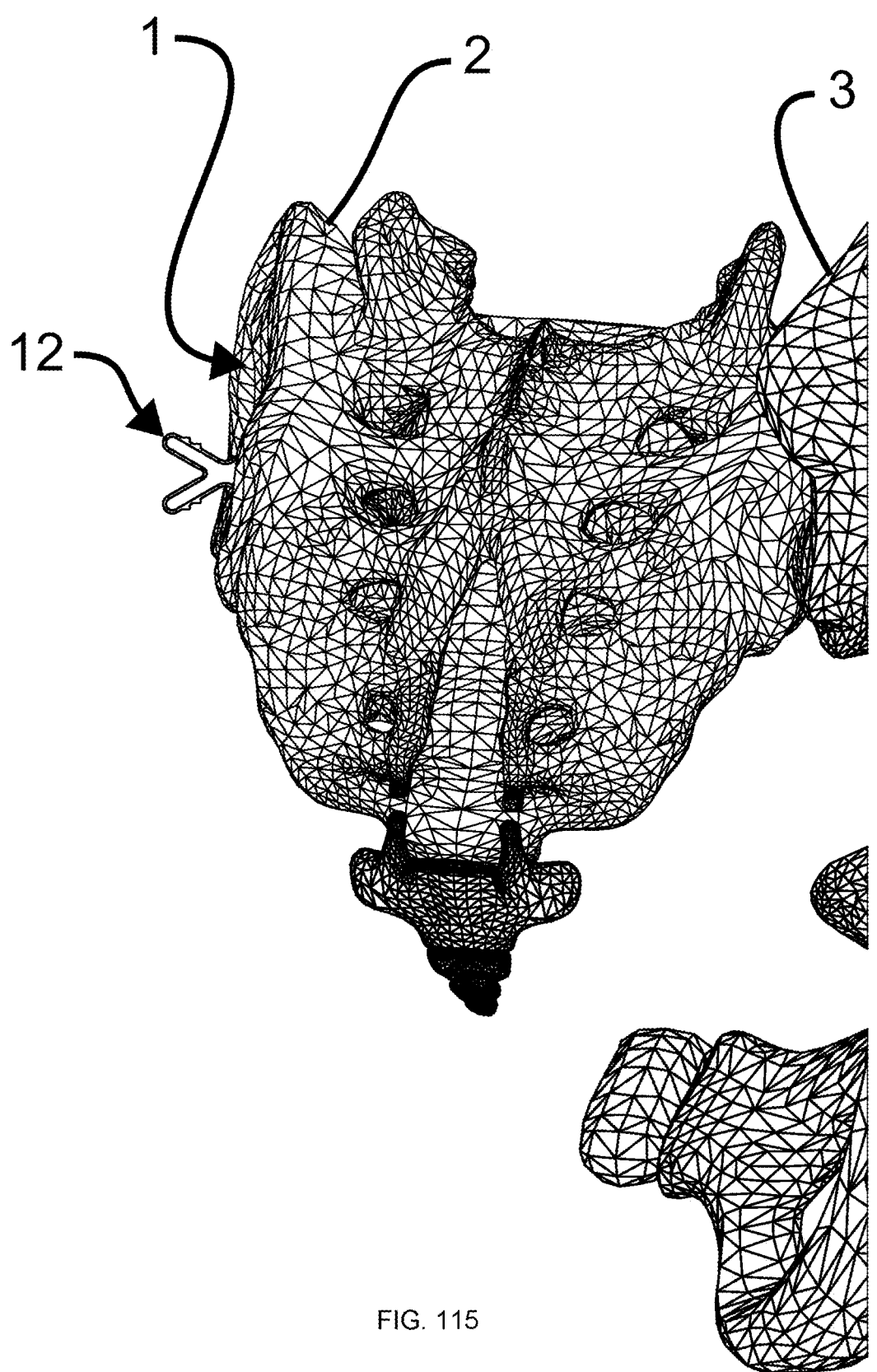
Figures 116A, 116B:
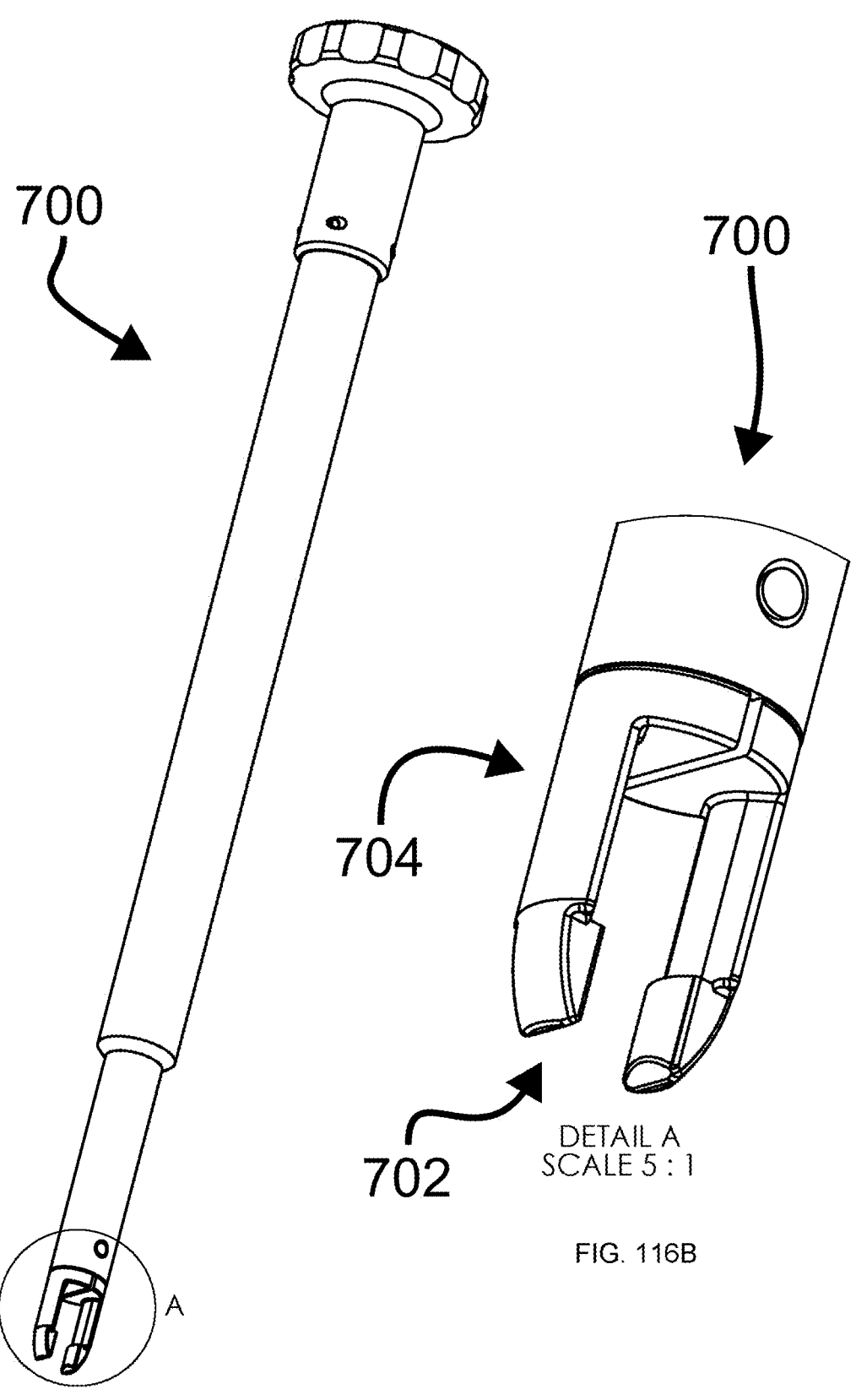
Figures 117A, 117B, 117C:
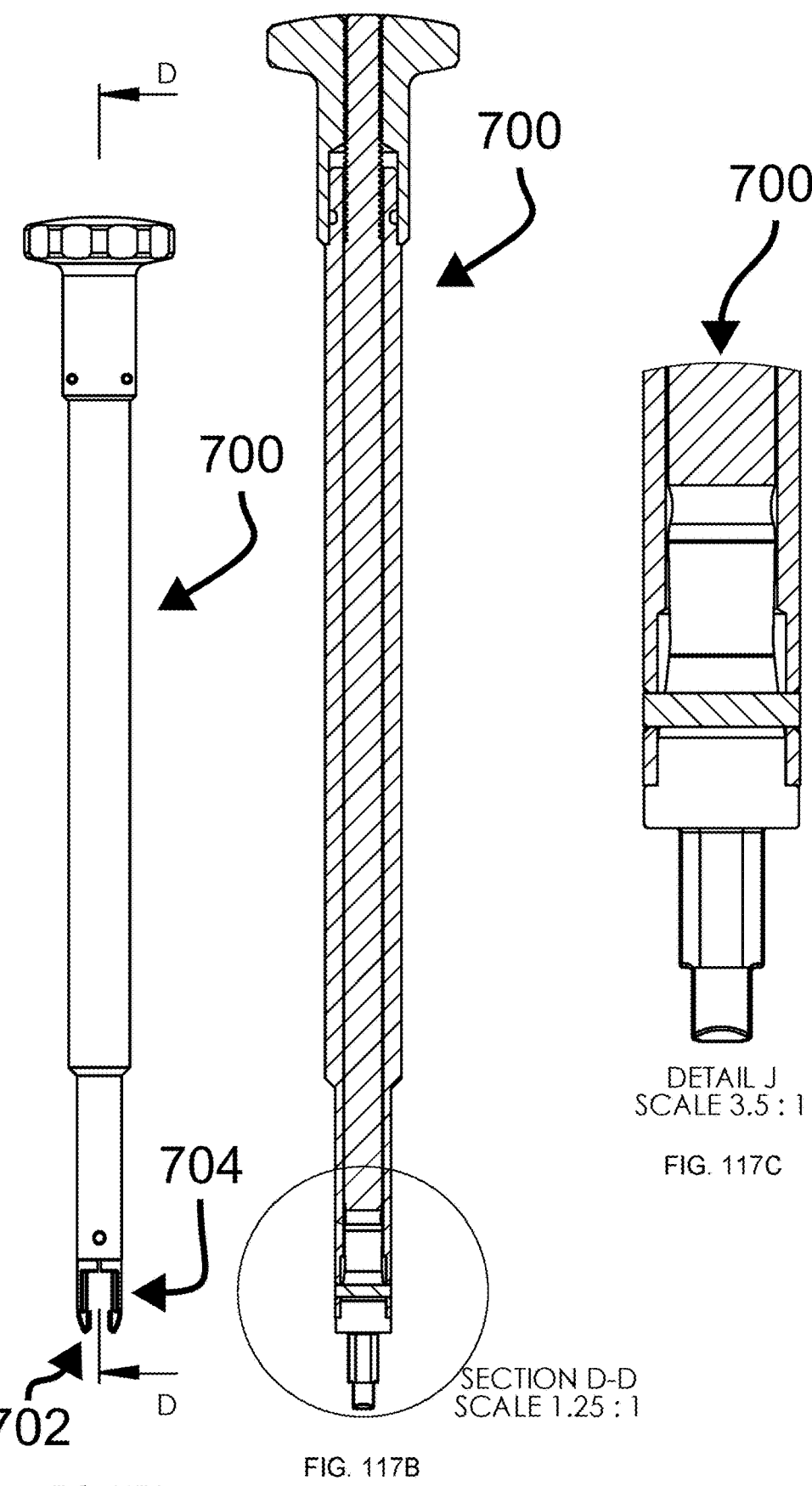
Figures 118A, 118B, 118C, 118D, 118E:
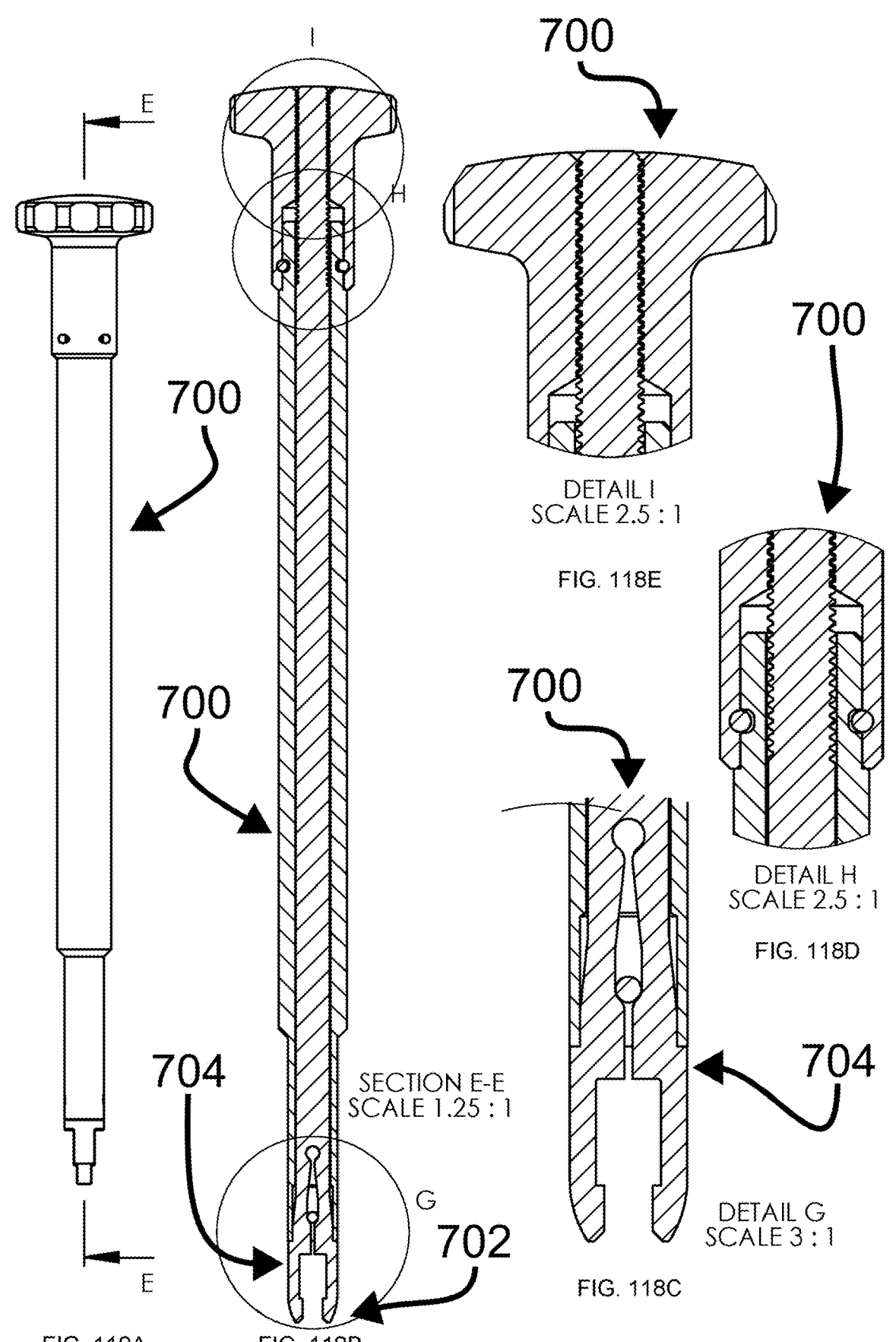
Figure 119:
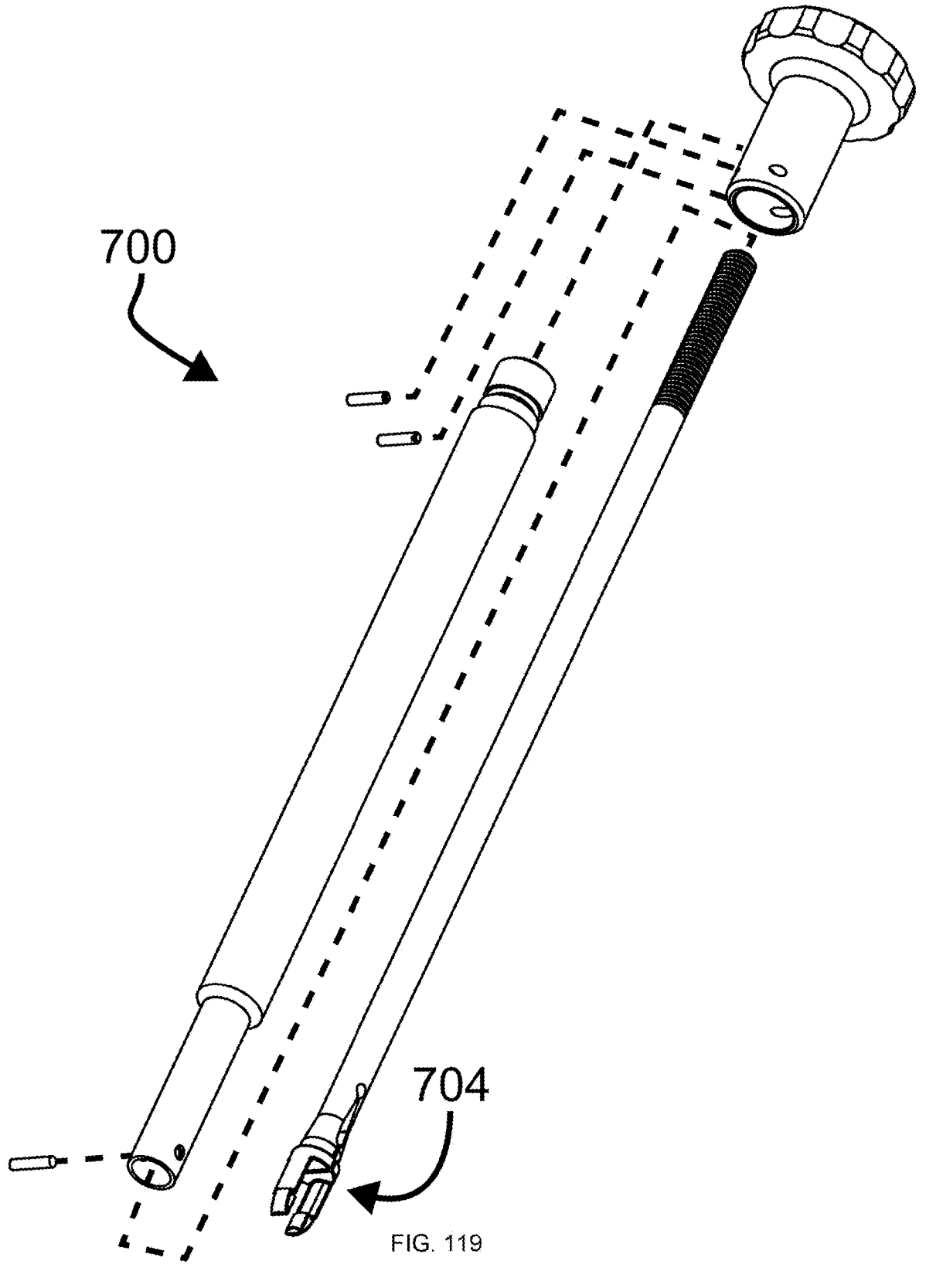

The present application incorporates by reference the following patent applications in their entireties: Ser. No. 12/998,712 filed on May 23, 2011; Ser. No. 13/135,381 filed on Jul. 1, 2011; Ser. No. 14/127,119 filed on Dec. 17, 2013; Ser. No. 13/236,411 filed on Sep. 19, 2011; Ser. No. 13/475, 695 filed on May 18, 2012; Ser. No. 13/945,053 filed on Jul. 18, 2013; Ser. No. 13/946,790 filed on Jul. 19, 2013; Ser. No. 14/344,876 filed on Mar. 13, 2014; Ser. No. 14/216,975 filed on Mar. 17, 2014; Ser. No. 14/681,882 filed on Apr. 8, 2015; Ser. No. 15/061,524 filed on Mar. 4, 2016; Ser. No. 15/178, 244 filed on Jun. 9, 2016; Ser. No. 15/178,291 filed on Jun. 9, 2016; Ser. No. 15/216,472 filed on Jul. 21, 2016; Ser. No. 15/664,608 filed on Jul. 31, 2017; Ser. No. 15/664,862 filed on Jul. 31, 2017; Ser. No. 14/514,221 filed on Oct. 14, 2014, now U.S. Pat. No. 9,826,986; Ser. No. 14/723,384 filed on May 27, 2015; Ser. No. 14/567,956 filed on Dec. 14, 2014; Ser. No. 14/447,612 filed Jul. 31, 2014; Ser. No. 14/413,318 filed Jan. 7, 2015; Ser. No. 15/418,633 filed on Jan. 27, 2017; 62/608,476 filed Dec. 20, 2017; 62/609,095 filed Dec. 21, 2017; 62/632,635 filed Feb. 20, 2018; 62/640,026 filed Mar. 8, 2018; Ser. No. 16/133,605 filed Sep. 17, 2018; U.S. patent application Ser. No. 16/544,193 filed Aug. 19, 2019; U.S. patent application Ser. No. 16/455,308 filed on Jun. 27, 2019; U.S. patent application Ser. No. 16/431,301 filed on Jun. 4, 2019; U.S. provisional patent application Ser. No.

62/854,041 filed May 29, 2019; and U.S. patent application Ser. No. 16/282,114 filed Feb. 21, 2019.

Implementations of the present disclosure involve a system for preparing a sacroiliac joint for fusion. In particular, the system may include a preparation tool for removing articular cartilage from the sacroiliac joint space, abrading of the articular surfaces to enhance bony fusion, and removal of portions of the cortical, subchondral or cancellous bone for implantation of a fusion device. The preparation tool may include an anchoring arm that is configured to direct an anchoring element for transverse delivery through the sacroiliac joint space. The anchor may be delivered into the joint space before, during, or after the joint space is prepared for implant delivery. Alternatively, an implant may not be delivered into the joint and instead, e.g., bone paste or slurry may be introduced into the prepared sacroiliac joint before or after anchor placement. And, the anchor may be delivered cranial, caudal, in front of, behind, above, below, next to, up to, near, adjacent, away from, through, or in-line with the eventual placement of the implant. The preparation tool is configured to quickly, accurately and reliably prepare the joint space for insertion of an implant.

Implementations of the present disclosure may further include radiographic tools adapted to confirm placement of the joint implant and anchors prior to their implantation. According to particular embodiments, a radiographic tool may include a radiographic implant template (not shown) positioned near, up to or within the patient's body in order to approximate the orientation, location, size, configuration and implantation trajectory of the implant and employed either: i) prior to the incision of the patient's skin, ii) prior to the preparation of the sacroiliac joint, iii) prior to the creation of the central portion of the implant receiving space, iv) prior to the creation of substantially the entire implant receiving space, v) after placement of a pin or other guidance instrument (e.g., joint finder) into the sacroiliac joint, vi) after the preparation of the sacroiliac joint, vii) after the creation of the central portion of the implant receiving space, viii) after the creation of substantially the entire implant receiving space; for example, the implant template may include a shape comprising a cross section of the implant and may further comprise an overlapping pattern of implant sizes or configurations in order to determine, e.g., desired implant size or configuration in relation to the sacroiliac joint an surrounding anatomy. As an example, such tools may be used after removing articular cartilage but prior to abrading or otherwise removing the cortical, subchondral or cancellous bone of the joint. The tools may be used before making cuts for keels or other members extending beyond the portion of the implant at the plane of the joint and after preparing the plane of the sacroiliac joint in order to create at least a portion of the implant receiving space, which, e.g., may approximate the shape and size of the portion of the implant to be situated therein and, e.g., may be configured to accommodate a cylindrical body, a rectangular body. In other aspects the implant receiving space may be fully prepared before employing the radiographic tools. The radiographic tools generally include radiopaque markers or structures that are viewable using a radiography system, such as a fluoroscope or X-ray. By aligning the radiopaque markers/structures with anatomical features of the patient or other radiopaque elements of the tools, parameters for implanting the anchors (such as anchor configuration and size, location, orientation, and depth) may be determined and confirmed prior to the substantial tissue removal required for implanting the joint implant and/or the anchor.

The drawing sheets illustrate certain tools and methods of use for treating a sacroiliac joint.

The cutting tool may be configured as a dual serrated edge blade powered by an oscillating tool. For example, an ultrasonically powered system may be employed and as a non-limiting example, may include an ultrasonic oscillating tool which is configured to couple longitudinal vibration with torsional oscillation such as the SONOPET Ultrasonic Aspirator available from STRYKER.

The cutting tool may be constrained and guided by a guide block.

The foregoing merely illustrates the principles of the embodiments described herein. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the embodiments described herein and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A sacroiliac joint implant comprising:
a distal end, a proximal end opposite the distal end, and a longitudinal axis extending centrally between the distal end and the proximal end,
a first planar member comprising a first iliac member, a first sacral member extending from the first iliac member at a first midsection thereof, a first iliac side edge, a first sacral side edge opposite the first iliac side edge, a first iliac distal edge, a first sacral distal edge joined with the first iliac distal edge, a first iliac proximal edge, a first sacral proximal edge joining the first iliac proximal edge, a first iliac top surface, a first iliac bottom surface opposite the first iliac top surface, a first sacral top surface, and a first sacral bottom surface opposite the first sacral top surface, and a first aperture extending from the first iliac top surface and the first sacral top surface through the first planar member to the first iliac bottom surface and the first sacral bottom surface,
wherein the first iliac top surface and the first sacral bottom surface each include at least one first fin extending between the proximal end and the distal end and terminating at a first distal section, the at least one first fin comprising a first trough and a first crest, the first trough positioned farther outward than the first crest from the longitudinal axis, the first distal section comprising an outward flaring of both the first trough and the first crest away from the longitudinal axis,
a second planar member joined with the first planar member to form a generally X-shape cross-section transverse to the longitudinal axis.

2. The sacroiliac joint implant of claim 1, wherein the X-shape is a flattened X-shape.

3. The sacroiliac joint implant of claim 1, wherein the second planar member comprises a second iliac member, a second sacral member extending from the second iliac member at a second midsection thereof, a second iliac side edge, a second sacral side edge opposite the second iliac side edge, a second iliac distal edge, a second sacral distal edge joined with the second iliac distal edge, a second iliac proximal edge, a second sacral proximal edge joining the second iliac proximal edge, a second iliac top surface, a second iliac bottom surface opposite the second iliac top surface, a second sacral top surface, and a second sacral bottom surface opposite the second sacral top surface, and a second aperture extending from the second iliac top surface and the second sacral top surface through the second planar member to the second iliac bottom surface and the second sacral bottom surface, wherein the first planar member and the second planar member are joined at the first and second midsections, respectively.

4. The sacroiliac joint implant of claim 3, wherein the second sacral top surface and the second iliac bottom surface each include at least one second fin extending between the proximal end and the distal end and terminating at a second distal section, the at least one second fin comprising a second trough and a second crest, the second trough positioned farther outward than the second crest from the longitudinal axis, the second distal section comprising an outward flaring of both the second trough and the second crest away from the longitudinal axis.

5. The sacroiliac joint implant of claim 4, wherein a first obtuse angle is formed between the first iliac member and the second sacral member.

6. The sacroiliac joint implant of claim 5, wherein a second obtuse angle is formed between the second iliac member and the first sacral member.

7. The sacroiliac joint implant of claim 4, wherein a first acute angle is formed between the first iliac member and the second iliac member.

8. The sacroiliac joint implant of claim 5, wherein a first acute angle is formed between the first iliac member and the second iliac member.

9. The sacroiliac joint implant of claim 1, wherein the first distal section is beveled.

10. The sacroiliac joint implant of claim 4, wherein the first distal section and the second distal section are beveled.

11. The sacroiliac joint implant of claim 4, wherein each of the first iliac side edge, the first sacral side edge, the second iliac side edge, and the second sacral side edge includes a plurality of ridges thereon.

12. The sacroiliac joint implant of claim 11, wherein each of the plurality of ridges includes a distal face that is non-perpendicular to the longitudinal axis and a proximal face that is perpendicular to the longitudinal axis.

13. The sacroiliac joint implant of claim 1, wherein the outward flaring is about 7.5 degrees relative to the longitudinal axis.

14. The sacroiliac joint implant of claim 1, wherein each of the first iliac member and the first sacral member includes a distal section, a proximal section, and a transition point between the distal section and the proximal section, the distal section angling outward relative to the longitudinal axis at the transition point such that the distal end of the sacroiliac joint implant is wider than the proximal end of the implant.

15. The sacroiliac joint implant of claim 1, wherein the first iliac bottom surface and the first sacral top surface are devoid of the at least one first fin.

16. The sacroiliac joint implant of claim 4, wherein the first iliac bottom surface and the first sacral top surface are devoid of the at least one first fin, and wherein the second sacral bottom surface and the second iliac top surface are devoid of the at least one second fin.

17. The sacroiliac joint implant of claim 3, wherein the first aperture extends through the longitudinal axis and through a midpoint between the proximal end and the distal end.

18. The sacroiliac joint implant of claim 1, wherein the first trough includes a plurality of apertures extending through the first planar member.

19. A sacroiliac joint implant comprising:
a distal end, a proximal end opposite the distal end, and a longitudinal axis extending centrally between the distal end and the proximal end,
an iliac side, a sacral side adjacent the iliac side, a top surface extending across the iliac side and the sacral side, a bottom surface opposite the top surface and extending across the iliac side and the sacral side, an iliac side surface, a sacral side surface opposite the iliac side surface, a first aperture extending from the top surface to the bottom surface, a second aperture extending from the iliac side surface to the sacral side surface and extending through the first aperture, and
wherein each of the sacral side and the iliac side includes, on the top surface, at least one first fin extending between the proximal end and the distal end and terminating at a first distal section, the at least one first fin comprising a first trough and a first crest, the first trough positioned farther outward than the first crest from the longitudinal axis, the first distal section comprising an outward flaring of both the first trough and the first crest away from the longitudinal axis.

20. The sacroiliac joint implant of claim 19, wherein each of the sacral side and the iliac side includes, on the bottom surface, at least one second fin extending between the proximal end and the distal end and terminating at a second distal section, the at least one second fin comprising a second trough and a second crest, the second trough positioned farther outward than the second crest from the longitudinal axis, the second distal section comprising an outward flaring of both the second trough and the second crest away from the longitudinal axis.

21. The sacroiliac joint implant of claim 20, wherein the outward flaring is about 7.5 degrees relative to the longitudinal axis.

22. The sacroiliac joint implant of claim 20, wherein each of the iliac side surface and the sacral side surface includes a distal section, a proximal section, and a transition point between the distal section and the proximal section, the distal section angling outward relative to the longitudinal axis at the transition point such that the distal end of the sacroiliac joint implant is wider than the proximal end of the implant.

23. The sacroiliac joint implant of claim 22, wherein the sacroiliac joint implant defines a generally X-shaped body having an opened midsection defined by the first and second apertures.

24. A sacroiliac joint implant comprising:
a distal end, a proximal end opposite the distal end, and a longitudinal axis extending centrally between the distal end and the proximal end, and an implant body extending a length between the distal and proximal ends and comprising:
a central core portion disposed along the longitudinal axis,
a first, second, third, and fourth fixation member each of which extends outwardly from and connects to the central core portion and each of which extends the length, wherein each of the first fixation member and the second fixation member comprises at least one exterior surface having at least one stepped projection disposed thereon and extending along the implant body between the proximal and distal ends,
wherein each of the at least one stepped projection comprises a riser portion and a tread portion, the riser portion extending outward from the at least one exterior surface from which it is disposed and the tread portion extending generally perpendicular to the riser portion; and
wherein each of the at least one stepped projection, while extending along the implant body between the proximal and distal ends, extends parallel to the longitudinal axis from the proximal end up until a transition point where each of the at least one stepped projection then forms a diverging angle to the longitudinal axis.

25. The sacroiliac joint implant of claim 24, wherein the first, second, third, and fourth fixation members are arranged around the longitudinal axis such that a first obtuse angle is formed between the first fixation member and the second fixation member, a first acute angle is formed between the second fixation member and the third fixation member, and a second acute angle is formed between the fourth fixation member and the first fixation member.

26. The sacroiliac joint implant of claim 24, wherein the implant body defines a generally X-shaped cross-section as viewed along the longitudinal axis.

27. The sacroiliac joint implant of claim 24, further comprising a first window positioned between the proximal and distal ends and extending generally perpendicular to the longitudinal axis and extending through each of the first, second, third and fourth fixation members and the central core portion, and a second window positioned between the proximal and distal ends and extending generally perpendicular to both the longitudinal axis and the first window and extending through the central core portion, wherein the first and second windows are coincident with each other.

28. A sacroiliac joint implant comprising:
a distal end, a proximal end opposite the distal end, and a longitudinal axis extending centrally between the distal end and the proximal end, and an implant body extending a length between the distal and proximal ends and comprising:
a central core portion disposed along the longitudinal axis,
a first, second, third, and fourth fixation member each of which extends outwardly from and connects to the central core portion and each of which extends the length, wherein each of the first fixation member and the second fixation member comprises at least one exterior surface having at least one trough disposed thereon and extending along the implant body between the proximal and distal ends; and
wherein each of the at least one trough, while extending along the implant body from the proximal end to distal end, forms a diverging angle to the longitudinal axis such that a distal trough portion is located farther from the longitudinal axis than a proximal trough portion.

29. The sacroiliac joint implant of claim 28, wherein each of the at least one trough extends parallel to the longitudinal axis from the proximal end up until a transition point where each of the at least one trough then forms the diverging angle to the longitudinal axis.

30. The sacroiliac joint implant of claim 28, wherein the first, second, third, and fourth fixation members are arranged around the longitudinal axis such that a first obtuse angle is formed between the first fixation member and the second fixation member, a first acute angle is formed between the second fixation member and the third fixation member, and a second acute angle is formed between the fourth fixation member and the first fixation member.

31. The sacroiliac joint implant of claim 28, wherein the implant body defines a generally X-shaped cross-section as viewed along the longitudinal axis.

32. The sacroiliac joint implant of claim 28, further comprising a first window positioned between the proximal and distal ends and extending generally perpendicular to the longitudinal axis and extending through each of the first, second, third and fourth fixation members and the central core portion, and a second window positioned between the proximal and distal ends and extending generally perpendicular to both the longitudinal axis and the first window and extending through the central core portion, wherein the first and second windows are coincident with each other.

* * * * *